(12) United States Patent
Meyer et al.

(10) Patent No.: US 11,406,617 B2
(45) Date of Patent: *Aug. 9, 2022

(54) COMPOUNDS FOR THE TREATMENT OF BOVINE OR SWINE RESPIRATORY DISEASE

(71) Applicant: Intervet Inc., Madison, NJ (US)

(72) Inventors: Thorsten Meyer, Wiesbaden (DE); Ralf Warrass, Alzey (DE); Joachim Ullrich, Stadecken-Elsheim (DE); Michael Berger, Wiesbaden (DE); Michael Linder, Ingelheim (DE)

(73) Assignee: Intervet Inc., Madison, NJ (US)

( * ) Notice: Subject to any disclaimer, the term of this patent is extended or adjusted under 35 U.S.C. 154(b) by 387 days.

This patent is subject to a terminal disclaimer.

(21) Appl. No.: 16/472,084

(22) PCT Filed: Dec. 22, 2017

(86) PCT No.: PCT/EP2017/084364
§ 371 (c)(1),
(2) Date: Jun. 20, 2019

(87) PCT Pub. No.: WO2018/115432
PCT Pub. Date: Jun. 28, 2018

(65) Prior Publication Data
US 2020/0085779 A1    Mar. 19, 2020

(30) Foreign Application Priority Data
Dec. 23, 2016 (EP) .................................. 16206843

(51) Int. Cl.
| | |
|---|---|
| *A61K 31/27* | (2006.01) |
| *A61P 31/04* | (2006.01) |
| *A61P 11/00* | (2006.01) |
| *A61K 9/00* | (2006.01) |
| *A61K 31/166* | (2006.01) |
| *A61K 31/222* | (2006.01) |
| *A61K 31/357* | (2006.01) |
| *A61K 31/40* | (2006.01) |
| *A61K 31/445* | (2006.01) |
| *A61K 31/472* | (2006.01) |
| *A61K 31/495* | (2006.01) |
| *A61K 31/5377* | (2006.01) |
| *A61K 31/54* | (2006.01) |
| *A61K 31/695* | (2006.01) |

(52) U.S. Cl.
CPC ............ *A61K 31/27* (2013.01); *A61K 9/0019* (2013.01); *A61K 31/166* (2013.01); *A61K 31/222* (2013.01); *A61K 31/357* (2013.01); *A61K 31/40* (2013.01); *A61K 31/445* (2013.01); *A61K 31/472* (2013.01); *A61K 31/495* (2013.01); *A61K 31/5377* (2013.01); *A61K 31/54* (2013.01); *A61K 31/695* (2013.01); *A61P 11/00* (2018.01); *A61P 31/04* (2018.01)

(58) Field of Classification Search
CPC ................................. A61K 31/27; A61P 31/04
See application file for complete search history.

(56) References Cited

U.S. PATENT DOCUMENTS 8,084,615 B2 * 12/2011 Andersen .............. C07C 311/19
546/309
9,073,821 B2   7/2015 Takashima et al.

FOREIGN PATENT DOCUMENTS

| JP | 2006519772 A | 8/2006 |
|---|---|---|
| JP | 2010530372 A | 9/2010 |
| JP | 2020514270 A | 5/2020 |
| RU | 2012149216 A | 5/2014 |
| WO | 2004062601 A2 | 7/2004 |
| WO | 2008154642 A2 | 12/2008 |
| WO | 2012/031298 A2 | 3/2012 |
| WO | 2013/170030 A1 | 11/2013 |
| WO | 2014165075 A1 | 10/2014 |
| WO | 2018115421 A1 | 6/2018 |

OTHER PUBLICATIONS

Angen et al., Proposal of *Histophilus somni* gen. nov., sp. nov., International Journal of Systematic and Evolutionary Microbiology, 2003, pp. 1449-1456, vol. 53.
Barb, Adam W. et al., Inhibition of lipid A Biosynthesis as the Primary Mechanism of CHIR-090 Antibiotic Activity in *Escherichia coli*, Biochemistry, 2007, pp. 3793-3802, 46(12).
European Search report for 16206843.1, dated Oct. 2, 2017, 9 pages.
Gao, N. et al., Overexpression of Pseudomonas aeruginosa LpxC with its inhibitors in an acrB-deficient *Escherichia coli* strain, Protein Expression and Purification, 2014, pp. 57-64, 104.
International Search report and written opinion for PCT/EP2017/084364 dated Jan. 4, 2019, 13 pages.
Kurasaki, H. et al., LpxC Inhibitors: Design, Synthesis, and Biological Evaluation of Oxazolidinones as Gram-negative Antibacterial Agents, ACS Med. Chem. Lett., 2016, pp. 623-628, 7.
Lee, C-J. et al., Structural Basis of the Promiscuous Inhibitor Susceptibility of *Escherichia coli* LpxC, ACS Chem. Biol., 2014, pp. 237-246, 9.
Liang, X. et al., Synthesis, structure and antibiotic activity of aryl-substituted LpxC inhibitors, J Med Chem., 2013, pp. 6954-6966, 56(17).
Rose, S et al, Multiplex PCR To Identify Macrolide Resistance Determinants in Mannheimia haemolytica and Pasteurella multocida, Antimicrobial Agents and Chemotherapy, 2012, pp. 3664-3669, vol. 56 No. 7.

(Continued)

*Primary Examiner* — Yong S. Chong
(74) *Attorney, Agent, or Firm* — David J. Kerwick

(57) ABSTRACT

The present invention provides compounds for use in the treatment of respiratory diseases of animals, especially Bovine or Swine Respiratory disease (BRD and SRD).

2 Claims, 4 Drawing Sheets

(56) References Cited

OTHER PUBLICATIONS

Stephens, L et al, Morphological, Biochemical, Antigenic, and Cytochemical Relationships Among Haemophilus somnus, Haemophilus agni, Haemophilus haemoglobinophilus, Histophilus ovis, and Actinobacillus seminis, Journal of Clinical Microbiology,, 1983, p. 728-737, vol. 17, No. 5.

Titecat, M. et al., High susceptibility of MDR and XDR Gram-negative pathogens to biphenyl-diacetylene-based difluoromethyl-allo-threonyl-hydroxamate LpxC inhibitors, J. Antimicrob. Chemother., Jun. 20, 2016, pp. 2874-2882, 71.

Belikov, V.G., Pharmaceutical Chemistry, Moscow MEDpress-inform, 2007, 27-29, 4th Edition.

Belikov, V.G., Pharmaceutical Chemistry, Moscow MEDpress-inform, 2007, 27-29, 4th Edition, machine translation.

Ministry of Agriculture, Forestry and Fisheries, Guidebook for Antimicrobial Treatment in Bovine Respiratory Disease (BRDC), Mar. 2016, https://www.maff.go.jp/nval/yakuzai/pdf/brdc_guidebook.pdf, 40 pages.

Partial English translation of Ministry of Agriculture, Forestry and Fisheries, Guidebook for Antimicrobial Treatment in Bovine Respiratory Disease (BRDC), Mar. 2016, https://www.maff.go.jp/nval/yakuzai/pdf/brdc_guidebook.pdf, 1 pages.

Yamamoto, K., Porcine Respiratory Disease Complex (PRDC), Proc. Jpn. Pig. Vet. Soc., 2003, 7-8, 43.

Vamamoto, Takashi, Porcine Respiratory Disease Complex (PRDC), Proc. Jpn. Pig Vet. Soc., 2003, Partial translation of pp. 7-8, 43.

\* cited by examiner

Figure 1: General behavior [score]
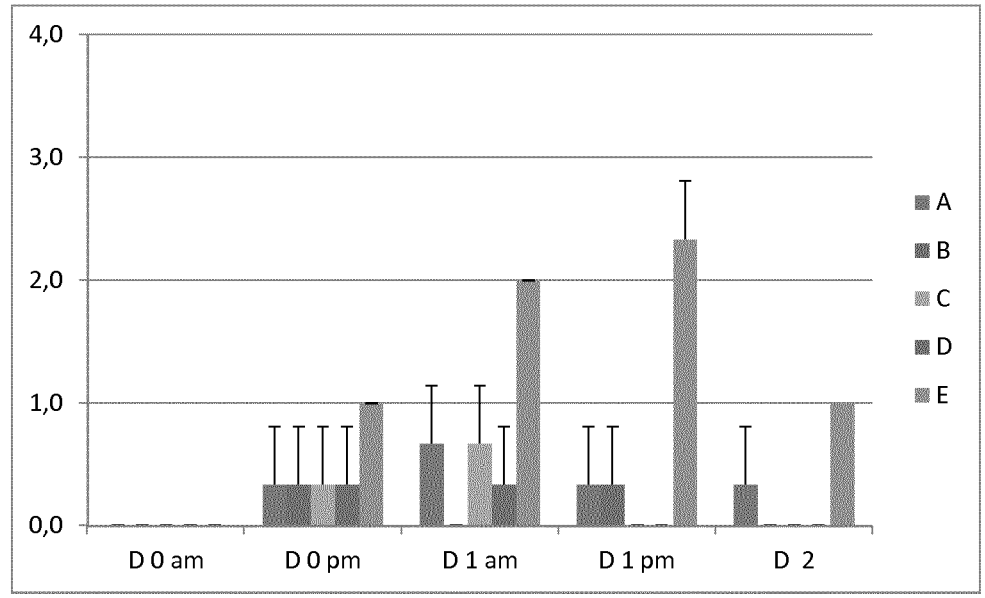
A =C.105; B =C.189; C =C.326; D= Enrofloxacin; E= Placebo
On D 1 pm 2 out of 3 animals of group E were euthanized for humane reason.
Figure 2: Lung scores, including grade and % of consolidation
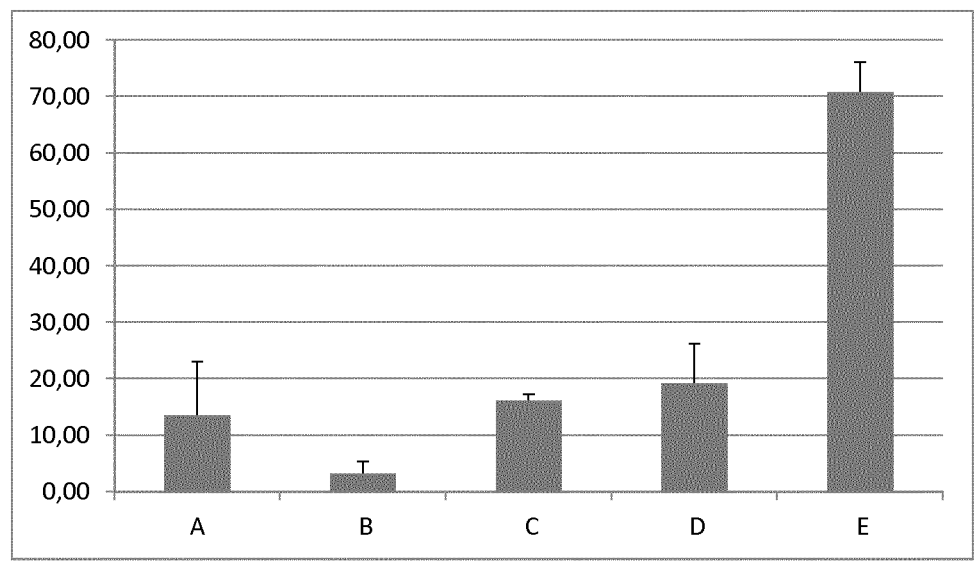
A =C.105; B =C.189; C =C.326; D= Enrofloxacin; E= Placebo

Figure 3: Lung body mass ratio [%]
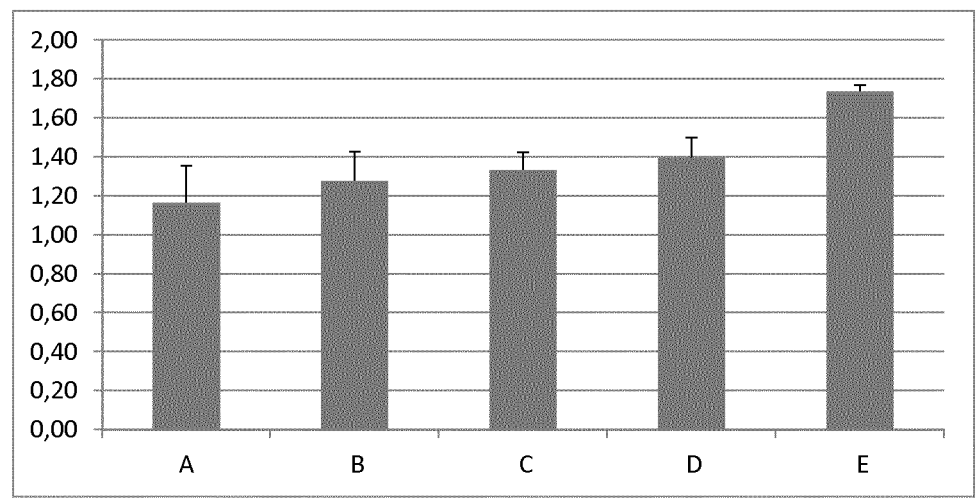
A =C.105; B =C.189; C =C.326; D= Enrofloxacin; E= Placebo
Figure 4: Bacteria re-isolated from lung [CFU/g, geometrical means]
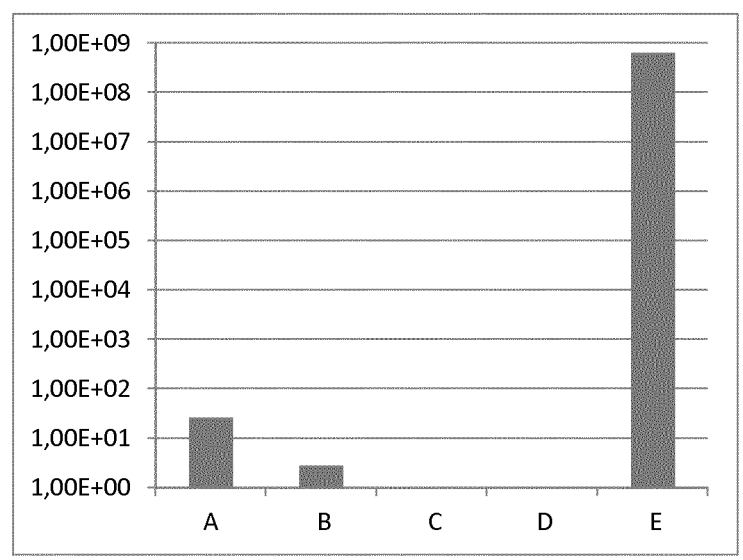
A =C.105; B =C.189; C =C.326; D= Enrofloxacin; E= Placebo

Figure 5: General behavior [score]
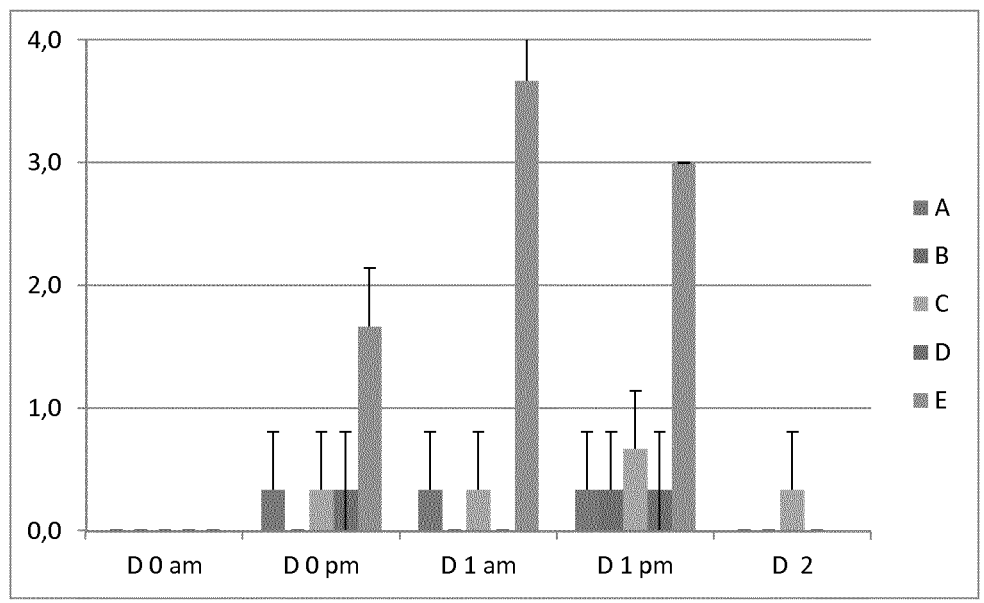
A = C.231; B = C.329, 10 mg/kg; C = C.329, 5 mg/kg; D Enrofloxacin; E Placebo
On D 1 pm 2 out of 3 animals of group E had died or been euthanized for humane reason.
On D 2 all animals of group E had died or been euthanized for humane reason.
Figure 6: Lung scores, including grade and % of consolidation
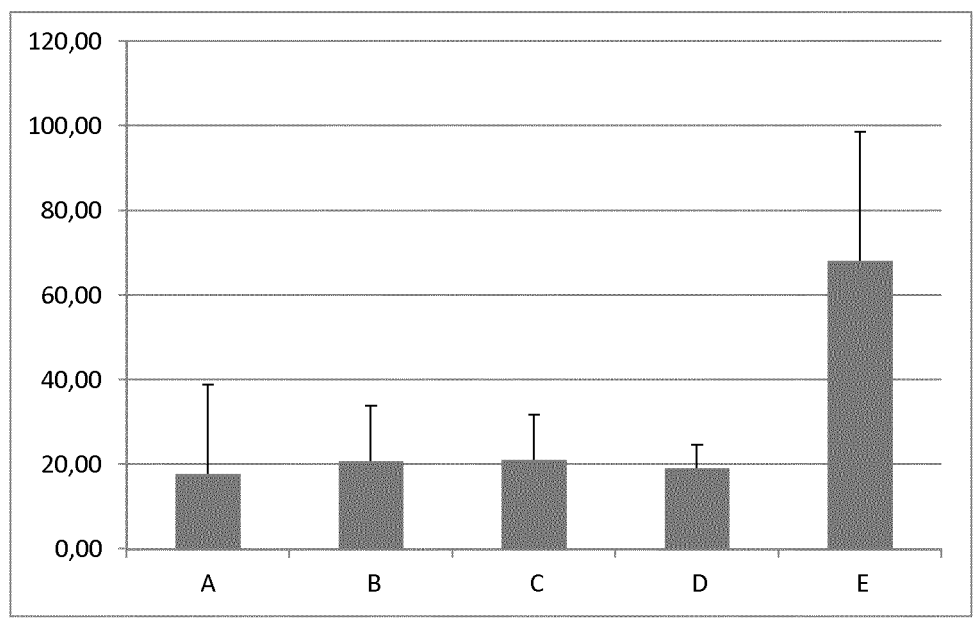
A = C.231; B = C.329, 10 mg/kg; C = C.329, 5 mg/kg; D Enrofloxacin; E Placebo Figure 7: Lung body mass ratio [%]
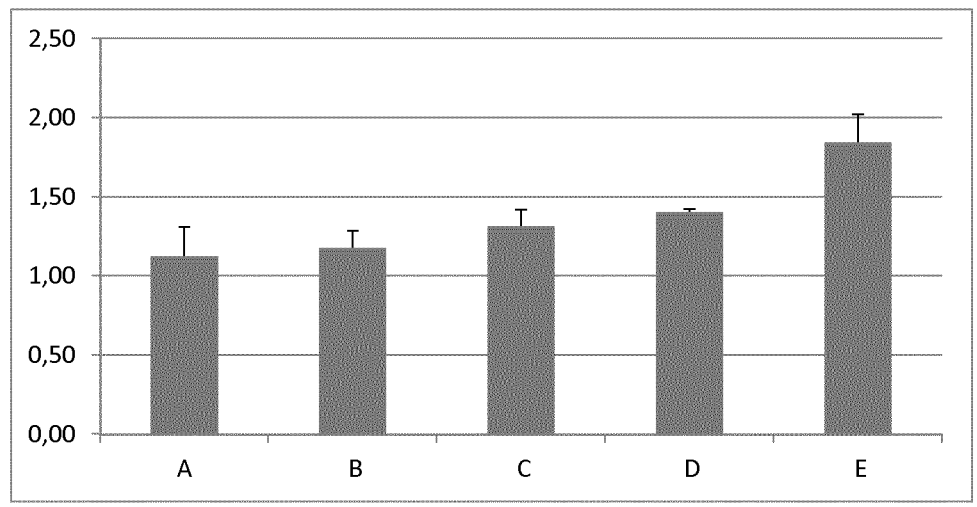
A =C.231; B = C.329, 10 mg/kg; C = C.329, 5 mg/kg; D Enrofloxacin; E Placebo
Figure 8: Bacteria re-isolated from lung [CFU/g, geometrical means]
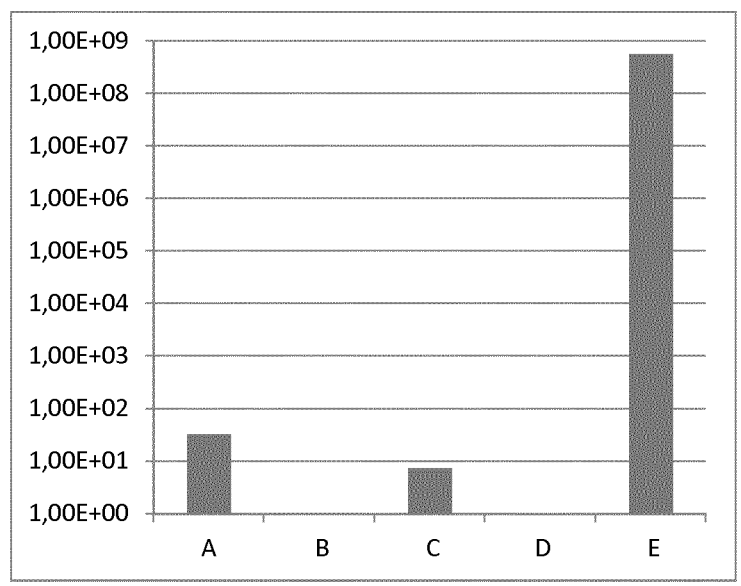
A =C.231; B = C.329, 10 mg/kg; C = C.329, 5 mg/kg; D Enrofloxacin; E Placebo

COMPOUNDS FOR THE TREATMENT OF BOVINE OR SWINE RESPIRATORY DISEASE

CROSS-REFERENCE TO RELATED APPLICATIONS

This application is a national stage entry under 35 U.S.C. § 371 of PCT/EP2017/084364, filed on Dec. 22, 2017, which claims priority to EP 16206843.1, filed on Dec. 23, 2016; the content of PCT/EP2017/084364 is hereby incorporated by reference in its entirety.

The present invention relates to compounds for use in the treatment of diseases of animals, especially Bovine or Swine Respiratory disease (BRD and SRD).

BACKGROUND

Bovine respiratory disease (BRD) is the most common and costly disease affecting beef cattle in the world. Bovine respiratory disease (BRD) has a multifactorial etiology and develops as a result of complex interactions between environmental factors, host factors, and pathogens. Environmental factors (e.g., weaning, transport, commingling, crowding, inclement weather, dust, and inadequate ventilation) serve as stressors that adversely affect the immune and nonimmune defense mechanisms of the host. In addition, certain environmental factors (e.g., crowding and inadequate ventilation) can enhance the transmission of infectious agents among animals. It is a complex, bacterial infection that causes Enzootic pneumonia in calves and other bovine animals and can possibly be fatal. The infection is usually a sum of three codependent factors: Stress, an underlying viral infection, and a new bacterial infection. The diagnosis of the disease is complex since there are multiple possible causes.

The disease manifests itself most often in calves within four weeks of weaning, when calves are sorted and often sold to different farms. This gives it a common nickname, "Shipping Fever" or "Shipping fever pneumonia". The four key clinical signs of the disease are depression, decreasing appetite, respiratory signs and raise in temperature.

*Mannheimia haemolytica*, *Pasteurella multocida*, *Histophilus somni*, and *Mycoplasma bovis* are the bacterial agents that have been most consistently implicated in BRD. Viral agents include Bovine Viral Diarrhea (BVD), Infectious Bovine Rhinotracheitis (IBR), Bovine Respiratory Synctial Virus (BRSV), and Parainfluenza Type-3 Virus (P1-3).

*Pasteurella* is a genus of Gram-negative, facultatively anaerobic bacteria. *Pasteurella* species are non-motile and pleomorphic. The genus is named after the Louis Pasteur who first identified the bacteria now known as *Pasteurella multocida* as the agent of chicken cholera. Many *Pasteurella* species are zoonotic pathogens, and humans can acquire an infection from domestic animal bites. *Pasteurella multocida* is the most frequent causative agent in human of *Pasteurella* infection. *Pasteurella multocida* is the cause of a range of diseases in mammals and birds, including fowl cholera in poultry, atrophic rhinitis in pigs, and bovine hemorrhagic septicemia in cattle and buffalo.

*Histophilus somni* is also known as *Haemophilus agni*, *Histophilus ovis*, *Haemophilus somnus*, and *Haemophilus somnifer*. Stephens et al (Stephens L R, Humphrey J D, Little P B, Barnum D A. Morphological, biochemical, antigenic, and cytochemical relationships among *Haemophilus somnus*, *Haemophilus agni*, *Haemophilus haemoglobinophilus*, *Histophilus ovis*, and *Actinobacillus seminis*. J Clin Microbiol. 1983; 17:728-737) found that these organisms had similar morphology and biochemical reactions, as well as common antigens, and suggested that they should be considered members of a single taxon within the family Pasteurellaceae.

*Histophilus somni* is a bacterium that lives in the nasal passages of cattle. Generally speaking, *H. somni* infects vascular tissue (blood vessels) and endothelium of organs, causing inflammation, thrombosis (formation of a vascular obstruction) that interrupts the blood supply, and causes local cellular death.

*H. somni* typically colonize in the respiratory tract, reproductive tract, and circulatory system of many herd animals such as cattle, sheep, and American bison. If *H. somni* infects the lungs, pneumonia can result in rapid death. If *H. somni* gains access to the bloodstream, it spreads throughout the body, a condition known as septicemia. Involvement of the central nervous system, whereby blood flow to the spinal cord and brain is affected, results in a syndrome known as thromboembolic meningoencepahlitis (TEME). The respiratory syndrome is often preceded by primary infection with viral pathogens, with respiratory signs sometimes followed by TEME.

Phylogenetic analyses, utilizing the 16s ribosomal DNA (rDNA) and RNA polymerase B (rpoB) gene sequences, have shown that *Histophilus somni* differs significantly from *Haemophilus influenzae*, the type species of the genus *Haemophilus* (Angen O, Ahrens P, Kuhnert P, Christensen H, Mutters R. Proposal of *Histophilus somni* gen. nov., sp. nov for the three species incertae sedis '*Haemophilus somnus*', '*Haemophilus agni*' and '*Histophilus ovis*' Int. J. Syst. Evol. Microbiol. 2003; 53: (1449-1456).

*Mannheimia haemolytica* is a species of the *Mannheimia* genus. *Mannheimia haemolytica* is a gram negative bacterium normally found in the upper respiratory tract of healthy cattle, sheep and wild sheep. *Mannheimia haemolytica* was formerly known as: *Pasteurella haemolytica*. *M. haemolytica* descends into the lungs when cattle experience stress such as shipping, weaning, overcrowding, or viral infections and causes fibrinous and necrotizing bronchopneumonia, a chief component of the bovine respiratory disease (BRD). *M. haemolytica* is the bacterium most commonly isolated from the lungs of cattle affected with BRD in the United States.

Vaccinations exist for several biological BRD precursors, but the multitude of possible precursors complicates the process of choosing a vaccine regime. Bacteria may be treated with common antibiotics. Fear of antibiotic resistance caution the use of broad spectrum antibiotics and instead prefer compounds that selectively kill bacteria. There exists a need for such compounds that treat bovine respiratory disease (BRD) associated with *Mannheimia haemolytica*, *Pasteurella multocida* and *Histophilus somni*.

Preferably these compounds are active against the bacterial causes of BRD. Preferably the compounds are active against *Mannheimia haemolytica*, *Pasteurella multocida* and *Histophilus somni*. Preferably the compounds are also active against resistant (e.g. macrolide) strains of these bacteria.

Such strains for *Mannheimia haemolytica* and *Pasteurella multocida* are e.g. described in Rose S, et al: "Multiplex PCR to identify macrolide resistance determinants in *Mannheimia haemolytica* and *Pasteurella multocida* "Antimicrobial Agents and Chemotherapy, 56, 7 (2012) p. 3664-3669.

Respiratory disease in swine is arguably the most important health concern for swine producers today. As with respiratory disease in humans and other species, respiratory disease in swine is often the result of a combination of primary and opportunistic infectious agents. In addition, adverse environmental and management conditions play an important role in the multifactorial nature of respiratory disease in pigs.

The term swine respiratory disease (SRD) was used to describe pneumonia of multiple etiology causing clinical disease and failure to gain weight later in the finishing process (15 to 20 weeks of age).

*Actinobacillus pleuropneumoniae* is a gram-negative bacterium which is the most common cause of pleuropneumonia in pigs. Outbreaks of *A. pleuropneumoniae* are usually precipitated by stress, environmental changes, or viral or mycoplasmal infection. The disease may present clinically as a peracute form with sudden death; an acute form with clinical signs characterized by fever, lethargy, dyspnea, cyanosis, recumbency, and froth from the nose; or a sub-acute/chronic form which develops after disappearance of acute signs with intermittent cough, slow growth, and exercise intolerance.

*P. multocida* is a gram-negative bacterium which is a cause of atrophic rhinitis and pneumonia in pigs.

*Bordetella bronchiseptica* is a gram-negative bacterium that causes rhinitis and mild to moderate turbinate atrophy and predisposes to infection with toxigenic strains of *P. multocida* which causes the progressive form of atrophic rhinitis.

*Mycoplasma hyopneumoniae* is the primary pathogen associated with enzootic pneumonia, which occurs when *M. hyopneumoniae* is combined with opportunistic bacteria such as *P. multocida*.

*Haemophilus parasuis* is a gram-negative bacterium which causes polyserositis (Glasser's disease) and pneumonia in swine. Clinical signs include fever, anorexia, swollen joints with lameness, dyspnea, and central nervous system signs. Because of the incomplete efficacy of vaccines, antibacterials are needed to treat *H. parasuis* infections.

Consequently there is a need for compounds for the treatment and control of swine respiratory disease (SRD). Preferably these compounds are active against the bacterial causes of SRD especially when associated with *Pasteurella multocida, Actinobacillus pleuropneumoniae, Bordetella bronchiseptica* or *Haemophilus parasuis*. Preferably the compounds are active against *Pasteurella multocida* and *Actinobacillus pleuropneumoniae*. Preferably the compounds are also active against *Bordetella bronchiseptica*. In one embodiment they are active against *Mycoplasma* spp.

It is therefore desirable, that such antibacterial compounds have an effect on such bacterial pathogens involved in BRD and/or SRD but are not active against pathogens (especially multiresistant to common antibacterials) that are important in human health, such as *Straphylococcus* spp. and *Streptrococcus* spp., *Acinetobacter* spp., especially *Acinetobacter baumanii*.

SUMMARY OF THE INVENTION

Surprisingly it was found that at least one of the objects can be met by providing a compound according to the formula (I):

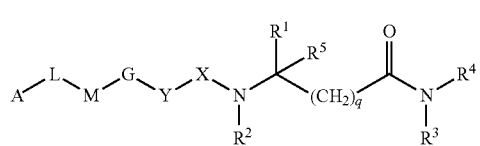

or a stereoisomer, pharmaceutically acceptable salt, ester, solvate, or prodrug thereof, for use in the treatment of bovine respiratory disease (BRD)—especially if associated with *Mannheimia haemolytica, Pasteurella multocida* and *Histophilus somni*- or swine respiratory disease (SRD), especially if associated with *Pasteurella multocida, Actinobacillus pleuropneumoniae* or *Haemophilus parasuis*, wherein A is selected from the group consisting of $NR^{A1}R^{A2}$, or $NO_2$;

wherein
$R^{A1}$, $R^{A2}$ are independently selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$—, carbonyl, —O(=O)—$OR^{A5}$—, halogen atom, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, —$SR^{A5}$—, —$SO_2R^{A5}$—, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from H, or $C_{1-6}$-alkyl L is absent or selected from the group consisting of $C_{1-6}$-alkyl, $C_{2-6}$-alkenyl, $C_{2-6}$-alkynyl, $C_{3-10}$-cycloalkyl, aryl, heterocyclyl, heteroaryl, —$(NR^{L3})_{0-1}$—$(CH_2)_{0-4}$—$NR^{L3}$—$(CH_2)_{0-4}$—, —$(NR^{L3})_{0-1}$—$(CR^{L1}R^{L2})_{0-4}$—$NR^{L3}$—$(CR^{L1}R^{L2})$—, —$(CR^{L1}R^{L2})_{0-4}$—O—$(CR^{L1}R^{L2})$—, —$(CH_2)_{0-4}$—$NR^{L3}$—$(CR^{L1}R^{L2})$—C(=O)NH—$(CH_2)_{0-4}$—, —C(=O)—$(CR^{L1}R^{L2})$—$NR^{L3}$C(=O)—, —C(=O)$NR^{L3}$—, —$NR^{L3}$C(=O)—, —$NR^{L3}$—C(=O)—$NR^{L3}$—
wherein
$R^{L1}$, $R^{L2}$, $R^{L3}$, are independently selected from the group consisting of H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or $R^{L1}$, $L^{L3}$ together with the atoms to which they are attached can form a saturated or unsaturated heterocyclic ring having 3 to 8 ring atoms, wherein 1, 2, or 3, ring atoms are selected from N, S, and O;

M is selected from the group consisting of
$C_{3-10}$-cycloalkyl, aryl, heterocyclyl, heteroaryl, $C_{2-4}$alkenyl, $C_{2-4}$alkynyl, —C($R^{M1}$)=C($R^{M1}$)—C≡C—, —C($R^{M1}$)=C($R^{M1}$)—, wherein each cycloalkyl, aryl, heterocyclyl, or heteroaryl is optionally substituted with a substituent selected from the group consisting of
$C_{1-6}$-alkyl, $C_{3-8}$-cycloalky, $C_{1-6}$-alkyloxy, $NR^{M2}R^{M3}$, carbonyl, —O(=O)—$OR^{M2}$, halo, halo-$C_{1-6}$-alkyl, $C_{1-6}$-alkyloxy-$C_1$-$C_6$-alkyl, aryl, heteroaryl, $C_1$-$C_6$-alkyl substituted with aryl, cyano, hydroxy, —$SR^2$, —SO$_2$R$^{M4}$, —OSO$_2$R$^{M4}$, —SO$_2$NR$^{M2}$R$^{M3}$, —C(=O)NR$^{M2}$R$^{M3}$—, hydroxy-C$_{1-6}$-alkyl;
wherein R$^{M1}$ is selected from the group consisting of H, C$_{1-6}$-alkyl, halo, hydroxyl, and amino;
wherein R$^{M2}$, R$^{M3}$ are independently selected from the group consisting of H, and C$_{1-6}$-alkyl;
wherein R$^{M4}$ is selected from the group consisting of H, C$_{1-6}$-alkyl, and amino;
G is selected from the group consisting of
—(C(R$^{G2}$R$^{G3}$)$_{0-4}$—O—(C(R$^{G2}$R$^{G3}$)$_{0-4}$—, —(C(R$^{G2}$R$^{G3}$)$_{0-4}$—S—(R$^{G2}$R$^{G3}$)$_{0-4}$—, —(C(R$^{G2}$R$^{G3}$)$_{0-4}$—NR$^{G1}$—(C(R$^{G2}$R$^{G3}$)$_{0-4}$—, —C(=O)—, —NR$^{G1}$C(=O)—, —C(=O)NR$^{G1}$—, —(C(R$^{G2}$R$^{3}$)$_{0-4}$—NR$^{G2}$—C(R$^{G2}$R$^{G3}$)—C(=O)NR$^{G1}$—,
—CR$^{G2}$=CR$^{G2}$—, —CR$^{G2}$=CR$^{G2}$—CR$^{G2}$=CR$^{G2}$—, —C≡C—, —C≡C—C≡C—, —CR$^{G2}$=CR$^{G2}$—C≡C—, —C≡C—CR$^{G2}$=CR$^{G2}$, —C(=O)—C=C—, —C≡C—C(=O)—, —SO$_2$—, —S(=O)—, —S(=O)C(R$^{G2}$R$^{G3}$)—. —C(R$^{G2}$R$^{G3}$)S(=O)—, —C(R$^{G2}$R$^{G3}$)—SO$_2$—, —SO$_2$C(R$^{G2}$R$^{G3}$)—;
wherein
R$^{G1}$ is H or C$_{1-6}$-alkyl
each R$^{G2}$, R$^{G3}$ is independently selected from the group consisting of
H, halogen atom, or C$_{1-6}$-alkyl;
Y is selected from the group consisting of
C$_{3-10}$-cycloalkyl, aryl, heterocyclyl, heteroaryl,
wherein each cycloalkyl, aryl, heterocyclyl, or heteroaryl is optionally substituted with a substituent selected from the group consisting of
C$_{1-6}$-alkyl, C$_{3-8}$-cycloalky, C$_{1-6}$-alkyloxy, NR$^{Y1}$R$^{Y2}$, carbonyl, —C(=O)—OR$^{Y1}$, halo, halo-C$_{1-6}$-alkyl, C$_{1-6}$-alkyloxy-C$_{1}$-C$_{6}$-alkyl, aryl, heterocyclyl, C$_{1}$-C$_{6}$-alkyl substituted with aryl, cyano, hydroxy, —SR$^{Y2}$, —SO$_2$R$^{Y3}$, —OSO$_2$R$^{Y3}$, —SO$_2$NR$^{Y1}$R$^{Y2}$, —C(=O)NR$^{Y2}$R$^{Y3}$—, hydroxy-C$_{1-6}$-alkyl;
wherein R$^{Y1}$, R$^{Y2}$ are independently selected from the group consisting of H, and C$_{1-6}$-alkyl;
wherein R$^{Y3}$ is selected from the group consisting of H, C$_{1-6}$-alkyl, and amino;
X is absent or selected from the group consisting of
—C(=O)—, —C$_{1-6}$-alkyl-C(=O)—, —C$_{2-6}$-alkenyl-C(=O)—, —C$_{2-6}$-alkynyl-C(=O)—, and —(C(R$^{X1}$)$_2$—, —S(=O)—, —SO$_2$—;
wherein
R$^{X1}$, is selected from the group consisting of
H, halogen atom, substituted C$_{1-6}$-alkyl, or un-substituted C$_{1-6}$-alkyl;
wherein the substituents on the substituted C$_{1-6}$-alkyl may be selected from the group consisting of halogen, hydroxyl, alkoxy, aryloxy, thiol, C$_{1-6}$-alkyl, carbonyl, —SR, —SO$_2$R$^{X5}$, SO$_2$NR$^{X3}$R$^{X4}$, —C(=O)NR$^{X3}$R$^{X4}$, cyano, —NR$^{X3}$R$^{X4}$, cyano, —NR$^{X3}$R$^{X4}$, —C(=O)—OR$^{X3}$, aryl, heteroaryl, heterocycle, C$_{3-8}$-cycloalkyl;
wherein R$^{X3}$, R$^{X4}$ are independently selected from the group consisting of H, or C$_{1-6}$-alkyl;
wherein R$^{X5}$ is selected from the group consisting of H, C$_{1-6}$-alkyl, and amine;
R$^1$ is selected from the group consisting of
H, C$_{1-6}$-alkyl, C$_{2-6}$-alkenyl, C$_{2-6}$-alkynyl, C$_{3-10}$-cycloalkyl, C(=O)R$^9$, C(=N—OR$^8$)R$^8$, aryl, heterocyclyl, heteroaryl, C$_1$-C$_6$-alkyl substituted with aryl, C$_1$-C$_6$-alkyl substituted with heteroaryl, C$_1$-C$_6$-alkyl substituted with heterocyclyl;

wherein each alkyl, alkenyl, alkynyl, cycloalkyl, aryl, heterocyclyl, heteroaryl, is optionally substituted with a substituent selected from the group consisting of
C$_{1-6}$-alkyl, C$_{3-8}$-cycloalky, C$_{1-6}$-alkyloxy, NR$^6$R$^7$, carbonyl, nitro, C(=O)OR$^9$, halogen, halo-C$_{1-6}$-alkyl, C$_{1-6}$-alkyloxy-C$_1$-C$_6$-alkyl, cyano, hydroxy, —SR$^8$, —SO$_2$R$^8$, SO$_2$NR$^6$R$^7$, —C(=O)NR$^6$R$^7$—;
wherein R$^6$, R$^7$, R$^8$ are independently selected from the group consisting of H or C$_{1-6}$-alkyl;
wherein R$^9$ is selected from the group consisting of H, hydroxyl, or C$_{1-6}$-alkyl;
R$^2$, R$^3$ are independently selected from the group consisting of
H atom, substituted C$_{1-6}$-alkyl, or un-substituted C$_{1-6}$-alkyl;
wherein the substituents on the substituted C$_{1-6}$-alkyl may be selected from the group consisting of halogen, hydroxyl, alkoxy, aryloxy, thiol, C$_{1-6}$-alkyl, carbonyl, —SR, —SO$_2$R$^8$, —C(=O)NR$^6$R$^7$, cyano, —NR$^6$R, —C(=O)—OR$^6$, aryl, heteroaryl, heterocycle, C$_{3-8}$-cycloalkyl;
q is 0, 1, 2, 3, or 4;
R$^4$ is selected from the group consisting of
H, C$_{1-6}$-alkyl, C$_{2-6}$-alkenyl, C$_{2-6}$-alkynyl, C$_{3-10}$-cycloalkyl, —OR$^8$, C(=O)OR$^9$C(=O)R$^9$, aryl, heterocyclyl, heteroaryl, C$_1$-C$_6$-alkyl substituted with aryl, C$_1$-C$_6$-alkyl substituted with heteroaryl, C$_1$-C$_6$-alkyl substituted with heterocyclyl;
wherein each alkyl, alkenyl, alkynyl, cycloalkyl, aryl, heterocyclyl, heteroaryl, is optionally substituted with a substituent selected from the group consisting of
C$_{3-8}$-cycloalky, C$_{1-6}$-alkyloxy, NR$^6$R$^7$, carbonyl, nitro, C(=O)OR$^9$, halogen, halo-C$_{1-6}$-alkyl, C$_{1-6}$-alkyloxy-C$_1$-C$_6$-alkyl, cyano, hydroxy, —SR$^8$, —SO$_2$R, SO$_2$NR$^6$R$^7$, —C(=O)NR$^5$R$^6$;
R$^5$ is selected from the group consisting of H, and C$_{1-6}$-alkyl;
R$^6$, R$^7$, R$^8$ are independently selected from the group consisting of H, and C$_{1-6}$-alkyl;
wherein R$^9$ is selected from the group consisting of H, hydroxyl, or C$_{1-6}$-alkyl.

In one embodiment of the invention and/or embodiments thereof, A is selected from the group consisting of NR$^{41}$R$^{42}$, or NO$_2$.

In another embodiment of the invention and/or embodiments thereof A is NR$^{41}$R$^{42}$.

In yet another embodiment of the invention and/or embodiments thereof, the compounds are according to formula (II).

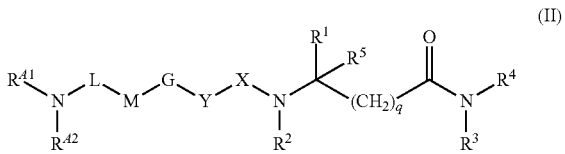

(II)

or a stereoisomer, pharmaceutically acceptable salt, ester, solvate, or prodrug thereof, for use in the treatment of bovine respiratory disease (BRD)—especially if associated with *Mannheimia haemolytica, Pasteurella multocida* and *Histophilus somni*- or swine respiratory disease (SRD), especially if associated with *Pasteurella multocida, Actinobacillus pleuropneumoniae* or *Haemophilus parasuis*, wherein $R^{A1}$, $R^{A2}$ are independently selected from
- H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or
- $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
- wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
    - $C_{1-6}$-alkyl, $C_{3-8}$-cycloalky, $C_{1-6}$-alkyloxy, —$NR^{A3}R^{A4}$—, carbonyl, —$O(=O)$—$OR^{A5}$—, halogen atom, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, —$SO_2R^{A5}$—, $SO_2NR^{A3}R^{A4}$, —$C(=O)NR^{A3}R^{A4}$—, $C_{1-6}$-alkyl substituted with hydroxy;
- wherein
    - $R^{A3}$, $R^{A4}$, $R^{A5}$ are independently chosen from H, or $C_{1-6}$-alkyl;
L is absent or selected from the group consisting of
$C_{1-6}$-alkyl, $C_{2-6}$-alkenyl, $C_{2-6}$-alkynyl, $C_{3-10}$-cycloalkyl, aryl, heterocyclyl, heteroaryl, —$(NR^{L3})_{0-1}$—$(CH_2)_{0-4}$—$NR^{L3}$—$(CH_2)_{0-4}$—, —$(NR^{L3})_{0-1}$—$(CR^{L1}R^{L2})_{0-4}$—$NR^{L3}$—$(CR^{L1}R^{L2})$—, —$(CR^{L1}R^{L2})_{0-4}$—O—$(CR^{L1}R^{L2})$—, —$(CH_2)_{0-4}$—$NR^{L3}$—$(CR^{L1}R^{L2})$—$C(=O)NH$—$(CH_2)_{0-4}$—, —$C(=O)$—$(CR^{L1}R^{L2})$—$NR^{L3}C(=O)$—, —$C(=O)NR^{L3}$—, —$NR^{L3}C(=O)$—, —$NR^{L3}$—, —$SO_2NR^{L3}$—, $NR^{L3}$—$C(=O)$—$NR^{L3}$—
wherein
- $R^{L1}$, $R^{L2}$, $R^{L3}$, are independently selected from the group consisting of
    - H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or
- $R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O;
M is selected from the group consisting of
$C_{3-10}$-cycloalkyl, aryl, heterocyclyl, heteroaryl, $C_{2-4}$alkenyl, $C_{2-4}$alkynyl, —$C(R^{M1})=C(R^{M1})$—$C\equiv C$—, —$C(R^{M1})=C(R^{M1})$—,
wherein each cycloalkyl, aryl, heterocyclyl, or heteroaryl is optionally substituted with a substituent selected from the group consisting of
- $C_{1-6}$-alkyl, $C_{3-8}$-cycloalky, $C_{1-6}$-alkyloxy, $NR^{M2}R^{M3}$, carbonyl, —$C(=O)$—$OR^{M2}$, halo, halo-$C_{1-6}$-alkyl, $C_{1-6}$-alkyloxy-$C_1$-$C_6$-alkyl, aryl, heteroaryl, $C_1$-$C_6$-alkyl substituted with aryl, cyano, hydroxy, —$SR^2$, —$SO_2R^{M4}$, —$OSO_2R^{M4}$, —$SO_2NR^{M2}R^{M3}$, —$C(=O)NR^{M2}R^{M3}$—, hydroxy-$C_{1-6}$-alkyl;
wherein $R^{M1}$ is selected from the group consisting of H, $C_{1-6}$-alkyl, halo, hydroxyl, and amino;
wherein $R^{M2}$, $R^{M3}$ are independently selected from the group consisting of H, and $C_{1-6}$-alkyl;
wherein $R^{M4}$ is selected from the group consisting of H, $C_{1-6}$-alkyl, and amino;
G is selected from the group consisting of
—$(C(R^{G2}R^{G3})_{0-4}$—O—$(C(R^{G2}R^{G3})_{0-4}$—, —$(C(R^{G2}R^{G3})_{0-4}$—S—$(C(R^{G2}R^{G3})_{0-4}$—, —$(C(R^{G2}R^{G3})_{0-4}$— $NR^{G1}$—$(C(R^{R2}R^{G3})_{0-4}$—, —$C(=O)$—, —$NR^{G1}C(=O)$—, —$C(=O)NR^{G1}$—, —$(C(R^{G2}R^{G3})_{0-4}$—$NR^{G1}$—$C(R^2R^{G3})$—$C(=O)NR^{G1}$—,
—$CR^{G2}=CR^{G2}$—, —$CR^{G2}=CR^{G2}$—$CR^{G2}=CR^{G2}$—, —$C=C$—, —$C\equiv C$—$C\equiv C$—, —$CR^{G2}=CR^{G2}$—$C=C$—, —$C\equiv C$—$CR^{G2}=CR^{G2}$, —$C(=O)$—$C\equiv C$—, —$C\equiv C$—$C(=O)$— —$SO_2$—, —$S(=O)$—, —$S(=O)C(R^{G2}R^{G3})$—. —$C(R^{G2}R^{G3})S(=O)$—, —$C(R^{G2}R^{G3})$—$SO_2$—, —$SO_2C(R^{G2}R^{G3})$—;
wherein
$R^{G1}$ is H or $C_{1-6}$-alkyl
each $R^{G2}$, $R^{G3}$ is independently selected from the group consisting of
H, halogen atom, or $C_{1-6}$-alkyl;
Y is selected from the group consisting of
$C_{3-10}$-cycloalkyl, aryl, heterocyclyl, heteroaryl,
wherein each cycloalkyl, aryl, heterocyclyl, or heteroaryl is optionally substituted with a substituent selected from the group consisting of
- $C_{1-6}$-alkyl, $C_{3-8}$-cycloalky, $C_{1-6}$-alkyloxy, $NR^{Y1}R^{Y2}$, carbonyl, —$C(=O)$—$OR^{Y1}$, halo, halo-$C_{1-6}$-alkyl, $C_{1-6}$-alkyloxy-$C_1$-$C_6$-alkyl, aryl, heteroaryl, $C_1$-$C_6$-alkyl substituted with aryl, cyano, hydroxy, —$SR^2$, —$SO_2R^{Y3}$, —$OSO_2R^{Y3}$, —$SO_2NR^{Y1}R^{Y2}$, —$C(=O)NR^{M2}R^{M3}$—, hydroxy-$C_{1-6}$-alkyl;
wherein $R^{Y1}$, $R^{Y2}$ are independently selected from the group consisting of H, and $C_{1-6}$-alkyl;
wherein $R^{Y3}$ is selected from the group consisting of H, $C_{1-6}$-alkyl, and amino;
X is absent or selected from the group consisting of
—$C(=O)$—, —$C_{2-6}$-alkenyl-$C(=O)$—, —$C_{2-6}$-alkynyl-$C(=O)$—, and —$(C(R^{X1})_2$—, —$S(=O)$—, —$SO_2$—,
wherein
$R^{X1}$, $R^{X2}$, is selected from the group consisting of
- H, halogen atom, substituted $C_{1-6}$-alkyl, or un-substituted $C_{1-6}$-alkyl;
- wherein the substituents on the substituted $C_{1-6}$-alkyl may be selected from the group consisting of halogen, hydroxyl, alkoxy, aryloxy, thiol, $C_{1-6}$-alkyl, carbonyl, —$SR^{X3}$, —$SO_2R^{X5}$, $SO_2NR^{X3}R^{X4}$, —$C(=O)NR^{X3}R^{X''}$, cyano, —$NR^{X3}R^{X4}$, —$C(=O)$—$OR^{X3}$, aryl, heteroaryl, heterocycle, $C_{3-8}$-cycloalkyl;
- wherein $R^{X3}$, $R^{X4}$ are independently selected from the group consisting of H, or $C_{1-6}$-alkyl;
- wherein $R^{X5}$ is selected from the group consisting of H, $C_{1-6}$-alkyl, and amine;
$R^1$ is selected from the group consisting of
H, $C_{1-6}$-alkyl, $C_{2-6}$-alkenyl, $C_{2-6}$-alkynyl, $C_{3-10}$-cycloalkyl, $C(=O)R^9$, $C(=N$—$OR^8)R^8$, aryl, heterocyclyl, heteroaryl, $C_1$-$C_6$-alkyl substituted with aryl, $C_1$-$C_6$-alkyl substituted with heteroaryl, $C_1$-$C_6$-alkyl substituted with heterocyclyl,
wherein each alkyl, alkenyl, alkynyl, cycloalkyl, aryl, heterocyclyl, heteroaryl, is optionally substituted with a substituent selected from the group consisting of
- $C_{1-6}$-alkyl, $C_{3-8}$-cycloalky, $C_{1-6}$-alkyloxy, $NR^6R^7$, carbonyl, nitro, $C(=O)OR^9$, halogen, halo-$C_{1-6}$-alkyl, $C_{1-6}$-alkyloxy-$C_1$-$C_6$-alkyl, cyano, hydroxy, —$SR^8$, —$SO_2R^8$, $SO_2NR^6R^7$, —$O(=O)NR^6R^7$—;
wherein $R^6$, $R^7$, $R^8$ are independently chosen from H, or $C_{1-6}$-alkyl;
wherein $R^9$ is selected from the group consisting of H, hydroxyl, or $C_{1-6}$-alkyl;

$R^2$, $R^3$ is selected from the group consisting of
H, atom, substituted $C_{1-6}$-alkyl, or un-substituted $C_{1-6}$-alkyl;
   wherein the substituents on the substituted $C_{1-6}$-alkyl may be selected from the group consisting of halogen, hydroxyl, alkoxy, aryloxy, thiol, $C_{1-6}$-alkyl, carbonyl, —SR, —SO$_2$R$^8$, SO$_2$NR$^6$R$^7$, —C(=O)NR$^6$R$^7$, cyano, —NR$^6$R$^7$, —C(=O)—OR$^6$, aryl, heteroaryl, heterocycle, $C_{3-8}$-cycloalkyl;
q is 0, 1, 2, 3, or 4;
$R^4$ is selected from the group consisting of
H, $C_{1-6}$-alkyl, $C_{2-6}$-alkenyl, $C_{2-6}$-alkynyl, $C_{3-10}$-cycloalkyl, —OR$^8$, C(=O)OR$^9$, C(=O)R$^9$, aryl, heterocyclyl, heteroaryl, $C_1$-$C_6$-alkyl substituted with aryl, $C_1$-$C_6$-alkyl substituted with heteroaryl, $C_1$-$C_6$-alkyl substituted with heterocyclyl;
   wherein each alkyl, alkenyl, alkynyl, cycloalkyl, aryl, heterocyclyl, heteroaryl, is optionally substituted with a substituent selected from the group consisting of
      $C_{1-6}$-alkyl, $C_{3-8}$-cycloalky, $C_{1-6}$-alkyloxy, NR$^6$R$^7$, carbonyl, nitro, C(=O)OR$^9$, halogen, halo-$C_{1-6}$-alkyloxy-$C_1$-$C_6$-alkyl, cyano, hydroxy, —SR$^8$, —SO$_2$R$^8$, SO$_2$NR$^6$R$^7$, —C(=O)NR$^5$R$^6$;
$R^5$ is selected from the group consisting of H, and $C_{1-6}$-alkyl;
$R^6$, $R^7$, $R^8$ are independently selected from the group consisting of H, and $C_{1-6}$-alkyl;
   wherein $R^9$ is selected from the group consisting of H, hydroxyl, or $C_{1-6}$-alkyl Suitably, in an embodiment of the invention and/or embodiments thereof, $R^{A1}$, $R^{A2}$ are independently selected from the group consisting of
   H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or
   $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
      wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
         $C_{1-6}$-alkyl, $C_{3-8}$-cycloalky, $C_{1-6}$-alkyloxy, —NR$^{A3}$R$^{A4}$, carbonyl, —C(=O)—OR$^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —SR$^{A5}$, —SO$_2$R$^{A5}$, SO$_2$NR$^{A3}$R$^{A4}$, —C(=O)NR$^{A3}$R$^{A4}$, $C_{1-6}$-alkyl substituted with hydroxy;
      wherein
         $R^{A3}$, $R^{A4}$, $R^{A5}$ are independently chosen from
            H, or $C_{1-6}$-alkyl.

In yet another embodiment of the invention and/or embodiments thereof, $R^{A1}$, $R^{A2}$ are independently selected from
   H, $C_{1-6}$-alkyl, $C_{2-6}$-alkenyl, $C_{2-6}$-alkynyl, $C_{3-10}$-cycloalkyl, $C_{1-6}$-alkyloxy-$C_1$-$C_6$-alkyl, substituted with aryl, $C_1$-$C_5$-alkyl substituted with heteroaryl, $C_1$-$C_5$-alkyl substituted with heterocyclyl, or
   $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O.

In yet another embodiment of the invention and/or embodiments thereof, $R^{A1}$, $R^{A2}$ are independently selected from
   H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or
   $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O.

In yet another embodiment of the invention and/or embodiments thereof q is 0, or 1. Preferably q is 0.

In yet another embodiment of the invention and/or embodiments thereof L is selected from the group consisting of
   $C_{1-6}$-alkyl, $C_{2-6}$-alkenyl, $C_{2-6}$-alkynyl, $C_{3-10}$-cycloalkyl, —(NR$^{L3}$)$_{0-1}$—(CH$_2$)$_{0-4}$—NR$^{L3}$—(CH$_2$)$_{0-4}$—, OR$^{L3}$)$_{0-1}$—(CR$^{L1}$R$^{L2}$)$_{0-4}$—NR$^{L3}$—(CR$^{L1}$R$^{L2}$)—, —(CR$^{L1}$R$^{L2}$)$_{0-4}$—O—(CR$^{L1}$R$^{L2}$)—, —(CH$_2$)$_{0-4}$—NR$^{L3}$—(CR$^{L1}$R$^{L2}$)—C(=O)NH—(CH$_2$)$_{0-4}$—, —C(=O)—(CR$^{L1}$R$^{L2}$)—NR$^{L3}$C(=O)—, —C(=O)NR$^{L3}$—, —NR$^{L3}$C(=))—, —NR$^{L3}$—, —SO$_2$NR$^{L3}$—, NR$^{L3}$—C(=O)—NR$^{L3}$—
wherein
   $R^{L1}$, $R^{L2}$, $R^{L3}$, are independently selected from the group consisting of
      H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or
   $R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O.

In yet another embodiment of the invention and/or embodiments thereof L is selected from the group consisting of
   $C_{1-6}$-alkyl, $C_{2-6}$-alkenyl, $C_{2-6}$-alkynyl, $C_{3-10}$-cycloalkyl, —NR$^{L3}$—,
wherein
   $R^{L3}$, is selected from the group consisting of
      H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl.

Suitably L is selected from the group consisting of $C_{1-6}$-alkyl, or $C_{2-6}$-alkenyl. Preferably L is —CH$_2$—, —CH$_2$CH$_2$—, —CH$_2$CH$_2$CH$_2$—, or —CH$_2$CH$_2$CH$_2$CH$_2$—, more preferably L is —CH$_2$—, —CH$_2$CH$_2$—, or —CH$_2$CH$_2$CH$_2$—, more preferably L is —CH$_2$—, or —CH$_2$CH$_2$—.

In another embodiment of the invention and/or embodiments thereof M is selected from the group consisting of
   $C_{3-10}$-cycloalkyl, aryl, heterocyclyl, heteroaryl, $C_{2-4}$alkenyl, $C_{2-4}$alkynyl, —C(R$^{M1}$)=C(R$^{M1}$)—C≡C—, —C(R$^{M1}$)=C(R$^{M1}$)—,
   wherein each cycloalkyl, aryl, heterocyclyl, or heteroaryl is optionally substituted with a substituent selected from the group consisting of
      $C_{1-6}$-alkyl, $C_{3-8}$-cycloalky, $C_{1-6}$-alkyloxy, NR$^{M2}$R$^{M3}$, carbonyl, —C(=O)—OR$^{M2}$, halo, halo-$C_{1-6}$-alkyl, $C_{1-6}$-alkyloxy-$C_1$-$C_6$-alkyl, aryl, heterocyclyl, $C_1$-$C_6$-alkyl substituted with aryl, cyano, hydroxy, —SR$^2$, —SO$_2$R$^{M4}$, —OSO$_2$R$^{M4}$, —SO$_2$NR$^{M2}$R$^{M3}$, —C(=O)NR$^{M2}$R$^{M3}$—, hydroxy-$C_{1-6}$-alkyl;

wherein $R^{M1}$ is selected from the group consisting of H, $C_{1-6}$-alkyl, halo, hydroxyl, and amino;

wherein $R^{M2}$, $R^{M3}$ are independently selected from the group consisting of H, and $C_{1-6}$-alkyl;

wherein $R^{M4}$ is selected from the group consisting of H, $C_{1-6}$-alkyl, and amino.

Suitably M is selected from the group consisting of $C_{3-10}$-cycloalkyl, aryl, heterocyclyl, heteroaryl, $C_{2-4}$ alkenyl, $C_{2-4}$alkynyl, —C($R^{M1}$)=C($R^{M1}$)—C≡C—, —C($R^{M1}$)=C($R^{M1}$)—. More suitably M is selected from the group consisting of aryl, heterocyclyl, heteroaryl, —C($R^{M1}$)=C($R^{M1}$)—C≡C—, —C($R^{M1}$)=C($R^{M1}$)—. More suitably M is selected from the group consisting of aryl, heteroaryl, —C($R^{M1}$)=C($R^{M1}$)—C≡C—, —C($R^{M1}$)=C($R^{M1}$)—.

In another embodiment of the invention and/or embodiments thereof G is selected from the group consisting of
—(C($R^{G2}R^{G3}$)$_{0-4}$—O—(C($R^{G2}R^{G3}$)$_{0-4}$—, —(C($R^{G2}R^{G3}$)$_{0-4}$—S—(C($R^{G2}R^{G3}$)$_{0-4}$—, —(C($R^{G2}R^{G3}$)$_{0-4}$—N$R^{G1}$—(C($R^{G2}R^{G3}$)$_{0-4}$—, —C(=O)—, —N$R^{G1}$C(=O)—, —C(=O)N$R^{G1}$—, —(C($R^{G2}R^{G3}$)$_{0-4}$—N$R^{G1}$—C($R^{G2}R^{G3}$)—C(=O)N$R^{G1}$—,
—C$R^{G2}$=C$R^{G2}$—, —C$R^{G2}$=C$R^{G2}$—C$R^{G2}$=C$R^{G2}$—, —C≡C—, —C≡C—C≡C—,
—C$R^{G2}$—C≡C—, —C≡C—C$R^{G2}$=C$R^{G2}$, —C(=O)—C≡C—, —C≡C—C(=O)— —SO$_2$—, —S(=O)—, —S(=O)C($R^{G2}R^{G3}$)—. —C($R^{G2}R^{G3}$)S(=O)—, —C($R^{G2}R^{G3}$)—SO$_2$—, —SO$_2$C($R^{G2}R^{G3}$)—;
wherein
$R^{G1}$ is H or $C_{1-6}$-alkyl
each $R^{G2}$, $R^{G3}$ is independently selected from the group consisting of
H, halogen atom, or $C_{1-6}$-alkyl.

Suitably G is selected from the group consisting of C$R^{G2}$=C$R^{G2}$—, —C$R^{G2}$=C$R^{G2}$—C$R^{G2}$=C$R^{G2}$—, —C≡C—, —C≡C—C=O—, —C$R^{G2}$=C$R^{G2}$—C≡C—, —C≡C—C$R^{G2}$=C$R^{G2}$, —C(=O)—C≡C—, —C≡C—C(=O)—, wherein $R^{G2}$ is selected from the group consisting of H, halogen atom, or $C_{1-6}$-alkyl.

In suitable embodiments, G is selected from the group consisting of C$R^{G2}$=C$R^{G2}$—, —C$R^{G2}$=C$R^{G2}$—C$R^{G2}$=C$R^{G2}$—, —C≡C—, —C≡C—C≡C—, —C≡C—C$R^{G2}$=C$R^{G2}$, wherein $R^{G2}$ is selected from the group consisting of H, halogen atom, or $C_{1-6}$-alkyl.

In some embodiments of the invention and/or embodiments thereof the compound is a compound according to formula (X)

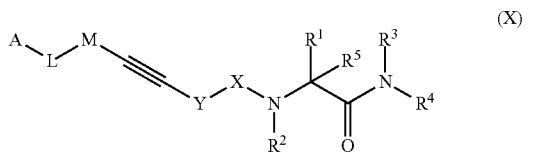

(X)

or a stereoisomer, pharmaceutically acceptable salt, ester, solvate, or prodrug thereof, for use in the treatment of bovine respiratory disease (BRD) especially if associated with *Mannheimia haemolytica, Pasteurella multocida* and *Histophilus somni*- or swine respiratory disease (SRD), especially if associated with *Pasteurella multocida, Actinobacillus pleuropneumoniae* or *Haemophilus parasuis*, wherein A, L, M, Y, X, q, $R^1$, $R^2$, $R^3$, $R^4$, and $R^5$, are defined as in any of the embodiments described herein.

In some embodiments of the invention and/or embodiments thereof, Y is selected from the group consisting of $C_{3-10}$-cycloalkyl, aryl, heterocyclyl, heteroaryl,
wherein each cycloalkyl, aryl, heterocyclyl, or heteroaryl is optionally substituted with a substituent selected from the group consisting of
$C_{1-6}$-alkyl, $C_{3-8}$-cycloalky, $C_{1-6}$-alkyloxy, NR$^{Y1}$R$^{Y2}$, carbonyl, —C(=O)—OR$^{Y1}$, halo, halo-$C_{1-6}$-alkyl, $C_{1-6}$-alkyloxy-$C_1$-$C_6$-alkyl, aryl, heteroaryl, $C_1$-$C_6$-alkyl substituted with aryl, cyano, hydroxy, —SR$^2$, —SO$_2$R$^{Y3}$, —OSO$_2$R$^{Y3}$, —SO$_2$NR$^{Y1}$R$^{Y2}$, —O(=O)NR$^{M2}$R$^{M3}$—, hydroxy-$C_{1-6}$-alkyl;
wherein R$^{Y1}$, R$^{Y2}$ are independently selected from the group consisting of H, and $C_{1-6}$-alkyl;
wherein R$^{Y3}$ is selected from the group consisting of H, $C_{1-6}$-alkyl, and amino.

In embodiments of the invention and/or embodiments thereof, Y is selected from
aryl, or heteroaryl. Suitably Y is aryl. Suitably Y is phenyl. Suitably Y is para-phenyl.

In some embodiments of the invention and/or embodiments thereof the cycloalkyl, aryl, heterocyclyl, or heteroaryl of Y is optionally substituted with a substituent selected from the group consisting of
$C_{1-6}$-alkyl, $C_{1-6}$-alkyloxy, NR$^{Y1}$R$^{Y2}$, carbonyl, —C(=O)—OR$^{Y1}$, halo, halo-$C_{1-6}$-alkyl, $C_{1-6}$-alkyloxy-$C_1$-$C_6$-alkyl, $C_1$-$C_6$-alkyl substituted with aryl, cyano, hydroxy, —SR$^{Y2}$, —SO$_2$R$^{Y3}$, —OSO$_2$R$^{Y3}$, —SO$_2$NR$^{Y1}$R$^{Y2}$, —C(=O)NR$^{M2}$R$^{M3}$—, hydroxy-$C_{1-6}$-alkyl.

Suitably the cycloalkyl, aryl, heterocyclyl, or heteroaryl of Y is optionally substituted with a substituent selected from the group consisting of $C_{1-6}$-alkyl, halo, halo-$C_{1-6}$-alkyl, hydroxy-$C_{1-6}$-alkyl. Suitably, the cycloalkyl, aryl, heterocyclyl, or heteroaryl of Y is not substituted.

In some embodiments of the invention and/or embodiments thereof the compound is a compound according to formula (XII)

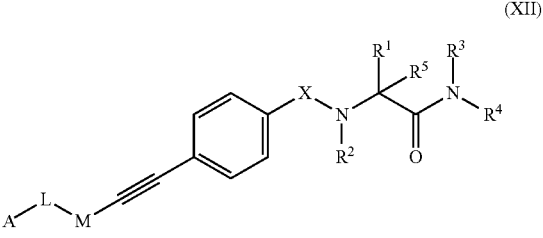

(XII)

or a stereoisomer, pharmaceutically acceptable salt, ester, solvate, or prodrug thereof, for use in the treatment of bovine respiratory disease (BRD) especially if associated with *Mannheimia haemolytica, Pasteurella multocida* and *Histophilus somni*- or swine respiratory disease (SRD), especially if associated with *Pasteurella multocida, Actinobacillus pleuropneumoniae* or *Haemophilus parasuis*, wherein A, L, M, X, $R^1$, $R^2$, $R^3$, $R^4$, and $R^5$, are defined as in any of the embodiments described herein.

In some embodiments of the invention and embodiments thereof, X is selected from the group consisting of
—C(=O)—, $C_{1-6}$-alkyl-C(=O)—, —$C_{2-6}$-alkenyl-C(=O)—, —$C_{2-6}$-alkynyl-C(=O)—, and —(C(R$^{X1}$)$_2$—, —S(=O)—, —SO$_2$—;

wherein $R^{X1}$, $R^{X2}$, is selected from the group consisting of
H, halogen atom, substituted $C_{1-6}$-alkyl, or un-substituted $C_{1-6}$-alkyl;
wherein the substituents on the substituted $C_{1-6}$-alkyl may be selected from the group consisting of halogen, hydroxyl, alkoxy, aryloxy, thiol, $C_{1-6}$-alkyl, carbonyl, —$SR^{X3}$, —$SO_2R^{X5}$, $SO_2NR^{X3}R^{X4}$, —$C(=O)NR^{X3}R^{X4}$, cyano, —$NR^{X3}R^{X4}$, —$C(=O)$—$OR^{X3}$, aryl, heteroaryl, heterocycle, $C_{3-8}$-cycloalkyl;
wherein $R^{X3}$, $R^{X4}$ are independently selected from the group consisting of H, or $C_{1-6}$-alkyl;
wherein $R^{X5}$ is selected from the group consisting of H, $C_{1-6}$-alkyl, and amine.

Suitably X is selected from the group consisting of —$C(=O)$—, —$C_{1-6}$-alkyl-$C(=O)$—, $S(=O)$—, —$SO_2$—. Suitably X is selected from —$C(=O)$—, and $S(=O)$—.

In some embodiments of the invention and/or embodiments thereof the compound is a compound according to formula (XV)

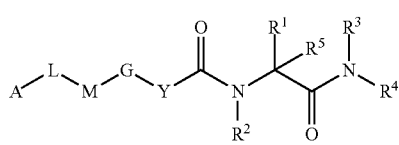

(XV)

or a stereoisomer, pharmaceutically acceptable salt, ester, solvate, or prodrug thereof, for use in the treatment of bovine respiratory disease (BRD) especially if associated with *Mannheimia haemolytica, Pasteurella multocida* and *Histophilus somni-* or swine respiratory disease (SRD), especially if associated with *Pasteurella multocida, Actinobacillus pleuropneumoniae* or *Haemophilus parasuis*, wherein A, L, M, G, Y, $R^1$, $R^2$, $R^3$, $R^4$, and $R^5$, are defined as in any of the embodiments described herein.

In another embodiments of the invention and/or embodiments thereof $R^2$, $R^3$ is independently selected from the group consisting of H, substituted $C_{1-6}$-alkyl, or un-substituted $C_{1-6}$-alkyl. Suitably $R^2$ and $R^3$ are H.

In embodiments of the invention and/or embodiments thereof $R^4$ is selected from the group consisting of H, $C_{2-6}$-alkenyl, $C_{2-6}$-alkynyl, $C_{3-10}$-cycloalkyl, —$OR^8$, $C(=O)OR^9$, $C(=O)R^9$, aryl, heterocyclyl, heteroaryl, $C_1$-$C_6$-alkyl substituted with aryl, $C_1$-$C_6$-alkyl substituted with heteroaryl, $C_1$-$C_6$-alkyl substituted with heterocyclyl,
wherein each alkyl, alkenyl, alkynyl, cycloalkyl, aryl, heterocyclyl, heteroaryl, is optionally substituted with a substituent selected from the group consisting of
$C_{1-6}$-alkyl, $C_{3-8}$-cycloalky, $C_{1-6}$-alkyloxy, $NR^6R^7$, carbonyl, nitro, $C(=O)OR^9$, halogen, halo-$C_{1-6}$-alkyl, $C_{1-6}$-alkyloxy-$C_1$-$C_6$-alkyl, cyano, hydroxy, —$SR^8$, —$SO_2R$, $SO_2NR^6R^7$, —$C(=O)NR^5R^6$.

Suitably In embodiments of the invention and/or embodiments thereof $R^4$ is selected from the group consisting of H, $C_{1-6}$-alkyl, —$OR^8$, $C(=O)OR^9$, $C(=O)R^9$. More suitably $R^4$ is selected from the group consisting of H, —$OR^8$. Suitably $R^4$ is —$OR^8$, more suitably $R^8$ is OH.

In embodiments of the invention and/or embodiments thereof $R^1$ is selected from the group consisting of H, $C_{1-6}$-alkyl, $C_{2-6}$-alkenyl, $C_{2-6}$-alkynyl, $C_{3-10}$-cycloalkyl, $C(=O)R^9$, $C(=N$—$OR^8)R^8$, aryl, heterocyclyl, heteroaryl, $C_1$-$C_6$-alkyl substituted with aryl, $C_1$-$C_6$-alkyl substituted with heteroaryl, $C_1$-$C_6$-alkyl substituted with heterocyclyl,
wherein each alkyl, alkenyl, alkynyl, cycloalkyl, aryl, heterocyclyl, heteroaryl, is optionally substituted with a substituent selected from the group consisting of
$C_{1-6}$-alkyl, $C_{3-8}$-cycloalky, $C_{1-6}$-alkyloxy, —$NR^6R^7$, carbonyl, nitro, $C(=O)OR^9$, halogen, halo-$C_{1-6}$-alkyl, $C_{1-6}$-alkyloxy-$C_1$-$C_6$-alkyl, cyano, hydroxy, —$SR^8$, —$SO_2R^8$, $SO_2NR^6R^7$, —$C(=O)NR^6R^7$—.

In embodiments of the invention and/or embodiments thereof $R^1$ is selected from the group consisting of H, $C_{1-6}$-alkyl, $C_{2-6}$-alkenyl, $C_{2-6}$-alkynyl, $C_{3-10}$-cycloalkyl, $C(=O)R^9$, $C(=N$—$OR^8)R^8$. Suitably $R^1$ is selected from the group consisting of $C_{1-6}$-alkyl, $C(=O)R^9$, $C(=N$—$OR^8)R^8$.

In embodiments of the invention and/or embodiments thereof the alkyl, alkenyl, alkynyl, cycloalkyl, aryl, heterocyclyl, heteroaryl, of $R^1$ is optionally substituted with a substituent selected from the group consisting of $C_{1-6}$-alkyl, —$NR^6R^7$, carbonyl, nitro, $C(=O)OR^9$, halogen, cyano, hydroxy, —$SR^8$, —$SO_2R^8$, $SO_2NR^6R^7$, —$C(=O)NR^6R^7$—.

In embodiments of the invention and/or embodiments thereof the alkyl, alkenyl, alkynyl, cycloalkyl, aryl, heterocyclyl, heteroaryl, of $R^1$ is optionally substituted with a substituent selected from the group consisting of $C_{1-6}$-alkyl, —$NR^6R^7$, nitro, hydroxy, —$SR^8$, $SO_2NR^6R^7$, —$SO_2R^8$.

In embodiments of the invention and/or embodiments thereof $R^1$ is selected from the group consisting of $C(=O)R^9$, $C(=N$—$OR^8)R^8$, wherein the alkyl is optionally substituted with a substituent selected from the group consisting of $C_{1-6}$-alkyl, —$NR^6R^7$, carbonyl, nitro, $C(=O)OR^9$, halogen, cyano, hydroxy, —$SR^8$, —$SO_2R^8$, $SO_2NR^6R$, —$C(=O)NR^6R^7$—.

In some embodiments of the invention and/or embodiments thereof the compound is a compound according to formula

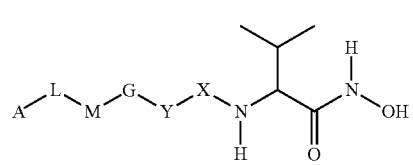

(XIX)

or a stereoisomer, pharmaceutically acceptable salt, ester, solvate, or prodrug thereof for use in the treatment of bovine respiratory disease (BRD) especially if associated with *Mannheimia haemolytica, Pasteurella multocida* and *Histophilus somni-* or swine respiratory disease (SRD), especially if associated with *Pasteurella multocida, Actinobacillus pleuropneumoniae* or *Haemophilus parasuis*, wherein A, L, M, G, Y, and X, are defined as in any of the embodiments described herein.

In some embodiments of the invention and/or embodiments thereof the compound is a compound according to formula

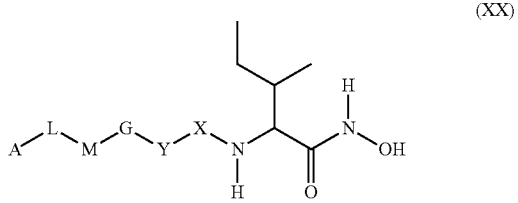

(XX)

or a stereoisomer, pharmaceutically acceptable salt, ester, solvate, or prodrug thereof, for use in the treatment of bovine respiratory disease (BRD) especially if associated with *Mannheimia haemolytica, Pasteurella multocida* and *Histophilus somni*- or swine respiratory disease (SRD), especially if associated with *Pasteurella multocida, Actinobacillus pleuropneumoniae* or *Haemophilus parasuis*, wherein A, L, M, G, Y, and X, are defined as in any of the embodiments described herein.

In some embodiments of the invention and/or embodiments thereof the compound is a compound according to formula

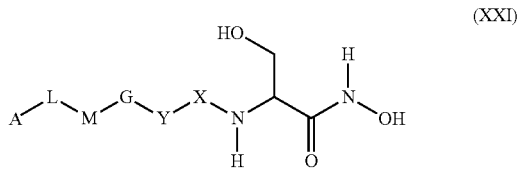

(XXI)

or a stereoisomer, pharmaceutically acceptable salt, ester, solvate, or prodrug thereof, for use in the treatment of bovine respiratory disease (BRD) especially if associated with *Mannheimia haemolytica, Pasteurella multocida* and *Histophilus somni*- or swine respiratory disease (SRD), especially if associated with *Pasteurella multocida, Actinobacillus pleuropneumoniae* or *Haemophilus parasuis*, wherein A, L, M, G, Y, and X, are defined as in any of the embodiments described herein.

In some embodiments of the invention and/or embodiments thereof the compound is a compound according to formula

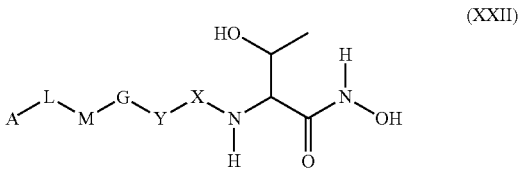

(XXII)

or a stereoisomer, pharmaceutically acceptable salt, ester, solvate, or prodrug thereof, for use in the treatment of bovine respiratory disease (BRD) especially if associated with *Mannheimia haemolytica, Pasteurella multocida* and *Histophilus somni*- or swine respiratory disease (SRD), especially if associated with *Pasteurella multocida, Actinobacillus pleuropneumoniae* or *Haemophilus parasuis*, wherein A, L, M, G, Y, and X, are defined as in any of the embodiments described herein.

In some embodiments of the invention and/or embodiments thereof the compound is a compound according to formula

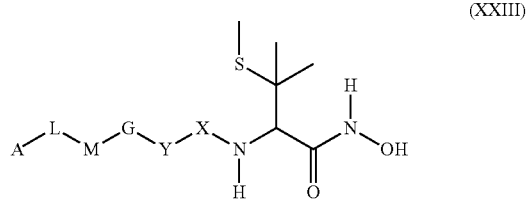

(XXIII)

or a stereoisomer, pharmaceutically acceptable salt, ester, solvate, or prodrug thereof, for use in the treatment of bovine respiratory disease (BRD) especially if associated with *Mannheimia haemolytica, Pasteurella multocida* and *Histophilus somni*- or swine respiratory disease (SRD), especially if associated with *Pasteurella multocida, Actinobacillus pleuropneumoniae* or *Haemophilus parasuis*, wherein A, L, M, G, Y, and X, are defined as in any of the embodiments described herein.

In some embodiments of the invention and/or embodiments thereof the compound is a compound according to formula

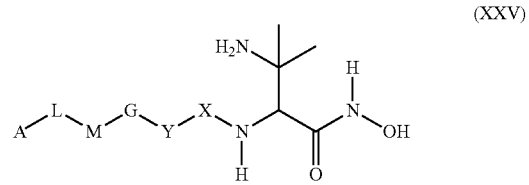

(XXV)

or a stereoisomer, pharmaceutically acceptable salt, ester, solvate, or prodrug thereof, for use in the treatment of bovine respiratory disease (BRD) especially if associated with *Mannheimia haemolytica, Pasteurella multocida* and *Histophilus somni*- or swine respiratory disease (SRD), especially if associated with *Pasteurella multocida, Actinobacillus pleuropneumoniae* or *Haemophilus parasuis*, wherein A, L, M, G, Y, and X, are defined as in any of the embodiments described herein.

In some embodiments of the invention and/or embodiments thereof the compound is a compound according to formula

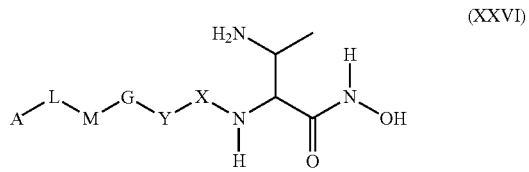

(XXVI)

or a stereoisomer, pharmaceutically acceptable salt, ester, solvate, or prodrug thereof, for use in the treatment of bovine respiratory disease (BRD) especially if associated with *Mannheimia haemolytica, Pasteurella multocida* and *Histophilus somni*- or swine respiratory disease (SRD), especially if associated with *Pasteurella multocida, Actinobacillus pleuropneumoniae* or *Haemophilus parasuis*, wherein A, L, M, G, Y, and X, are defined as in any of the embodiments described herein.

In some embodiments of the invention and/or embodiments thereof the compound is a compound according to formula (XXVII)

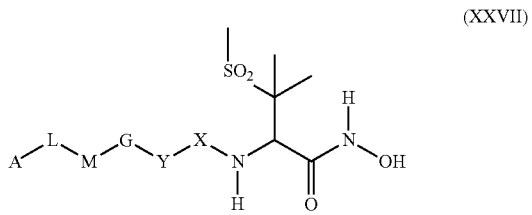

(XXX)

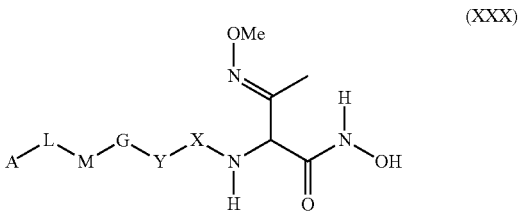

or a stereoisomer, pharmaceutically acceptable salt, ester, solvate, or prodrug thereof, for use in the treatment of bovine respiratory disease (BRD) especially if associated with *Mannheimia haemolytica, Pasteurella multocida* and *Histophilus somni-* or swine respiratory disease (SRD), especially if associated with *Pasteurella multocida, Actinobacillus pleuropneumoniae* or *Haemophilus parasuis*, wherein A, L, M, G, Y, and X, are defined as in any of the embodiments described herein.

In some embodiments of the invention and/or embodiments thereof the compound is a compound according to formula (XXVIII)

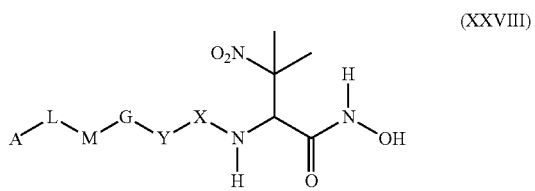

or a stereoisomer, pharmaceutically acceptable salt, ester, solvate, or prodrug thereof for use in the treatment of bovine respiratory disease (BRD) especially if associated with *Mannheimia haemolytica, Pasteurella multocida* and *Histophilus somni-* or swine respiratory disease (SRD), especially if associated with *Pasteurella multocida, Actinobacillus pleuropneumoniae* or *Haemophilus parasuis*, wherein A, L, M, G, Y, and X, are defined as in any of the embodiments described herein.

In some embodiments of the invention and/or embodiments thereof the compound is a compound according to formula (XXIX)

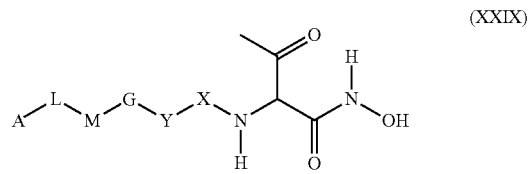

or a stereoisomer, pharmaceutically acceptable salt, ester, solvate, or prodrug thereof, for use in the treatment of bovine respiratory disease (BRD) especially if associated with *Mannheimia haemolytica, Pasteurella multocida* and *Histophilus somni-* or swine respiratory disease (SRD), especially if associated with *Pasteurella multocida, Actinobacillus pleuropneumoniae* or *Haemophilus parasuis*, wherein A, L, M, G, Y, and X, are defined as in any of the embodiments described herein.

In some embodiments of the invention and/or embodiments thereof the compound is a compound according to formula or a stereoisomer, pharmaceutically acceptable salt, ester, solvate, or prodrug thereof, for use in the treatment of bovine respiratory disease (BRD) especially if associated with *Mannheimia haemolytica, Pasteurella multocida* and *Histophilus somni-* or swine respiratory disease (SRD), especially if associated with *Pasteurella multocida, Actinobacillus pleuropneumoniae* or *Haemophilus parasuis*, wherein A, L, M, G, Y, and X, are defined as in any of the embodiments described herein.

In one embodiment the compound as defined above is for use in the treatment or prevention of bovine respiratory disease. In another embodiment the compound as defined above is for use in the treatment or prevention of swine respiratory disease Another embodiment is the use of a compound as defined above in the manufacturing of a medicament for the treatment or prevention of bovine respiratory disease or of swine respiratory disease.

DETAILED DESCRIPTION

It was found that compounds according to formula (I) or the stereoisomer, pharmaceutically acceptable salt, ester, solvate, or prodrug thereof, are useful in the treatment or prevention of an infection by bacterial pathogens involved in Bovine Respiratory disease, such as *Mannheimia haemolytica, Histophilus somni*, and *Pasteurella multicocida*. In particular the compounds according to the invention and/or any embodiments thereof are useful in the treatment of of bovine respiratory disease (BRD)—especially if associated with *Mannheimia haemolytica, Pasteurella multocida* and *Histophilus somni-* or swine respiratory disease (SRD), especially if associated with *Pasteurella multocida, Actinobacillus pleuropneumoniae, Bordetella bronchiseptica* or *Haemophilus parasuis.*

In one embodiment the compounds can be used to treat Glässers Disease in swine caused by *Haemophilus parasuis.*

It has now been further found that, surprisingly, the agent of the invention is particularly effective in the therapy of veterinary diseases, the expression of which is enhanced by increased stocking density or stress, such as bovine respiratory disease and swine respiratory disease complex. It has been further found that such compounds can be used in the treatment of enzootic pneumonia in swine, secondary pneumonia in swine associated with *Pasteurella multocida, Actinobacillus pleuropneumoniae* and/or *Haemophilus parasuis* infection, enzootic pneumonia in lambs and sheep and cattle (Shipping Fever, Transit Fever, Calf Respiratory Complex, Bovine Pneumonic Pasteurellosis) associated with *Mannheimia haemolytica* infection.

Increasingly there is a fear of multi-resistant bacteria. There is therefore a need for a specific antibiotic that can be used in an infection of a specific bacterium. Advantageously the compounds according to the invention and/or any embodiments thereof is effective against *Mannheimia haemolytica, Histophilus somni* and/or *Pasteurella multicocida* but not against other pathogen bacteria that are especially relevant in human health, such as *Actinetobcacter baumanii* or *Stapylococcus* spp. or *Streptococcus* spp.

The inventors found that the compounds of the inventions meet such needs and are therefore very useful in the treatment (and prevention) of bovine respiratory disease and/or swine respiratory disease.

The following abbreviations and definitions are used throughout this application:

Generally, reference to a certain element such as hydrogen or H is meant to include all isotopes of that element. For example, if an R group is defined to include hydrogen or H, it also includes deuterium and tritium.

The phrase "alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following that are provided by way of example:—$CH(CH_3)_2$, —$CH(CH_3)(CH_2CH_3)$, —$CH(CH_2CH_3)_2$, —$C(CH_3)_3$, —$C(CH_2CH_3)_3$, —$CH_2CH(CH_3)_2$, —$CH_2CH(CH_3)(CH_2CH_3)$, —$CH_2CH(CH_2CH_3)_2$, —$CH_2C(CH_3)_3$, —$CH_2C(CH_2CH_3)_3$, —$CH(CH_3)CH(CH_3)(CH_2CH_3)$, —$CH_2CH_2CH(CH_3)_2$, —$CH_2CH_2CH(CH_2CH_3)$, —$CH_2CH_2CH(CH_2CH_3)_2$, —$CH_2CH_2C(CH_3)_3$, —$CH_2CH_2C(CH_2CH_3)_3$, —$CH(CH_3)CH_2CH(CH_3)_2$, —$CH(CH_3)CH(CH_3)CH(CH_3)_2$, —$CH(CH_2CH_3)CH(CH_3)CH(CH_3)(CH_2CH_3)$, and others. Thus the phrase "alkyl groups' includes primary alkyl groups, secondary alkyl groups, and tertiary alkyl groups. Preferred alkyl groups include straight and branched chain alkyl groups having 1 to 12 carbon atoms.

The phrase "substituted alkyl" refers to an alkyl group as defined above in which one or more bonds to a carbon (s) or hydrogen (s) are replaced by a bond to non-hydrogen and non-carbon atoms. If not further defined the "substituted alkyl" may be substituted by a group such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon (s) or hydrogen (s) atom is replaced by a higher-order bond (e.g., a double- or triple-bond) to a heteroatom such as oxygen in oxo, carbonyl, carboxyl, and ester groups; nitrogen in groups such as imines, oximes, hydrazones, and nitriles. Substituted alkyl groups further include alkyl groups in which one or more bonds to a carbon (s) or hydrogen (s) atoms is replaced by a bond to an aryl, heterocyclyl group, or cycloalkyl group. Exemplary substituted alkyl groups include, among others, alkyl groups in which one or more bonds to a carbon or hydrogen atom is/are replaced by one or more bonds to fluorine atoms.

Another exemplary substituted alkyl group is the trifluoromethyl group and other alkyl groups that contain the trifluoromethyl group. Other exemplary substituted alkyl groups include those in which one or more bonds to a carbon or hydrogen atom is replaced by a bond to an oxygen atom such that the substituted alkyl group contains a hydroxyl, alkoxy, or aryloxy group. Still other exemplary substituted alkyl groups include alkyl groups that have an amine, or a substituted or unsubstituted alkylamine, dialkylamine, arylamine, (alkyl) (aryl) amine, diarylamine, heterocyclylamine, diheterocyclylamine, (alkyl) (heterocyclyl) amine, or (aryl) (heterocyclyl) amine group.

The phrase "alkenyl" refers to straight and branched chain and cyclic groups such as those described with respect to alkyl groups as defined above, except that at least one double bond exists between two carbon atoms. Examples include, but are not limited to vinyl, —$CH=C(H)(CH_3)$, —$CH=C(CH_3)_2$, —$C(CH_3)=C(H)_2$, —$C(CH)=C(H)(CH_3)$, —$C(CH_2CH_3)=CH_2$, cyclohexenyl, cyclopentenyl, cyclohexadienyl, butadienyl, pentadienyl, and hexadienyl among others.

The phrase "substituted alkenyl" has the same meaning with respect to alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

The phrase "alkynyl" refers to straight and branched chain groups such as those described with respect to alkyl groups as defined above, except that at least one triple bond exists between two carbon atoms. Examples include, but are not limited to —$C\equiv C(H)$, —$C\equiv C(CH_3)$, —$C\equiv C(CH_2CH_3)$, —$C(H_2)CEC(H)$, —$C(H)_2C\equiv C(CH_3)$, and —$C(H)_2C\equiv C(CH_2CH_3)$ among others.

The phrase "substituted alkynyl" has the same meaning with respect to alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

The phrase "cycloalkyl" refers to a non-aromatic monocyclic or polycyclic alkyl group consisting solely of carbon and hydrogen atoms, and which may be saturated or unsaturated. Cycloalkyl may include fused or bridged ring systems, having from three to fifteen carbon atoms, preferably having from three to ten carbon atoms ($C_3$-$C_{10}$-cycloalkyl), and which may be saturated or unsaturated. Monocyclic radicals include, for example, cyclopropyl, cyclobutyl, cyclopentyl, cyclohexyl, cycloheptyl, cyclooctyl, and the like. Polycyclic radicals include, for example, adamantine, norbornane, decalinyl, 7,7-dimethyl-bicyclo[2.2.1]heptanyl, and the like. If not further defined, cycloalkyl may be substituted with substituents as indicated above with substituted alkyl group.

The phrase "heterocyclic ring" refers to both aromatic, "heteroaryl" and nonaromatic, "heterocyclyl", ring compounds including monocyclic, bicyclic, and polycyclic ring compounds such as, but not limited to, quinuclidinyl, containing 3 or more ring members of which one or more is a heteroatom such as, but not limited to, N, O, and S.

Heterocyclyl refers to a 3- to 18-membered non-aromatic ring radical which consists of two to seventeen carbon atoms and from one to ten heteroatoms selected from the group consisting of nitrogen, oxygen and sulfur. Unless stated otherwise specifically in the specification, the heterocyclyl radical may be a monocyclic, bicyclic or polycyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Although the phrase "unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl (e.g. 4H-1, 2,4-triazolyl, lu-1, 2, 3-triazolyl, 2H-1,2,3-triazolyl etc.), tetrazolyl, (e.g. 1H-tetrazolyl, 2H tetrazolyl, etc.); saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl (e.g. 1,2, 4-oxadiazolyl, 1,3, 4-oxadiazolyl, 1,2, 5-oxadiazolyl, etc.); saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2, 3-thiadiazolyl, 1,2, 4-thiadiazolyl, 1,3, 4-thiadiazolyl, 1,2, 5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1, 4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1, 3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1, 4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1, 1-dioxide. Exemplary heterocyclyl groups contain 5 or 6 ring members. Other exemplary heterocyclyl groups include morpholine, piperazine, piperidine, imidazole, pyrazole, 1,2, 3-triazole, 1,2, 4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

The phrase "substituted heterocyclyl" refers to a heterocyclyl group as defined above in which one of the ring members is bonded to a non-hydrogen atom such as described above with respect to substituted alkyl groups and substituted aryl groups. Examples, include, but are not limited to, 2-methylbenzimidazolyl, 5-methylbenzimidazolyl, 5-chlorobenzthiazolyl, 1-methyl piperazinyl, and 2-chloropyridyl among others.

The phrase "aryl" refers to aryl groups that do not contain heteroatoms. Thus the phrase includes, but is not limited to, groups such as phenyl, biphenyl, anthracenyl, naphtlienyl by way of example. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. An exemplary unsubstituted aryl group is phenyl. Unsubstituted aryl groups may be bonded to one or more carbon atom(s), oxygen atom(s), nitrogen atom(s), and/or sulfur atom (s) in the parent compound, however.

The phrase "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, and hydroxyphenyl among others. If not further defined the "substituted aryl group" may be substituted by a group such as straight and branched chain alkyl groups, —$CH_3$, —$C_2H_5$, —$CH_2OH$, —OH, —$OCH_3$, —$OC_2H_5$, —$OCF_3$, —CN, —$NO_2$, —$CO_2H$, —$CO_2CH_3$, —$CONH_2$, —$NH_2$, —F, —Cl, Br, —CF3, —$N(CH_3)_2$, —$NHSO_2CH_3$, —$NHCOCH_3$.

The term "heteroaryl", as used herein, refers to a cyclic or bicyclic aromatic radical having from five to ten ring atoms in each ring of which one atom of the cyclic or bicyclic ring is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and naphthyridinyl, and the like.

The term "substituted heteroaryl" as used herein refers to a heteroaryl group as defined herein substituted by independent replacement of one, two or three of the hydrogen atoms thereon. Exemplary substituents may include Cl, Br, F, I, OH, CN, $C_{1-3}$-alkyl, $C_{1-6}$-alkoxy, $C_{1-6}$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

Exemplary substituents include straight and branched chain alkyl groups, —$CH_3$, —$C_2H_5$, —$CH_2OH$, —OH, —OCH$_3$, —OC$_2$H$_5$, —OCF$_3$, —CN, —NO$_2$, —CO$_2$H, —CO$_2$CH$_3$, —CONH$_2$, —NH$_2$, —F, —Cl, —Br, —CF$_3$, —N(CH$_3$)$_2$, —NHSO$_2$CH$_3$, —NHCOCH$_3$.

The term "biaryl" refers to a group or substituent to which two aryl groups, which are not condensed to each other, are bound. Exemplary biaryl compounds include, for example, phenylbenzene, diphenyldiazene, 4-methylthio-1-phenylbenzene, phenoxybenzene, (2-phenylethynyl) benzene, diphenyl ketone, (4-phenylbuta-1,3-diynyl)benzene, phenylbenzylamine, (phenylmethoxy)benzene, and the like. Preferred optionally substituted biaryl groups include: 2-(phenylamino)-N-[4-(2-phenylethynyl) phenyl]acetamide, 1,4-diphenylbenzene, N-[4-(2-phenylethynyl) phenyl]-2-[benzylamino]acetamide, 2-amino-N-[4-(2-phenylethynyl) phenyl]propanamide, 2-amino-N-[4-(2-phenylethynyl) phenyl]acetamide, 2-(cyclopropylamino)-N-[4-(2-phenylethynyl) phenyl]acetamide, 2-(ethylamino)-N-[4-(2-phenylethynyl) phenyl]acetamide, 2-[(2-methylpropyl) amino]-N-[4-(2-phenylethynyl) phenyl] acetamide, 5-phenyl-2H-benzo [d]1, 3-dioxolene, 2-chloro-1-methoxy4-phenylbenzene, 2-[(imidazolylmethyl) amino]-N-[4-(2-phenylethynyl) phenyl]acetamide, 4-phenyl-1-phenoxybenzene, N-(2-aminoethyl) [4-(2-phenylethynyl) phenyl]carboxamide, 2-{[(4-fluorophenyl) methyl]amino}-N-[4-(2-phenylethynyl) phenyl]acetamide, 2-{[(4-methylphenyl) methyl]amino}-N-[4-(2-phenylethynyl) phenyl] acetamide, 4-phenyl-1-(trifluoromethyl) benzene, 1-butyl-4-phenylbenzene, 2-(cyclohexylamino)-N-[4-(2-phenylethynyl) phenyl]acetamide, 2-(ethylmethylamino)-N-[4-(2-phenylethynyl) phenyl]acetamide, 2-(butylamino)-N-[4-(2-phenylethynyl) phenyl]acetamide, N-[4-(2-phenylethynyl) phenyl]-2-(4-pyridylamino) acetamide, N-[4-(2-phenylethynyl) phenyl]-2-(quinuclidin-3-ylamino) acetamide, N-[4-(2-phenylethynyl) phenyl]pyrrolidin-2-yl-carboxamide, 2-amino-3-methyl-N-[4-(2-phenylethynyl) phenyl]butanamide, 4-(4-phenylbuta-1, 3-diynyl) phenylamine, 2-(dimethylamino)-N-[4-(4-phenylbuta-1, 3-diynyl) phenyl]acetamide, 2-(ethylamino)-N-[4-(4-phenylbuta-1, 3-diynyl) phenyl]acetamide, 4-ethyl-1-phenylbenzene, 1-[4-(2-phenylethynyl) phenyl]ethan-1-one, N-(1-carbamoyl-2-hydroxypropyl) [4-(4-phenylbuta-1, 3-diynyl) phenyl] carboxamide, N-[4-(2-phenylethynyl) phenyl]propanamide, 4-methoxyphenyl phenyl ketone, phenyl-N-benzamide, (tert-butoxy)-N-[(4-phenylphenyl) methyl]carboxamide, 2-(3-phenylphenoxy) ethanehydroxamic acid, 3-phenylphenyl propanoate, 1-(4-ethoxyphenyl)-4-methoxybenzene, and [4-(2-phenylethynyl) phenyl]pyrrole.

The term "heteroarylaryl" refers to a biaryl group where one of the aryl groups is a heteroaryl group. Exemplary heteroarylaryl groups include, for example, 2-phenylpyridine, phenylpyrrole, 3-(2-phenylethynyl) pyridine, phenylpyrazole, 5-(2-phenylethynyl)-1, 3-dihydropyrinnidine-2,4-dione, 4-phenyl-1, 2,3-thiadiazole, 2-(2-phenylethynyl) pyrazine, 2-phenylthiophene, phenylimidazole, 3-(2-piperazinylphenyl)furan, 3-(2, 4-dichlorophenyl)-4-methylpyrrole, and the like. Optionally substituted heteroarylaryl groups include: 5-(2-phenylethynyl) pyrimidine-2-ylamine, 1-methoxy-4-(2-thienyl) benzene, 1-methoxy-3-(2-thienyl) benzene, 5-methyl-2-phenylpyridine, 5-methyl-3-phenylisoxazole, 2-[3-(trifluoromethyl) phenyl]furan, 3-fluoro-5-(2-furyl)-2-methoxy-1-prop-2-enylbenzene, (hydroxyimino) (5-phenyl (2-thienyl)) methane, 5-[(4-methylpiperazinyl) methyl]-2-phenylthiophene, 2-(4-ethylphenyl) thiophene, 4-methylthio-1-(2-thienyl) benzene, 2-(3-nitrophenyl) thiophene, (tert-butoxy)-N-[(5-phenyl (3-pyridyl)) methyl]carboxamide, hydroxy-N-[(5-phenyl (3-pyridyl)) methyl]amide, 2-(phenyhnethylthio) pyridine, and benzylimidazole.

The term "heteroarylheteroaryl" refers to a biaryl group where both of the aryl groups is a heteroaryl group. Exemplary heteroarylheteroaryl groups include, for example, 3-pyridylimidazole, 2-imidazolylpyrazine, and the like. Preferred optionally substituted heteroarylheteroaryl groups include: 2-(4-piperazinyl-3-pyridyl) furan, diethyl (3-pyrazin-2-yl (4-pyridyl)) amine, and dimethyl {2-[2-(5-methylpyrazin-2-yl) ethynyl](4-pyridyl)}amine.

"Optionally substituted" refers to the optional replacement of hydrogen with one or more monovalent or divalent radicals. Optionally substituted groups include those described herein, for each group in which a distinct definition for substitution is supplied. Additionally, suitable substitution groups include, for example, hydroxyl, nitro, amino, imino, cyano, halo, thio, thioamido, amidino, imidino, oxo, oxamidino, methoxamidino, imidino, guanidino, sulfonamido, carboxyl, formyl, alkyl, substituted alkyl, haloloweralkyl, loweralkoxy, haloloweralkoxy, loweralkoxyalkyl, alkylcarbonyl, arylcarbonyl, aralkylcarbonyl, heteroarylcarbonyl, heteroaralkylcarbonyl, alkylthio, aminoalkyl, cyanoalkyl, benzyl, pyridyl, pyrazolyl, pyrrole, thiophene, imidazolyl, and the like.

The term "protected" with respect to hydroxyl groups, amine groups, and sulfhydryl groups refers to forms of these functionalities that are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999) that can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropyl-chlorosilane, triethylchlorosilane; substituted methyl and ethyl ethers such as, but not limited to methoxymethyl ether, methythiomethyl ether, benzyloxymethyl ether, t-butoxymethyl ether, 2-nnethoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoracetate.

Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioether such as S-benzyl thioether, and S-4-picolyl thioether; substituted S-methyl derivatives such as hemithio, dithio and aminothio acetals; and others.

A "pharmaceutically acceptable salt" includes a salt with an inorganic base, organic base, inorganic acid, organic acid, or basic or acidic amino acid.

Examples of often suitable inorganic acids for making (pharmaceutically acceptable) salts include hydrochloric, hydrobromic, hydroiodic, nitric, carbonic, sulfuric, and phosphoric acid. Examples of often suitable organic acids for making (pharmaceutically acceptable) salts generally include, for example, aliphatic, cycloaliphatic, aromatic, araliphatic, heterocyclic, carboxylic, and sulfonic classes of organic acids. Specific examples of often suitable organic acids include cholic, sorbic, lauric, acetic, trifluoroacetic, formic, propionic, succinic, glycolic, gluconic, digluconic, lactic, malic, tartaric acid, citric, ascorbic, glucuronic, maleic, fumaric, pyruvic, aspartic, glutamic, aryl carboxylic acid (e.g., benzoic), anthranilic acid, mesylic, stearic, salicylic, p-hydroxybenzoic, phenylacetic, mandelic, embonic (pamoic), alkylsulfonic (e.g., ethanesulfonic), arylsulfonic (e.g., benzenesulfonic), pantothenic, 2-hydroxyethanesulfonic, sulfanilic, cyclohexylaminosulfonic, β-hydroxybutyric, galactaric, galacturonic, adipic, alginic, butyric, camphoric, camphorsulfonic, cyclopentanepropionic, dodecylsulfic, glycoheptanoic, glycerophosphic, heptanoic, hexanoic, nicotinic, 2-naphthalesulfonic, oxalic, palmoic, pectinic, 3-phenylpropionic, picric, pivalic, thiocyanic, tosylic, and undecanoic acid. In some such embodiments, for example, the salt comprises a trifluoroacetate, mesylate, or tosylate salt. In other embodiments, the salt comprises a hydrochloric acid salt. In general, a base addition salt can be prepared by reacting a free acid compound with an approximately stoichiometric amount of an inorganic or organic base. Examples of base addition salts may include, for example, metallic salts and organic salts. Metallic salts, for example, include alkali metal (group 1a) salts, alkaline earth metal (group IIa) salts, and other physiologically acceptable metal salts. Such salts may be made from aluminum, calcium, lithium, magnesium, potassium, sodium, and zinc. For example, a free acid compound may be mixed with sodium hydroxide to form such a base addition salt. Organic salts may be made from amines, such as trimethylamine, diethylamine, N,N'-dibenzylethylenediamine, chloroprocaine, ethanolamine, diethanolamine, ethylenediamine, meglumine (N-methylglucamine), and procaine. Basic nitrogen-containing groups may be quaternized with agents such as C1-C6-alkyl halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

As salts of basic amino acids, the instant invention includes, for example, arginine, lysine and ornithine. Acidic amino acids include, for example, aspartic acid and glutamic acid.

As used herein, the term "pharmaceutically acceptable ester" refers to esters that hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms.

Representative examples of particular esters include, but are not limited to, formates, acetates, propionates, butyrates, acrylates and ethylsuccinates.

The term "prodrug" refers to compounds that are rapidly transformed in vivo to yield the parent compound of the above formula, for example by hydrolysis in blood. A thorough discussion is provided in T. Higuchi and V. Stella, Pro-drugs as Novel Delivery Systems, Vol. 14 of the A. C. S. Symposium Series, and in Edward B. Roche, ed., Bioreversible Carriers in Drug Design, American Pharmaceutical Association and Pergamon Press, 1987, both of which are incorporated herein by reference.

The term "pharmaceutically acceptable prodrugs" as used herein refers to those prodrugs of the compounds of the present invention that are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the invention.

The term "antibacterial agent" refers to agents synthesized or modified in the laboratory that have either bactericidal or bacteriostatic activity.

A "bacteriostatic" agent in this context will inhibit the growth of (pathogenic) bacteria, such as e.g. relevant bacteria for BRD or SRD such as e.g. *Mannheimia haemolytica, Histophilus somni*, and/or *Pasteurella multocida*.

The term "inhibiting the growth" indicates that the rate of increase in the numbers of a population of a particular bacterium is reduced. Thus, the term includes situations in which the bacterial population increases but at a reduced rate, as well as situations where the growth of the population is stopped, as well as situations where the numbers of the bacteria in the population are reduced or the population even eliminated. If an enzyme activity assay is used to screen for inhibitors, one can make modifications in uptake/efflux, solubility, half-life, etc. to compounds in order to correlate enzyme inhibition with growth inhibition. The activity of antibacterial agents is not necessarily limited to bacteria but may also encompass activity against parasites, virus, and fungi.

The compounds of the current invention are administered to treat or prevent infections (or infectious disease) of an animal (or make a medicament to treat or prevent infections—or infectious disease—of an animal) involved in bovine respiratory disease or swine respiratory disease. In one embodiment one or more, preferably one compound according to this invention is administered to treat bovine respiratory disease or swine respiratory disease (or make a medicament to treat bovine respiratory disease or swine respiratory disease).

The term "infectious disease" includes conditions associated with or caused by one or more (bacterial) pathogens; said conditions include clinical conditions and sub-clinical conditions.

The term "treatment" as used herein refers to reversing, alleviating, inhibiting the progress of a disease, disorder or condition. In case of BRD or SRD this means that the clinical symptoms, both general (e.g. depression, increased body temperature, high heart frequency, reduced feed consumption) and respiratory (e.g. high breathing rate- and laborious breathing quality) are alleviated. A further indication of the success of "treatment" is the diminishing or prevention of pathomorphological findings after slaughter of the animal, this means prevention of tissue damage. In addition, in case of infectious diseases that are caused by bacteria, treatment encompasses bacteriological cure of the animal, this means that no, or a reduced number of pathogens can be isolated from blood, or tissue of the treated animal.

The term "treatment of" thus includes both the treatment of bovine respiratory disease or swine respiratory disease and the treatment of sub-clinical conditions connected with infections of an animal with (bacterial) pathogens involved in bovine respiratory disease or swine respiratory disease complex. The treatment of an infection or infectious disease generally implies the suppression of bacteria in the animal below that level at which economic loss occurs.

Sub-clinical conditions are typically conditions not directly leading to clinical symptoms in the infected animal but leading to economic losses. Such economic losses can be e.g. by depression of growth in young animals, lower feed efficiency, lower weight gain in meat producing animals, lower milk production in dairy ruminants, or lower wool-production in sheep.

Thus the invention provides a method of treating a (bacterial) infection, that leads to a treatment of bovine respiratory disease or swine respiratory disease and, in one embodiment includes the treatment of sub-clinical conditions connected with infections of an animal with (bacterial) pathogens involved in bovine respiratory disease or swine respiratory disease complex, which comprises administering to the animal an antibacterial effective amount of one or more compounds according to this invention.

In a preferred embodiment the compounds according to this invention are used to treat a bacterial infection, such as an infection caused by one or more pathogens, being gram negative bacteria selected from the group consisting of *Pasteurella* spp., *Mannheimia* spp. and/or *Histophilus* spp. infections are controlled so that (at least) an bacteriostatic effect for such pathogens is achieved.

"Treating (bacterial) infections" means, that a compound has a bacteriostatic (inhibit the growth or multiplication of pathogen bacteria) or a bactericidal (kill) effect. The in vitro microbiological determination of whether an antibacterial agent is bactericidal or bacteriostatic may be influenced by growth conditions, bacterial density, test duration, and extent of reduction in bacterial numbers.

Quantitative susceptibility testing is usually performed by making 2-fold dilutions of the test antibacterial compound in a liquid culture medium, inoculating it with a standard number of microorganisms, and incubating it at 35° C.-37° C. for 18-24 h. The amount of antibacterial that inhibits visible growth (inhibitory phase) of the microorganism is called the "MIC."

In the following the use of the compounds as disclosed and covered by the general structures disclosed in this application for use in the treatment of bovine respiratory disease (BRD) especially if associated with *Mannheimia haemolytica*, *Pasteurella multocida* and *Histophilus somni* or swine respiratory disease (SRD), especially if associated with *Pasteurella multocida*, *Actinobacilusr pleuropneumoniae* or *Histophilus somni* or *Haemophilus parasuis* is sometimes referred to as "use according to the invention".

Furthermore the present invention provides compounds for use in the treatment of an infection by *Mannheimia haemolytica Histophilus somni*, pharmaceutical formulations including the compounds for use in the treatment of an infection by *Mannheimia haemolytica* and/or *Histophilus somni* and/or *Pasteurella multocida*, and methods of treating an infection by *Mannheimia haemolytica* and/or *Histophilus somni* and/or *Pasteurella multocida*.

Furthermore the present invention provides compounds for use in the treatment of Bovine Respiratory Disease or Swine respiratory Disease, pharmaceutical formulations including the compounds for use in the treatment of Bovine Respiratory Disease or Swine respiratory Disease, and methods of treating Bovine Respiratory Disease or Swine respiratory Disease.

It has been shown by the inventors that the compounds of the current invention as disclosed and defined earlier are especially suitable for the treatment (and prevention) of respiratory disease, especially in bovine and porcine (swine) animals.

As indicated in the examples compounds of the current invention show very high in-vitro activity against the relevant bacterial pathogens that are involved in the aetiology of important respiratory diseases of livestock, especially bovine respiratory disease and swine respiratory disease, including *Pasteurella multocida*, *Histophilus somni* and *Mannheimia haemolytica*. On the other hand, these compounds do not show activity against important pathogens that are relevant for human health, and are therefore especially useful for use in veterinary medicine, especially in livestock animals such as cattle and swine. At the same time the compounds show acceptable toxicity that allow a therapeutic window for the use as medicament for animals. Furthermore the administration of the compounds resulted in high concentrations in the target tissue for such diseases, i.e. the lungs and bronchial swabs.

The observed in-vitro activity was confirmed in model animals and in target animals (cattle).

The compounds of this invention exhibit unexpectedly high antibacterial activity against *Pasteurella multocida, Mannheimia haemolytica* and *Histophilus somni*. For example, representative compounds were tested against relevant pathoges for BRD and SRD, including *Pasteurella multocida, Mannheimia haemolytica* and *Histophilus somni*, using a conventional broth-dilution assay. This information can be found in Example 1 and 2. The minimal inhibitory concentrations (MIC's) of representative compounds against specific tested strains of these species are summarized in Tables 1 and 2.

Examples 3 and 4 show $MIC_{50}$ and $MIC_{90}$ data that represent the concentration at which minimum 50% or 90% of the isolates are inhibited for *A. pleuropneumoniae, B. bronchoseptica, H. somni, M. haemolytica, P. multocida* and *H. parasuis*.

Representative compounds of the current invention have been also tested in vivo in a mouse septicemia model *Pasteurella multocida*, see Example 5.

Respresentative compounds were tested in one of the target animals, in cattle, were clinical and/or bacteriological cure after experimentally induced *Mannheimia haemolytica* infection was observed, see Examples 6, 7 and 8. The efficacy of a representative compound in diseased naturally infected cattle under feedlot conditions was investigated in Example 9.

On the other hand the compounds of the invention have a very beneficial spectrum of activity, covering most of the relevant BRD and SRD pathogens but do not display activity against *Acinetobacter baumanii*, a pathogen that is especially relevant in human health. Therefore the use as an antibacterial compound for treatment in livestock animals is especially attractive because there is no risk of causing resistance in this relevant human pathogen. The MIC of representative compounds against *Actinobacter baumanii* and *Staphylococcus aureus* is disclosed in Example 2.

Furthermore it has been found that the compounds as described in this specification (sometimes referred to as the compounds of the current invention) do not show significant activity against anaerobic bacteria such as *Fusobacterium* spp. and therefore no or only very limited effect on the bacterial flora of the gut is expected, which is beneficial because it reduced frequently observed side effects of antibiotic therapy such as diarrhea.

Therefore the compounds as described in this specification are especially useful in the treatment of respiratory diseases of lifestock animals, especially cattle, swine (and small ruminants such as sheep and goat), such as BRD and SRD because they have such beneficial effects as described above.

The invention provides a compound for use according to the invention and/or embodiments thereof, wherein A is selected from the group consisting of $NR^{A1}R^{A2}$, and $NO_2$
wherein
- $R^{A1}R^{A2}$ are independently selected from the group consisting of
  - H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heterocyclyl, $C_1$-$C_6$-alkyl substituted with heterocyclyl, or
  - $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
- wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
  - $C_{1-6}$-alkyl, $C_{3-8}$-cycloalky, $C_{1-6}$-alkyloxy, $-NR^{A3}R^{A4}$, carbonyl, $-C(=O)-OR^{A5}$, halogen atom, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, $-SR^{A5}$, $-SO_2R^{A5}$, $SO_2NR^6R^7$, $-C(=O)NR^{A3}R^{A4}$, $C_{1-6}$-alkyl substituted with hydroxy;
- wherein
  - $R^{A3}$, $R^{A4}$, $R^{A5}$ are independently chosen from
  - H, or $C_{1-6}$-alkyl.

Suitably, in an embodiment of the invention and/or embodiments thereof the alkyl, alkenyl, alkynyl, cycloalkyl, aryl, heterocyclyl, heteroaryl, alkyloxy of A, $R^{A1}$, $R^{A2}$ or the heterocyclic ring formed by $R^{A1}$, $R^{A2}$ together with the N atom to which they are attached is optionally substituted with a substituent selected from the group consisting of
- $C_{1-6}$-alkyl, $C_{3-8}$-cycloalky, $-NR^{A3}R^{A4}$, carbonyl, halogen, $C_{1-6}$-alkyl substituted with halo, aryl, heteroaryl, $C_1$-$C_6$-alkyl substituted with aryl, cyano, hydroxy, $-SR^{A5}$, $-SO_2R^{A5}$, $SO_2NR^{A3}R^{A4}$, $-C(=O)NR^{A3}R^{A4}$, $C_{1-6}$-alkyl substituted with hydroxyl.
- wherein
  - $R^{A3}$, $R^{A4}$, $R^{A5}$ are independently chosen from
  - H, or $C_{1-6}$-alkyl.

Optionally, in an embodiment of the invention and/or embodiments thereof the alkyl, alkenyl, alkynyl, cycloalkyl, aryl, heterocyclyl, heteroaryl, alkyloxy of A, $R^{A1}$, $R^2$ or the heterocyclic ring formed by $R^{A1}$, $R^{A2}$ together with the N atom to which they are attached is optionally substituted with a substituent selected from the group consisting of
- $C_{1-6}$-alkyl, $-NR^{A3}R^{A4}$, carbonyl, halogen, cyano, hydroxy, $-SR^{A5}$, $-SO_2R^{A5}$, $SO_2NR^6R^7$, $-C(=O)NR^{A3}R^{A4}$;
- wherein
  - $R^{A3}$, $R^{A4}$, $R^{A5}$ are independently chosen from
  - H, or $C_{1-6}$-alkyl.

Optionally, in an embodiment of the invention and/or embodiments thereof the alkyl, alkenyl, alkynyl, cycloalkyl, aryl, heterocyclyl, heteroaryl, alkyloxy of A, $R^{A1}$; $R^{A2}$, or the heterocyclic ring formed by $R^{A1}$, $R^{A2}$ together with the N atom to which they are attached is optionally substituted with a substituent selected from the group consisting of
- $C_{1-6}$-alkyl, carbonyl, halogen, amino, cyano, hydroxyl.

Optionally, in an embodiment of the invention and/or embodiments thereof, A is selected from the group consisting of
- $NR^{A1}R^{A2}$, and $NO_2$.

Optionally
- $R^{A1}$, $R^{A2}$ are independently selected from the group consisting of
  - H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$alkyl, $C_1$-$C_6$-alkyl substituted with aryl, $C_1$-$C_6$-alkyl substituted with heterocyclyl, or
  - $R^{A1}$, $R^{A2}$ (together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
- wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
  - $C_{1-6}$-alkyl, $C_{3-8}$-cycloalky, $-NR^{A3}R^{A4}$, carbonyl, halogen, $C_{1-6}$-alkyl substituted with halo, aryl, heteroaryl, $C_1$-$C_6$-alkyl substituted with aryl, cyano, hydroxy, $-SR^{A5}$, $-SO_2R^{A5}$, $SO_2NR^{A3}R^{A4}$, $-C(=O)NR^{A3}K^{A4}$, $C_{1-6}$-alkyl substituted with hydroxy;
- wherein
  - $R^{A3}$, $R^{A4}$, $R^{A5}$ are independently chosen from
  - H, or $C_{1-6}$-alkyl.

Optionally,
- $R^{A1}R^{A2}$ are independently selected from the group consisting of
  - H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heterocyclyl, or
  - $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
- wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of $C_{1-6}$-alkyl, $-NR^{A3}R^{A4}$, carbonyl, halogen, cyano, hydroxy, $-SR^{A5}$, $-SO_2R^{A5}$, $SO_2NR^6R^7$, $-C(=O)NR^{A3}R^{A4}$;
- wherein
  - $R^{A3}$, $R^{A4}$, $R^{A5}$ are independently chosen from
  - H, or $C_{1-6}$-alkyl.

Optionally
- $R^{A1}$, $R^{A2}$ are independently selected from the group consisting of
  - H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heterocyclyl, or
  - $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
- wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
  - $C_{1-6}$-alkyl, carbonyl, halogen, amino, cyano, hydroxyl.

Optionally, in an embodiment of the invention and/or embodiments thereof, A is $NR^{41}R^{42}$, wherein $R^{41}$, $R^{42}$ are independently selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{41}$, $R^{42}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{41}$, $R^{42}$ together with the N atom to which they are attached is $R^{42}$ optionally substituted with a substituent selected from the group consisting of $C_{1-6}$-alkyl, $C_{3-8}$-cycloalky, $C_{1-6}$-alkyloxy, —$NR^{43}R^{44}$, carbonyl, —O(=O)—$OR^{45}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{45}$, —$SO_2R^{45}$, $SO_2NR^{43}R^{44}$, —C(=O)$NR^{43}R^{44}$, $C_{1-6}$-alkyl substituted with hydroxy;

wherein $R^{43}$, $R^{44}$, $R^{45}$ are independently chosen from

H, or $C_{1-6}$-alkyl.

Optionally, in an embodiment of the invention and/or embodiments thereof, A is $NR^{41}R^{42}$, wherein $R^{41}$, $R^{42}$ are independently selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{41}$, $R^{42}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{41}$, $R^{42}$ together with the N atom to which they are attached is optionally substituted with a substituent selected from the group consisting of $C_{3-8}$-cycloalky, —$NR^{43}R^{44}$, carbonyl, halogen, $C_{1-6}$-alkyl substituted with halo, aryl, heteroaryl, $C_1$-$C_6$-alkyl substituted with aryl, cyano, hydroxy, —$SR^{45}$, —$SO_2R^{45}$, $SO_2NR^{43}R^{44}$, —C(=O)$NR^{43}R^{44}$, $C_{1-6}$-alkyl substituted with hydroxy;

wherein $R^{43}$, $R^{44}$, $R^{45}$ are independently chosen from

H, or $C_{1-6}$-alkyl.

Optionally, in an embodiment of the invention and/or embodiments thereof, A is $NR^{41}R^{42}$, wherein $R^{41}$, $R^{42}$ are independently selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{41}$, $R^{42}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{41}$, $R^{42}$ together with the N atom to which they are attached is optionally substituted with a substituent selected from the group consisting of $C_{1-6}$-alkyl, —$NR^{43}R^{44}$, carbonyl, halogen, cyano, hydroxy, —$SR^{45}$, —$SO_2R^{45}$, $SO_2NR^{43}R^{44}$, C(=O)$NR^{43}R^{44}$;

wherein $R^{43}$, $R^{44}$, $R^{45}$ are independently chosen from

H, or $C_{1-6}$-alkyl.

Optionally, in an embodiment of the invention and/or embodiments thereof, A is $NR^{41}R^{42}$, wherein $R^{41}R^{42}$ are independently selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{41}$, $R^{42}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{41}$, $R^{42}$ together with the N atom to which they are attached is optionally substituted with a substituent selected from the group consisting of $C_{1-6}$-alkyl, carbonyl, halogen, amino, cyano, hydroxyl.

Optionally, in an embodiment of the invention and/or embodiments thereof, $R^{41}$, $R^{42}$ are independently selected from the group consisting of H, $C_{1-6}$-alkyl, $C_{2-6}$-alkenyl, $C_{2-6}$-alkynyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{41}$, $R^{42}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

Optionally, in an embodiment of the invention and/or embodiments thereof, $R^{41}$ is H or $C_{1-6}$-alkyl.

Optionally, in an embodiment of the invention and/or embodiments thereof $R^{42}$ is selected from the group consisting of H, $C_{1-6}$-alkyl, $C_{2-6}$-alkenyl, $C_{2-6}$-alkynyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{42}$ together with $R^{41}$ and the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

In an embodiment of the invention and/or embodiments thereof, the compounds are according to formula (II).

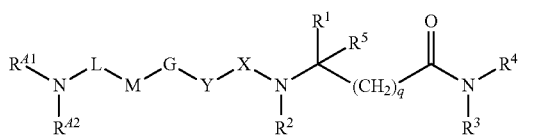

(II)

or a stereoisomer, pharmaceutically acceptable salt, ester, solvate, or prodrug thereof, use according to the invention, wherein $R^{A1}$, $R^{A2}$ are independently selected from
H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$—, carbonyl, —C(=O)—$OR^{A5}$—, halogen atom, $C_{1-6}$-alkyl substituted with halo, $C_{1-6}$-alkyloxy-$C_1$-$C_6$—, aryl, heterocyclyl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$—, $C_{1-6}$-alkyl substituted with hydroxy;

wherein
$R_{A3}$, $R^{A4}$, $R^{A5}$ are independently chosen from
H, or $C_{1-6}$-alkyl;

L is absent or selected from the group consisting of
$C_{1-6}$-alkyl, $C_{2-6}$-alkenyl, $C_{2-6}$-alkynyl, $C_{3-10}$-cycloalkyl, aryl, heterocyclyl, heteroaryl, —$(NR^{L3})_{0-1}$—$(CH_2)_{0-4}$—$NR^{L3}$—$(CH_2)_{0-4}$—, —(NR—$(CR^{L1}R^{L2})_{0-4}$—$NR^3$—$(CR^{L1}R^{L2})$—, —$(CR^{L1}R^{L2})_{0-4}$—O—$(CR^{L1}R^{L2})$—, —$(CH_2)_{0-4}$—$NR^{L3}$—$(CR^{L1}R^{L2})$—C(=O)NH—$(CH_2)_{0-4}$—, —C(=O)—$(CR^{L1}R^{L2})$—$NR^{L3}$C(=O)—, —C(=O)$NR^{L3}$—, —$NR^{L3}$C(=O)—, —$NR^{L3}$—, —$SO_2NR^{L3}$—, —C(=O)—$NR^{L3}$— wherein
$R^{L1}$, $R^{L2}$, $R^{L3}$, are independently selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or $R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O;

M is selected from the group consisting of
$C_{3-10}$-cycloalkyl, aryl, heterocyclyl, heteroaryl, $C_{2-4}$alkenyl, $C_{2-4}$alkynyl, —C($R^{M1}$)=C($R^{M1}$)—C≡C—, —C($R^{M1}$)=C($R^{M1}$)—, wherein each cycloalkyl, aryl, heterocyclyl, or heteroaryl is optionally substituted with a substituent selected from the group consisting of $C_{3-8}$-cycloalky, $C_{1-6}$-alkyloxy, $NR^{M2}R^{M3}$, carbonyl, —O(=O)—$OR^{M2}$, halo, halo-$C_{1-6}$-alkyl, $C_{1-6}$-alkyloxy-$C_1$-$C_6$-alkyl, aryl, heteroaryl, $C_1$-$C_6$-alkyl substituted with aryl, cyano, hydroxy, —$SR^2$, —$SO_2R^{M4}$, —$OSO_2R^{M4}$, —$SO_2NR^{M2}R^{M3}$, —C(=O)$NR^{M2}R^{M3}$—, hydroxy-$C_{1-6}$-alkyl;

wherein $R^{M1}$ is selected from the group consisting of H, $C_{1-6}$-alkyl, halo, hydroxyl, and amino;

wherein $R^{M2}$, $R^{M3}$ are independently selected from the group consisting of H, and $C_{1-6}$-alkyl;

wherein $R^{M4}$ is selected from the group consisting of H, $C_{1-6}$-alkyl, and amino;

G is selected from the group consisting of
—$(C(R^{G2}R^{G3})_{0-4}$—O—$(C(R^{G2}R^{G3})_{0-4}$—, —$(C(R^{G2}R^{G3})_{0-4}$—S—$(C(R^{G2}R^{G3})_{0-4}$—, —$(C(R^{G2}R^{G3})_{0-4}$—$NR^{G1}$—$(C(R^{G2}R^{G3})_{0-4}$—, —C(=O)—, —$NR^{G1}$C(=O)—, —C(=O)$NR^{G1}$—, —$(C(R^{G2}R^3)_{0-4}$—$NR^{G1}$—$C(R^{G2}R^{G3})$—C(=O)$NR^{G1}$—, —$CR^{G2}$=$CR^{G2}$—, —$CR^{G2}$=$CR^{G2}$—$CR^{G2}$=$CR^{G2}$—, —C≡C—, —C≡C—C≡C—, —$CR^{G2}$=$CR^{G2}$—C≡C—, —C≡C—$CR^{G2}$=$CR^{G2}$, —C(=O)—C≡C—, —C≡O—C(=O)—, —$SO_2$—, —S(=O)—, —S(=O)$C(R^{G2}R^{G3})$—, —$C(R^{G2}R^{G3})$S(=O)—, —$C(R^{G2}R^{G3})$—$SC_2$—, —$SC_2C(R^{G2}R^{G3})$—;

wherein
$R^{G1}$ is H or $C_{1-6}$-alkyl
each $R^{G2}$, $R^{G3}$ is independently selected from the group consisting of
H, halogen atom, or $C_{1-6}$-alkyl;

Y is selected from the group consisting of
$C_{3-10}$-cycloalkyl, aryl, heterocyclyl, heteroaryl,
wherein each cycloalkyl, aryl, heterocyclyl, or heteroaryl is optionally substituted with a substituent selected from the group consisting of $C_{1-6}$-alkyl, $C_{3-8}$-cycloalky, $C_{1-6}$-alkyloxy, $NR^{Y1}R^{Y2}$, carbonyl, —C(=O)—$OR^{Y1}$, halo, halo-$C_{1-6}$-alkyl, $C_{1-6}$-alkyloxy-$C_1$-$C_6$-alkyl, aryl, heteroaryl, $C_1$-$C_6$-alkyl substituted with aryl, cyano, hydroxy, —$SR^2$, —$SO_2R^{Y3}$, —$OSO_2R^{Y3}$, —$SO_2NR^{Y1}R^{Y2}$, —C(=O)$NR^{M2}R^{M3}$—, hydroxy-$C_{1-6}$-alkyl;

wherein $R^{Y1}$, $R^{Y2}$ are independently selected from the group consisting of H, and $C_{1-6}$-alkyl; wherein $R^{Y3}$ is selected from the group consisting of H, $C_{1-6}$-alkyl, and amino;

X is absent or selected from the group consisting of
—C(=O)—, —$C_{1-6}$-alkyl-C(=O)—, —$C_{2-6}$-alkenyl-C(=O)—, —$C_{2-6}$-alkynyl-C(=O)—, and —$(C(R^{X1})_2$—, —S(=O)—, —$SO_2$—;

wherein
$R^{X1}$, $R^{X2}$, is selected from the group consisting of
H, halogen atom, substituted $C_{1-6}$-alkyl, or un-substituted $C_{1-6}$-alkyl;
wherein the substituents on the substituted $C_{1-5}$-alkyl may be selected from the group consisting of halogen, hydroxyl, alkoxy, aryloxy, thiol, $C_{1-6}$-alkyl, carbonyl, —$SR^3$, —$SO_2R^{X5}$, —C(=O)$NR^{X3}R^{X4}$, cyano, —$NR^{X3}R^{X4}$, —O(=O)—$OR^{X3}$, aryl, heteroaryl, heterocycle, $C_{3-8}$-cycloalkyl;
wherein $R^{X3}$, $R^{X4}$ are independently selected from the group consisting of H, or $C_{1-6}$-alkyl;
wherein $R^{X5}$ is selected from the group consisting of H, $C_{1-6}$-alkyl, and amine;

$R^1$ is selected from the group consisting of
H, $C_{1-6}$-alkyl, $C_{2-6}$-alkenyl, $C_{2-6}$-alkynyl, $C_{3-10}$-cycloalkyl, C(=O)$R^9$, C(=N—$OR^8$)$R^8$, aryl, heterocyclyl, heteroaryl, $C_1$-$C_6$-alkyl substituted with aryl, $C_1$-$C_6$-alkyl substituted with heteroaryl, $C_1$-$C_6$-alkyl substituted with heterocyclyl, wherein each alkyl, alkenyl, alkynyl, cycloalkyl, aryl, heterocyclyl, heteroaryl, is optionally substituted with a substituent selected from the group consisting of
$C_{1-6}$-alkyl, $C_{3-8}$-cycloalky, $C_{1-6}$-alkyloxy, $NR^6R^7$, carbonyl, nitro, $C(=O)OR^9$, halogen, halo-$C_{1-6}$-alkyl, $C_{1-6}$-alkyloxy-$C_1$-$C_6$-alkyl, cyano, hydroxy, —$SR^8$, —$SO_2R^8$, $SO_2NR^6R^7$, —$C(=O)NR^6R^7$—;
wherein $R^6$, $R^7$, $R^8$ are independently chosen from H, or $C_{1-6}$-alkyl;
wherein $R^9$ is selected from the group consisting of H, hydroxyl, or $C_{1-6}$-alkyl
$R^2$, $R^3$ is selected from the group consisting of
H, halogen atom, substituted $C_{1-6}$-alkyl, or un-substituted $C_{1-6}$-alkyl;
wherein the substituents on the substituted $C_{1-6}$-alkyl may be selected from the group consisting of halogen, hydroxyl, alkoxy, aryloxy, thiol, $C_{1-6}$-alkyl, carbonyl, —$S^8$, —$SO_2R^8$, $SO_2NR^6R^7$, —$C(=O)NR^6R^7$, cyano, —$NR^6R^7$, —$C(=O)$—$OR^6$, aryl, heteroaryl, heterocycle, $C_{3-8}$-cycloalkyl;
q is 0, 1, 2, 3, or 4;
$R^4$ is selected from the group consisting of
H, $C_{1-6}$-alkyl, $C_{2-6}$-alkenyl, $C_{2-6}$-alkynyl, $C_{3-10}$-cycloalkyl, —$OR^8$, $C(=O)OR^9$, $C(=O)R^9$, aryl, heterocyclyl, heteroaryl, $C_1$-$C_6$-alkyl substituted with aryl, $C_1$-$C_6$-alkyl substituted with heteroaryl, $C_1$-$C_6$-alkyl substituted with heterocyclyl
wherein each alkyl, alkenyl, alkynyl, cycloalkyl, aryl, heterocyclyl, heteroaryl, is optionally substituted with a substituent selected from the group consisting of
$C_{1-6}$-alkyl, $C_{3-8}$-cycloalkyl, $C_{1-6}$-alkyloxy, $NR^6R^7$, carbonyl, nitro, $C(=O)OR^9$, halogen, amino, halo-$C_{1-6}$-alkyl, $C_{1-6}$-alkyloxy-$C_1$-$C_6$-alkyl, cyano, hydroxy, —$SR^8$, —$SO_2R^8$, $SO_2NR^6R^7$, —$C(=O)NR^5R^6$;
$R^5$ is selected from the group consisting of H, and $C_{1-6}$-alkyl;
$R^6$, $R^7$, $R^8$ are independently selected from the group consisting of H, and $C_{1-6}$-alkyl;
wherein $R^9$ is selected from the group consisting of H, hydroxyl, or $C_{1-6}$-alkyl Suitably, in an embodiment of the invention and/or embodiments thereof, $R^{41}$, $R^{42}$ are independently selected from the group consisting of
H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or
$R^{41}$, $R^{42}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, alkynyl, cycloalkyl, aryl, heterocyclyl, heteroaryl, alkyloxy or the heterocyclic ring formed by $R^{41}$, $R^{42}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{43}R^{44}$, carbonyl, —$C(=O)$—$OR^{45}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{45}$, —$SO_2R^{45}$, $SO_2NR^{44}R^{45}$, —$C(=O)NR^{43}R^{44}$, $C_{1-6}$-alkyl substituted with hydroxy;
wherein
$R^{43}$, $R^{44}$, $R^{45}$ are independently chosen from
H, or $C_{1-6}$-alkyl.

Suitably, in an embodiment of the invention and/or embodiments thereof, $R^{41}$, $R^{42}$ are independently selected from the group consisting of
H, $C_{1-6}$-alkyl, $C_{2-6}$-alkenyl, $C_{3-10}$-cycloalkyl$C_{1-6}$-alkyloxy-$C_1$-$C_6$-alkyl, $C_1$-$C_6$-alkyl substituted with aryl, $C_1$-$C_6$-alkyl substituted with heteroaryl;
wherein the alkyl, alkenyl, cycloalkyl, aryl, heteroaryl, or alkyloxy is optionally substituted with a substituent selected from the group consisting of
$C_{1-6}$-alkyl, $C_{3-8}$-cycloalky, $C_{1-6}$-alkyloxy, —$NR^{43}R^{44}$, carbonyl, —$C(=O)$—$OR^{45}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{45}$, —$SO_2R^{45}$, $SO_2NR^{44}R^{45}$, —$C(=O)NR^{43}R^{44}$, $C_{1-6}$-alkyl substituted with hydroxy;
wherein
$R^{43}$, $R^{44}$, $R^{45}$ are independently chosen from
H, or $C_{1-6}$-alkyl.

Suitably, in an embodiment of the invention and/or embodiments thereof, $R^{41}$, $R^{42}$ are independently selected from the group consisting of
H, $C_{1-6}$-alkyl, $C_{2-6}$-alkenyl, $C_{3-10}$-cycloalkyl$C_{1-6}$-alkyloxy-$C_1$-$C_6$-alkyl, $C_1$-$C_6$-alkyl substituted with aryl, $C_1$-$C_6$-alkyl substituted with heteroaryl;
wherein the alkyl, alkenyl, cycloalkyl, aryl, heteroaryl, or alkyloxy is optionally substituted with a substituent selected from the group consisting of
$C_{1-6}$-alkyl, $C_{3-8}$-cycloalky, $C_{1-6}$-alkyloxy, —$NR^{43}R^{44}$, carbonyl, halogen atom, cyano, hydroxy, —$SR^{45}$, —$SO_2R^{45}$, $SO_2NR^{44}R^{45}$, —$C(=O)NR^{43}R^{44}$, $C_{1-6}$-alkyl substituted with hydroxy;
wherein
$R^{43}$, $R^{44}$, $R^{45}$ are independently chosen from
H, or $C_{1-6}$-alkyl.

In yet another embodiment of the invention and/or embodiments thereof, $R^{41}$, $R^{42}$ together with the N atom to which they are attached can form a saturated or unsaturated heterocyclic ring having 3 to 10 ring atoms, wherein 1 ring atom is N and wherein 0, 1, 2, or 3 further ring atoms are selected from N, S, and O.

In yet another embodiment of the invention and/or embodiments thereof, $R^{41}$, $R^{42}$ together with the N atom to which they are attached can form a saturated or unsaturated heterocyclic ring having 3 to 8 ring atoms, wherein 1 ring atom is N and wherein 0, 1, 2, or 3 further ring atoms are selected from N, S, and O.

In yet another embodiment of the invention and/or embodiments thereof, $R^{41}$, $R^{42}$ together with the N atom to which they are attached can form a saturated or unsaturated heterocyclic ring selected from the group consisting of azetidinyl, azetyl, diazetidinyl, pyrrolidinyl, pyrrolinyl, pyrrolyl, pyrazolidinyl, imidazolidinyl, pyrazolinyl, imidazolinyl, pyrazolyl, imidazolyl, triazolyl, tetrazolyl, oxazolyl, isoxazolyl, isothiazolyl, thiazolyl, oxoadiazolyl, thiadiazolyl, oxazolidonyl, piperidinyl, pyridinyl, piperazinyl, pyridazinyl, pyrimidinyl, pyrazinyl, triazinyl, morpholinyl, oxazinyl, thiomorpholinyl, thiazinyl, thiomorpholinyl dioxide, indolyl, indolinyl, isoindolyl, benzimidazolyl, azaindolyl, azepanyl, tetrahydroisoquinolinyl, tetrahydroquinolinyl, decahydroisoquinolinyl, decahydroquinolinyl, quinolonyl, isoquinolinyl.

In yet another embodiment of the invention and/or embodiments thereof, $R^{41}$, $R^{42}$ together with the N atom to which they are attached can form a saturated or unsaturated heterocyclic ring selected from the group consisting of pyrrolidinyl, pyrrolinyl, pyrrolyl, pyrazolidinyl, imidazolidinyl, pyrazolinyl, imidazolinyl, pyrazolyl, imidazolyl, triazolyl, tetrazolyl, oxazolyl, isoxazolyl, isothiazolyl, thiazolyl, thiadiazolyl, oxazolidonyl, piperidinyl, pyridinyl, piperazinyl, pyridazinyl, pyrimidinyl, pyrazinyl, triazinyl, morpholinyl, thiomorpholinyl, thiazinyl, thiomorpholinyl dioxide, indolyl, indolinyl, benzimidazolyl, azepanyl, tetrahydroisoquinolinyl, tetrahydroquinolinyl, decahydroisoquinolinyl, decahydroquinolinyl, quinolonyl, isoquinolinyl.

In yet another embodiment of the invention and/or embodiments thereof, $R^{A1}$, $R^{A2}$ together with the N atom to which they are attached can form a saturated or unsaturated heterocyclic ring selected from the group consisting of pyrrolidinyl, pyrrolinyl, pyrrolyl, imidazolidinyl, pyrazolinyl, imidazolinyl, pyrazolyl, imidazolyl, oxazolyl, isoxazolyl, thiazolyl, thiadiazolyl, piperidinyl, pyridinyl, piperazinyl, pyrimidinyl, pyrazinyl, morpholinyl, thiomorpholinyl, thiomorpholinyl dioxide, indolinyl, benzimidazolyl, azepanyl, tetrahydroisoquinolinyl, tetrahydroquinolinyl, decahydroisoquinolinyl, decahydroquinolinyl, quinolonyl, isoquinolinyl.

In yet another embodiment of the invention and/or embodiments thereof, $R^{A1}$, $R^{A2}$ together with the N atom to which they are attached can form a saturated or unsaturated heterocyclic ring selected from the group consisting of pyrrolidinyl, pyrrolinyl, pyrrolyl, imidazolidinyl, pyrazolinyl, imidazolinyl, pyrazolyl, imidazolyl, oxazolyl, isoxazolyl, thiazolyl, thiadiazolyl, piperidinyl, pyridinyl, piperazinyl, pyrimidinyl, pyrazinyl, morpholinyl, thiomorpholinyl, thiomorpholinyl dioxide, indolinyl, benzimidazolyl, azepanyl, tetrahydroisoquinolinyl, tetrahydroquinolinyl, decahydroisoquinolinyl, decahydroquinolinyl, quinolonyl, isoquinolinyl.

In yet another embodiment of the invention and/or embodiments thereof, $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl, In yet another embodiment of the invention and/or embodiments thereof, $R^{A2}$ is hydrogen or $C_{1-6}$alkyl.

In case $R^{A1}$, $R^{A2}$ together with the N atom to which they are attached do not form a heterocyclic ring, then $R^{A2}$ is hydrogen or $C_{1-6}$alkyl.

In yet another embodiment of the invention and/or embodiments thereof, $R^{A2}$ is hydrogen or $C_{1-6}$alkyl and $R^{A1}$ is selected from the group consisting of
H, $C_{1-6}$-alkyl, $C_{2-6}$-alkenyl, $C_{3-10}$-cycloalkyl$C_{1-6}$-alkyloxy-$C_1$-$C_6$-alkyl, $C_1$-$C_6$-alkyl substituted with aryl, $C_1$-$C_6$-alkyl substituted with heteroaryl;
wherein the alkyl, alkenyl, cycloalkyl, aryl, heteroaryl, or alkyloxy is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A4}R^{A5}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In yet another embodiment of the invention and/or embodiments thereof, $R^{A2}$ is hydrogen or $C_{1-6}$alkyl and $R^{A1}$ is selected from the group consisting of
H, $C_{1-6}$-alkyl, $C_{2-6}$-alkenyl, $C_{3-10}$-cycloalkyl$C_{1-6}$-alkyloxy-$C_1$-$C_6$-alkyl, $C_1$-$C_6$-alkyl substituted with aryl, $C_1$-$C_6$-alkyl substituted with heteroaryl;
wherein the alkyl, alkenyl, cycloalkyl, aryl, heteroaryl, or alkyloxy is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, halogen atom, cyano, hydroxy, —$SR^{A5}$, —$SO_2R^{A5}$, $SO_2NR^{A4}R^{A5}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

Suitably, in an embodiment of the invention and/or embodiments thereof $NR^{A1}R^{A2}$ is selected from the group consisting of

(a-1)

(a-2)

(a3)

(a-4)

(a-5)

(a-6)

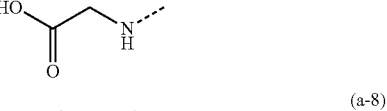
(a-7)

(a-8)

(a-9)

(a-10)

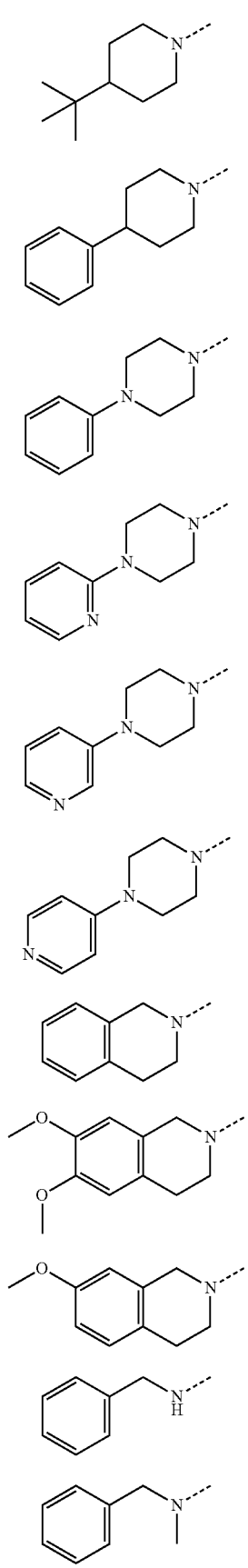
(a-11)
(a-12)
(a-13)
(a-14)
(a-15)
(a-16)
(a-17)
(a-18)
(a-19)
(a-20)
(a-21)
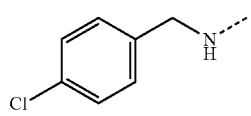
(a-22)
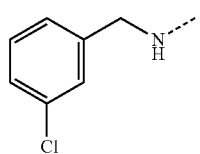
(a-23)
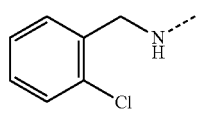
(a-24)
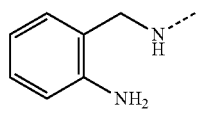
(a-25)
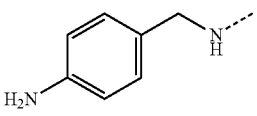
(a-26)
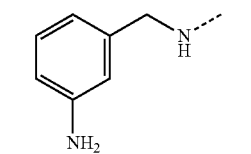
(a-27)
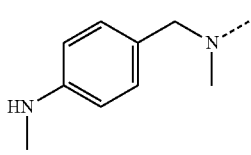
(a-28)
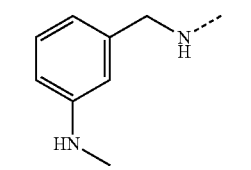
(a-29)
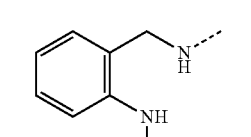
(a-30)
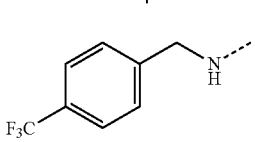
(a-31)
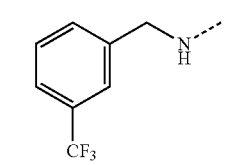
(a-32)

-continued
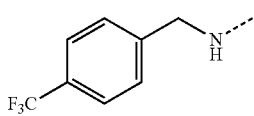 (a-33)
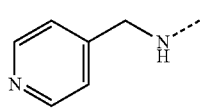 (a-34)
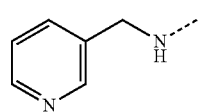 (a35)
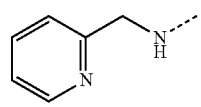 (a36)
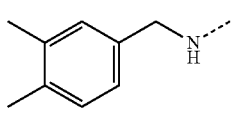 (a-37)
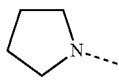 (a-38)
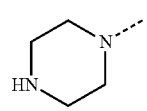 (a-39)
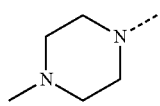 (a-40)
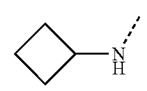 (a-41)
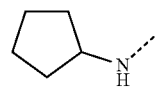 (a-42)
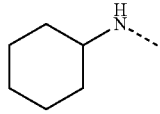 (a-43)
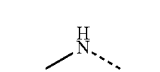 (a-44)
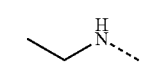 (a-45)
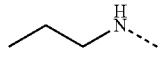 (a-46)
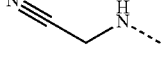 (a-47)
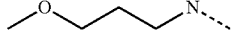 (a-48)
-continued
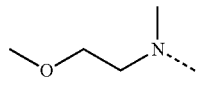 (a-49)
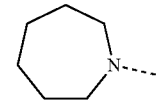 (a-50)
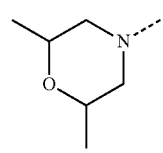 (a-51)
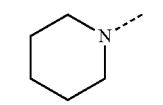 (a-52)
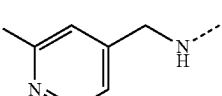 (a-53)
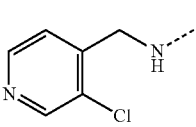 (a-54)
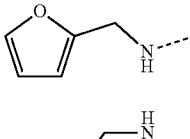 (a-55)
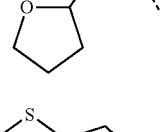 (a-56)
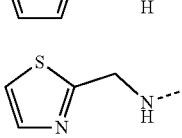 (a-57)
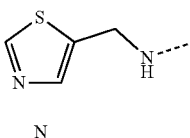 (a-58)
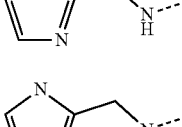 (a-59)
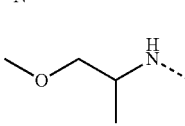 (a-60)
(a-61)
(a-62)

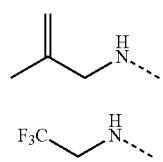
(a-63)
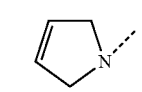
(a-64)
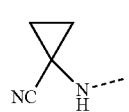
(a-65)
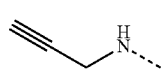
(a-66)
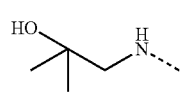
(a-67)
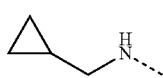
(a-68)
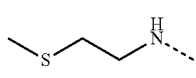
(a-69)
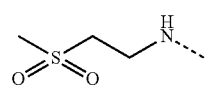
(a-70)
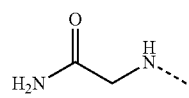
(a-71)
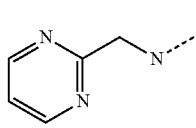
(a-72)
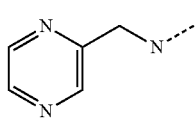
(a-73)
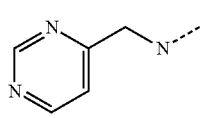
(a-74)
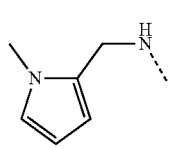
(a75)
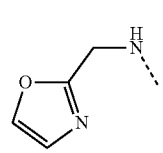
(a76)
(a-77)
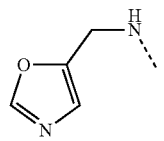
(a-78)
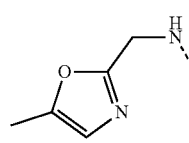
(a-79)
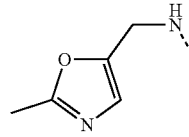
(a-80)
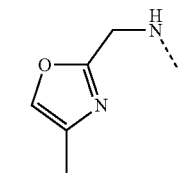
(a-81)
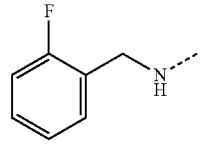
(a-82)
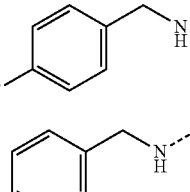
(a-83)
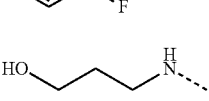
(a-84)
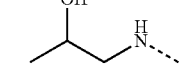
(a-85)
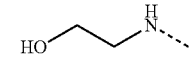
(a-86)
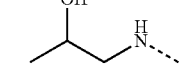
(a-87)
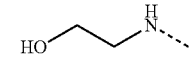
(a-88)
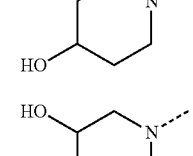
(a-89)
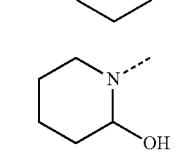
(a-90)

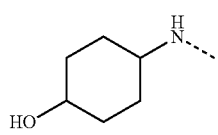 (a-91)
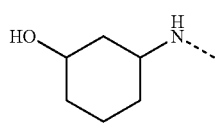 (a-92)
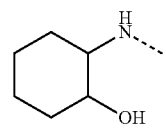 (a-93)
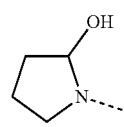 (a-94)
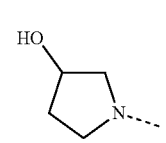 (a-95)
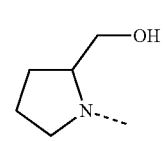 (a-96)
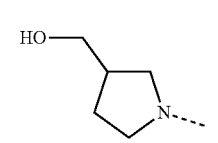 (a-97)
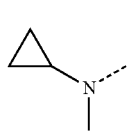 (a-98)
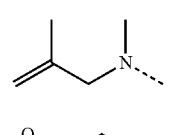 (a-99)
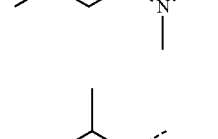 (a-100)
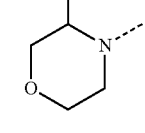 (a-101)
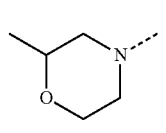 (a-102)
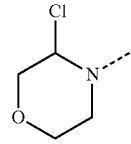 (a-103)
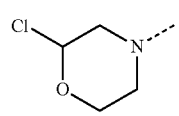 (a-104)
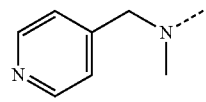 (a-105)
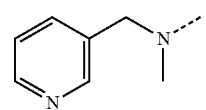 (a-106)
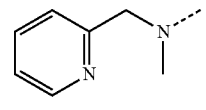 (a-107)
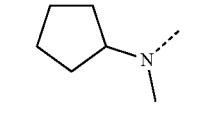 (a-108)
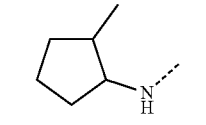 (a-109)
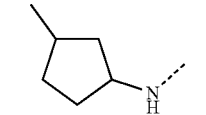 (a-110)
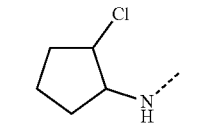 (a-111)
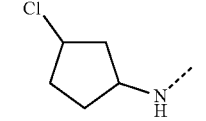 (a-112)
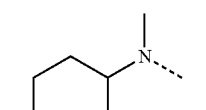 (a-113)
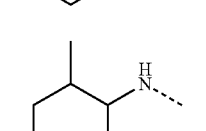 (a-114)

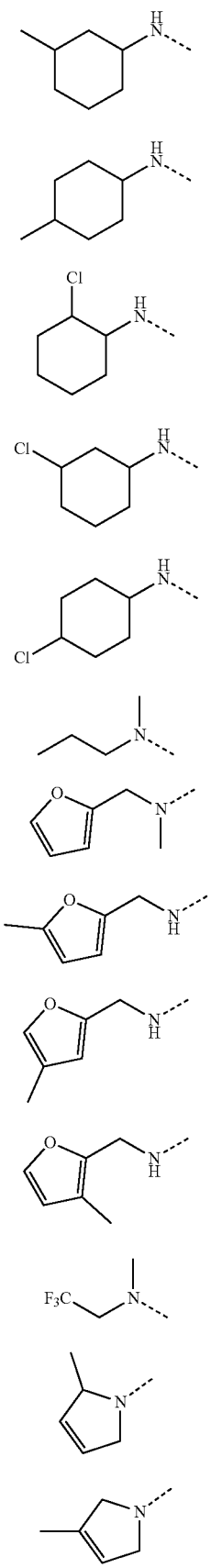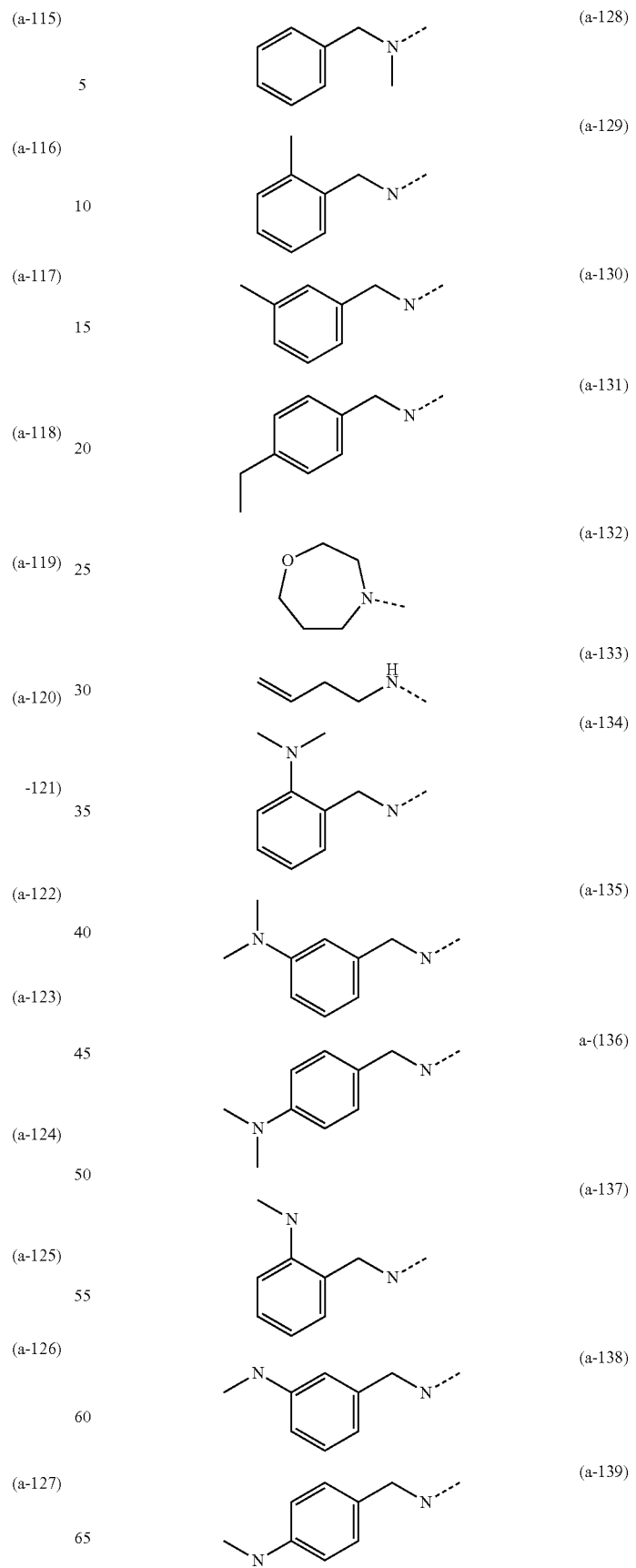

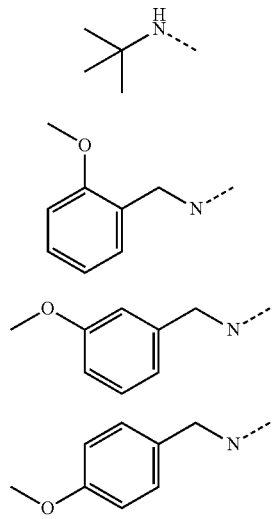

Suitably, in an embodiment of the invention and/or embodiments thereof $NR^{41}R^{42}$ is selected from the group consisting of (a-1), (a-3), (a-5), (a-9), (a-20), (a-21), (a-22), (a-23), (a-24), (a-25), (a-26), (a-27), (a-28), (a-29), (a-30), (a-31), (a-33), (a-34), (a-35), (a-36), (a-42), (a-43), (a-46), (a-55), (a-64), (a-65), (a-82), (a-83), (a-84), (a-98), (a-99), (a-100), (a-101), (a-102), (a-103), (a-104), (a-105), (a-106), (a-107), (a-108), (a-109), (a-110), (a-111), (a-112), (a-113), (a-114), (a-115), (a-116), (a-117), (a-118), (a-119), (a-120), (a-121), (a-122), (a-123), (a-124), (a-125), (a126), (a-127), (a-128), (a-129), (a-130), and (a-131).

Suitably, in an embodiment of the invention and/or embodiments thereof $NR^{41}R^{42}$ is selected from the group consisting of (a-1), (a-3), (a-5), (a-9), (a-20), (a-34), (a-35), (a-36), (a-42), (a-46), (a-55), (a-64), (a-65), (a-98), (a-99), (a-100), (a-103), (a-104), (a-105), (a-106), (a-107), (a-108), (a-120), (a-121), (a-125), (a126), and (a-128).

Suitably, in an embodiment of the invention and/or embodiments thereof $NR^{41}R^{42}$ is selected from the group consisting of (a-1), (a-3), (a-5), (a-9), (a-20), (a-34), (a-35), (a-36), (a-42), (a-46), (a-55), (a-64), and (a-65).

Suitably, in an embodiment of the invention and/or embodiments thereof $NR^{41}R^{42}$ is selected from the group consisting of (a-1), (a-3), (a-5), (a-20), (a-34), (a-35), (a-36), (a-46), (a-55), and (a-65).

In another embodiment, q is 0, 1, 2, 3, or 4. Suitably, q is 0, 1, 2, or 3. In yet another embodiment q is 0, 1, or 2. Suitably, q is 0, or 1.

Suitably the present invention provides compounds according to formula (III)

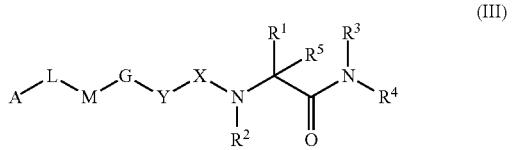

or a stereoisomer, pharmaceutically acceptable salt, ester, solvate, or prodrug thereof, use according to the invention, wherein A, L, M, G, Y, X, $R^1$, $R^2$, $R^3$, $R^4$, and $R^5$ are defined as in any of the embodiments described herein.

Suitably the present invention provides compounds according to formula (IV)

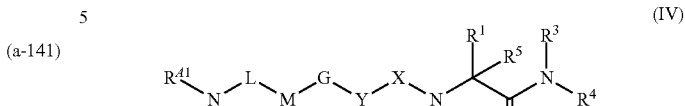

or a stereoisomer, pharmaceutically acceptable salt, ester, solvate, or prodrug thereof, use according to the invention, wherein L, M, G, Y, X, $R^1$, $R^2$, $R^3$, $R^4$, $R^5$, $R^{41}$, and $R^{42}$ are defined as in any of the embodiments described herein.

In embodiments, L is selected from the group consisting of $C_{2-6}$-alkenyl, $C_{2-6}$-alkynyl, $C_{3-10}$-cycloalkyl, aryl, heterocyclyl, heteroaryl, —$(NR^{L3})_{0-1}$—$(CH_2)_{0-4}$—$NR^{L3}$—$(CH_2)_{0-4}$—, —$(NR^{L3})_{0-1}$—$(CR^{L1}R^{L2})_{0-4}$—$NR^{L3}$—$(CR^{L1}R^{L2})$—, —$(CR^{L1}R^{L2})_{0-4}$—O—$(CR^{L1}R^{L2})$—, —$(CH_2)_{0-4}$—$NR^{L3}$—$(CR^{L1}R^{L2})$—$C(=O)NH$—$(CH_2)_{0-4}$—, —$C(=O)$—$(CR^{L1}R^{L2})$—$NR^{L3}C(=O)$—, —$C(=O)NR^{L3}$—, —$NR^{L3}C(=O)$—, $NR^{L3}$—$C(=O)$—$NR^{L3}$— wherein $R^{L1}$, $R^{L2}$, $R^{L3}$, are independently selected from the group consisting of H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or $R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O.

In embodiments, L is selected from the group consisting of $C_{1-6}$-alkyl, $C_{2-6}$-alkenyl, $C_{2-6}$-alkynyl, $C_{3-10}$-cycloalkyl, aryl, heterocyclyl, heteroaryl, $(CH_2)_{0-4}$—$NR^{L3}$—$(CH_2)_{0-4}$—, —$(NR^{L3})_{0-1}$—$(CR^{L1}R^{L2})_{0-4}$—$NR^{L3}$—$(CR^{L1}R^{L2})$—, —$(CR^{L1}R^{L2})_{0-4}$—O—$(CR^{L1}R^{L2})$—, —$(CH_2)_{0-4}$—$NR^{L3}$—$(CR^{L1}R^{L2})$—$C(=O)NH$—$(CH_2)_{0-4}$—, —$C(=O)$—$(CR^{L1}R^{L2})$—$NR^{L3}C(=O)$—, —$C(=O)NR^{L3}$—, —$NR^{L3}C(=O)$—, $NR^{L3}$—$C(=O)$—$NR^{L3}$— wherein $R^{L1}$, $R^{L2}$, $R^{L3}$, are independently selected from the group consisting of H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or $R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O.

In embodiments, L is selected from the group consisting of $C_{1-6}$-alkyl, $C_{2-6}$-alkenyl, $C_{2-6}$-alkynyl, $C_{3-10}$-cycloalkyl, —$(NR^{L3})_{0-1}$—$(CH_2)_{0-4}$—$NR^{L3}$—$(CH_2)_{0-4}$—, —$(NR^{L3})_{0-1}$—$(CR^{L1}R^{L2})_{0-4}$—$NR^{L3}$—$(CR^{L1}R^{L2})$—, —$(CR^{L1}R^{L2})_{0-4}$—O—$(CR^{L1}R^{L2})$—, —$(CH_2)_{0-4}$—$NR^{L3}$—$(CR^{L1}R^{L2})$—$C(=O)NH$—$(CH_2)_{0-4}$—, —$C(=O)$—$(CR^{L1}R^{L2})$—$NR^{L3}C(=O)$—, —$C(=O)NR^{L3}$—, —$NR^{L3}C(=O)$—, —$NR^{L3}$—, —$SO_2NR^{L3}$—, $NR^{L3}$—$C(=O)$—$NR^{L3}$— wherein
$R^{L1}$, $R^{L2}$, $R^{L3}$, are independently selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or
$R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O.

In embodiments, L is absent or selected from the group consisting of
$C_{1-6}$-alkyl, $C_{2-6}$-alkenyl, $C_{2-6}$-alkynyl, $C_{3-10}$-cycloalkyl, —(NR$^{L3}$)$_{0-1}$—(CH$_2$)$_{0-4}$—NR$^{L3}$—(CH$_2$)$_{0-4}$—, —(NR$^{L3}$)$_{0-1}$—(CR$^{L1}$R$^{L2}$)$_{0-4}$—NR$^{L3}$—(CR$^{L1}$R$^{L2}$)—, —(CR$^{L1}$R$^2$)$_{0-4}$—O—(CR$^{L1}$R$^{L2}$), —NR$^{L3}$—, —SO$_2$NR$^{L3}$—,
wherein
$R^{L1}$, $R^{L2}$, $R^{L3}$ are independently selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or
$R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O.

In embodiments, L is absent or selected from the group consisting of
$C_{1-6}$-alkyl, $C_{2-6}$-alkenyl, $C_{2-6}$-alkynyl, $C_{3-10}$-cycloalkyl, wherein
$R^{L3}$, is selected from the group consisting of
H, $C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl.

Suitably L is absent or selected from the group consisting of $C_{1-6}$-alkyl, or $C_{2-6}$-alkenyl.
Suitably L is $C_{1-6}$-alkyl. Suitably L is CH$_2$—, —CH$_2$CH$_2$—, —CH$_2$CH$_2$CH$_2$—, or —CH$_2$CH$_2$CH$_2$CH$_2$—. Suitably L is CH$_2$—, —CH$_2$CH$_2$—, or —CH$_2$CH$_2$CH$_2$—. Suitably L is CH$_2$—, or —CH$_2$CH$_2$—.
Suitably L is absent.
In some embodiments, L is not absent.
Suitably L is selected from the group consisting of
$C_{1-6}$-alkyl, $C_{2-6}$-alkenyl, $C_{2-6}$-alkynyl, $C_{3-10}$-cycloalkyl, aryl, heterocyclyl, heteroaryl, —(NR$^{L3}$)$_{0-1}$—(CH$_2$)$_{0-4}$—NR$^{L3}$—(CH$_2$)$_{0-4}$—, —(NR$^{L3}$)$_{0-1}$—(CR$^{L1}$R$^{L2}$)$_{0-4}$—NR$^{L3}$—(CR$^{L1}$R$^{L2}$)—, —(CR$^{L1}$R$^{L2}$)$_{0-4}$—O—(CR$^{L1}$R$^{L2}$)—, —(CH$_2$)$_{0-4}$—NR$^{L3}$—(CR$^{L1}$R$^{L2}$)—C(=O)NH—(CH$_2$)$_{0-4}$—, —C(=O)—(CR$^{L1}$R$^{L2}$)—NR$^{L3}$C(=O)—, —C(=O)NR$^{L3}$—, —NR$^{L3}$C(=O)—, —NR$^{L3}$—, —SO$_2$NR$^{L3}$—C(=O)—NR$^{L3}$—
wherein
$R^{L1}$, $R^{L2}$, $R^{L3}$ are independently selected from the group consisting of
H, $C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or
$R^{L3}$ together with the atoms to which they are attached can form a saturated or unsaturated heterocyclic ring having 3 to 8 ring atoms, wherein 1, 2, or 3, ring atoms are selected from N, S, and O;

In some embodiments of the invention and/or embodiments thereof the compound is a compound according to formula

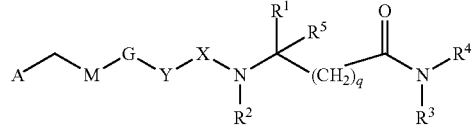

(V)

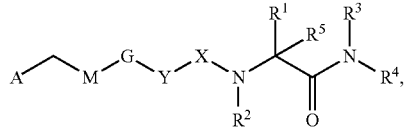

(VI)

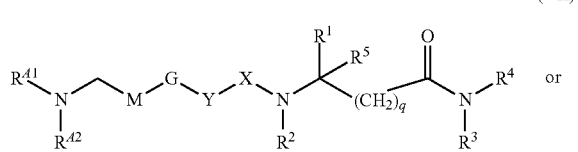

(VII)

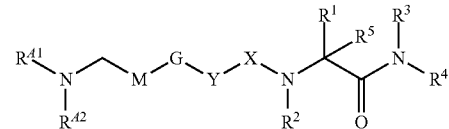

(VIII)

or a stereoisomer, pharmaceutically acceptable salt, ester, solvate, or prodrug thereof, use according to the invention, wherein A, M, G, Y, X, q, $R^1$, $R^2$, $R^3$, $R^4$, $R^5$, $R^{41}$, and $R^{42}$ are defined as in any of the embodiments described herein.

In some embodiments, M is selected from the group consisting of
$C_{3-10}$-cycloalkyl, aryl, heterocyclyl, heteroaryl, $C_{2-4}$alkenyl, $C_{2-4}$alkynyl, —C(R$^{M1}$)=C(R$^{M1}$)—C≡C—, —C(R$^{M1}$)=C(R$^{M1}$)—,
wherein each cycloalkyl, aryl, heterocyclyl, or heteroaryl is optionally substituted with a substituent selected from the group consisting of
$C_{1-6}$-alkyl, $C_{3-8}$-cycloalky, $C_{1-6}$-alkyloxy, NR$^{M2}$R$^{M3}$, carbonyl, —C(=O)—OR$^{M2}$, halo, halo-$C_{1-6}$-alkyl, $C_{1-6}$-alkyloxy-$C_1$-$C_6$-alkyl, aryl, heteroaryl, $C_1$-$C_6$-alkyl substituted with aryl, cyano, hydroxy, —SR$^2$, —SO$_2$R$^{M4}$, SO$_2$NR$^{M2}$R$^{M3}$, —OSO$_2$R$^{M4}$, —SO$_2$NR$^{M2}$R$^{M3}$, —C(=O)NR$^{M2}$R$^{M3}$—, hydroxy-$C_{1-6}$-alkyl;
wherein $R^{M1}$ is selected from the group consisting of H, $C_{1-6}$-alkyl, halo, hydroxyl, and amino;
wherein $R^{M2}$, $R^{M3}$ are independently selected from the group consisting of H, and $C_{1-6}$-alkyl;
wherein $R^{M4}$ is selected from the group consisting of H, $C_{1-6}$-alkyl, and amino.

In some embodiments, M is selected from the group consisting of
$C_{3-10}$-cycloalkyl, aryl, heterocyclyl, heteroaryl, $C_{2-4}$alkenyl, $C_{2-4}$alkynyl, —C(R$^{M1}$)=C(R$^{M1}$)—C≡C—, —C(R$^{M1}$)=C(R$^{M}$)—.

Suitably M is selected from the group consisting of aryl, heterocyclyl, heteroaryl, —C(R$^{M1}$)=C(R$^{M1}$)—C≡C—, —C(R$^{M1}$)=C(R$^{M1}$)—.
Suitably M is selected from the group consisting of aryl, heteroaryl, —C(R$^{M1}$)=C(R$^{M1}$)—C≡C—, —C(R$^{M1}$)=C(R$^{M1}$)—.
Suitably M is selected from the group consisting of phenyl, thiazolyl, pyridinyl, pyrimidinyl, thiophenyl, furanyl, pyrrolyl, imidazolyl, oxazolyl, pyrazinyl, pyranyl, thiopyranyl, oxazinyl, thiazynyl, —C(R$^{M1}$)=C(R$^{M1}$)—C≡C—, —C(R$^{M1}$)=C(R$^{M1}$)—.

Suitably M is selected from the group consisting of phenyl, thiazolyl, pyridinyl, pyrimidinyl, thiophenyl, furanyl, pyrrolyl, imidazolyl, oxazolyl, pyrazinyl, —C(R$^{M1}$)=C(R$^{M1}$)—C≡C—, —C(R$^{M1}$)=C(R$^{M1}$)—.

Suitably M is selected from the group consisting of phenyl, thiazolyl, pyridinyl, pyrimidinyl, thiophenyl, furanyl, —C(R$^{M1}$)=C(R$^{M1}$)—C≡C—, —C(R$^{M1}$)=C(R$^{M1}$)—.

Suitably M is selected from the group consisting of phenyl, thiazolyl, pyridinyl, pyrimidinyl, thiophenyl, furanyl, —C(H)=C(H)—C≡C—, —C(H)=C(H)—.

Suitably the cycloalkyl, aryl, heterocyclyl, or heteroaryl of M is optionally substituted with a substituent selected from the group consisting of C$_{1-6}$-alkyloxy, NR$^{M2}$R$^{M3}$, carbonyl, —C(=O)—OR$^{M2}$, halo, halo-C$_{1-6}$-alkyl, C$_{1-6}$-alkyloxy-C$_1$-C$_6$-alkyl, C$_1$-C$_6$-alkyl substituted with aryl, cyano, hydroxy, —SR$^{M2}$, —SO$_2$R$^{M4}$, —OSO$_2$R$^{M4}$, —SO$_2$NR$^{M2}$R$^{M3}$, —C(=O)NR$^{M2}$R$^{M3}$—, hydroxy-C$_{1-6}$-alkyl.

Suitably the cycloalkyl, aryl, heterocyclyl, or heteroaryl of M is optionally substituted with a substituent selected from the group consisting of C$_{1-6}$-alkyloxy, NR$^{M2}$R$^{M3}$, carbonyl, —C(=O)—OR$^{M2}$, halo, halo-C$_{1-6}$-alkyl, C$_{1-6}$-alkyloxy-C$_1$-C$_6$-alkyl, C$_1$-C$_6$-alkyl substituted with aryl, cyano, hydroxy, —SR$^{M2}$, —SO$_2$R$^{M4}$, —OSO$_2$R$^{M4}$, —SO$_2$NR$^{M2}$R$^{M3}$, —C(=O)NR$^{M2}$R$^{M3}$—, hydroxy-C$_{1-6}$-alkyl.

Suitably the cycloalkyl, aryl, heterocyclyl, or heteroaryl of M is optionally substituted with a substituent selected from the group consisting of C$_{1-6}$-alkyl, halo, halo-C$_{1-6}$-alkyl, C$_{1-6}$-alkyloxy-C$_1$-C$_6$-alkyl, C$_1$-C$_6$-alkyl substituted with aryl, cyano, hydroxy, —SR$^{M2}$, —SO$_2$R$^{M4}$, —OSO$_2$R$^{M4}$, —SO$_2$NR$^{t2}$R$^{M3}$, hydroxy-C$_{1-6}$-alkyl.

Suitably the cycloalkyl, aryl, heterocyclyl, or heteroaryl of M is optionally substituted with a substituent selected from the group consisting of C$_{1-6}$-alkyl, halo, halo-C$_{1-6}$-alkyl, hydroxy-C$_{1-6}$-alkyl.

Suitably R$^{M1}$ is selected from the group consisting of H, C$_{1-6}$-alkyl, halo, hydroxyl, and amino. Suitably R$^{M1}$ is selected from the group consisting of H, C$_{1-6}$-alkyl, and halo. Suitably R$^{M1}$ is selected from the group consisting of H, and C$_{1-6}$-alkyl.

Suitably R$^{M4}$ is selected from the group consisting of H, C$_{1-6}$-alkyl, and amino. Suitably R$^{M4}$ is selected from the group consisting of H, and C$_{1-6}$-alkyl.

Particular suitable groups of M are selected from the group consisting of

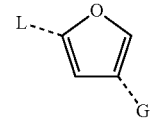
(m-1)

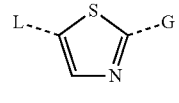
(m-2)

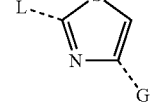
(m-3)

-continued

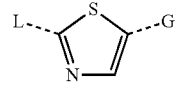
(m-4)

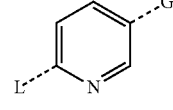
(m-5)

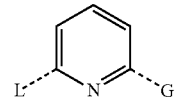
(m-6)

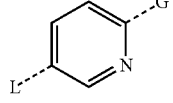
(m-7)

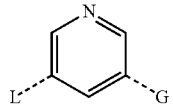
(m-8)

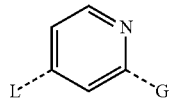
(m-9)

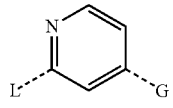
(m-10)

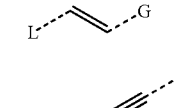
(m-11)

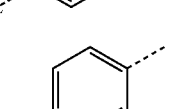
(m-12)

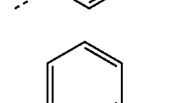
(m-13)

(m-14)

(m-15)

(m-16)

(m-17)

Particular suitable groups of M are selected from the group consisting of
(m-1), (m-3), (m-5), (m-8), (m-14), (m-15), (m-16), (m-17).

Particular suitable groups of M are selected from the group consisting of
(m-1), (m-8), (m-16).

In embodiments of the invention and embodiments thereof, G is selected from the group consisting of
—(C(R$^{G2}$R$^{G3}$)$_{0-4}$—O—(C(R$^{G2}$R$^{G3}$)$_{0-4}$—, —(C(R$^{G2}$R$^{G3}$)$_{0-4}$—S—C(R$^{G2}$R$^{G3}$)$_{0-4}$—, —(C(R$^{G2}$R$^{G3}$)$_{0-4}$—NR$^{G1}$—(C(R$^{G2}$R$^{G3}$)$_{0-4}$—, —C(=O)—, —NR$^{G1}$C(=O)—, —C(=O)NR$^{G1}$—, —(C(R$^{G2}$R$^{G3}$)$_{0-4}$—NR$^{G1}$—C(R$^{G2}$R$^{G3}$)—C(=O)NR$^{G1}$—,
—CR$^{G2}$=CR$^{G2}$—, —CR$^{G2}$=CR$^{G2}$—CR$^{G2}$=CR$^{G2}$—, —C≡C—, —C≡C—C≡C—, —CR$^{G2}$=CR$^{G2}$—C≡C—, —C≡C—CR$^{G2}$=CR$^{G2}$, —C(=O)—C≡C—, —C≡C—C(=O)—SO$_2$—, —S(=O)—, —S(=O)C(R$^{G2}$R$^{G3}$)—. —C(R$^{G2}$R$^{G3}$)S(=O)—, —C(R$^{G2}$R$^{G3}$)—SO$_2$—, —SC$_2$C(R$^{G2}$R$^{G3}$)—;
wherein
R$^{G1}$ is H or C$_{1-6}$-alkyl
each R$^{G2}$, R$^{G3}$ is independently selected from the group consisting of
H, halogen atom, or C$_{1-6}$-alkyl.

Suitably G is selected from the group consisting of
CR$^{G2}$=CR$^{G2}$—, —CR$^{G2}$=CR$^{G2}$—CR$^{G2}$=CR$^{G2}$—, —C≡C—, —C≡C—C≡C—, —CR$^{G2}$=CR$^{G2}$—C≡C—, —C≡C—CR$^{G2}$=CR$^{G2}$, —C(=O)—C≡C—, —C≡C—C(=O)—.
wherein
R$^{G2}$ is selected from the group consisting of
H, halogen atom, or C$_{1-6}$-alkyl Suitably G is selected from the group consisting of
—C=O—, —C≡C—C≡C—, —CR$^{G2}$=CR$^{G2}$—C≡C—, —C≡C—CR$^{G2}$=CR$^{G2}$,
wherein
R$^{G2}$ is selected from the group consisting of
H, halogen atom, or C$_{1-6}$-alkyl.

In some embodiments of the invention and/or embodiments thereof the compound is a compound according to formula

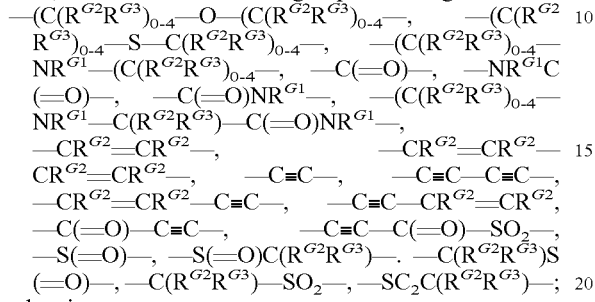

(IX)

(X)

or a stereoisomer, pharmaceutically acceptable salt, ester, solvate, or prodrug thereof, use according to the invention, wherein A, L, M, Y, X, q, R$^1$, R$^2$, R$^3$, R$^4$, and R$^5$, are defined as in any of the embodiments described herein.

In embodiments of the invention and embodiments thereof, Y is selected from the group consisting of
C$_{3-10}$-cycloalkyl, aryl, heterocyclyl, heteroaryl,
wherein each cycloalkyl, aryl, heterocyclyl, or heteroaryl is optionally substituted with a substituent selected from the group consisting of
C$_{3-8}$-cycloalky, C$_{1-6}$-alkyloxy, NR$^{Y1}$R$^{Y2}$, carbonyl, —C(=O)—OR$^{Y1}$, halo, halo-C$_{1-6}$-alkyl, C$_{1-6}$-alkyloxy-C$_1$-C$_6$-alkyl, aryl, heteroaryl, C$_9$-C$_6$-alkyl substituted with aryl, cyano, hydroxy, —SR$^2$, —SO$_2$R$^{Y3}$, —OSO$_2$R$^{Y3}$, —SO$_2$NR$^{Y1}$R$^{Y2}$, —C(=O)NR$^{M2}$R$^{M3}$—, hydroxy-C$_{1-6}$-alkyl;
wherein R$^{Y1}$, R$^{Y2}$ are independently selected from the group consisting of H, and C$_{1-6}$-alkyl;
wherein R$^{Y3}$ is selected from the group consisting of H, C$_{1-6}$-alkyl, and amino.

In embodiments of the invention and/or embodiments thereof, Y is selected from aryl, or heteroaryl.

Suitably Y is aryl. Suitably Y is phenyl. Suitably Y is para-phenyl.

Suitably the cycloalkyl, aryl, heterocyclyl, or heteroaryl of Y is optionally substituted with a substituent selected from the group consisting of
C$_{1-6}$-alkyl, C$_{1-6}$-alkyloxy, NR$^{Y1}$R$^{Y2}$, carbonyl, —C(=O)—OR$^{Y1}$, halo, halo-C$_{1-6}$-alkyl, C$_{1-6}$-alkyloxy-C$_1$-C$_6$-alkyl, C$_1$-C$_6$-alkyl substituted with aryl, cyano, hydroxy, —SR$^{Y2}$, —SO$_2$R$^{Y3}$, —OSO$_2$R$^{Y3}$, —SO$_2$NR$^{Y1}$R$^{Y2}$, —C(=O)NR$^{M2}$R$^{M3}$—, hydroxy-C$_{1-6}$-alkyl.

Suitably the cycloalkyl, aryl, heterocyclyl, or heteroaryl of Y is optionally substituted with a substituent selected from the group consisting of
C$_{1-6}$-alkyl, C$_{1-6}$-alkyloxy, NR$^{Y1}$R$^{Y2}$, carbonyl, —C(=O)—OR$^{Y1}$, halo, halo-C$_{1-6}$-alkyl, C$_{1-6}$-alkyloxy-C$_1$-C$_6$-alkyl, C$_1$-C$_6$-alkyl substituted with aryl, cyano, hydroxy, —SR$^{Y2}$, —SO$_2$R$^{Y3}$, —OSO$_2$R$^{Y3}$, —SO$_2$NR$^{Y1}$R$^{Y2}$, —C(=O)NR$^{M2}$R$^{M3}$—, hydroxy-C$_{1-6}$-alkyl.

Suitably the cycloalkyl, aryl, heterocyclyl, or heteroaryl of Y is optionally substituted with a substituent selected from the group consisting of
C$_{1-6}$-alkyl, NR$^{Y1}$R$^{Y2}$, halo, halo-C$_{1-6}$-alkyl, C$_{1-6}$-alkyloxy-C$_1$-C$_6$-alkyl, C$_1$-C$_6$-alkyl substituted with aryl, cyano, hydroxy, hydroxy-C$_{1-6}$-alkyl.

Suitably the cycloalkyl, aryl, heterocyclyl, or heteroaryl of Y is optionally substituted with a substituent selected from the group consisting of
C$_{1-6}$-alkyl, halo, halo-C$_{1-6}$-alkyl, hydroxy-C$_{1-6}$-alkyl.

Suitably, the cycloalkyl, aryl, heterocyclyl, or heteroaryl of Y is not substituted.

In some embodiments of the invention and/or embodiments thereof the compound is a compound according to formula

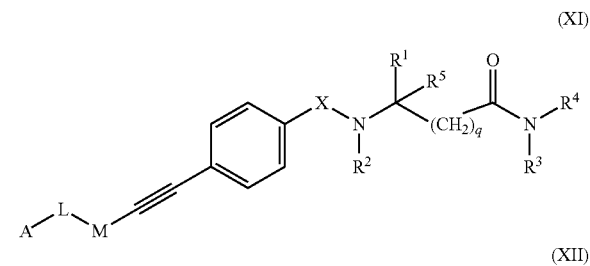

(XI)

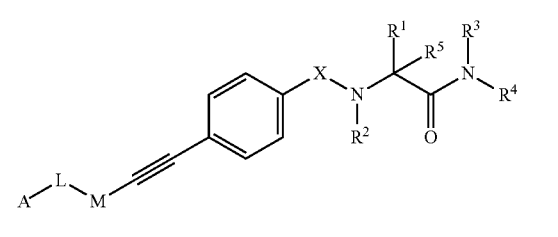

(XII)

or a stereoisomer, pharmaceutically acceptable salt, solvate, or prodrug thereof, use according to the invention, wherein A, L, M, X, q, $R^1$, $R^2$, $R^3$, $R^4$, and $R^5$, are defined as in any of the embodiments described herein.

In embodiments of the invention and embodiments thereof, X is selected from the group consisting of
—C(=O)—, —$C_{2-6}$-alkenyl-C(=O)—, —$C_{2-6}$-alkynyl-C(=O)—, and —$(C(R^{X1})_2)$—, —S(=O)—, —$SO_2$—;
wherein
$R^{X2}$, is selected from the group consisting of
H, halogen atom, substituted $C_{1-6}$-alkyl, or un-substituted $C_{1-6}$-alkyl;
wherein the substituents on the substituted $C_{1-6}$-alkyl may be selected from the group consisting of halogen, hydroxyl, alkoxy, aryloxy, thiol, $C_{1-6}$-alkyl, carbonyl, —$SR^3$, —$SO_2R^{X5}$, $SO_2NR^{X3}R^{X4}$, —C(=O)$NR^{X3}R^{X4}$, cyano, —$NR^{X3}R^{X4}$, —C(=O)—$OR^{X3}$, aryl, heteroaryl, heterocycle, $C_{3-8}$-cycloalkyl;
wherein $R^{X3}$, $R^{X4}$ are independently selected from the group consisting of H, or $C_{1-6}$-alkyl;
wherein $R^{X5}$ is selected from the group consisting of H, $C_{1-6}$-alkyl, and amine.

Suitably X is selected from the group consisting of —C(=O)—, S(=O)—, —$SO_2$—. Suitably X is selected from —C(=O)—, and S(=O)—.

Suitably $R^{X1}$, $R^{X2}$, are independently selected from the group consisting of H, halogen atom, substituted $C_{1-6}$-alkyl, or un-substituted $C_{1-6}$-alkyl;
wherein the substituents on the substituted $C_{1-6}$-alkyl may be selected from the group consisting of halogen, hydroxyl, alkoxy, carbonyl, —$SR^{X3}$, —$SO_2R^{X5}$, $SO_2NRX^3R^{X4}$, —C(=O)$NR^{A3}R^{X4}$, cyano, —$NR^{X3}R^{X4}$, —C(=O)—$OR^{X3}$.

Suitably the substituents on the substituted $C_{1-6}$-alkyl of X is selected from the group consisting of halogen, hydroxyl, carbonyl, —$SR^{X3}$, —$SO_2R^{X5}$, $SO_2NR^{X3}R^{X4}$, —O(=O)$NR^{X3}R^{X4}$, —$NR^{X3}R^{X4}$.

Suitably the substituents on the substituted $C_{1-6}$-alkyl of X is selected from the group consisting of halogen or amino.

Suitably $R^{X1}$, $R^{X2}$, are independently selected from the group consisting of H, halogen atom, or un-substituted $C_{1-6}$-alkyl.

Suitably, $R^{X3}$, $R^{X4}$ are independently selected from the group consisting of H, or $C_{1-6}$-alkyl;

Suitably $R^{X5}$ is selected from the group consisting of H, $C_{1-6}$-alkyl, and amine.

In some embodiments of the invention and/or embodiments thereof the compound is a compound according to formula

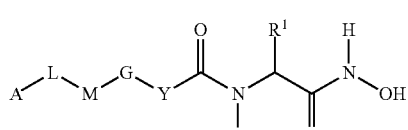

(XIII)

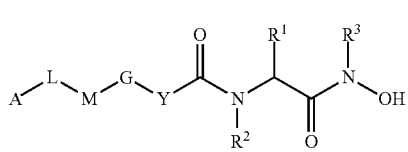

(XIV)

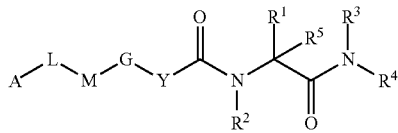

(XV)

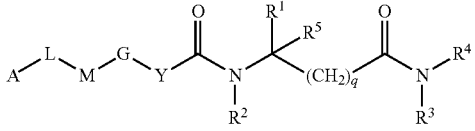

(XVI)

or a stereoisomer, pharmaceutically acceptable salt, solvate, or prodrug thereof, use according to the invention, wherein A, L, M, G, Y, q, $R^1$, $R^2$, $R^3$, $R^4$, and $R^5$, are defined as in any of the embodiments described herein.

In suitable embodiments of the invention and/or embodiments thereof $R^5$ is selected from the group consisting of H, and $C_{1-6}$-alkyl. Suitably $R^5$ is H.

In embodiments of the invention and/or embodiments thereof $R^2$, $R^3$ is independently selected from the group consisting of
H, substituted $C_{1-6}$-alkyl, or un-substituted $C_{1-6}$-alkyl;
wherein the substituents on the substituted $C_{1-6}$-alkyl may be selected from the group consisting of halogen, hydroxyl, alkoxy, aryloxy, thiol, $C_{1-6}$-alkyl, carbonyl, —$SR^6$, —$SO_2R^8$, $SO_2NR^{X3}R^{X4}$, —C(=O)$NR^6R^7$, cyano, —$NR^6R^7$, —C(=O)—$OR^6$, aryl, heteroaryl, heterocycle, $C_{3-8}$-cycloalkyl.

Suitably $R^2$, $R^3$ is independently selected from the group consisting of H, substituted $C_{1-6}$-alkyl, or un-substituted $C_{1-6}$-alkyl. Suitably $R^2$ and $R^3$ are H.

In some embodiment, the substituents on the substituted $C_{1-6}$-alkyl of $R^2$ and/or $R^3$ may be selected from the group consisting of halogen, hydroxyl, alkoxy, aryloxy, thiol, $C_{1-6}$-alkyl, carbonyl, —$SR^8$, —$SO_2R^8$, $SO_2NR^6R^7$, —C(=O)$NR^6R^7$, cyano, —$NR^6R^7$, —C(=O)—$OR^6$, aryl, heteroaryl, heterocycle, $C_{3-8}$-cycloalkyl.

In some embodiment, the substituents on the substituted $C_{1-6}$-alkyl of $R^2$ and/or $R^3$ may be selected from the group consisting of halogen, hydroxyl, $C_{1-6}$-alkyl, carbonyl, —$SR^8$, —$SO_2R^8$, $SO_2NR^6R^7$, —C(=O)$NR^6R^7$, cyano, —$NR^6R^7$, —O(=O)—OR.

In some embodiment, the substituents on the substituted $C_{1-6}$-alkyl of $R^2$ and/or $R^3$ may be selected from the group consisting of halogen, hydroxyl, $C_{1-6}$-alkyl, —$NR^6R^7$.

In embodiments of the invention and/or embodiments thereof $R^4$ is selected from the group consisting of H, $C_{2-6}$-alkenyl, $C_{2-6}$-alkynyl, $C_{3-10}$-cycloalkyl, —$OR^8$, C(=O)$OR^9$, C(=O)$R^9$, aryl, heterocyclyl, heteroaryl, $C_1$-$C_6$-alkyl substituted with aryl, $C_1$-$C_6$-alkyl substituted with heteroaryl, $C_1$-$C_6$-alkyl substituted with heterocyclyl
wherein each alkyl, alkenyl, alkynyl, cycloalkyl, aryl, heterocyclyl, heteroaryl, is optionally substituted with a substituent selected from the group consisting of
$C_{1-6}$-alkyl, $C_{3-8}$-cycloalky, $C_{1-6}$-alkyloxy, $NR^6R^7$, carbonyl, nitro, C(=O)$OR^9$, halogen, halo-$C_{1-6}$-alkyl, $C_{1-6}$-alkyloxy-$C_1$-$C_6$-alkyl, cyano, hydroxy, —$SR^8$, —$SO_2R$, $SO_2NR^6R^7$, —C(=O)$NR^5R^6$.

In embodiments of the invention and/or embodiments thereof $R^4$ is selected from the group consisting of H, $C_{1-6}$-alkyl, $C_{2-6}$-alkenyl, $C_{2-6}$-alkynyl, —$OR^8$, C(=O)$OR^9$, C(=O)$R^9$, $C_1$-$C_6$-alkyl substituted with aryl, $C_1$-$C_6$-alkyl substituted with heteroaryl, $C_1$-$C_6$-alkyl substituted with heterocyclyl.

In embodiments of the invention and/or embodiments thereof $R^4$ is selected from the group consisting of H, —$OR^8$, $C(=O)OR^9$, $C(=O)R^9$.

In embodiments of the invention and/or embodiments thereof $R^4$ is selected from the group consisting of H, —$OR^8$. Suitably $R^4$ is —$OR^8$, more suitably $R^8$ is OH.

In embodiments of the invention and/or embodiments thereof the alkyl, alkenyl, alkynyl, cycloalkyl, aryl, heterocyclyl, heteroaryl, of $R^4$ is optionally substituted with a substituent selected from the group consisting of $C_{1-6}$-alkyl, $C_{3-8}$-cycloalky, $C_{1-6}$-alkyloxy, $NR^6R^7$, carbonyl, nitro, $C(=O)OR^9$, halogen, halo-$C_{1-6}$-alkyl, $C_{1-6}$-alkyloxy-$C_1$-$C_6$-alkyl, cyano, hydroxy, —$SR^8$, —$SO_2R^8$, $SO_2NR^6R^7$, —$C(=O)NR^5R^6$.

In embodiments of the invention and/or embodiments thereof the alkyl, alkenyl, alkynyl, cycloalkyl, aryl, heterocyclyl, heteroaryl, of $R^4$ is optionally substituted with a substituent selected from the group consisting of $C_{1-6}$-alkyl, $C_{3-8}$-cycloalky, $NR^6R^7$, carbonyl, nitro, halogen, halo-$C_{1-6}$-alkyl, $C_{1-6}$-alkyloxy-$C_1$-$C_6$-alkyl, cyano, hydroxy.

In embodiments of the invention and/or embodiments thereof the alkyl, alkenyl, alkynyl, cycloalkyl, aryl, heterocyclyl, heteroaryl, of $R^4$ is optionally substituted with a substituent selected from the group consisting of $C_{1-6}$-alkyl, $NR^6R^7$, halogen, cyano, hydroxy.

In embodiments of the invention and/or embodiments thereof the alkyl, alkenyl, alkynyl, cycloalkyl, aryl, heterocyclyl, heteroaryl, of $R^4$ is optionally substituted with a substituent selected from the group consisting of $C_{1-6}$-alkyl, $NR^6R^7$, halogen.

In some embodiments of the invention and/or embodiments thereof the compound is a compound according to formula

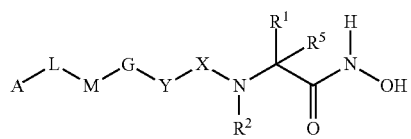

(XVII)

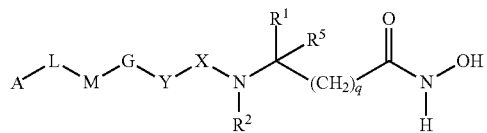

(XVIII)

or a stereoisomer, pharmaceutically acceptable salt, ester, solvate, or prodrug thereof, use according to the invention, wherein A, L, M, G, Y, X, q, $R^1$, $R^2$, and $R^5$, are defined as in any of the embodiments described herein.

In embodiments of the invention and/or embodiments thereof $R^1$ is selected from the group consisting of H, $C_{2-6}$-alkenyl, $C_{2-6}$-alkynyl, $C_{3-10}$-cycloalkyl, $C(=O)R^9$, $C(=N-OR^8)R^8$, aryl, heterocyclyl, heteroaryl, $C_1$-$C_6$-alkyl substituted with aryl, $C_1$-$C_6$-alkyl substituted with heteroaryl, $C_1$-$C_6$-alkyl substituted with heterocyclyl, wherein each alkyl, alkenyl, alkynyl, cycloalkyl, aryl, heterocyclyl, heteroaryl, is optionally substituted with a substituent selected from the group consisting of $C_{1-6}$-alkyl, $C_{3-8}$-cycloalky, $C_{1-6}$-alkyloxy, —$NR^6R^7$, carbonyl, nitro, $C(=O)OR^9$, halogen, halo-$C_{1-6}$-alkyl, $C_{1-6}$-alkyloxy-$C_1$-$C_6$-alkyl, cyano, hydroxy, —$SR^8$, —$SO_2R^8$, $SO_2NR^6R^7$, —$C(=O)NR^6R^7$—.

In embodiments of the invention and/or embodiments thereof $R^1$ is selected from the group consisting of H, $C_{1-6}$-alkyl, $C_{2-6}$-alkenyl, $C_{2-6}$-alkynyl, $C_{3-10}$-cycloalkyl, $C(=O)R^9$, $C(=N-OR^8)R^8$.

In embodiments of the invention and/or embodiments thereof $R^1$ is selected from the group consisting of H, $C_{2-6}$-alkenyl, $C(=O)R^9$, $C(=N-OR^8)R^8$.

In embodiments of the invention and/or embodiments thereof $R^1$ is selected from the group consisting of H, $C_{1-6}$ alkyl, $C_{2-6}$-alkenyl, $C(=O)R^9$, $C(=N-OR^8)R^8$.

In embodiments of the invention and/or embodiments thereof $R^1$ is selected from the group consisting of H, $C_{2-6}$-alkenyl.

In embodiments of the invention and/or embodiments thereof the alkyl, alkenyl, alkynyl, cycloalkyl, aryl, heterocyclyl, heteroaryl, of $R^1$ is optionally substituted with a substituent selected from the group consisting of $C_{1-6}$-alkyl, $C_{3-8}$-cycloalky, $C_{1-6}$-alkyloxy, —$NR^6R^7$, carbonyl, nitro, $C(=O)OR^9$, halogen, halo-$C_{1-6}$-alkyl, $C_{1-6}$-alkyloxy-$C_1$-$C_6$-alkyl, cyano, hydroxy, —$SR^8$, —$SO_2R^8$, $SO_2NR^6R^7$, —$O(=O)NR^6R^7$.

In embodiments of the invention and/or embodiments thereof the alkyl, alkenyl, alkynyl, cycloalkyl, aryl, heterocyclyl, heteroaryl, of $R^1$ is optionally substituted with a substituent selected from the group consisting of $C_{1-6}$-alkyl, —$NR^6R^7$, carbonyl, nitro, $C(=O)OR^9$, halogen, cyano, hydroxy, —$SR^8$, —$SO_2R^8$, $SO_2NR^6R^7$, —$C(=O)NR^6R^7$.

In embodiments of the invention and/or embodiments thereof the alkyl, alkenyl, alkynyl, cycloalkyl, aryl, heterocyclyl, heteroaryl, of $R^1$ is optionally substituted with a substituent selected from the group consisting of $C_{1-6}$-alkyl, —$NR^6R^7$, nitro, hydroxy, —$SR^8$, —$SO_2R^8$, $SO_2NR^6R^7$.

In embodiments of the invention and/or embodiments thereof the alkyl, alkenyl, alkynyl, cycloalkyl, aryl, heterocyclyl, heteroaryl, of $R^1$ is optionally substituted with a substituent selected from the group consisting of $C_{1-6}$-alkyl, nitro, —$SR^8$, —$SO_2R^8$, $SO_2NR^6R^7$.

In embodiments of the invention and/or embodiments thereof $R^1$ is selected from the group consisting of $C_{1-6}$-alkyl, $C(=O)R^9$, $C(=N-OR^8)R^8$, wherein the alkyl is optionally substituted with a substituent selected from the group consisting of $C_{1-6}$-alkyl, —$NR^6R^7$, carbonyl, nitro, $C(=O)OR^9$, halogen, cyano, hydroxy, —$SR^8$, —$SO_2R^8$, $SO_2NR^6R^7$, —$C(=O)NR^6R^7$.

In embodiments of the invention and/or embodiments thereof $R^1$ is selected from the group consisting of $C_{1-6}$-alkyl, $C(=O)R^9$, $C(=N-OR^8)R^8$, wherein the alkyl is optionally substituted with a substituent selected from the group consisting of $C_{1-3}$-alkyl, nitro, hydroxy, —$SO_2R^8$, $SO_2NR^6R^7$, —$SR^8$.

In embodiments of the invention and/or embodiments thereof $R^1$ is $C_{1-6}$-alkyl, wherein the alkyl is optionally substituted with a substituent selected from the group consisting of $C_{1-3}$-alkyl, nitro, amino, hydroxy, —$SO_2R^8$, $SO_2NR^6R^7$, —$SR^8$.

In embodiments of the invention and/or embodiments thereof $R^1$ is $C_{1-6}$-alkyl, wherein the alkyl is optionally substituted with a substituent selected from the group consisting of $C_{1-3}$-alkyl, $SO_2R^8$, $SO_2NR^6R^7$, —$SR^8$.

In embodiments of the invention and/or embodiments thereof $R^6$, $R^7$ are independently selected from the group consisting of H, and $C_{1-6}$-alkyl.

In embodiments of the invention and/or embodiments thereof $R^8$ is selected from the group consisting of H, $C_{1-6}$-alkyl, and amine. Suitably $R^8$ is H or $C_{1-6}$-alkyl.

In some embodiments of the invention and/or embodiments thereof the compound is a compound according to formula

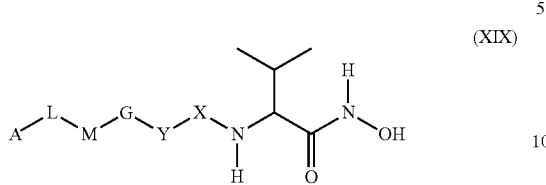

(XIX)

or a stereoisomer, pharmaceutically acceptable salt, ester, solvate, or prodrug thereof, use according to the invention, wherein A, L, M, G, Y, and X, are defined as in any of the embodiments described herein.

In some embodiments of the invention and/or embodiments thereof the compound is a compound according to formula (XIX) or a stereoisomer, pharmaceutically acceptable salt, ester, solvate, or prodrug thereof, use according to the invention, wherein A is selected from the group consisting of
NR$^{A1}$R$^{A2}$, and NO$_2$,
wherein
R$^{A1}$, R$^{A2}$ are independently selected from the group consisting of
H, C$_{1-6}$-alkyl, C$_{2-6}$-alkenyl, C$_{2-6}$-alkynyl, C$_{3-10}$-cycloalkyl, aryl, heterocyclyl, heteroaryl, C$_{1-6}$-alkyloxy-C$_1$-C$_6$-alkyl, C$_1$-C$_6$-alkyl substituted with aryl, C$_1$-C$_6$-alkyl substituted with heteroaryl, C$_1$-C$_6$-alkyl substituted with heterocyclyl, or
R$^A$, R$^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, alkynyl, cycloalkyl, aryl, heterocyclyl, heteroaryl, alkyloxy or the heterocyclic ring formed by R$^{A1}$, R$^{A2}$ together with the N atom to which they are attached is optionally substituted with a substituent selected from the group consisting of
C$_{3-8}$-cycloalky, C$_{1-6}$-alkyloxy, —NR$^{A3}$R$^{A4}$, carbonyl, —C(=O)—OR$^{A5}$, halogen atom, C$_{1-6}$-alkyl substituted with halo, C$_{1-6}$-alkyloxy-C$_1$-C$_6$—, aryl, heteroaryl, C$_1$-C$_6$-alkyl substituted with aryl, cyano, hydroxy, —SR$^{A5}$, —SO$_2$R$^{A5}$, SO$_2$NR$^{A3}$R$^{A4}$, C(=O)NR$^{A3}$R$^{A4}$, C$_{1-6}$-alkyl substituted with hydroxy;
wherein
R$^{A3}$, R$^{A4}$, R$^{A5}$ are independently chosen from
H, or C$_{1-6}$-alkyl;
L is selected from the group consisting of
C$_{1-6}$-alkyl, C$_{2-6}$-alkenyl, C$_{2-6}$-alkynyl, C$_{3-10}$-cycloalkyl, —(NR$^{L3}$)$_{0-1}$—(CH$_2$)$_{0-4}$—NR$^{L3}$—(CH$_2$)$_{0-4}$—NR$^{L3}$—(CH$_2$)$_{0-4}$—, —(NR$^{L3}$)$_{0-1}$—(CR$^{L1}$R$^{L2}$)$_{0-4}$—NR$^{L3}$—(CR$^{L1}$R$^{L2}$)—, —(CR$^{L1}$R$^{L2}$)—, —(CH$_2$)$_{0-4}$—NR$^{L3}$—(CR$^{L1}$R$^{L2}$)—C(=O)NH—(CH$_2$)$_{0-4}$—, —(=O)—(CR$^{L1}$R$^{L2}$)—NR$^{L3}$C(=O)—, —C(=O)NR$^{L3}$—, —NR$^{L3}$C(=O)—, —NR$^{L3}$—, —SO$_2$NR$^{L3}$—, NR$^{L3}$—C(=O)—NR$^{L3}$—
wherein
R$^{L1}$, R$^{L2}$, R$^{L3}$ are independently selected from the group consisting of
H, C$_{1-6}$-alkyl, halo-C$_{1-6}$-alkyl, C$_1$-C$_6$-alkyl substituted with aryl, C$_1$-C$_6$-alkyl substituted with heteroaryl, C$_1$-C$_6$-alkyl substituted with heterocyclyl; or R$^{L1}$, R$^{L3}$ together with the atoms to which they are attached can form a saturated or unsaturated heterocyclic ring having 3 to 8 ring atoms, wherein 1, 2, or 3, ring atoms are selected from N, S, and O;
M is selected from the group consisting of
C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—;
G is selected from the group consisting of
CR$^{G2}$=CR$^{G2}$—, —CR$^{G2}$=CR$^{G2}$—CR$^{G2}$=CR$^{G2}$—, —C≡C—, —C≡C—C≡C—, —CR$^{G2}$=CR$^{G2}$—C≡C—, —C≡C—CR$^{G2}$=CR$^{G2}$, —C(=O)—C≡C—, —C≡C—C(=O)—.
wherein
R$^{G2}$ is selected from the group consisting of
H, halogen atom, or C$_{1-6}$-alkyl;
Y is selected from aryl, or heteroaryl;
and
X is selected from the group consisting of —C(=O)—, and —S(=O).

In some embodiments of the invention and/or embodiments thereof the compound is a compound according to formula (XIX) or a stereoisomer, pharmaceutically acceptable salt, ester, solvate, or prodrug thereof, use according to the invention, wherein A is selected from the group consisting of
NR$^{A1}$R$^{A2}$, and NO$_2$;
L is selected from the group consisting of
C$_{1-6}$-alkyl, C$_{2-6}$-alkenyl, C$_{2-6}$-alkynyl, C$_{3-10}$-cycloalkyl,
wherein
R$^{L3}$, is selected from the group consisting of
H, C$_{1-6}$-alkyl, halo-C$_{1-6}$-alkyl, C$_1$-C$_6$-alkyl substituted with aryl, C$_1$-C$_6$-alkyl substituted with heteroaryl, C$_1$-C$_6$-alkyl substituted with heterocyclyl.
M is selected from the group consisting of
C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—;
G is selected from the group consisting of
CR$^{G2}$=CR$^{G2}$—, —C≡C—, —C≡C—C≡C—, —CR$^{G2}$=CR$^{G2}$—C≡C—, —C≡C—CR$^{G2}$=CR$^{G2}$;
wherein
R$^{G2}$ is selected from the group consisting of
H, halogen atom, or C$_{1-6}$-alkyl;
Y is selected from aryl, or heteroaryl;
X is selected from the group consisting of —C(=O)—, and —S(=O).

In some embodiments of the invention and/or embodiments thereof the compound is a compound according to formula (XIX) or a stereoisomer, pharmaceutically acceptable salt, ester, solvate, or prodrug thereof, use according to the invention, wherein A is NR$^{A1}$R$^{A2}$;
L is selected from the group consisting of —CH$_2$—, —CH$_2$CH$_2$—, —CH$_2$CH$_2$CH$_2$—, and —CH$_2$CH$_2$CH$_2$CH$_2$—;
M is selected from the group consisting of
C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—;
G is selected from the group consisting of
—C≡C—, —C≡C—C≡C—
Y is selected from aryl, or heteroaryl;
X is selected from the group consisting of —C(=O)—, and —S(=O);

$R^{A1}$, $R^{A2}$ are independently selected from the group consisting of
- H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or
- $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
  - wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
    $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
  wherein
  $R^{A3}$, $R^{A4}$, $R^{A5}$ are independently chosen from
  H, or $C_{1-6}$-alkyl.

In some embodiments of the invention and/or embodiments thereof the compound is a compound according to formula (XIX) or a stereoisomer, pharmaceutically acceptable salt, ester, solvate, or prodrug thereof, use according to the invention, wherein
A is $NR^{A1}$, $R^{A2}$;
L is selected from the group consisting of —$CH_2$—, —$CH_2CH_2$—, —$CH_2CH_2CH_2$—, and —$CH_2CH_2CH_2CH_2$—;
M is selected from the group consisting of
$C_{3-10}$-cycloalkyl, aryl, heterocyclyl, heteroaryl, $C_{2-4}$alkenyl, $C_{2-4}$alkynyl, —C($R^{M1}$)=C($R^{M1}$)—C≡C—, —C($R^{M1}$)=C($R^{M1}$)—;
G is selected from the group consisting of
—C≡C—, —C≡C—C≡C—
Y is selected from aryl, or heteroaryl;
X is selected from the group consisting of —C(=O)—, and —S(=O);
$R^{A1}$, $R^{A2}$ are independently selected from the group consisting of
- H, $C_{1-6}$-alkyl, $C_{2-6}$-alkenyl, $C_{3-10}$-cycloalkyl$C_{1-6}$-alkyloxy-$C_1$-$C_6$-alkyl, $C_1$-$C_6$-alkyl substituted with aryl, $C_1$-$C_6$-alkyl substituted with heteroaryl, or
- $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
  - wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
    $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
  wherein
  $R^{A3}$, $R^{A4}$, $R^{A5}$ are independently chosen from
  H, or $C_{1-6}$-alkyl.

In some embodiments of the invention and/or embodiments thereof the compound is a compound according to formula (XIX) or a stereoisomer, pharmaceutically acceptable salt, ester, solvate, or prodrug thereof, use according to the invention, wherein
A is $NR^{A1}R^{A2}$;
L is selected from the group consisting of —$CH_2$—, and —$CH_2CH_2$—;
M is selected from the group consisting of
aryl, heteroaryl, —C($R^{M1}$)=C($R^{M1}$)—C≡C—, —O($R^{M1}$)=C($R^{M1}$)—;
G is selected from the group consisting of
—C≡C—, —C≡C—C≡C—
Y is aryl;
X is selected from the group consisting of —C(=O)—, and —S(=O);
$R^{A1}$, $R^{A2}$ are independently selected from the group consisting of
- H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or
- $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
  - wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
    $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R$ C(=O)$NR^{A3}R^{A4}$, $C_{1-6}$-alkyl substituted with hydroxy;
  wherein
  $R^{A3}$, $R^{A4}$, $R^{A5}$ are independently chosen from
  H, or $C_{1-6}$-alkyl.

In some embodiments of the invention and/or embodiments thereof the compound is a compound according to formula (XIX) or a stereoisomer, pharmaceutically acceptable salt, ester, solvate, or prodrug thereof, use according to the invention, wherein
A is $NR^{A1}R^{A2}$;
L is selected from the group consisting of —$CH_2$—, and —$CH_2CH_2$—;
M is selected from the group consisting of
phenyl, thiazolyl, pyridinyl, pyrimidinyl, thiophenyl, furanyl, pyrrolyl, imidazolyl, oxazolyl, pyrazinyl, —C($R^{M1}$)=C($R^M$)—C≡C—, —C($R^{M1}$)=C($R^{M1}$)—.
G is selected from the group consisting of
—C≡O—, —C≡C—C≡C—
Y is phenyl;
X is selected from the group consisting of —C(=O)—, and —S(=O);
$R^{A1}$, $R^{A2}$ are independently selected from the group consisting of
- H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or R$^{A1}$, R$^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by R$^{A1}$, R$^{A2}$ together with the N atom to which they are attached is optionally substituted with a substituent selected from the group consisting of $C_{1-6}$-alkyl, $C_{3-8}$-cycloalky, $C_{1-6}$-alkyloxy, —NR$^{A3}$R$^{A4}$, carbonyl, —C(=O)—OR$^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —SR$^{A5}$, —SO$_2$R$^{A5}$, SO$_2$NR$^{A3}$R$^{A4}$, —C(=O)NR$^{A3}$R$^{A4}$, $C_{1-6}$-alkyl substituted with hydroxy;

wherein

R$^{A3}$, R$^{A4}$, R$^{A5}$ are independently chosen from

H, or $C_{1-6}$-alkyl.

In some embodiments of the invention and/or embodiments thereof the compound is a compound according to formula (XIX) or a stereoisomer, pharmaceutically acceptable salt, ester, solvate, or prodrug thereof, use according to the invention, wherein A is NR$^{A1}$R$^{A2}$;

L is selected from the group consisting of CH$_2$—, and —CH$_2$CH$_2$—;

M is selected from the group consisting of phenyl, thiazolyl, pyridinyl, pyrimidinyl, thiophenyl, furanyl, pyrrolyl, imidazolyl, oxazolyl, pyrazinyl, —C(R$^{M1}$)=C(R$^M$)—C≡C—, —C(R$^{M1}$)=C(R$^{M1}$)—.

G is selected from the group consisting of

—C≡C—, —C≡C—C≡C—

Y is phenyl;

X is selected from the group consisting of —C(=O)—, and —S(=O);

R$^{A1}$ is selected from the group consisting of $C_{1-6}$-alkyl, $C_{2-6}$-alkenyl, $C_{3-10}$-cycloalkyl, $C_{1-6}$-alkyloxy-$C_1$-$C_6$alkyl, $C_1$-$C_6$-alkyl substituted with aryl, $C_1$-$C_6$-alkyl substituted with heteroaryl, R$^{A2}$ is hydrogen or $C_{1-6}$alkyl or R$^{A1}$, R$^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by R$^{A1}$, R$^{A2}$ together with the N atom to which they are attached is optionally substituted with a substituent selected from the group consisting of $C_{1-6}$-alkyl, $C_{3-8}$-cycloalky, $C_{1-6}$-alkyloxy, —NR$^{A3}$R$^{A4}$, carbonyl, —C(=O)—OR$^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —SR$^{A5}$, —SO$_2$R$^{A5}$, SO$_2$NR$^{A3}$R$^{A4}$, C(=O)NR$^{A3}$R$^{A4}$, $C_{1-6}$-alkyl substituted with hydroxy;

wherein

R$^{A3}$, R$^{A4}$, R$^{A5}$ are independently chosen from

H, or $C_{1-6}$-alkyl.

In some embodiments of the invention and/or embodiments thereof the compound is a compound according to formula

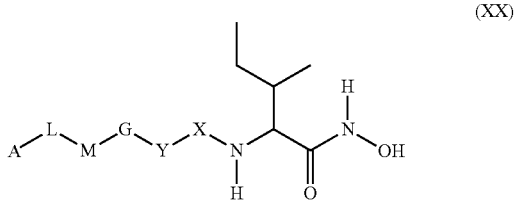

(XX)

or a stereoisomer, pharmaceutically acceptable salt, ester, solvate, or prodrug thereof, use according to the invention, wherein A, L, M, G, Y, and X, are defined as in any of the embodiments described herein.

In some embodiments of the invention and/or embodiments thereof the compound is a compound according to formula (XX) or a stereoisomer, pharmaceutically acceptable salt, ester, solvate, or prodrug thereof, use according to the invention, wherein A is selected from the group consisting of

NR$^{A1}$R$^{A2}$, NO$_2$, wherein

R$^{A1}$, R$^{A2}$ are independently selected from the group consisting of

H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or R$^{A1}$, R$^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkenyl, cycloalkyl, aryl, heterocyclyl, heteroaryl, alkyloxy or the heterocyclic ring formed by R$^{A1}$, R$^{A2}$ together with the N atom to which they are attached is optionally substituted with a substituent selected from the group consisting of $C_{1-6}$ alkyl, $C_{3-8}$-cycloalky, $C_{1-6}$-alkyloxy, —NR$^{A3}$R$^{A4}$, carbonyl, —C(=O)—OR$^{A5}$, halogen atom, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, —SR$^{A5}$, —SO$_2$R$^{A5}$, SO$_2$NR$^{A3}$R$^{A4}$, —C(=O)NR$^{A3}$R$^{A4}$, $C_{1-6}$-alkyl substituted with hydroxy;

wherein

R$^{A3}$, R$^{A4}$, R$^{A5}$ are independently chosen from

H, or $C_{1-6}$-alkyl;

L is selected from the group consisting of $C_{2-6}$-alkenyl, $C_{2-6}$-alkynyl, $C_{3-10}$-cycloalkyl, —(NR$^{L3}$)$_{0-1}$—(CH$_2$)$_{0-4}$—NR$^{L3}$—(CH$_2$)$_{0-4}$—, —(NR$^{L3}$)$_{0-1}$—(CR$^{L1}$R$^{L2}$)$_{0-4}$—NR$^{L3}$—(CR$^{L1}$R$^{L2}$)—, —(CR$^{L1}$R$^{L2}$)$_{0-4}$—O—(CR$^{L1}$R$^{L2}$)—, —(CH$_2$)$_{0-4}$—NR$^{L3}$—(CR$^{L1}$R$^{L2}$)—C(=O)NH—(CH$_2$)$_{0-4}$—, —C(=O)—(CR$^{L1}$R$^{L2}$)NR$^{L3}$C(=O)—, —C(=O)NR$^{L3}$—, —NR$^{L3}$C(=O)—, —SO$_2$NR$^{L3}$—, NR$^{L3}$—C(=O)—NR$^{L3}$— wherein $R^{L1}$, $R^{L2}$, $R^{L3}$, are independently selected from the group consisting of H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or $R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O;

M is selected from the group consisting of $C_{3-10}$-cycloalkyl, aryl, heterocyclyl, heteroaryl, $C_{2-4}$alkenyl, $C_{2-4}$alkynyl, —C($R^{M1}$)=C($R^{M1}$)—C≡C—, —C($R^{M1}$)=C($R^{M1}$)—;

G is selected from the group consisting of $CR^{G2}$=$CR^{G2}$—, —$CR^{G2}$=$CR^{G2}$—$CR^{G2}$=$CR^{G2}$—, —C≡C—, —C≡C—C≡C—, —$CR^{G2}$=$CR^{G2}$—C≡C—, —C≡C—$CR^{G2}$=$CR^{G2}$, —C(=O)—C≡C—, —C≡C—C(=O)—.

wherein $R^{G2}$ is selected from the group consisting of

H, halogen atom, or $C_{1-6}$-alkyl;

Y is selected from aryl, or heteroaryl; and

X is selected from the group consisting of —C(=O)—, and —S(=O).

In some embodiments of the invention and/or embodiments thereof the compound is a compound according to formula (XX) or a stereoisomer, pharmaceutically acceptable salt, ester, solvate, or prodrug thereof, use according to the invention, wherein A is selected from the group consisting of $NR^{41}R^{42}$, and $NO_2$;

L is selected from the group consisting of $C_{1-6}$-alkyl, $C_{2-6}$-alkenyl, $C_{2-6}$-alkynyl, $C_{3-10}$-cycloalkyl, wherein $R^{L3}$, is selected from the group consisting of H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl.

M is selected from the group consisting of $C_{3-10}$-cycloalkyl, aryl, heterocyclyl, heteroaryl, $C_{2-4}$alkenyl, $C_{2-4}$alkynyl, —C($R^{M1}$)=C($R^{M1}$)—C≡C—, —C($R^{M1}$)=C($R^{M1}$)—;

G is selected from the group consisting of $CR^{G2}$=$CR^{G2}$—, —C≡C—, —C≡C—C≡C—, —$CR^{G2}$=$CR^{G2}$—C≡C—, —C≡C—$CR^{G2}$=$CR^{G2}$;

wherein $R^{G2}$ is selected from the group consisting of

H, halogen atom, or $C_{1-6}$-alkyl;

Y is selected from aryl, or heteroaryl;

X is selected from the group consisting of —C(=O)—, and —S(=O).

In some embodiments of the invention and/or embodiments thereof the compound is a compound according to formula (XX) or a stereoisomer, pharmaceutically acceptable salt, ester, solvate, or prodrug thereof, use according to the invention, wherein A is $NR^{41}R^{42}$;

L is selected from the group consisting of —CH$_2$—, —CH$_2$CH$_2$—, —CH$_2$CH$_2$CH$_2$—, and —CH$_2$CH$_2$CH$_2$CH$_2$—;

M is selected from the group consisting of $C_{3-10}$-cycloalkyl, aryl, heterocyclyl, heteroaryl, $C_{2-4}$alkenyl, $C_{2-4}$alkynyl, —C($R^{M1}$)=C($R^{M1}$)—C≡C—, —C($R^{M1}$)=C($R^{M1}$)—;

G is selected from the group consisting of

—C≡C—, —C≡C—C≡C—

Y is selected from aryl, or heteroaryl;

X is selected from the group consisting of —C(=O)—, and —S(=O);

$R^{41}$, $R^{42}$ are independently selected from the group consisting of

H, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{41}$, $R^{42}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{41}$, $R^{42}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{43}R^{44}$, carbonyl, —C(=O)—$OR^{45}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{45}$, —$SO_2R^{45}$, $SO_2NR^{43}R^{44}$, —C(=O)$NR^{43}R^{44}$, $C_{1-6}$-alkyl substituted with hydroxy;

wherein $R^{43}$, $R^{44}$, $R^{45}$ are independently chosen from

H, or $C_{1-6}$-alkyl.

In some embodiments of the invention and/or embodiments thereof the compound is a compound according to formula (XX) or a stereoisomer, pharmaceutically acceptable salt, ester, solvate, or prodrug thereof, use according to the invention, wherein A is $NR^{41}R^{42}$;

L is selected from the group consisting of —CH$_2$—, —CH$_2$CH$_2$—, —CH$_2$CH$_2$CH$_2$—, and —CH$_2$CH$_2$CH$_2$CH$_2$—;

M is selected from the group consisting of $C_{3-10}$-cycloalkyl, aryl, heterocyclyl, heteroaryl, $C_{2-4}$alkenyl, $C_{2-4}$alkynyl, —C($R^{M1}$)=C($R^{M1}$)—C≡C—, —C($R^{M1}$)=C($R^{M1}$)—;

G is selected from the group consisting of

—C≡C—, —C≡C—C≡C—

Y is selected from aryl, or heteroaryl;

X is selected from the group consisting of —C(=O)—, and —S(=O);

$R^{41}$, $R^{42}$ are independently selected from the group consisting of

H, $C_{1-6}$-alkyl, $C_{2-6}$-alkenyl, $C_{3-10}$-cycloalkyl$C_{1-6}$-alkyloxy-$C_1$-$C_6$-alkyl, $C_1$-$C_6$-alkyl substituted with aryl, $C_1$-$C_6$-alkyl substituted with heteroaryl, or $R^{41}$, $R^{42}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, cycloalkyl, aryl, heteroaryl, or alkyloxy or the heterocyclic ring formed by $R^{41}$, $R^{42}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{43}R^{44}$, carbonyl, —C(=O)—$OR^{45}$, halogen atom, $C_{1-6}$-alkyl substituted with halo, $C_{1-6}$- alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_1NR^{A3}R^{A4}$, —$C(=O)NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XX) or a stereoisomer, pharmaceutically acceptable salt, ester, solvate, or prodrug thereof, use according to the invention, wherein A is $NR^{A1}R^{A2}$;
L is selected from the group consisting of $CH_2$—, and —$CH_2CH_2$—;
M is selected from the group consisting of
aryl, heteroaryl, —$C(R^{M1})=C(R^{M1})$—$C\equiv C$—, —$C(R^{M1})=C(R^{M1})$—;
G is selected from the group consisting of
—$C\equiv C$—, —$C\equiv C$—$C\equiv C$—
Y is aryl;
X is selected from the group consisting of —$C(=O)$—, and —$S(=O)$;
$R^{A1}$, $R^{A2}$ are independently selected from the group consisting of
H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^M$, carbonyl, —$C(=O)$—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —$C(=O)NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XX) or a stereoisomer, pharmaceutically acceptable salt, ester, solvate, or prodrug thereof, use according to the invention, wherein A is $NR^{A1}R^{A2}$;
L is selected from the group consisting of $CH_2$—, and —$CH_2CH_2$—;
M is selected from the group consisting of
phenyl, thiazolyl, pyridinyl, pyrimidinyl, thiophenyl, furanyl, pyrrolyl, imidazolyl, oxazolyl, pyrazinyl, —$C(R^{M1})=C(R^M)$—$C\equiv C$—, —$C(R^{M1})=C(R^{M1})$—.
G is selected from the group consisting of
—$C\equiv C$—, —$C\equiv C$—$C\equiv C$—
Y is phenyl;
X is selected from the group consisting of —$C(=O)$—, and —$S(=O)$;

$R^{A1}$, $R^{A2}$ are independently selected from the group consisting of
H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —$C(=O)$—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —$C(=O)NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XX) or a stereoisomer, pharmaceutically acceptable salt, ester, solvate, or prodrug thereof, use according to the invention, wherein A is $NR^{A1}$, $R^{A2}$;
L is selected from the group consisting of $CH_2$—, and —$CH_2CH_2$—;
M is selected from the group consisting of
phenyl, thiazolyl, pyridinyl, pyrimidinyl, thiophenyl, furanyl, pyrrolyl, imidazolyl, oxazolyl, pyrazinyl, —$C(R^{M1})=C(R^M)$—$C\equiv C$—, —$C(R^{M1})=C(R^{M1})$—.
G is selected from the group consisting of
—$C\equiv C$—, —$C\equiv C$—$C\equiv C$—
Y is phenyl;
X is selected from the group consisting of —$C(=O)$—, and —$S(=O)$;
$R^{A1}$ is selected from the group consisting of
$C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl,
$R^{A2}$ is hydrogen or $C_{1-6}$alkyl
or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^M$, carbonyl, —$C(=O)$—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —$C(=O)NR^{A3}R^{A4}$, $C_{1-6}$-alkyl substituted with hydroxy;

wherein
$R^{A3}$, $R^{A4}$, $R^{A5}$ are independently chosen from
H, or $C_{1-6}$-alkyl.

In some embodiments of the invention and/or embodiments thereof the compound is a compound according to formula

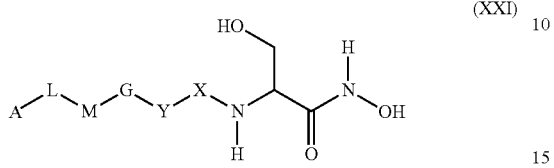

(XXI)

or a stereoisomer, pharmaceutically acceptable salt, ester, solvate, or prodrug thereof, use according to the invention, wherein A, L, M, G, Y, and X, are defined as in any of the embodiments described herein.

In some embodiments of the invention and/or embodiments thereof the compound is a compound according to formula (XXI) or a stereoisomer, pharmaceutically acceptable salt, ester, solvate, or prodrug thereof, use according to the invention, wherein A is selected from the group consisting of
$HNR^{A1}R^{A2}$, and $NO_2$,
wherein
$R^{A1}$, $R^{A2}$ are independently selected from the group consisting of
H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or
$R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
$C_{1-6}$-cycloalky, $C_{1-6}$-alkyloxy, $-NR^{A3}R^{A4}$, carbonyl, $-C(=O)-OR^{A5}$, halogen atom, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, $-SR^{A5}$, $-SO_2R^{A5}$, $SO_2NR^{A3}R^{A4}$, $-C(=O)NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl;
L is selected from the group consisting of
$C_{1-6}$-alkyl, $C_{2-6}$-alkenyl, $C_{2-6}$-alkynyl, $C_{3-10}$-cycloalkyl, $-(NR^{L3})_{0-1}-(CH_2)_{0-4}-NR^{L3}-(CH_2)_{0-4}-$, $-(NR^{L3})_{0-1}-(CR^{L1}R^{L2})_{0-4}-NR^{L3}-(CR^{L1}R^{L2})-$, $-(CR^{L1}R^{L2})_{0-4}-O-(CR^{L1}R^{L2})-$, $-(CH_2)_{0-4}-NR^{L3}-(CR^{L1}R^{L2})-C(=O)NH-(CH_2)_{0-4}-$, $-C(=O)-(CR^{L1}R^{L2})NR^{L3}C(=O)-$, $-C(=O)NR^{L3}-$, $-NR^{L3}C(=O)-$, $-SO_2NR^{L3}-$, $NR^{L3}-C(=O)-NR^{L3}-$ wherein
$R^{L1}$, $R^{L2}$, $R^{L3}$ are independently selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or
$R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O;
M is selected from the group consisting of
$C_{3-10}$-cycloalkyl, aryl, heterocyclyl, heteroaryl, $C_{2-4}$alkenyl, $C_{2-4}$alkynyl, $-C(R^{M1})=C(R^{M1})-C\equiv C-$, $-C(R^{M1})=C(R^{M1})-$;
G is selected from the group consisting of
$CR^{G2}=CR^{G2}-$, $-CR^{G2}=CR^{G2}-CR^{G2}=CR^{G2}-$, $-C\equiv C-$, $-C\equiv C-C\equiv C-$, $-CR^{G2}=CR^{G2}-C\equiv C-$, $-C\equiv C-CR^{G2}=CR^{G2}$, $-C(=O)-C\equiv C-$, $-C\equiv C-C(=O)-$.
wherein
$R^{G2}$ is selected from the group consisting of
H, halogen atom, or $C_{1-6}$-alkyl;
Y is selected from aryl, or heteroaryl;
and
X is selected from the group consisting of $-C(=O)-$, and $-S(=O)$.

In some embodiments of the invention and/or embodiments thereof the compound is a compound according to formula (XXI) or a stereoisomer, pharmaceutically acceptable salt, ester, solvate, or prodrug thereof, use according to the invention, wherein A is selected from the group consisting of
$HNR^{A1}R^{A2}$, and $NO_2$; and $NO_2$;
L is selected from the group consisting of
$C_{1-6}$-alkyl, $C_{2-6}$-alkenyl, $C_{2-6}$-alkynyl, $C_{3-10}$-cycloalkyl,
wherein
$R^{L3}$, is selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl;
M is selected from the group consisting of
$C_{3-10}$-cycloalkyl, aryl, heterocyclyl, heteroaryl, $C_{2-4}$alkenyl, $C_{2-4}$alkynyl, $-C(R^{M1})=C(R^{M1})-C\equiv C-$, $-C(R^{M1})=C(R^{M1})-$;
G is selected from the group consisting of
$CR^{G2}=CR^{G2}-$, $-C\equiv C-$, $-C\equiv C-C\equiv C-$, $-CR^{G2}=CR^{G2}-C\equiv C-$, $-C\equiv C-CR^{G2}=CR^{G2}$;
wherein
$R^{G2}$ is selected from the group consisting of
H, halogen atom, or $C_{1-6}$-alkyl;
Y is selected from aryl, or heteroaryl;
X is selected from the group consisting of $-C(=O)-$, and $-S(=O)$.

In some embodiments of the invention and/or embodiments thereof the compound is a compound according to formula (XXI) or a stereoisomer, pharmaceutically acceptable salt, ester, solvate, or prodrug thereof, use according to the invention, wherein A is $NR^{A1}R^{A2}$;
L is selected from the group consisting of $-CH_2-$, $-CH_2CH_2-$, $-CH_2CH_2CH_2-$, and $-CH_2CH_2CH_2CH_2-$;
M is selected from the group consisting of
$C_{3-10}$-cycloalkyl, aryl, heterocyclyl, heteroaryl, $C_{2-4}$alkenyl, $C_{2-4}$alkynyl, $-C(R^{M1})=C(R^{M1})-C\equiv C-$, $-C(R^{M1})=C(R^{M1})-$;

G is selected from the group consisting of
—C≡C—, —C≡C—C≡C—

Y is selected from aryl, or heteroaryl;

X is selected from the group consisting of —C(=O)—, and —S(=O);

$R^{A1}$, $R^{A2}$ are independently selected from the group consisting of

H, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^1$, A together with the N atom to which they are attached $R^{A2}$ is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXI) or a stereoisomer, pharmaceutically acceptable salt, ester, solvate, or prodrug thereof, use according to the invention, wherein A is $NR^{A1}R^{A2}$;

L is selected from the group consisting of —$CH_2$—, —$CH_2CH_2$—, —$CH_2CH_2CH_2$—, and —$CH_2CH_2CH_2CH_2$—;

M is selected from the group consisting of $C_{3-10}$-cycloalkyl, aryl, heterocyclyl, heteroaryl, $C_{2-4}$alkenyl, $C_{2-4}$alkynyl, —C($R^{M1}$)=C($R^{M1}$)—C≡C—, —C($R^{M1}$)=C($R^{M1}$)—;

G is selected from the group consisting of
—C≡C—, —C≡C—C≡C—

Y is selected from aryl, or heteroaryl;

X is selected from the group consisting of —C(=O)—, and —S(=O);

$R^{A1}$, $R^{A2}$ are independently selected from the group consisting of

H, $C_{1-6}$-alkyl, $C_{2-6}$-alkenyl, $C_{3-10}$-cycloalkyl$C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —$SO_2NR^{A3}R^{A4}$, —C(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXI) or a stereoisomer, pharmaceutically acceptable salt, ester, solvate, or prodrug thereof, use according to the invention, wherein A is $NR^{A1}R^{A2}$;

L is selected from the group consisting of $CH_2$—, and —$CH_2CH_2$—;

M is selected from the group consisting of aryl, heteroaryl, —C($R^{M1}$)=C($R^{M1}$)—C≡C—, —C($R^{M1}$)=C($R^{M1}$)—;

G is selected from the group consisting of
—C≡C—, —C≡C—C≡C—

Y is aryl;

X is selected from the group consisting of —C(=O)—, and —S(=O);

$R^{A1}$, $R^{A2}$ are independently selected from the group consisting of

H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXI) or a stereoisomer, pharmaceutically acceptable salt, ester, solvate, or prodrug thereof, use according to the invention, wherein A is $NR^{A1}R^{A2}$;

L is selected from the group consisting of $CH_2$—, and —$CH_2CH_2$—;

M is selected from the group consisting of phenyl, thiazolyl, pyridinyl, pyrimidinyl, thiophenyl, furanyl, pyrrolyl, imidazolyl, oxazolyl, pyrazinyl, —C($R^{M1}$)=C($R^M$)—C≡C—, —C($R^{M1}$)=C($R^{M1}$)—.

G is selected from the group consisting of
—C≡C—, —C≡C—C≡C—

Y is phenyl;

X is selected from the group consisting of —C(=O)—, and —S(=O);

$R^{A1}$, $R^{A2}$ are independently selected from the group consisting of
H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXI) or a stereoisomer, pharmaceutically acceptable salt, ester, solvate, or prodrug thereof, use according to the invention, wherein A is $NR^{A1}$, $R^{A2}$;

L is selected from the group consisting of $CH_2$—, and —$CH_2CH_2$—;

M is selected from the group consisting of
phenyl, thiazolyl, pyridinyl, pyrimidinyl, thiophenyl, furanyl, pyrrolyl, imidazolyl, oxazolyl, pyrazinyl, —C($R^{M1}$)=C($R^M$)—C≡C—, —C($R^{M1}$)=C($R^{M1}$)—.

G is selected from the group consisting of
—C≡C—, —C≡C—C≡C—

Y is phenyl;

X is selected from the group consisting of —C(=O)—, and —S(=O);

$R^{A1}$ is selected from the group consisting of
$C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, $R^{A2}$ is hydrogen or $C_{1-6}$alkyl or $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^M$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula

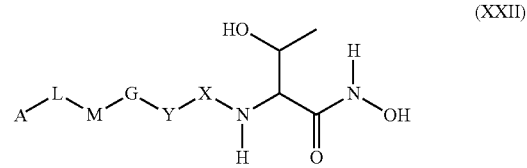

(XXII)

or a stereoisomer, pharmaceutically acceptable salt, solvate, or prodrug thereof, use according to the invention, wherein A, L, M, G, Y, and X, are defined as in any of the embodiments described herein.

In some embodiments of the invention and/or embodiments thereof the compound is a compound according to formula (XXII) or a stereoisomer, pharmaceutically acceptable salt, ester, solvate, or prodrug thereof, use according to the invention, wherein A is selected from the group consisting of
$NR^{A1}R^{A2}$, $NO_2$,
wherein
$R^{A1}$, $R^{A2}$ are independently selected from the group consisting of
H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
$C_{1-6}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl;

L is selected from the group consisting of
$C_{1-6}$-alkyl, $C_{2-6}$-alkenyl, $C_{2-6}$-alkynyl, $C_{3-10}$-cycloalkyl,
—$(NR^{L3})_{0-1}$—$(CH_2)_{0-4}$—$NR^{L3}$—$(CH_2)_{0-4}$—,
—$(NR^{L3})_{0-1}$—$(CR^{L1}R^{L2})_{0-4}$—$NR^{L3}$—$(CR^{L1}R^{L2})$—,
—$(CR^{L1}R^{L2})_{0-4}$—O—$(CR^{L1}R^{L2})$—, —$(CH_2)_{0-4}$—
$NR^{L3}$—$(CR^{L1}R^{L2})$—C(=O)NH—$(CH_2)_{0-4}$—, —C(=O)—(CR$^{L1}$R$^{L2}$)—NR$^{L3}$C(=O)—, —C(=O)NR$^{L3}$—, —NR$^{L3}$C(=O)—, —SO$_2$NR$^{L3}$—, NR$^{L3}$—C(=O)—NR$^{L3}$— wherein

R$^{L1}$, R$^{L2}$, R$^{L3}$ are independently selected from the group consisting of H, C$_{1-6}$-alkyl, halo-C$_{1-6}$-alkyl, C$_1$-C$_6$-alkyl substituted with aryl, C$_1$-C$_6$-alkyl substituted with heteroaryl, C$_1$-C$_6$-alkyl substituted with heterocyclyl; or R$^{L1}$, R$^{L3}$ together with the atoms to which they are attached can form a saturated or unsaturated heterocyclic ring having 3 to 8 ring atoms, wherein 1, 2, or 3, ring atoms are selected from N, S, and O;

M is selected from the group consisting of

C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—;

G is selected from the group consisting of

CR$^{G2}$=CR$^{G2}$—, —CR$^{G2}$=CR$^{G2}$—CR$^{G2}$=CR$^{G2}$—, —C≡C—, —C≡C—C≡C—, —CR$^{G2}$=CR$^{G2}$—C≡C—, —C≡C—CR$^{G2}$=CR$^{G2}$, —C(=O)—C≡C—, —C≡C—C(=O)—.

wherein

R$^{G2}$ is selected from the group consisting of

H, halogen atom, or C$_{1-6}$-alkyl;

Y is selected from aryl, or heteroaryl; and

X is selected from the group consisting of —C(=O)—, and —S(=O).

In some embodiments of the invention and/or embodiments thereof the compound is a compound according to formula (XXII) or a stereoisomer, pharmaceutically acceptable salt, ester, solvate, or prodrug thereof, use according to the invention, wherein A is selected from the group consisting of NR$^{A1}$R$^{A2}$, and NO$_2$;

L is selected from the group consisting of C$_{1-6}$-alkyl, C$_{2-6}$-alkenyl, C$_{2-6}$-alkynyl, C$_{3-10}$-cycloalkyl, wherein R$^{L3}$, is selected from the group consisting of H, C$_{1-6}$-alkyl, halo-C$_{1-6}$-alkyl, C$_1$-C$_6$-alkyl substituted with aryl, C$_1$-C$_6$-alkyl substituted with heteroaryl, C$_1$-C$_6$-alkyl substituted with heterocyclyl;

M is selected from the group consisting of

C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—;

G is selected from the group consisting of

CR$^{G2}$=CR$^{G2}$—, —C≡C—, —C≡C—C≡C—, —CR$^{G2}$=CR$^{G2}$—C≡C—, —C≡C—CR$^{G2}$=CR$^{G2}$;

wherein

R$^{G2}$ is selected from the group consisting of

H, halogen atom, or C$_{1-6}$-alkyl;

Y is selected from aryl, or heteroaryl;

X is selected from the group consisting of —C(=O)—, and —S(=O).

In some embodiments of the invention and/or embodiments thereof the compound is a compound according to formula (XXII) or a stereoisomer, pharmaceutically acceptable salt, ester, solvate, or prodrug thereof, use according to the invention, wherein A is NR$^{A1}$R$^{A2}$;

L is selected from the group consisting of —CH$_2$—, —CH$_2$CH$_2$—, —CH$_2$CH$_2$CH$_2$—, and —CH$_2$CH$_2$CH$_2$CH$_2$—;

M is selected from the group consisting of

C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—;

G is selected from the group consisting of

—C=O—, —C≡C—C≡C—;

Y is selected from aryl, or heteroaryl;

X is selected from the group consisting of —C(=O)—, and —S(=O);

R$^{A1}$, R$^{A2}$ are independently selected from the group consisting of

H, C$_{1-6}$-alkyl, C$_{2-6}$-alkenyl, C$_{2-6}$-alkynyl, C$_{3-10}$-cycloalkyl, aryl, heterocyclyl, heteroaryl, C$_{1-6}$-alkyloxy-C$_1$-C$_6$-alkyl, C$_1$-C$_6$-alkyl substituted with aryl, C$_1$-C$_6$-alkyl substituted with heteroaryl, C$_1$-C$_6$-alkyl substituted with heterocyclyl, or R$^{A1}$, R$^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by R$^{A1}$, R$^{A2}$ together with the N atom to which they are attached is optionally substituted with a substituent selected from the group consisting of C$_{1-6}$-alkyl, C$_{3-8}$-cycloalky, C$_{1-6}$-alkyloxy, —NR$^{A3}$R$^{A4}$, carbonyl, —C(=O)—OR$^{A5}$, halogen atom, C$_{1-6}$-alkyl substituted with halo, C$_{1-6}$-alkyloxy-C$_1$-C$_6$-alkyl, aryl, heteroaryl, C$_1$-C$_6$-alkyl substituted with aryl, cyano, hydroxy, —SR$^{A5}$, —SO$_2$R$^{A5}$, SO$_2$NR$^{A3}$R$^{A4}$, —C(=O)NR$^{A3}$R$^{A4}$, C$_{1-6}$-alkyl substituted with hydroxy;

wherein

R$^{A3}$, R$^{A4}$, R$^{A5}$ are independently chosen from

H, or C$_{1-6}$-alkyl.

In some embodiments of the invention and/or embodiments thereof the compound is a compound according to formula (XXII) or a stereoisomer, pharmaceutically acceptable salt, ester, solvate, or prodrug thereof, use according to the invention, wherein A is NR$^{A1}$, R$^{A2}$;

L is selected from the group consisting of —CH$_2$—, —CH$_2$CH$_2$—, —CH$_2$CH$_2$CH$_2$—, and —CH$_2$CH$_2$CH$_2$CH$_2$—;

M is selected from the group consisting of

C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^M$I)—;

G is selected from the group consisting of

—C≡C—, —C≡C—C≡C—

Y is selected from aryl, or heteroaryl;

X is selected from the group consisting of —C(=O)—, and —S(=O);

R$^{A1}$, R$^{A2}$ are independently selected from the group consisting of

H, C$_{1-6}$-alkyl, C$_{2-6}$-alkenyl, C$_{3-10}$-cycloalkylC$_{1-6}$-alkyloxy-C$_1$-C$_6$-alkyl, C$_1$-C$_6$-alkyl substituted with aryl, C$_1$-C$_6$-alkyl substituted with heteroaryl, or R$^{A1}$, R$^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, cycloalkyl, aryl, heteroaryl, or alkyloxy or the heterocyclic ring formed by R$^{A1}$, R$^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXII) or a stereoisomer, pharmaceutically acceptable salt, ester, solvate, or prodrug thereof, use according to the invention, wherein A is $NR^{A1}R^{A2}$;
L is selected from the group consisting of —$CH_2$—, and —$CH_2CH_2$—;
M is selected from the group consisting of
aryl, heteroaryl, —C($R^{M1}$)=C($R^{M1}$)—C≡C—, —C($R^{M1}$)=C($R^{M1}$)—;
G is selected from the group consisting of
—C≡C—, —C≡C—C≡C—
Y is aryl;
X is selected from the group consisting of —C(=O)—, and —S(=O);
$R^{A1}$, $R^{A2}$ are independently selected from the group consisting of
H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXII) or a stereoisomer, pharmaceutically acceptable salt, ester, solvate, or prodrug thereof, use according to the invention, wherein A is $NR^{A1}R^{A2}$;
L is selected from the group consisting of $CH_2$—, and —$CH_2CH_2$—;
M is selected from the group consisting of
phenyl, thiazolyl, pyridinyl, pyrimidinyl, thiophenyl, furanyl, pyrrolyl, imidazolyl, oxazolyl, pyrazinyl, —C($R^{M1}$)=C($R^{M1}$)—C≡C—, —C($R^{M1}$)=C($R^{M1}$)—.
G is selected from the group consisting of
—C≡C—, —C≡C—C≡C—;
Y is phenyl;
X is selected from the group consisting of —C(=O)—, and —S(=O);
$R^{A1}$, $R^{A2}$ are independently selected from the group consisting of
H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXII) or a stereoisomer, pharmaceutically acceptable salt, ester, solvate, or prodrug thereof, use according to the invention, wherein A is $NR^{A1}R^{A2}$;
L is selected from the group consisting of $CH_2$—, and —$CH_2CH_2$—;
M is selected from the group consisting of
phenyl, thiazolyl, pyridinyl, pyrimidinyl, thiophenyl, furanyl, pyrrolyl, imidazolyl, oxazolyl, pyrazinyl, —C($R^{M1}$)=C($R^M$)—C≡C—, —C($R^{M1}$)=C($R^{M1}$)—.
G is selected from the group consisting of
—C≡C—, —C≡C—C≡C—
Y is phenyl;
X is selected from the group consisting of —C(=O)—, and —S(=O);
$R^{A1}$ is selected from the group consisting of
$C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl,
$R^{A2}$ is hydrogen or $C_{1-6}$alkyl
or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$- alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —$C(=O)NR^{A3}R^{A4}$, $C_{1\text{-}6}$-alkyl substituted with hydroxy;
wherein
$R^{A3}$, $R^{A4}$, $R^{A5}$ are independently chosen from
H, or $C_{1\text{-}6}$-alkyl.

In some embodiments of the invention and/or embodiments thereof the compound is a compound according to formula

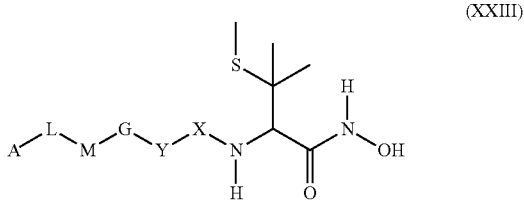

(XXIII)

or a stereoisomer, pharmaceutically acceptable salt, ester, solvate, or prodrug thereof, use according to the invention, wherein A, L, M, G, Y, and X, are defined as in any of the embodiments described herein.

In some embodiments of the invention and/or embodiments thereof the compound is a compound according to formula (XXIII) or a stereoisomer, pharmaceutically acceptable salt, ester, solvate, or prodrug thereof, use according to the invention, wherein
A is selected from the group consisting of
$NR^{A1}R^{A2}$, $NO_2$,
wherein
$R^{A1}$, $R^{A2}$ are independently selected from the group consisting of
H, $C_{1\text{-}6}$-alkyl, $C_{2\text{-}6}$-alkenyl, $C_{2\text{-}6}$-alkynyl, $C_{3\text{-}10}$-cycloalkyl, aryl, heterocyclyl, heteroaryl, $C_{1\text{-}6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or
$R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
$C_{1\text{-}6}$-alkyl, $C_{3\text{-}8}$-cycloalky, $C_{1\text{-}6}$-alkyloxy, —$NR^{A3}R^{A4}$, carbonyl, —$C(=O)$—$OR^{A5}$, halogen atom, $C_{1\text{-}6}$-alkyl substituted with halo, $C_{1\text{-}6}$-alkyloxy-$C_1$-$C_6$—, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —$C(=O)NR^{A3}R^{A4}$, $C_{1\text{-}6}$-alkyl substituted with hydroxy;
wherein
$R^{A3}$, $R^{A4}$, $R^{A5}$ are independently chosen from
H, or $C_{1\text{-}6}$-alkyl;
L is selected from the group consisting of
$C_{2\text{-}6}$-alkenyl, $C_{2\text{-}6}$-alkynyl, $C_{3\text{-}10}$-cycloalkyl, —$(NR^{L3})_{0\text{-}1}$—$(CH_2)_{0\text{-}4}$—$NR^{L3}$—$(CH_2)_{0\text{-}4}$—, —$(NR^{L3})_{0\text{-}1}$—$(CR^{L1}R^{L2})_{0\text{-}4}$—$NR^{L3}$—$(CR^{L1}R^{L2})$—, —$(CR^{L1}R^{L2})_{0\text{-}4}$—O—$(CR^{L1}R^{L2})$—, —$(CH_2)_{0\text{-}4}$—$NR^{L3}$—$(CR^{L1}R^{L2})$—$C(=O)NH$—$(CH_2)_{0\text{-}4}$—, —$C(=O)$—$(CR^{L1}R^{L2})NR^3C(=O)$—, —$C(=O)NR^{L3}$—, —$NR^{L3}C(=O)$—, —$SO_2NR^{L3}$—, $NR^{L3}$—$C(=O)$—$NR^{L3}$—
wherein
$R^{L1}$, $R^{L2}$, $R^{L3}$, are independently selected from the group consisting of
H, $C_{1\text{-}6}$-alkyl, halo-$C_{1\text{-}6}$-alkyl, $C_1$-$C_6$-alkyl substituted with aryl, $C_1$-$C_6$-alkyl substituted with heteroaryl, $C_1$-$C_6$-alkyl substituted with heterocyclyl; or
$R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O;
M is selected from the group consisting of
$C_{3\text{-}10}$-cycloalkyl, aryl, heterocyclyl, heteroaryl, $C_{2\text{-}4}$alkenyl, $C_{2\text{-}4}$alkynyl, —$C(R^{M1})=C(R^{M1})$—$C\equiv C$—, —$C(R^{M1})=C(R^{M1})$—;
G is selected from the group consisting of
$CR^{G2}=CR^{G2}$—, —$CR^{G2}=CR^{G2}$—$CR^{G2}=CR^{G2}$—, —$C\equiv C$—, —$C\equiv C$—$C\equiv C$—, —$CR^{G2}=CR^{G2}$—$C\equiv C$—, —$C\equiv C$—$CR^{G2}=CR^{G2}$, —$C(=O)$—$C\equiv C$—, —$C\equiv C$—$C(=O)$—;
wherein
$R^{G2}$ is selected from the group consisting of
H, halogen atom, or $C_{1\text{-}6}$-alkyl;
Y is selected from aryl, or heteroaryl;
and
X is selected from the group consisting of —$C(=O)$—, and —$S(=O)$.

In some embodiments of the invention and/or embodiments thereof the compound is a compound according to formula (XXIII) or a stereoisomer, pharmaceutically acceptable salt, ester, solvate, or prodrug thereof, use according to the invention, wherein
A is selected from the group consisting of
$NR^{A1}R^{A2}$, $NO_2$;
L is selected from the group consisting of
$C_{1\text{-}6}$-alkyl, $C_{2\text{-}6}$-alkenyl, $C_{2\text{-}6}$-alkynyl, $C_{3\text{-}10}$-cycloalkyl,
wherein
$R^{L3}$, is selected from the group consisting of
H, $C_{1\text{-}6}$-alkyl, halo-$C_{1\text{-}6}$-alkyl, $C_1$-$C_6$-alkyl substituted with aryl, $C_1$-$C_6$-alkyl substituted with heteroaryl, $C_1$-$C_6$-alkyl substituted with heterocyclyl;
M is selected from the group consisting of
$C_{3\text{-}10}$-cycloalkyl, aryl, heterocyclyl, heteroaryl, $C_{2\text{-}4}$alkenyl, $C_{2\text{-}4}$alkynyl, —$C(R^{M1})=C(R^{M1})$—$C\equiv C$—, —$C(R^{M1})=C(R^{M1})$—;
G is selected from the group consisting of
$CR^{G2}=CR^{G2}$—, —$C\equiv C$—, —$C\equiv C$—$C\equiv C$—, —$CR^{G2}=CR^{G2}$—$C\equiv C$—, —$C\equiv C$—$CR^{G2}=CR^{G2}$
wherein
$R^{G2}$ is selected from the group consisting of
H, halogen atom, or $C_{1\text{-}6}$-alkyl;
Y is selected from aryl, or heteroaryl;
X is selected from the group consisting of —$C(=O)$—, and —$S(=O)$.

In some embodiments of the invention and/or embodiments thereof the compound is a compound according to formula (XXIII) or a stereoisomer, pharmaceutically acceptable salt, ester, solvate, or prodrug thereof, use according to the invention, wherein
A is $NR^{A1}R^{A2}$;
L is selected from the group consisting of —$CH_2$—, —$CH_2CH_2$—, —$CH_2CH_2CH_2$—, and —$CH_2CH_2CH_2CH_2$—;

M is selected from the group consisting of
C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—;

G is selected from the group consisting of —C≡C—, —C≡C—C≡C—;

Y is selected from aryl, or heteroaryl;

X is selected from the group consisting of —C(=O)—, and —S(=O);

R$^{A1}$, R$^{A2}$ are independently selected from the group consisting of

H, C$_{1-6}$-alkyl, C$_{2-6}$-alkenyl, C$_{2-6}$-alkynyl, C$_{3-10}$-cycloalkyl, aryl, heterocyclyl, heteroaryl, C$_{1-6}$-alkyloxy-C$_1$-C$_6$-alkyl, C$_1$-C$_6$-alkyl substituted with aryl, C$_1$-C$_6$-alkyl substituted with heteroaryl, C$_1$-C$_6$-alkyl substituted with heterocyclyl, or R$^{A1}$, R$^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by R$^{A1}$, R$^{A2}$ together with the N atom to which they are attached is optionally substituted with a substituent selected from the group consisting of C$_{1-6}$-alkyl, C$_{3-8}$-cycloalky, C$_{1-6}$-alkyloxy, —NR$^{A3}$R$^{A4}$, carbonyl, —C(=O)—OR$^{A5}$, halogen atom, C$_{1-6}$-alkyl substituted with halo, C$_{1-6}$-alkyloxy-C$_1$-C$_6$-alkyl, aryl, heteroaryl, C$_1$-C$_6$-alkyl substituted with aryl, cyano, hydroxy, —SR$^{A5}$, —SO$_2$R$^{A5}$, SO$_2$NR$^{A3}$R$^{A4}$, —C(=O)NR$^{A3}$R$^{A4}$, C$_{1-6}$-alkyl substituted with hydroxy;

wherein

R$^{A3}$, R$^{A4}$, R$^{A5}$ are independently chosen from

H, or C$_{1-6}$-alkyl.

In some embodiments of the invention and/or embodiments thereof the compound is a compound according to formula (XXIII) or a stereoisomer, pharmaceutically acceptable salt, ester, solvate, or prodrug thereof, use according to the invention, wherein A is NR$^{A1}$, R$^{A2}$;

L is selected from the group consisting of —CH$_2$—, —CH$_2$CH$_2$—, —CH$_2$CH$_2$CH$_2$—, and —CH$_2$CH$_2$CH$_2$CH$_2$—;

M is selected from the group consisting of
C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—;

G is selected from the group consisting of —C≡C—, —C≡C—C≡C—;

Y is selected from aryl, or heteroaryl;

X is selected from the group consisting of —C(=O)—, and —S(=O);

R$^{A1}$, R$^{A2}$ are independently selected from the group consisting of

H, C$_{1-6}$-alkyl, C$_{2-6}$-alkenyl, C$_{3-10}$-cycloalkylC$_{1-6}$-alkyloxy-C$_1$-C$_6$-alkyl, C$_1$-C$_6$-alkyl substituted with aryl, C$_1$-C$_6$-alkyl substituted with heteroaryl, or R$^{A1}$, R$^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, cycloalkyl, aryl, heteroaryl, or alkyloxy or the heterocyclic ring formed by R$^{A1}$, R$^{A2}$ together with the N atom to which they are attached is optionally substituted with a substituent selected from the group consisting of C$_{1-6}$-alkyl, C$_{3-8}$-cycloalky, C$_{1-6}$-alkyloxy, —NR$^{A3}$R$^{A4}$, carbonyl, —C(=O)—OR$^{A5}$, halogen atom, C$_{1-6}$-alkyl substituted with halo, C$_{1-6}$-alkyloxy-C$_1$-C$_6$-alkyl, aryl, heteroaryl, C$_1$-C$_6$-alkyl substituted with aryl, cyano, hydroxy, —SR$^{A5}$, —SO$_2$R$^{A5}$, SO$_2$NR$^{A3}$R$^{A4}$, —C(=O)NR$^{A3}$R$^{A4}$, C$_{1-6}$-alkyl substituted with hydroxy;

wherein

R$^{A3}$, R$^{A4}$, R$^{A5}$ are independently chosen from

H, or C$_{1-6}$-alkyl.

In some embodiments of the invention and/or embodiments thereof the compound is a compound according to formula (XXIII) or a stereoisomer, pharmaceutically acceptable salt, ester, solvate, or prodrug thereof, use according to the invention, wherein A is NR$^{A1}$R$^{A2}$;

L is selected from the group consisting of —CH$_2$—, and —CH$_2$CH$_2$—;

M is selected from the group consisting of
aryl, heteroaryl, —C(R$^{M1}$)=C(R$^{M1}$)—C≡C—, —C(R$^{M1}$)=C(R$^{M1}$)—;

G is selected from the group consisting of —C≡C—, —C≡C—C≡C—;

Y is aryl;

X is selected from the group consisting of —C(=O)—, and —S(=O);

R$^{A1}$, R$^{A2}$ are independently selected from the group consisting of

H, C$_{1-6}$-alkyl, C$_{2-6}$-alkenyl, C$_{3-10}$-cycloalkyl, C$_{1-6}$-alkyloxy-C$_1$-C$_6$-alkyl, C$_1$-C$_6$-alkyl substituted with aryl, C$_1$-C$_6$-alkyl substituted with heteroaryl, or R$^{A1}$, R$^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by R$^{A1}$, R$^{A2}$ together with the N atom to which they are attached is optionally substituted with a substituent selected from the group consisting of C$_{1-6}$-alkyl, C$_{3-8}$-cycloalky, C$_{1-6}$-alkyloxy, —NR$^{A3}$R$^{A4}$, carbonyl, —C(=O)—OR$^{A5}$, halogen atom, C$_{1-6}$-alkyl substituted with halo, C$_{1-6}$-alkyloxy-C$_1$-C$_6$-alkyl, aryl, heteroaryl, C$_1$-C$_6$-alkyl substituted with aryl, cyano, hydroxy, —SR$^{A5}$, —SO$_2$R$^{A5}$, SO$_2$NR$^{A3}$R$^{A4}$, —C(=O)NR$^{A3}$R$^{A4}$, C$_{1-6}$-alkyl substituted with hydroxy;

wherein

R$^{A3}$, R$^{A4}$, R$^{A5}$ are independently chosen from

H, or C$_{1-6}$-alkyl.

In some embodiments of the invention and/or embodiments thereof the compound is a compound according to formula (XXIII) or a stereoisomer, pharmaceutically acceptable salt, ester, solvate, or prodrug thereof, use according to the invention, wherein A is NR$^{A1}$R$^{A2}$;

L is selected from the group consisting of CH$_2$—, and —CH$_2$CH$_2$—;

M is selected from the group consisting of
phenyl, thiazolyl, pyridinyl, pyrimidinyl, thiophenyl, furanyl, pyrrolyl, imidazolyl, oxazolyl, pyrazinyl, —C(R$^{M1}$)=C(R$^{M}$)—C≡C—, —C(R$^{M1}$)=C(R$^{M1}$)—.

G is selected from the group consisting of
—C≡C—, —C≡C—C≡C—;
Y is phenyl;
X is selected from the group consisting of —C(=O)—, and —S(=O);
$R^{A1}$, $R^{A2}$ are independently selected from the group consisting of
H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXIII) or a stereoisomer, pharmaceutically acceptable salt, ester, solvate, or prodrug thereof, use according to the invention, wherein
A is $NR^{A1}R^{A2}$;
L is selected from the group consisting of $CH_2$—, and —$CH_2CH_2$—;
M is selected from the group consisting of
phenyl, thiazolyl, pyridinyl, pyrimidinyl, thiophenyl, furanyl, pyrrolyl, imidazolyl, oxazolyl, pyrazinyl, —C($R^{M1}$)=C($R^{M1}$)—C≡C—, —C($R^{M1}$)=C($R^{M1}$)—.
G is selected from the group consisting of
—C≡C—, —C≡C—C≡C—;
Y is phenyl;
X is selected from the group consisting of —C(=O)—, and —S(=O);
$R^{A1}$ is selected from the group consisting of
$C_{1-6}$-alkyl, $C_{2-6}$-alkenyl, $C_{3-10}$-cycloalkyl, $C_1$-$C_6$-alkyl substituted with aryl, $C_1$-$C_6$-alkyl substituted with heteroaryl,
$R^{A2}$ is hydrogen or $C_{1-6}$alkyl
or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^6R^7$, C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula

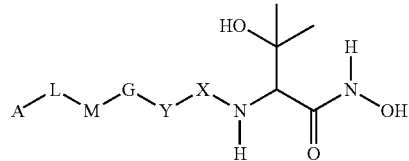

(XXIV)

or a stereoisomer, pharmaceutically acceptable salt, ester, solvate, or prodrug thereof, use according to the invention, wherein A, L, M, G, Y, and X, are defined as in any of the embodiments described herein.

In some embodiments of the invention and/or embodiments thereof the compound is a compound according to formula (XXIV) or a stereoisomer, pharmaceutically acceptable salt, ester, solvate, or prodrug thereof, use according to the invention, wherein
A is selected from the group consisting of
$NR^{A1}R^{A2}$, and $NO_2$,
wherein
$R^{A1}$, $R^{A2}$ are independently selected from the group consisting of
H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or
$R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl;
L is selected from the group consisting of
$C_{2-6}$-alkenyl, $C_{2-6}$-alkynyl, $C_{3-10}$-cycloalkyl, —$(NR^{L3})_{0-1}$—$(CH_2)_{0-4}$—$NR^{L3}$—$(CH_2)_{0-4}$—, —$(NR^{L3})_{0-1}$—$(CR^{L1}R^{L2})_{0-4}$—$NR^{L3}$—$(CR^{L1}R^{L2})$—, —$(CR^{L1}R^{L2})_{0-4}$—O—$(CR^{L1}R^{L2})$—, —$(CH_2)_{0-4}$—$NR^{L3}$—$(CR^{L1}R^{L2})$—C(=O)NH—$(CH_2)_{0-4}$—, —C(=O)—

$(CR^{L1}R^{L2})NR^3C(=O)-$, $-C(=O)NR^{L3}-$, $-NR^{L3}C(=O)-$, $-SO_2NR^3-$, $NR^{L3}-C(=O)-NR^{L3}-$ wherein
$R^{L1}$, $R^{L2}$, $R^{L3}$, are independently selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or
$R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O;

M is selected from the group consisting of
$C_{3-10}$-cycloalkyl, aryl, heterocyclyl, heteroaryl, $C_{2-4}$alkenyl, $C_{2-4}$alkynyl, $-C(R^{M1})=C(R^{M1})-C\equiv C-$, $-C(R^{M1})=C(R^{M1})-$;

G is selected from the group consisting of
$CR^{G2}=CR^{G2}-$, $-CR^{G2}=CR^{G2}-CR^{G2}=CR^{G2}-$, $-C\equiv C-$, $-C\equiv C-C\equiv C-$, $-CR^{G2}=CR^{G2}-C\equiv C-$, $-C\equiv C-CR^{G2}=CR^{G2}$, $-C(=O)-C\equiv C-$, $-C\equiv C-C(=O)-$;

wherein
$R^{G2}$ is selected from the group consisting of
H, halogen atom, or $C_{1-6}$-alkyl;

Y is selected from aryl, or heteroaryl;
and
X is selected from the group consisting of $-C(=O)-$, and $-S(=O)$.

In some embodiments of the invention and/or embodiments thereof the compound is a compound according to formula (XXIV) or a stereoisomer, pharmaceutically acceptable salt, ester, solvate, or prodrug thereof, use according to the invention, wherein A is selected from the group consisting of
$NR^{A1}R^{A2}$, and $NO_2$;

L is selected from the group consisting of
$C_{1-6}$-alkyl, $C_{2-6}$-alkenyl, $C_{2-6}$-alkynyl, $C_{3-10}$-cycloalkyl, $-NR^{L3}-$, wherein
$R^{L3}$, is selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl;

M is selected from the group consisting of
$C_{3-10}$-cycloalkyl, aryl, heterocyclyl, heteroaryl, $C_{2-4}$alkenyl, $C_{2-4}$alkynyl, $-C(R^{M1})=C(R^{M1})-C\equiv C-$, $-C(R^{M1})=C(R^{M1})-$;

G is selected from the group consisting of
$CR^{G2}=CR^{G2}-$, $-C\equiv C-$, $-C\equiv C-C\equiv C-$, $-CR^{G2}=CR^{G2}-C\equiv C-$, $-C\equiv C-CR^{G2}=CR^{G2}$ wherein
$R^{G2}$ is selected from the group consisting of
H, halogen atom, or $C_{1-6}$-alkyl;

Y is selected from aryl, or heteroaryl;
X is selected from the group consisting of $-C(=O)-$, and $-S(=O)$.

In some embodiments of the invention and/or embodiments thereof the compound is a compound according to formula (XXIV) or a stereoisomer, pharmaceutically acceptable salt, ester, solvate, or prodrug thereof, use according to the invention, wherein A is $NR^{A1}$, $R^{A2}$;

L is selected from the group consisting of $-CH_2-$, $-CH_2CH_2-$, $-CH_2CH_2CH_2-$, and $-CH_2CH_2CH_2CH_2-$;

M is selected from the group consisting of
$C_{3-10}$-cycloalkyl, aryl, heterocyclyl, heteroaryl, $C_{2-4}$alkenyl, $C_{2-4}$alkynyl, $-C(R^{M1})=C(R^{M1})-C\equiv C-$, $-C(R^{M1})=C(R^{M1})-$;

G is selected from the group consisting of
$-C\equiv C-$, $-C\equiv C-C\equiv C-$;

Y is selected from aryl, or heteroaryl;
X is selected from the group consisting of $-C(=O)-$, and $-S(=O)$;

$R^{A1}$, $R^{A2}$ are independently selected from the group consisting of
H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, $-NR^{A3}R^{A4}$, carbonyl, $-C(=O)-OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, $-SR^{A5}$, $-SO_2R^{A5}$, $SO_2NR^{A3}R^{A4}$, $-C(=O)NR^{A3}R^{A4}$, $C_{1-6}$-alkyl substituted with hydroxy;

wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXIV) or a stereoisomer, pharmaceutically acceptable salt, ester, solvate, or prodrug thereof, use according to the invention is, wherein A is $NR^{A1}$, $R^{A2}$;

L is selected from the group consisting of $-CH_2-$, $-CH_2CH_2-$, $-CH_2CH_2CH_2-$, and $-CH_2CH_2CH_2CH_2-$;

M is selected from the group consisting of
$C_{3-10}$-cycloalkyl, aryl, heterocyclyl, heteroaryl, $C_{2-4}$alkenyl, $C_{2-4}$alkynyl, $-C(R^{M1})=C(R^{M1})-C\equiv C-$, $-C(R^{M1})=C(R^{M1})-$;

G is selected from the group consisting of
$-C\equiv C-$, $-C\equiv C-C\equiv C-$;

Y is selected from aryl, or heteroaryl;
X is selected from the group consisting of $-C(=O)-$, and $-S(=O)$;

$R^{A1}$, $R^{A2}$ are independently selected from the group consisting of
H, $C_{1-6}$-alkyl, $C_{2-6}$-alkenyl, $C_{3-10}$-cycloalkyl$C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXIV) or a stereoisomer, pharmaceutically acceptable salt, ester, solvate, or prodrug thereof, use according to the invention, wherein A is $NR^{A1}R^{A2}$;
L is selected from the group consisting of —$CH_2$—, and —$CH_2CH_2$—;
M is selected from the group consisting of
aryl, heteroaryl, —$C(R^{M1})$=$C(R^{M1})$—C≡C—, —$C(R^{M1})$=$C(R^{M1})$—;
G is selected from the group consisting of
—C≡C—, —C≡C—C≡C—;
Y is aryl;
X is selected from the group consisting of —C(=O)—, and —S(=O);
$R^{A1}$, $R^{A2}$ are independently selected from the group consisting of
H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXIV) or a stereoisomer, pharmaceutically acceptable salt, ester, solvate, or prodrug thereof, use according to the invention, wherein A is $NR^{A1}R^{A2}$;
L is selected from the group consisting of $CH_2$—, and —$CH_2CH_2$—;
M is selected from the group consisting of
phenyl, thiazolyl, pyridinyl, pyrimidinyl, thiophenyl, furanyl, pyrrolyl, imidazolyl, oxazolyl, pyrazinyl, —$C(R^{M1})$=$C(R^{M1})$—C≡C—, —$C(R^{M1})$=$C(R^{M1})$—.
G is selected from the group consisting of
—C≡C—, —C≡C—C≡C—;
Y is phenyl;
X is selected from the group consisting of —C(=O)—, and —S(=O);
$R^{A1}$, $R^{A2}$ are independently selected from the group consisting of
H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXIV) or a stereoisomer, pharmaceutically acceptable salt, ester, solvate, or prodrug thereof, use according to the invention, wherein A is $NR^{A1}R^{A2}$;
L is selected from the group consisting of $CH_2$—, and —$CH_2CH_2$—;
M is selected from the group consisting of
phenyl, thiazolyl, pyridinyl, pyrimidinyl, thiophenyl, furanyl, pyrrolyl, imidazolyl, oxazolyl, pyrazinyl, —$C(R^{M1})$=$C(R^{M1})$—C≡C—, —$C(R^{M1})$=$C(R^{M1})$—.
G is selected from the group consisting of
—C≡C—, —C≡C—C≡C—;
Y is phenyl;
X is selected from the group consisting of —C(=O)—, and —S(=O);
$R^{A1}$ is selected from the group consisting of
$C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl,
$R^{A2}$ is hydrogen or $C_{1-6}$alkyl
or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$- alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A4}R^{A3}$, $R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula

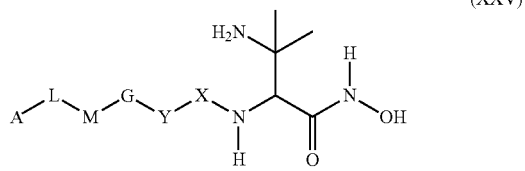

(XXV)

or a stereoisomer, pharmaceutically acceptable salt, ester, solvate, or prodrug thereof, use according to the invention, wherein A, L, M, G, Y, and X, are defined as in any of the embodiments described herein.

In some embodiments of the invention and/or embodiments thereof the compound is a compound according to formula (XXV) or a stereoisomer, pharmaceutically acceptable salt, ester, solvate, or prodrug thereof, use according to the invention, wherein A is selected from the group consisting of
$NR^{A1}R^{A2}$, and $NO_2$,
wherein
$R^{A1}$, $R^{A2}$ are independently selected from the group consisting of
H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or
$R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl;
L is selected from the group consisting of
$C_{2-6}$-alkenyl, $C_{2-6}$-alkynyl, $C_{3-10}$-cycloalkyl, —$(NR^{L3})_{0-1}$—$(CH_2)_{0-4}$—$NR^{L3}$—$(CH_2)_{0-4}$—, —$(NR^{L3})_{0-1}$—$(CR^{L1}R^{L2})_{0-4}$—$NR^{L3}$—$(CR^{L1}R^{L2})$—, —$(CR^{L1}R^{L2})_{0-4}$—O—$(CR^{L1}R^{L2})$—, —$(CH_2)_{0-4}$—$NR^{L3}$—$(CR^{L1}R^{L2})$—C(=O)NH—$(CH_2)_{0-4}$—, —C(=O)—$(CR^{L1}R^{L2})NR^{L3}C(=O)$—, —C(=O)$NR^{L3}$—, —$NR^{L3}C(=O)$—, —$SO_2NR^3$—, $NR^{1-3}$—C(=O)—$NR^{1-3}$—
wherein
$R^{L1}$, $R^{L2}$, $R^{L3}$, are independently selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or
$R^{L1}$, $R^{L3}$, together with the atoms to which they are attached can form a saturated or unsaturated heterocyclic ring having 3 to 8 ring atoms, wherein 1, 2, or 3, ring atoms are selected from N, S, and O;
M is selected from the group consisting of
$C_{3-10}$-cycloalkyl, aryl, heterocyclyl, heteroaryl, $C_{2-4}$alkenyl, $C_{2-4}$alkynyl, —C($R^{M1}$)=C($R^{M1}$)—C≡C—, —C($R^{M1}$)=C($R^{M1}$)—;
G is selected from the group consisting of
$CR^{G2}$=$CR^{G2}$—, —$CR^{G2}$=$CR^{G2}$—$CR^{G2}$=$CR^{G2}$—, —C≡C—, —C≡C—C≡C—, —$CR^{G2}$=$CR^{G2}$—C≡C—, —C≡C—$CR^{G2}$=$CR^{G2}$, —C(=O)—C≡C—, —C≡C—C(=O)—;
wherein
$R^{G2}$ is selected from the group consisting of
H, halogen atom, or $C_{1-6}$-alkyl;
Y is selected from aryl, or heteroaryl;
and
X is selected from the group consisting of —C(=O)—, and —S(=O).

In some embodiments of the invention and/or embodiments thereof the compound is a compound according to formula (XXV) or a stereoisomer, pharmaceutically acceptable salt, ester, solvate, or prodrug thereof, use according to the invention, wherein A is selected from the group consisting of
$NR^{A1}R^{A2}$, $NO_2$;
L is selected from the group consisting of
$C_{1-6}$-alkyl, $C_{2-6}$-alkenyl, $C_{2-6}$-alkynyl, $C_{3-10}$-cycloalkyl,
wherein
$R^{L3}$, is selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl.
M is selected from the group consisting of
$C_{3-10}$-cycloalkyl, aryl, heterocyclyl, heteroaryl, $C_{2-4}$alkenyl, $C_{2-4}$alkynyl, —C($R^{M1}$)=C($R^{M1}$)—C≡C—, —
G is selected from the group consisting of
$CR^{G2}$=$CR^{G2}$—, —C≡C—, —C≡C—C≡C—, —$CR^{G2}$=$CR^{G2}$—C≡C—, —C≡C—$CR^{G2}$=$CR^{G2}$
wherein
$R^{G2}$ is selected from the group consisting of
H, halogen atom, or $C_{1-6}$-alkyl;
Y is selected from aryl, or heteroaryl;
X is selected from the group consisting of —C(=O)—, and —S(=O).

In some embodiments of the invention and/or embodiments thereof the compound is a compound according to formula (XXV) or a stereoisomer, pharmaceutically acceptable salt, ester, solvate, or prodrug thereof, use according to the invention, wherein A is $NR^{A1}$, $R^{A2}$;
L is selected from the group consisting of —$CH_2$—, —$CH_2CH_2$—, —$CH_2CH_2CH_2$—, and —$CH_2CH_2CH_2CH_2$—;

M is selected from the group consisting of
$C_{3-10}$-cycloalkyl, aryl, heterocyclyl, heteroaryl, $C_{2-4}$-alkenyl, $C_{2-4}$alkynyl, —C(R$^{M1}$)═C(R$^{M1}$)—C≡C—, —C(R$^{M1}$)═C(R$^{M1}$)—;

G is selected from the group consisting of
—C≡C—, —C≡C—C≡C—;

Y is selected from aryl, or heteroaryl;

X is selected from the group consisting of —C(═O)—, and —S(═O);

R$^{A1}$, R$^{A2}$ are independently selected from the group consisting of
H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or R$^{A1}$, R$^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by R$^1$, R$^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —NR$^{A3}$R$^{A4}$, carbonyl, —C(═O)—OR$^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —SR$^{A5}$, —SO$_2$R$^{A5}$, SO$_2$NR$^{A3}$R$^{A4}$, —C(═O)NR$^{A3}$R$^{A4}$, $C_{1-6}$-alkyl substituted with hydroxy;

wherein
R$^{A3}$, R$^{A4}$, R$^{A5}$ are independently chosen from
H, or $C_{1-6}$-alkyl.

In some embodiments of the invention and/or embodiments thereof the compound is a compound according to formula (XXV) or a stereoisomer, pharmaceutically acceptable salt, ester, solvate, or prodrug thereof, use according to the invention, wherein A is NR$^{A1}$, R$^{A2}$;

L is selected from the group consisting of —CH$_2$—, —CH$_2$CH$_2$—, —CH$_2$CH$_2$CH$_2$—, and —CH$_2$CH$_2$CH$_2$CH$_2$—;

M is selected from the group consisting of
$C_{3-10}$-cycloalkyl, aryl, heterocyclyl, heteroaryl, $C_{2-4}$-alkenyl, $C_{2-4}$alkynyl, —C(R$^{M1}$)═C(R$^{M1}$)—C≡C—, —C(R$^{M1}$)═C(R$^{M1}$)—;

G is selected from the group consisting of
—C≡C—, —C≡C—C≡C—;

Y is selected from aryl, or heteroaryl;

X is selected from the group consisting of —C(═O)—, and —S(═O);

R$^{A1}$, R$^{A2}$ are independently selected from the group consisting of
H, $C_{1-6}$-alkyl, $C_{2-6}$-alkenyl, $C_{3-10}$-cycloalkyl$C_{1-6}$-alkyloxy-$C_1$-$C_6$-alkyl, $C_1$-$C_6$-alkyl substituted with aryl, $C_1$-$C_6$-alkyl substituted with heteroaryl, or R$^{A1}$, R$^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, cycloalkyl, aryl, heteroaryl, or alkyloxy or the heterocyclic ring formed by R$^{A1}$, R$^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —NR$^{A3}$R$^{A4}$, carbonyl, —C(═O)—OR$^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —SR$^{A5}$, —SO$_2$R$^{A5}$, SO$_2$NR$^{A3}$R$^{A4}$, —C(═O)NR$^{A3}$R$^{A4}$, $C_{1-6}$-alkyl substituted with hydroxy;

wherein
R$^{A3}$, R$^{A4}$, R$^{A5}$ are independently chosen from
H, or $C_{1-6}$-alkyl.

In some embodiments of the invention and/or embodiments thereof the compound is a compound according to formula (XXV) or a stereoisomer, pharmaceutically acceptable salt, ester, solvate, or prodrug thereof, use according to the invention, wherein A is NR$^{A1}$R$^{A2}$;

L is selected from the group consisting of —CH$_2$—, and —CH$_2$CH$_2$—;

M is selected from the group consisting of
aryl, heteroaryl, —C(R$^{M1}$)═C(R$^{M1}$)—C≡C—, —C(R$^{M1}$)═C(R$^{M1}$)—;

G is selected from the group consisting of
—C≡C—, —C≡C—C≡C—;

Y is aryl;

X is selected from the group consisting of —C(═O)—, and —S(═O);

R$^{A1}$, R$^{A2}$ are independently selected from the group consisting of
H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or R$^{A1}$R$^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by R$^{A1}$, R$^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —NR$^{A3}$R$^{A4}$, carbonyl, —C(═O)—OR$^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —SR$^{A5}$, —SO$_2$R$^{A5}$, SO$_2$NR$^{A3}$R$^{A4}$, —C(═O)NR$^{A3}$R$^{A4}$, $C_{1-6}$-alkyl substituted with hydroxy;

wherein
R$^{A3}$, R$^{A4}$, R$^{A5}$ are independently chosen from
H, or $C_{1-6}$-alkyl.

In some embodiments of the invention and/or embodiments thereof the compound is a compound according to formula (XXV) or a stereoisomer, pharmaceutically acceptable salt, ester, solvate, or prodrug thereof, use according to the invention, wherein A is NR$^{A1}$R$^{A2}$;

L is selected from the group consisting of CH$_2$—, and —CH$_2$CH$_2$—;

M is selected from the group consisting of
phenyl, thiazolyl, pyridinyl, pyrimidinyl, thiophenyl, furanyl, pyrrolyl, imidazolyl, oxazolyl, pyrazinyl, —C(R$^{M1}$)═C(R$^{M1}$)—C≡C—, —C(R$^{M1}$)═C(R$^{M1}$)—.

G is selected from the group consisting of
—C≡C—, —C≡C—C≡C—;
Y is phenyl;
X is selected from the group consisting of —C(=O)—, and —S(=O);
$R^{A1}$, $R^{A2}$ are independently selected from the group consisting of
H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXV) or a stereoisomer, pharmaceutically acceptable salt, ester, solvate, or prodrug thereof, use according to the invention, wherein
A is $NR^{A1}R^{A2}$;
L is selected from the group consisting of $CH_2$—, and —$CH_2CH_2$—;
M is selected from the group consisting of
phenyl, thiazolyl, pyridinyl, pyrimidinyl, thiophenyl, furanyl, pyrrolyl, imidazolyl, oxazolyl, pyrazinyl, —C($R^{M1}$)=C($R^{M1}$)—C≡C—, —C($R^{M1}$)=C($R^{M1}$)—.
G is selected from the group consisting of
—C≡C—, —C≡C—C≡C—;
Y is phenyl;
X is selected from the group consisting of —C(=O)—, and —S(=O);
$R^{A1}$ is selected from the group consisting of
$C_{1-6}$-alkyl, $C_{2-6}$-alkenyl, $C_{3-10}$-cycloalkyl, $C_1$-$C_6$-alkyl substituted with aryl, $C_1$-$C_6$-alkyl substituted with heteroaryl,
$R^{A2}$ is hydrogen or $C_{1-6}$alkyl
or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula

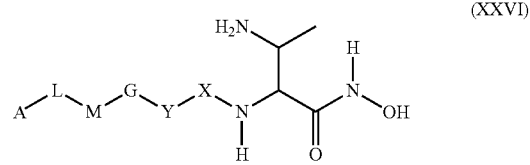

(XXVI)

or a stereoisomer, pharmaceutically acceptable salt, ester, solvate, or prodrug thereof, use according to the invention, wherein A, L, M, G, Y, and X, are defined as in any of the embodiments described herein.

In some embodiments of the invention and/or embodiments thereof the compound is a compound according to formula (XXVI) or a stereoisomer, pharmaceutically acceptable salt, ester, solvate, or prodrug thereof, use according to the invention, wherein
A is selected from the group consisting of
$NR^{A1}R^{A2}$, and $NO_2$,
wherein
$R^{A1}$, $R^{A2}$ are independently selected from the group consisting of
H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or
$R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl;
L is selected from the group consisting of
$C_{2-6}$-alkenyl, $C_{2-6}$-alkynyl, $C_{3-10}$-cycloalkyl, —$(NR^{L3})_{0-1}$—$(CH_2)_{0-4}$—$NR^{L3}$—$(CH_2)_{0-4}$—, —$(NR^{L3})_{0-1}$—$(CR^{L1}R^{L2})_{0-4}$—$NR^{L3}$—$(CR^{L1}R^{L2})$—, —$(CR^{L1}R^{L2})_{0-4}$—O—$(CR^{L1}R^L)$—, —$(CH_2)_{0-4}$—$NR^{L3}$—$(CR^{L1}R^{L2})$—C(=O)NH—$(CH_2)_{0-4}$—, —C(=O)—(CR$^{L1}$R$^{L2}$)NR$^{L3}$C(=O)—, —C(=O)NR$^{L3}$—, —NR$^{L3}$C(=O)—, —SO$_2$NR$^{L3}$—, NR$^{L3}$—C(=O)—NR$^{L3}$—
wherein
R$^{L1}$, R$^{L2}$, R$^{L3}$, are independently selected from the group consisting of
H, C$_{1-6}$-alkyl, halo-C$_{1-6}$-alkyl, C$_1$-C$_6$-alkyl substituted with aryl, C$_1$-C$_6$-alkyl substituted with heteroaryl, C$_1$-C$_6$-alkyl substituted with heterocyclyl; or
R$^{L1}$, R$^{L3}$ together with the atoms to which they are attached can form a saturated or unsaturated heterocyclic ring having 3 to 8 ring atoms, wherein 1, 2, or 3, ring atoms are selected from N, S, and O;
M is selected from the group consisting of
C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—;
G is selected from the group consisting of
CR$^{G2}$=CR$^{G2}$—, —CR$^{G2}$=CR$^{G2}$—CR$^{G2}$=CR$^{G2}$, —C≡C—, —C≡C—C≡C—, —CR$^{G2}$=CR$^{G2}$—C≡C—, —C≡C—CR$^{G2}$=CR$^{G2}$, —C(=O)—C≡C—, —C≡C—C(=O)—;
wherein
R$^{G2}$ is selected from the group consisting of
H, halogen atom, or C$_{1-6}$-alkyl;
Y is selected from aryl, or heteroaryl;
and
X is selected from the group consisting of —C(=O)—, and —S(=O).

In some embodiments of the invention and/or embodiments thereof the compound is a compound according to formula (XXVI) or a stereoisomer, pharmaceutically acceptable salt, ester, solvate, or prodrug thereof, use according to the invention, wherein
A is selected from the group consisting of
NR$^{A1}$R$^{A2}$, and NO$_2$;
L is selected from the group consisting of
C$_{1-6}$-alkyl, C$_{2-6}$-alkenyl, C$_{2-6}$-alkynyl, C$_{3-10}$-cycloalkyl, wherein
R$^{L3}$, is selected from the group consisting of
H, C$_{1-6}$-alkyl, halo-C$_{1-6}$-alkyl, C$_1$-C$_6$-alkyl substituted with aryl, C$_1$-C$_6$-alkyl substituted with heteroaryl, C$_1$-C$_6$-alkyl substituted with heterocyclyl.
M is selected from the group consisting of
C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—;
G is selected from the group consisting of
CR$^{G2}$=CR$^{G2}$—, —C≡C—, —C≡C—C≡C—, —CR$^{G2}$=CR$^{G2}$—C≡C—, —C≡C—CR$^{G2}$=CR$^{G2}$
wherein
R$^{G2}$ is selected from the group consisting of
H, halogen atom, or C$_{1-6}$-alkyl;
Y is selected from aryl, or heteroaryl;
X is selected from the group consisting of —C(=O)—, and —S(=O).

In some embodiments of the invention and/or embodiments thereof the compound is a compound according to formula (XXVI) or a stereoisomer, pharmaceutically acceptable salt, ester, solvate, or prodrug thereof, use according to the invention, wherein
A is NR$^{A1}$, R$^{A2}$;
L is selected from the group consisting of —CH$_2$—, —CH$_2$CH$_2$—, —CH$_2$CH$_2$CH$_2$—, and —CH$_2$CH$_2$CH$_2$CH$_2$—;

M is selected from the group consisting of
C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—;
G is selected from the group consisting of
—C=O—, —C≡C—C≡C—;
Y is selected from aryl, or heteroaryl;
X is selected from the group consisting of —C(=O)—, and —S(=O);
R$^{A1}$, R$^{A2}$ are independently selected from the group consisting of
H, C$_{1-6}$-alkyl, C$_{2-6}$-alkenyl, C$_{2-6}$-alkynyl, C$_{3-10}$-cycloalkyl, aryl, heterocyclyl, heteroaryl, C$_{1-6}$-alkyloxy-C$_1$-C$_6$-alkyl, C$_1$-C$_6$-alkyl substituted with aryl, C$_1$-C$_6$-alkyl substituted with heteroaryl, C$_1$-C$_6$-alkyl substituted with heterocyclyl, or
R$^{A1}$, R$^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, alkynyl, cycloalkyl, aryl, heterocyclyl, heteroaryl, alkyloxy or the heterocyclic ring formed by R$^1$, R$^{A2}$ together with the N atom to which they are attached is optionally substituted with a substituent selected from the group consisting of
C$_{1-6}$-alkyl, C$_{3-8}$-cycloalky, C$_{1-6}$-alkyloxy, —NR$^{A3}$R$^{A4}$, carbonyl, —C(=O)—OR$^{A5}$, halogen atom, C$_{1-6}$-alkyl substituted with halo, C$_{1-6}$-alkyloxy-C$_1$-C$_6$-alkyl, aryl, heteroaryl, C$_1$-C$_6$-alkyl substituted with aryl, cyano, hydroxy, —SR$^{A5}$, —SO$_2$R$^{A5}$, SO$_2$NR$^{A4}$R$^{A3}$, —C(=O)NR$^{A3}$R$^{A4}$, C$_{1-6}$-alkyl substituted with hydroxy;
wherein
R$^{A3}$, R$^{A4}$, R$^{A5}$ are independently chosen from
H, or C$_{1-6}$-alkyl.

In some embodiments of the invention and/or embodiments thereof the compound is a compound according to formula (XXVI) or a stereoisomer, pharmaceutically acceptable salt, ester, solvate, or prodrug thereof, use according to the invention, wherein
A is NR$^{A1}$, R$^{A2}$;
L is selected from the group consisting of —CH$_2$—, —CH$_2$CH$_2$—, —CH$_2$CH$_2$CH$_2$—, and —CH$_2$CH$_2$CH$_2$CH$_2$—;
M is selected from the group consisting of
C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—;
G is selected from the group consisting of
—C≡C—, —C≡C—C≡C—;
Y is selected from aryl, or heteroaryl;
X is selected from the group consisting of —C(=O)—, and —S(=O);
R$^{A1}$, R$^{A2}$ are independently selected from the group consisting of
H, C$_{1-6}$-alkyl, C$_{2-6}$-alkenyl, C$_{3-10}$-cycloalkylC$_{1-6}$-alkyloxy-C$_1$-C$_6$-alkyl, C$_1$-C$_6$-alkyl substituted with aryl, C$_1$-C$_6$-alkyl substituted with heteroaryl, or
R$^{A1}$, R$^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, cycloalkyl, aryl, heteroaryl, or alkyloxy or the heterocyclic ring formed by R$^{A1}$, R$^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXVI) or a stereoisomer, pharmaceutically acceptable salt, ester, solvate, or prodrug thereof, use according to the invention, wherein
A is $NR^{A1}R^{A2}$;
L is selected from the group consisting of —$CH_2$—, and —$CH_2CH_2$—;
M is selected from the group consisting of
aryl, heteroaryl, —C($R^{M1}$)=C($R^{M1}$)—C≡C—, —C($R^{M1}$)=C($R^{M1}$)—;
G is selected from the group consisting of
—C≡C—, —C≡C—C≡C—;
Y is aryl;
X is selected from the group consisting of —C(=O)—, and —S(=O);
$R^{A1}$, $R^{A2}$ are independently selected from the group consisting of
H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXVI) or a stereoisomer, pharmaceutically acceptable salt, ester, solvate, or prodrug thereof, use according to the invention, wherein
A is $NR^{A1}R^{A2}$;
L is selected from the group consisting of $CH_2$—, and —$CH_2CH_2$—;
M is selected from the group consisting of
phenyl, thiazolyl, pyridinyl, pyrimidinyl, thiophenyl, furanyl, pyrrolyl, imidazolyl, oxazolyl, pyrazinyl, —C($R^{M1}$)=C($R^{M1}$)—C≡C—, —C($R^{M1}$)=C($R^{M1}$)—.
G is selected from the group consisting of
—C≡C—, —C≡C—C≡C—;
Y is phenyl;
X is selected from the group consisting of —C(=O)—, and —S(=O);
$R^{A1}$, $R^{A2}$ are independently selected from the group consisting of
H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A4}R^{A3}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXVI) or a stereoisomer, pharmaceutically acceptable salt, ester, solvate, or prodrug thereof, use according to the invention, wherein
A is $NR^{A1}R^{A2}$;
L is selected from the group consisting of $CH_2$—, and —$CH_2CH_2$—;
M is selected from the group consisting of
phenyl, thiazolyl, pyridinyl, pyrimidinyl, thiophenyl, furanyl, pyrrolyl, imidazolyl, oxazolyl, pyrazinyl, —C($R^{M1}$)=C($R^{M1}$)—C≡C—, —C($R^{M1}$)=C($R^{M1}$)—.
G is selected from the group consisting of
—C≡C—, —C≡C—C≡C—;
Y is phenyl;
X is selected from the group consisting of —C(=O)—, and —S(=O);
$R^{A1}$ is selected from the group consisting of $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl,
K is hydrogen or $C_{1-6}$alkyl
or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$- alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula

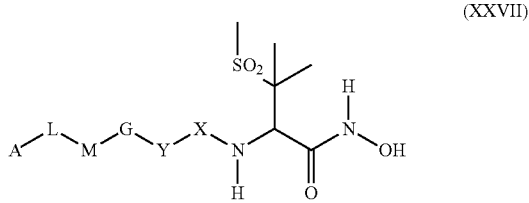

(XXVII)

or a stereoisomer, pharmaceutically acceptable salt, ester, solvate, or prodrug thereof, for use according to the invention wherein A, L, M, G, Y, and X, are defined as in any of the embodiments described herein.

In some embodiments of the invention and/or embodiments thereof the compound is a compound according to formula (XXVII) or a stereoisomer, pharmaceutically acceptable salt, ester, solvate, or prodrug thereof, for use according to the invention, wherein
A is selected from the group consisting of
$NR^{A1}R^{A2}$, and $NO_2$,
wherein
$R^{A1}$, $R^{A2}$ are independently selected from the group consisting of
H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or
$R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
$C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}$, $R^{A4}$, $C_{1-6}$-alkyl substituted with hydroxy;
wherein
$R^{A3}$, $R^{A4}$, $R^{A5}$ are independently chosen from
H, or $C_{1-6}$-alkyl;
L is selected from the group consisting of
$C_{1-6}$-alkyl, $C_{2-6}$-alkenyl, $C_{2-6}$-alkynyl, $C_{3-10}$-cycloalkyl, —$(NR^{L3})_{0-1}$—$(CH_2)_{0-4}$—$NR^{L3}$—$(CH_2)_{0-4}$—, —$(NR^{L3})_{0-1}$—$(CR^{L1}R^{L2})_{0-4}$—$NR^{L3}$—$(CR^{L1}R^{L2})$—, —$(CR^{L1}R^{L2})_{0-4}$—O—$(CR^{L1}R^{L2})$—, —$(CH_2)_{0-4}$—$NR^{L3}$—$(CR^{L1}R^{L2})$—C(=O)NH—$(CH_2)_{0-4}$—, —C(=O)—$(CR^{L1}R^{L2})NR^{L3}C$(=O)—, —C(=O)$NR^{L3}$—, —$NR^{L3}C$(=O)—, —$NR^{L3}$—, C(=O)—$NR^{L3}$—
wherein
$R^{L1}$, $R^{L2}$, $R^{L3}$, are independently selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or
$R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O;
M is selected from the group consisting of
$C_{3-10}$-cycloalkyl, aryl, heterocyclyl, heteroaryl, $C_{2-4}$alkenyl, $C_{2-4}$alkynyl, —C($R^{M1}$)=C($R^{M1}$)—C≡C—, —C($R^{M1}$)=C($R^{M1}$)—;
G is selected from the group consisting of
$CR^{G2}$=$CR^{G2}$—, —$CR^{G2}$=$CR^{G2}$—$CR^{G2}$=$CR^{G2}$—, —C≡C—, —C≡C—C≡C—, —$CR^{G2}$=$CR^{G2}$—C≡C—, —C≡C—$CR^{G2}$=$CR^{G2}$, —C(=O)—C≡C—, —C≡C—C(=O)—;
wherein
$R^{G2}$ is selected from the group consisting of
H, halogen atom, or $C_{1-6}$-alkyl;
Y is selected from aryl, or heteroaryl;
and
X is selected from the group consisting of —C(=O)—, and —S(=O).

In some embodiments of the invention and/or embodiments thereof the compound is a compound according to formula (XXVII) or a stereoisomer, pharmaceutically acceptable salt, ester, solvate, or prodrug thereof, for use according to the invention, wherein
A is selected from the group consisting of
$NR^{A1}R^{A2}$, and $NO_2$;
L is selected from the group consisting of
$C_{1-6}$-alkyl, $C_{2-6}$-alkenyl, $C_{2-6}$-alkynyl, $C_{3-10}$-cycloalkyl,
wherein
$R^{L3}$, is selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl.
M is selected from the group consisting of
$C_{3-10}$-cycloalkyl, aryl, heterocyclyl, heteroaryl, $C_{2-4}$alkenyl, $C_{2-4}$alkynyl, —C($R^{M1}$)=C($R^{M1}$)—C≡C—, —C($R^{M1}$)=C($R^{M1}$)—;
G is selected from the group consisting of
$CR^{G2}$=$CR^{G2}$—, —C≡C—, —C≡C—C≡C—, —$CR^{G2}$=$CR^{G2}$—C≡C—, —C≡C—$CR^{G2}$=$CR^{G2}$
wherein
$R^{G2}$ is selected from the group consisting of
H, halogen atom, or $C_{1-6}$-alkyl;
Y is selected from aryl, or heteroaryl;
X is selected from the group consisting of —C(=O)—, and —S(=O).

In some embodiments of the invention and/or embodiments thereof the compound is a compound according to formula (XXVII) or a stereoisomer, pharmaceutically acceptable salt, ester, solvate, or prodrug thereof, for use according to the invention, wherein
A is $NR^{A1}R^{A2}$;
L is selected from the group consisting of —$CH_2$—, —$CH_2CH_2$—, —$CH_2CH_2CH_2$—, and —$CH_2CH_2CH_2CH_2$—;

M is selected from the group consisting of
C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—;

G is selected from the group consisting of
—C≡C—, —C≡C—C≡C—;

Y is selected from aryl, or heteroaryl;

X is selected from the group consisting of —C(=O)—, and —S(=O);

R$^{A1}$, R$^{A2}$ are independently selected from the group consisting of
H, C$_{1-6}$-alkyl, C$_{2-6}$-alkenyl, C$_{2-6}$-alkynyl, C$_{3-10}$-cycloalkyl, aryl, heterocyclyl, heteroaryl, C$_{1-6}$-alkyloxy-C$_1$-C$_6$-alkyl, C$_1$-C$_6$-alkyl substituted with aryl, C$_1$-C$_6$-alkyl substituted with heteroaryl, C$_1$-C$_6$-alkyl substituted with heterocyclyl, or R$^{A1}$, R$^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by R$^{A1}$, R$^{A2}$ together with the N atom to which they are attached is optionally substituted with a substituent selected from the group consisting of
C$_{1-6}$-alkyl, C$_{3-8}$-cycloalky, C$_{1-6}$-alkyloxy, —NR$^{A3}$R$^{A4}$, carbonyl, —C(=O)—OR$^{A5}$, halogen atom, C$_{1-6}$-alkyl substituted with halo, C$_{1-6}$-alkyloxy-C$_1$-C$_6$-alkyl, aryl, heteroaryl, C$_1$-C$_6$-alkyl substituted with aryl, cyano, hydroxy, —SR$^{A5}$, —SO$_2$R$^{A5}$, SO$_2$NR$^{A3}$R$^{A4}$, —C(=O)NR$^{A3}$R$^{A4}$, C$_{1-6}$-alkyl substituted with hydroxy;

wherein
R$^{A3}$, R$^{A4}$, R$^{A5}$ are independently chosen from
H, or C$_{1-6}$-alkyl.

In some embodiments of the invention and/or embodiments thereof the compound is a compound according to formula (XXVII) or a stereoisomer, pharmaceutically acceptable salt, ester, solvate, or prodrug thereof, for use according to the invention, wherein A is NR$^{A1}$R$^{A2}$;

L is selected from the group consisting of —CH$_2$—, —CH$_2$CH$_2$—, —CH$_2$CH$_2$CH$_2$—, and —CH$_2$CH$_2$CH$_2$CH$_2$—;

M is selected from the group consisting of
C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—;

G is selected from the group consisting of
—C≡C—, —C≡C—C≡C—;

Y is selected from aryl, or heteroaryl;

X is selected from the group consisting of —C(=O)—, and —S(=O);

R$^{A1}$, R$^{A2}$ are independently selected from the group consisting of
H, C$_{1-6}$-alkyl, C$_{2-6}$-alkenyl, C$_{3-10}$-cycloalkylC$_{1-6}$-alkyloxy-C$_1$-C$_6$-alkyl, C$_1$-C$_6$-alkyl substituted with aryl, C$_1$-C$_6$-alkyl substituted with heteroaryl, or R$^{A1}$, R$^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, cycloalkyl, aryl, heteroaryl, or alkyloxy or the heterocyclic ring formed by R$^{A1}$, R$^{A2}$ together with the N atom to which they are attached is optionally substituted with a substituent selected from the group consisting of
C$_{1-6}$-alkyl, C$_{3-8}$-cycloalky, C$_{1-6}$-alkyloxy, —NR$^{A3}$R$^{A4}$, carbonyl, —C(=O)—OR$^{A5}$, halogen atom, C$_{1-6}$-alkyl substituted with halo, C$_{1-6}$-alkyloxy-C$_1$-C$_6$-alkyl, aryl, heteroaryl, C$_1$-C$_6$-alkyl substituted with aryl, cyano, hydroxy, —SR$^{A5}$, —SO$_2$R$^{A5}$, SO$_2$NR$^{A3}$R$^{A4}$, —C(=O)NR$^{A3}$R$^{A4}$, C$_{1-6}$-alkyl substituted with hydroxy;

wherein
R$^{A3}$, R$^{A4}$, R$^{A5}$ are independently chosen from
H, or C$_{1-6}$-alkyl.

In some embodiments of the invention and/or embodiments thereof the compound is a compound according to formula (XXVII) or a stereoisomer, pharmaceutically acceptable salt, ester, solvate, or prodrug thereof, for use according to the invention, wherein A is NR$^{A1}$R$^{A2}$;

L is selected from the group consisting of —CH$_2$—, and —CH$_2$CH$_2$—;

M is selected from the group consisting of
aryl, heteroaryl, —C(R$^{M1}$)=C(R$^{M1}$)—C≡C—, —C(R$^{M1}$)=C(R$^{M1}$)—;

G is selected from the group consisting of
—C≡C—, —C≡C—C≡C—;

Y is aryl;

X is selected from the group consisting of —C(=O)—, and —S(=O);

R$^{A1}$, R$^{A2}$ are independently selected from the group consisting of
H, C$_{1-6}$-alkyl, C$_{2-6}$-alkenyl, C$_{3-10}$-cycloalkyl, C$_{1-6}$-alkyloxy-C$_1$-C$_6$-alkyl, C$_1$-C$_6$-alkyl substituted with aryl, C$_1$-C$_6$-alkyl substituted with heteroaryl, or R$^{A1}$, R$^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by R$^{A1}$, R$^{A2}$ together with the N atom to which they are attached is optionally substituted with a substituent selected from the group consisting of
C$_{1-6}$-alkyl, C$_{3-8}$-cycloalky, C$_{1-6}$alkyloxy, —NR$^{A3}$R$^{A4}$, carbonyl, —C(=O)—OR$^{A5}$, halogen atom, C$_{1-6}$alkyl substituted with halo, C$_{1-6}$-alkyloxy-C$_1$-C$_6$alkyl, aryl, heteroaryl, C$_1$-C$_6$-alkyl substituted with aryl, cyano, hydroxy, —SR$^{A5}$, —SO$_2$R$^{A5}$, SO$_2$NR$^{A3}$R$^{A4}$, —C(=O)NR$^{A3}$R$^{A4}$, C$_{1-6}$-alkyl substituted with hydroxy;

wherein
R$^{A3}$, R$^{A4}$, R$^{A5}$ are independently chosen from
H, or C$_{1-6}$-alkyl.

In some embodiments of the invention and/or embodiments thereof the compound is a compound according to formula (XXVII) or a stereoisomer, pharmaceutically acceptable salt, ester, solvate, or prodrug thereof, for use according to the invention, wherein A is NR$^{A1}$R$^{A2}$;

L is selected from the group consisting of CH$_2$—, and —CH$_2$CH$_2$—;

M is selected from the group consisting of
phenyl, thiazolyl, pyridinyl, pyrimidinyl, thiophenyl, furanyl, pyrrolyl, imidazolyl, oxazolyl, pyrazinyl, —C(R$^{M1}$)=C(R$^{M1}$)—C≡C—, —C(R$^{M1}$)=C(R$^{M1}$)—.

G is selected from the group consisting of
—C≡C—, —C≡C—C≡C—;
Y is phenyl;
X is selected from the group consisting of —C(=O)—, and —S(=O);
$R^{A1}$, $R^{A2}$ are independently selected from the group consisting of
H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXVII) or a stereoisomer, pharmaceutically acceptable salt, ester, solvate, or prodrug thereof, for use according to the invention, wherein
A is $NR^{A1}$, $R^{A2}$;
L is selected from the group consisting of $CH_2$—, and —$CH_2CH_2$—;
M is selected from the group consisting of
phenyl, thiazolyl, pyridinyl, pyrimidinyl, thiophenyl, furanyl, pyrrolyl, imidazolyl, oxazolyl, pyrazinyl, —C($R^{M1}$)=C($R^{M1}$)—C≡C—, —C($R^{M1}$)=C($R^{M1}$)—.
G is selected from the group consisting of
—C≡C—, —C≡C—C≡C—;
Y is phenyl;
X is selected from the group consisting of —C(=O)—, and —S(=O);
$R^{A1}$ is selected from the group consisting of
$C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl,
$R^{A2}$ is hydrogen or $C_{1-6}$alkyl
or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula

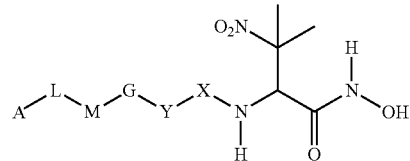

(XXVIII)

or a stereoisomer, pharmaceutically acceptable salt, ester, solvate, or prodrug thereof, for use according to the invention, wherein A, L, M, G, Y, and X, are defined as in any of the embodiments described herein.

In some embodiments of the invention and/or embodiments thereof the compound is a compound according to formula (XXVIII) or a stereoisomer, pharmaceutically acceptable salt, ester, solvate, or prodrug thereof, for use according to the invention, wherein
A is selected from the group consisting of
$NR^{A1}R^{A2}$, and $NO_2$,
wherein
$R^{A1}$, $R^{A2}$ are independently selected from the group consisting of
H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or
$R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, $SR^{A5}$, —$SC_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl;
L is selected from the group consisting of
$C_{1-6}$-alkyl, $C_{2-6}$-alkenyl, $C_{2-6}$-alkynyl, $C_{3-10}$-cycloalkyl, —($NR^{L3}$)$_{0-1}$—($CH_2$)$_{0-4}$—$NR^{L3}$—($CH_2$)$_{0-4}$—, —($NR^{L3}$)$_{0-1}$—($CR^{L1}R^{L2}$)$_{0-4}$—$NR^{L3}$—($CR^{L1}R^{L2}$)—, —($CR^{L1}R^{L2}$)$_{0-4}$—O—($CR^{L1}R^{L2}$)—, —($CH_2$)$_{0-4}$—$NR^{L2}$—($CR^{L1}R^{L2}$)—C(=O)NH—($CH_2$)$_{0-4}$—, —C(=O)—(CR$^{L1}$R$^{L2}$)NR$^{L3}$C(=O)—, —C(=O)NR$^{L3}$—, —NR$^{L3}$C(=O)—, —NR$^{L3}$—, —SO$_2$NR$^{L3}$—, NR$^{L3}$—C(=O)—NR$^{L3}$—
wherein
R$^{L1}$, R$^{L2}$, L$^{L3}$, are independently selected from the group consisting of
H, C$_{1-6}$-alkyl, halo-C$_{1-6}$-alkyl, C$_1$-C$_6$-alkyl substituted with aryl, C$_1$-C$_6$-alkyl substituted with heteroaryl, C$_1$-C$_6$-alkyl substituted with heterocyclyl; or
R$^{L1}$, R$^{L3}$ together with the atoms to which they are attached can form a saturated or unsaturated heterocyclic ring having 3 to 8 ring atoms, wherein 1, 2, or 3, ring atoms are selected from N, S, and O;
M is selected from the group consisting of
C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—;
G is selected from the group consisting of
CR$^{G2}$=CR$^{G2}$—, —CR$^{G2}$=CR$^{G2}$—CR$^{G2}$=CR$^{G2}$—, —C≡C—, —C≡C—C≡C—, —CR$^{G2}$=CR$^{G2}$—C≡C—, —C≡C—CR$^{G2}$=CR$^{G2}$, —C(=O)—C≡C—, —C≡C—C(=O)—;
wherein
R$^{G2}$ is selected from the group consisting of
H, halogen atom, or C$_{1-6}$-alkyl;
Y is selected from aryl, or heteroaryl;
and
X is selected from the group consisting of —C(=O)—, and —S(=O).

In some embodiments of the invention and/or embodiments thereof the compound is a compound according to formula (XXVIII) or a stereoisomer, pharmaceutically acceptable salt, ester, solvate, or prodrug thereof, for use according to the invention, wherein
A is selected from the group consisting of
NR$^{A1}$R$^{A2}$, NO$_2$;
L is selected from the group consisting of
C$_{1-6}$-alkyl, C$_{2-6}$-alkenyl, C$_{2-6}$-alkynyl, C$_{3-10}$-cycloalkyl,
wherein
R$^{L3}$, is selected from the group consisting of
H, C$_{1-6}$-alkyl, halo-C$_{1-6}$-alkyl, C$_1$-C$_6$-alkyl substituted with aryl, C$_1$-C$_6$-alkyl substituted with heteroaryl, C$_1$-C$_6$-alkyl substituted with heterocyclyl.
M is selected from the group consisting of
C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—;
G is selected from the group consisting of
CR$^{G2}$=CR$^{G2}$—, —C≡C—, —C≡C—C≡C—, —CR$^{G2}$=CR$^{G2}$—C≡C—, —C≡C—CR$^{G2}$=CR$^{G2}$
wherein
R$^{G2}$ is selected from the group consisting of
H, halogen atom, or C$_{1-6}$-alkyl;
Y is selected from aryl, or heteroaryl;
X is selected from the group consisting of —C(=O)—, and —S(=O).

In some embodiments of the invention and/or embodiments thereof the compound is a compound according to formula (XXVIII) or a stereoisomer, pharmaceutically acceptable salt, ester, solvate, or prodrug thereof, for use according to the invention, wherein
A is NR$^{A1}$R$^{A2}$;
L is selected from the group consisting of —CH$_2$—, —CH$_2$CH$_2$—, —CH$_2$CH$_2$CH$_2$—, and —CH$_2$CH$_2$CH$_2$CH$_2$—;

M is selected from the group consisting of
C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—;
G is selected from the group consisting of
—C≡C—, —C≡C—C≡C—;
Y is selected from aryl, or heteroaryl;
X is selected from the group consisting of —C(=O)—, and —S(=O);
R$^{A1}$, R$^{A2}$ are independently selected from the group consisting of
H, C$_{1-6}$-alkyl, C$_{2-6}$-alkenyl, C$_{2-6}$-alkynyl, C$_{3-10}$-cycloalkyl, aryl, heterocyclyl, heteroaryl, C$_{1-6}$-alkyloxy-C$_1$-C$_6$-alkyl, C$_1$-C$_6$-alkyl substituted with aryl, C$_1$-C$_6$-alkyl substituted with heteroaryl, C$_1$-C$_6$-alkyl substituted with heterocyclyl, or
R$^{A1}$, R$^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, alkynyl, cycloalkyl, aryl, heterocyclyl, heteroaryl, alkyloxy or the heterocyclic ring formed by R$^{A1}$, R$^{A2}$ together with the N atom to which they are attached is optionally substituted with a substituent selected from the group consisting of
C$_{1-6}$-alkyl, C$_{3-8}$-cycloalky, C$_{1-6}$-alkyloxy, —NR$^{A3}$R$^{A4}$, carbonyl, —C(=O)—OR$^{A5}$, halogen atom, C$_{1-6}$-alkyl substituted with halo, C$_{1-6}$-alkyloxy-C$_1$-C$_6$ alkyl, aryl, heteroaryl, C$_1$-C$_6$-alkyl substituted with aryl, cyano, hydroxy, —SR$^{A5}$, —SO$_2$R$^{A5}$, SO$_2$NR$^{A3}$R$^{A4}$, —C(=O)NR$^{A3}$R$^{A4}$, C$_{1-6}$-alkyl substituted with hydroxy;
wherein
R$^{A3}$, R$^{A4}$, R$^{A5}$ are independently chosen from
H, or C$_{1-6}$-alkyl.

In some embodiments of the invention and/or embodiments thereof the compound is a compound according to formula (XXVIII) or a stereoisomer, pharmaceutically acceptable salt, ester, solvate, or prodrug thereof, for use according to the invention, wherein
A is NR$^{A1}$R$^{A2}$;
L is selected from the group consisting of CH$_2$—, —CH$_2$CH$_2$—, —CH$_2$CH$_2$CH$_2$—, and CH$_2$CH$_2$CH$_2$CH$_2$—;
M is selected from the group consisting of
C$_{3-10}$-cycloalkyl, aryl, heterocyclyl, heteroaryl, C$_{2-4}$alkenyl, C$_{2-4}$alkynyl, —C(R$^{M1}$)=C(R$^{M1}$)—C≡C—, —C(R$^{M1}$)=C(R$^{M1}$)—;
G is selected from the group consisting of
—C≡C—, —C≡C—C≡C—;
Y is selected from aryl, or heteroaryl;
X is selected from the group consisting of —C(=O)—, and —S(=O);
R$^{A1}$, R$^{A2}$ are independently selected from the group consisting of
H, C$_{1-6}$-alkyl, C$_{2-6}$-alkenyl, C$_{3-10}$-cycloalkylC$_{1-6}$-alkyloxy-C$_1$-C$_6$-alkyl, C$_1$-C$_6$-alkyl substituted with aryl, C$_1$-C$_6$-alkyl substituted with heteroaryl, or
R$^{A1}$, R$^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, cycloalkyl, aryl, heteroaryl, or alkyloxy or the heterocyclic ring formed by R$^{A1}$, R$^{A2}$ together with the N atom to which they are attached is optionally substituted with a substituent selected from the group consisting of $C_{1-6}$-alkyl, $C_{3-8}$-cycloalky, $C_{1-6}$-alkyloxy, —NR$^{A3}$R$^{A4}$, carbonyl, —C(=O)—OR$^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —SR$^{A5}$, —SO$_2$R$^{A5}$, SO$_2$NR$^{A3}$R$^{A4}$, —C(=O)NR$^{A3}$R$^{A4}$, $C_{1-6}$-alkyl substituted with hydroxy;

wherein

R$^{A3}$, R$^{A4}$, R$^{A5}$ are independently chosen from

H, or $C_{1-6}$-alkyl.

In some embodiments of the invention and/or embodiments thereof the compound is a compound according to formula (XXVIII) or a stereoisomer, pharmaceutically acceptable salt, ester, solvate, or prodrug thereof, for use according to the invention, wherein A is NR$^{A1}$R$^{A2}$;

L is selected from the group consisting of CH$_2$—, and —CH$_2$CH$_2$—;

M is selected from the group consisting of aryl, heteroaryl, —C(R$^{M1}$)=C(R$^{M1}$)—C≡C—, —C(R$^{M1}$)=C(R$^{M1}$)—;

G is selected from the group consisting of

—C≡C—, —C≡C—C≡C—;

Y is aryl;

X is selected from the group consisting of —C(=O)—, and —S(=O);

R$^{A1}$, R$^{A2}$ are independently selected from the group consisting of

H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or R$^{A1}$, R$^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by R$^{A1}$, R$^{A2}$ together with the N atom to which they are attached is optionally substituted with a substituent selected from the group consisting of $C_{1-6}$-alkyl, $C_{3-8}$-cycloalky, $C_{1-6}$-alkyloxy, —NR$^{A3}$R$^{A4}$, carbonyl, —C(=O)—OR$^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —SR$^{A5}$, —SO$_2$R$^{A5}$, SO$_2$NR$^{A3}$R$^{A4}$, —C(=O)NR$^{A3}$R$^{A4}$, $C_{1-6}$-alkyl substituted with hydroxy;

wherein

R$^{A3}$, R$^{A4}$, R$^{A5}$ are independently chosen from

H, or $C_{1-6}$-alkyl.

In some embodiments of the invention and/or embodiments thereof the compound is a compound according to formula (XXVIII) or a stereoisomer, pharmaceutically acceptable salt, ester, solvate, or prodrug thereof, for use according to the invention, wherein A is NR$^{A1}$R$^{A2}$;

L is selected from the group consisting of CH$_2$—, and —CH$_2$CH$_2$—;

M is selected from the group consisting of phenyl, thiazolyl, pyridinyl, pyrimidinyl, thiophenyl, furanyl, pyrrolyl, imidazolyl, oxazolyl, pyrazinyl, —C(R$^{M1}$)=C(R$^{M1}$)—C≡C—, —C(R$^{M1}$)=C(R$^{M1}$)—.

G is selected from the group consisting of

—C≡C—, —C≡C—C≡C—;

Y is phenyl;

X is selected from the group consisting of —C(=O)—, and —S(=O);

R$^{A1}$, R$^{A2}$ are independently selected from the group consisting of

H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or R$^{A1}$, R$^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by R$^{A1}$, R$^{A2}$ together with the N atom to which they are attached is optionally substituted with a substituent selected from the group consisting of $C_{1-6}$-alkyl, $C_{3-8}$-cycloalky, $C_{1-6}$-alkyloxy, —NR$^{A3}$R$^{A4}$, carbonyl, —C(=O)—OR$^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —SR$^{A5}$, —SO$_2$R$^{A5}$, SO$_2$NR$^{A3}$R$^{A4}$, —C(=O)NR$^{A3}$R$^{A4}$, $C_{1-6}$-alkyl substituted with hydroxy;

wherein

R$^{A3}$, R$^{A4}$, R$^{A5}$ are independently chosen from

H, or $C_{1-6}$-alkyl.

In some embodiments of the invention and/or embodiments thereof the compound is a compound according to formula (XXVIII) or a stereoisomer, pharmaceutically acceptable salt, ester, solvate, or prodrug thereof, for use according to the invention, wherein A is NR$^{A1}$R$^{A2}$;

L is selected from the group consisting of CH$_2$—, and —CH$_2$CH$_2$—;

M is selected from the group consisting of phenyl, thiazolyl, pyridinyl, pyrimidinyl, thiophenyl, furanyl, pyrrolyl, imidazolyl, oxazolyl, pyrazinyl, —C(R$^{M1}$)=C(R$^{M1}$)—C≡C—, —C(R$^{M1}$)=C(R$^{M1}$)—.

G is selected from the group consisting of

—C≡C—, —C≡C—C≡C—;

Y is phenyl;

X is selected from the group consisting of —C(=O)—, and —S(=O);

R$^{A1}$ is selected from the group consisting of $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, R$^{A2}$ is hydrogen or $C_{1-6}$alkyl or R$^{A1}$, R$^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by R$^{A1}$, R$^{A2}$ together with the N atom to which they are attached is optionally substituted with a substituent selected from the group consisting of $C_{1-6}$-alkyl, $C_{3-8}$-cycloalky, $C_{1-6}$-alkyloxy, —NR$^{A3}$R$^{A4}$, carbonyl, —C(=O)—OR$^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —SR$^{A5}$, —$SO_2R^{A5}$, $SO_2NR^{A3}R^{A4}$, —$C(=O)NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula

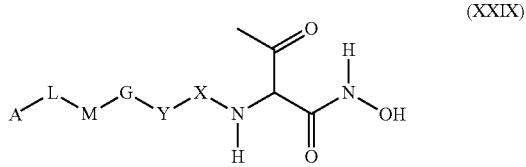

(XXIX)

or a stereoisomer, pharmaceutically acceptable salt, ester, solvate, or prodrug thereof, for use according to the invention, wherein A, L, M, G, Y, and X, are defined as in any of the embodiments described herein.

In some embodiments of the invention and/or embodiments thereof the compound is a compound according to formula (XXIX) or a stereoisomer, pharmaceutically acceptable salt, ester, solvate, or prodrug thereof, for use according to the invention, wherein A is selected from the group consisting of
$NR^{A1}R^{A2}$, and $NO_2$,
wherein
$R^{A1}$, $R^{A2}$ are independently selected from the group consisting of
H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or
$R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —$C(=O)$—$OR^{A5}$, halogen atom, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —$C(=O)NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl;
L is selected from the group consisting of
$C_{1-6}$-alkyl, $C_{2-6}$-alkenyl, $C_{2-6}$-alkynyl, $C_{3-10}$-cycloalkyl, —$(NR^{L3})_{0-1}$—$(CH_2)_{0-4}$—$NR^{L3}$—$(CH_2)_{0-4}$—, —$(NR^{L3})_{0-1}$—$(CR^{L1}R^{L2})_{0-4}$—$NR^{L3}$—$(CR^{L1}R^{L2})$—, —$(CR^{L1}R^{L2})_{0-4}$—O—$(CR^{L1}R^{L2})$—, —$(CH_2)_{0-4}$—$NR^{L3}$—$(CR^{L1}R^{L2})$—$C(=O)NH$—$(CH_2)_{0-4}$—, —$C(=O)$—$(CR^{L1}R^{L2})$—, —$(CR^{L1}R^{L2})_{0-4}$—O—$(CR^{L1}R^{L2})$—, —$(CH_2)_{0-4}$—$NR^{L3}$—$(CR^{L1}R^{L2})$—$C(=O)NH$—$C(=O)$—$NR^{L3}$— wherein
$R^{L1}$, $R^{L2}$, $R^{L3}$ are independently selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or
$R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O;
M is selected from the group consisting of
$C_{3-10}$-cycloalkyl, aryl, heterocyclyl, heteroaryl, $C_{2-4}$alkenyl, $C_{2-4}$alkynyl, —$C(R^{M1})=C(R^{M1})$—C≡C—, —$C(R^{M1})=C(R^{M1})$—;
G is selected from the group consisting of
$CR^{G2}=CR^{G2}$—, —$CR^{G2}=CR^{G2}$—$CR^{G2}=CR^{G2}$—, —C≡C—, —C≡C—C≡C—, —$CR^{G2}=CR^{G2}$—C≡C—, —C≡C—$CR^{G2}=CR^{G2}$, —C(=O)—C≡C—, —C≡C—C(=O)—;
wherein
$R^{G2}$ is selected from the group consisting of
H, halogen atom, or $C_{1-6}$-alkyl;
Y is selected from aryl, or heteroaryl;
and
X is selected from the group consisting of —C(=O)—, and —S(=O).

In some embodiments of the invention and/or embodiments thereof the compound is a compound according to formula (XXIX) or a stereoisomer, pharmaceutically acceptable salt, ester, solvate, or prodrug thereof, for use according to the invention, wherein
A is selected from the group consisting of
$NR^{A1}R^{A2}$, and $NO_2$;
L is selected from the group consisting of
$C_{1-6}$-alkyl, $C_{2-6}$-alkenyl, $C_{2-6}$-alkynyl, $C_{3-10}$-cycloalkyl, —$NR^{L3}$—,
wherein
$R^{L3}$, is selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl.
M is selected from the group consisting of
$C_{3-10}$-cycloalkyl, aryl, heterocyclyl, heteroaryl, $C_{2-4}$alkenyl, $C_{2-4}$alkynyl, —$C(R^{M1})=C(R^{M1})$—C≡C—, —$C(R^{M1})=C(R^{M1})$—;
G is selected from the group consisting of
$CR^{G2}=CR^{G2}$—, —C≡C—, —C≡C—C≡C—, —$CR^{G2}=CR^{G2}$—C≡C—, —C≡C—$CR^{G2}=CR^{G2}$
wherein
$R^{G2}$ is selected from the group consisting of
H, halogen atom, or $C_{1-6}$-alkyl;
Y is selected from aryl, or heteroaryl;
X is selected from the group consisting of —C(=O)—, and —S(=O).

In some embodiments of the invention and/or embodiments thereof the compound is a compound according to formula (XXIX) or a stereoisomer, pharmaceutically acceptable salt, ester, solvate, or prodrug thereof, for use according to the invention, wherein
A is $NR^{A1}R^{A2}$;
L is selected from the group consisting of —$CH_2$—, —$CH_2CH_2$—, —$CH_2CH_2CH_2$—, and —$CH_2CH_2CH_2CH_2$—;
M is selected from the group consisting of
$C_{3-10}$-cycloalkyl, aryl, heterocyclyl, heteroaryl, $C_{2-4}$alkenyl, $C_{2-4}$alkynyl, —$C(R^{M1})=C(R^{M1})$—C≡C—, —$C(R^{M1})=C(R^{M1})$—;

G is selected from the group consisting of
—C≡C—, —C≡C—C≡C—;
Y is selected from aryl, or heteroaryl;
X is selected from the group consisting of —C(═O)—, and —S(═O);
$R^{A1}$, $R^{A2}$ are independently selected from the group consisting of
H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or
$R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(═O)—$OR^{A5}$, halogen atom, $C_{1-6}$-alkyl substituted with halo, $C_{1-6}$-alkyloxy-$C_1$-$C_6$ alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(═O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXIX) or a stereoisomer, pharmaceutically acceptable salt, ester, solvate, or prodrug thereof, for use according to the invention, wherein
A is $NR^{A1}R^{A2}$;
L is selected from the group consisting of $CH_2$—, —$CH_2CH_2$—, —$CH_2CH_2CH_2$—, and $CH_2CH_2CH_2CH_2$—;
M is selected from the group consisting of
$C_{3-10}$-cycloalkyl, aryl, heterocyclyl, heteroaryl, $C_{2-4}$alkenyl, $C_{2-4}$alkynyl, —C($R^{M1}$)═C($R^{M1}$)—C≡C—, —C($R^{M1}$)═C($R^{M1}$)—;
G is selected from the group consisting of
—C≡C—, —C≡C—C≡C—;
Y is selected from aryl, or heteroaryl;
X is selected from the group consisting of —C(═O)—, and —S(═O);
$R^{A1}$, $R^{A2}$ are independently selected from the group consisting of
H, $C_{1-6}$-alkyl, $C_{2-6}$-alkenyl, $C_{3-10}$-cycloalkyl$C_{1-6}$-alkyloxy-$C_1$-$C_6$-alkyl, $C_1$-$C_6$-alkyl substituted with aryl, $C_1$-$C_6$-alkyl substituted with heteroaryl, or
$R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(═O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, C(═O)$NR^{A3}$ $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXIX) or a stereoisomer, pharmaceutically acceptable salt, ester, solvate, or prodrug thereof, for use according to the invention, wherein
A is $NR^{A1}R^{A2}$;
L is selected from the group consisting of $CH_2$—, and —$CH_2CH_2$—;
M is selected from the group consisting of
aryl, heteroaryl, —C($R^{M1}$)═C($R^{M1}$)—C≡C—, —O($R^{M1}$)═C($R^{M1}$)—;
G is selected from the group consisting of
—C≡C—, —C≡C—C≡C—;
Y is aryl;
X is selected from the group consisting of —C(═O)—, and —S(═O);
$R^{A1}$, $R^{A2}$ are independently selected from the group consisting of
H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(═O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(═O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXIX) or a stereoisomer, pharmaceutically acceptable salt, ester, solvate, or prodrug thereof, for use according to the invention, wherein
A is $NR^{A1}R^{A2}$;
L is selected from the group consisting of $CH_2$—, and —$CH_2CH_2$—;
M is selected from the group consisting of
phenyl, thiazolyl, pyridinyl, pyrimidinyl, thiophenyl, furanyl, pyrrolyl, imidazolyl, oxazolyl, pyrazinyl, —C($R^{M1}$)═C($R^{M1}$)—C≡C—, —C($R^{M1}$)═C($R^{M1}$)—.
G is selected from the group consisting of
—C≡C—, —C≡C—C≡C—;
Y is phenyl;
X is selected from the group consisting of —C(═O)—, and —S(═O);

$R^{A1}$, $R^{A2}$ are independently selected from the group consisting of

H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXIX) or a stereoisomer, pharmaceutically acceptable salt, ester, solvate, or prodrug thereof, for use according to the invention, wherein A is $NR^{A1}R^{A2}$;
L is selected from the group consisting of $CH_2$—, and —$CH_2CH_2$—;
M is selected from the group consisting of
phenyl, thiazol'l, pyridinyl, pyrimidinyl, thiophenyl, furanyl, pyrrolyl, imidazolyl, oxazolyl, pyrazinyl, —C($R^{M1}$)=C($R^{M1}$)—C≡C—, —C($R^{M1}$)=C($R^{M1}$)—.
G is selected from the group consisting of
—C≡O—, —C≡C—C≡C—;
Y is phenyl;
X is selected from the group consisting of —C(=O)—, and —S(=O);
$R^{A1}$ is selected from the group consisting of
$C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl,
$R^{A2}$ is hydrogen or $C_{1-6}$alkyl
or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;

wherein
$R^{A3}$, $R^{A4}$, $R^{A5}$ are independently chosen from
H, or $C_{1-6}$-alkyl.

In some embodiments of the invention and/or embodiments thereof the compound is a compound according to formula

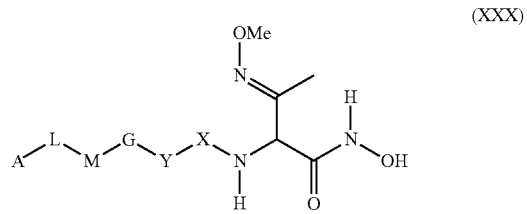

(XXX)

or a stereoisomer, pharmaceutically acceptable salt, ester, solvate, or prodrug thereof, for use according to the invention, wherein A, L, M, G, Y, and X, are defined as in any of the embodiments described herein.

In some embodiments of the invention and/or embodiments thereof the compound is a compound according to formula (XXX) or a stereoisomer, pharmaceutically acceptable salt, ester, solvate, or prodrug thereof, for use according to the invention, wherein A is selected from the group consisting of
$NR^{A1}R^{A2}$, and $NO_2$,
wherein
$R^{A1}$, $R^{A2}$ are independently selected from the group consisting of
H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or
$R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl;
L is selected from the group consisting of
$C_{1-6}$-alkyl, $C_{2-6}$-alkenyl, $C_{2-6}$-alkynyl, $C_{3-10}$-cycloalkyl, —($NR^{L3}$)$_{0-1}$—($CH_2$)$_{0-4}$—$NR^{L3}$—($CH_2$)$_{0-4}$—, —($NR^{L3}$)$_{0-1}$—($CR^{L1}R^{L2}$)$_{0-4}$—$NR^{L3}$—($CR^{L1}R^{L2}$)—, —($CR^{L1}R^{L2}$)$_{0-4}$—O—($CR^{L1}R^{L2}$)—, —($CH_2$)$_{0-4}$—$NR^{L3}$—($CR^{L1}R^{L2}$)—C(=O)NH—($CH_2$)$_{0-4}$—, —C(=O)—($CR^{L1}R^{L2}$)—$NR^{L3}$C(=O)—, —C(=O)$NR^{L3}$—, —$NR^{L3}$C(=O)—, —$NR^{L3}$—, —$SO_2NR^{L3}$—, $NR^{L3}$—C(=O)—$NR^{L3}$— wherein
$R^{L1}$, $R^{L2}$, $R^{L3}$ are independently selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl; or
$R^{L1}$, $R^{L3}$ together with the atoms to which they are attached can form a saturated or unsaturated heterocyclic ring having 3 to 8 ring atoms, wherein 1, 2, or 3, ring atoms are selected from N, S, and O;
M is selected from the group consisting of
$C_{3-10}$-cycloalkyl, aryl, heterocyclyl, heteroaryl, $C_{2-4}$alkenyl, $C_{2-4}$alkynyl, —C($R^{M1}$)=C($R^{M1}$)—C≡C—, —C($R^{M1}$)=C($R^{M1}$)—;
G is selected from the group consisting of
$R^{G2}$=$CR^{G2}$—, —$CR^{G2}$=$CR^{G2}$—$CR^{G2}$=$CR^{G2}$—, —C≡C—, —C≡C—C≡C—, —$CR^{G2}$=$CR^{G2}$—C≡C—, —C≡C—$CR^{G2}$=$CR^{G2}$, —C(=O)—C≡C—, —C≡C—C(=O)—;
wherein
$R^{G2}$ is selected from the group consisting of
H, halogen atom, or $C_{1-6}$-alkyl;
Y is selected from aryl, or heteroaryl; and
X is selected from the group consisting of —C(=O)—, and —S(=O).

In some embodiments of the invention and/or embodiments thereof the compound is a compound according to formula (XXX) or a stereoisomer, pharmaceutically acceptable salt, ester, solvate, or prodrug thereof, for use according to the invention, wherein
A is selected from the group consisting of
$NR^{A1}R^{A2}$, and $NO_2$;
L is selected from the group consisting of
$C_{1-6}$-alkyl, $C_{2-6}$-alkenyl, $C_{2-6}$-alkynyl, $C_{3-10}$-cycloalkyl, —$NR^{L3}$—,
wherein
$R^{L3}$, is selected from the group consisting of
H, $C_{1-6}$-alkyl, halo-$C_{1-6}$-alkyl, $C_1$-$C_6$-alkyl substituted with aryl, $C_1$-$C_6$-alkyl substituted with heteroaryl, $C_1$-$C_6$-alkyl substituted with heterocyclyl;
M is selected from the group consisting of
$C_{3-10}$-cycloalkyl, aryl, heterocyclyl, heteroaryl, $C_{2-4}$alkenyl, $C_{2-4}$alkynyl, —C($R^{M1}$)=C($R^{M1}$)—C≡C—, —C($R^{M1}$)=C($R^{M1}$)—;
G is selected from the group consisting of
$R^{G2}$=$CR^{G2}$—, —C≡C—, —C≡C—C≡C—, —$CR^{G2}$=$CR^{G2}$—C≡C—, —C≡C—$CR^{G2}$=$CR^{G2}$
wherein
$R^{G2}$ is selected from the group consisting of
H, halogen atom, or $C_{1-6}$-alkyl;
Y is selected from aryl, or heteroaryl;
X is selected from the group consisting of —C(=O)—, and —S(=O).

In some embodiments of the invention and/or embodiments thereof the compound is a compound according to formula (XXX) or a stereoisomer, pharmaceutically acceptable salt, ester, solvate, or prodrug thereof, for use according to the invention, wherein
A is $NR^{A1}R^{A2}$;
L is selected from the group consisting of $CH_2$—, —$CH_2CH_2$—, —$CH_2CH_2CH_2$—, and $CH_2CH_2CH_2CH_2$—;
M is selected from the group consisting of
$C_{3-10}$-cycloalkyl, aryl, heterocyclyl, heteroaryl, $C_{2-4}$alkenyl, $C_{2-4}$alkynyl, —C($R^{M1}$)=C($R^{M1}$)—C≡C—, —C($R^{M1}$)=C($R^{M1}$)—;
G is selected from the group consisting of
—C≡C—, —C≡C—C≡C—;
Y is selected from aryl, or heteroaryl;
X is selected from the group consisting of —C(=O)—, and —S(=O);
$R^{A1}$, $R^{A2}$ are independently selected from the group consisting of
H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or
$R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXX) or a stereoisomer, pharmaceutically acceptable salt, ester, solvate, or prodrug thereof, for use according to the invention, wherein
A is $NR^{A1}R^{A2}$;
L is selected from the group consisting of —$CH_2$—, —$CH_2CH_2$—, —$CH_2CH_2CH_2$—, and —$CH_2CH_2CH_2CH_2$—;
M is selected from the group consisting of
$C_{3-10}$-cycloalkyl, aryl, heterocyclyl, heteroaryl, $C_{2-4}$alkenyl, $C_{2-4}$alkynyl, —C($R^{M1}$)=C($R^{M1}$)—C≡C—, —C($R^{M1}$)=C($R^{M1}$)—;
G is selected from the group consisting of
—C≡C—, —C≡C—C≡C—;
Y is selected from aryl, or heteroaryl;
X is selected from the group consisting of —C(=O)—, and —S(=O);
$R^{A1}$, $R^{A2}$ are independently selected from the group consisting of
H, $C_{1-6}$-alkyl, $C_{2-6}$-alkenyl, $C_{3-10}$-cycloalkyl$C_{1-6}$-alkyloxy-$C_1$-$C_6$-alkyl, $C_1$-$C_6$-alkyl substituted with aryl, $C_1$-$C_6$-alkyl substituted with heteroaryl, or
$R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$- alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXX) or a stereoisomer, pharmaceutically acceptable salt, ester, solvate, or prodrug thereof, for use according to the invention, wherein
A is $NR^{A1}R^{A2}$;
L is selected from the group consisting of —$CH_2$—, and —$CH_2CH_2$—;
M is selected from the group consisting of
aryl, heteroaryl, —C($R^{M1}$)=C($R^{M1}$)—C≡C—, —C($R^{M1}$)=C($R^{M1}$)—;
G is selected from the group consisting of
—C≡C—, —C≡C—C≡C—;
Y is aryl;
X is selected from the group consisting of —C(=O)—, and —S(=O);
$R^{A1}$, $R^{A2}$ are independently selected from the group consisting of
H, $C_{1-6}$-alkyl, $C_{2-6}$-alkenyl, $C_{3-10}$-cycloalkyl, $C_{1-6}$-alkyloxy-$C_1$-$C_6$alkyl, $C_1$-$C_6$-alkyl substituted with aryl, $C_1$-$C_6$-alkyl substituted with heteroaryl, or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXX) or a stereoisomer, pharmaceutically acceptable salt, ester, solvate, or prodrug thereof, for use according to the invention, wherein
A is $NR^{A1}R^{A2}$;
L is selected from the group consisting of $CH_2$—, and —$CH_2CH_2$—;
M is selected from the group consisting of
phenyl, thiazolyl, pyridinyl, pyrimidinyl, thiophenyl, furanyl, pyrrolyl, imidazolyl, oxazolyl, pyrazinyl, —C($R^{M1}$)=C($R^{M1}$)—C≡C—, —C($R^{M1}$)=C($R^{M1}$)—.
G is selected from the group consisting of
—C≡C—, —C≡C—C≡C—;
Y is phenyl;
X is selected from the group consisting of —C(=O)—, and —S(=O);
$R^{A1}$, $R^{A2}$ are independently selected from the group consisting of
H, $C_{1-6}$-alkyl, $C_{2-6}$-alkenyl, $C_{3-10}$-cycloalkyl, $C_{1-6}$-alkyloxy-$C_1$-$C_6$alkyl, $C_1$-$C_6$-alkyl substituted with aryl, $C_1$-$C_6$-alkyl substituted with heteroaryl, or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXX) or a stereoisomer, pharmaceutically acceptable salt, ester, solvate, or prodrug thereof, for use according to the invention, wherein
A is $NR^{A1}R^{A2}$;
L is selected from the group consisting of $CH_2$—, and —$CH_2CH_2$—;
M is selected from the group consisting of
phenyl, thiazolyl, pyridinyl, pyrimidinyl, thiophenyl, furanyl, pyrrolyl, imidazolyl, oxazolyl, pyrazinyl, —C($R^{M1}$)=C($R^{M1}$)—C≡C—, —C($R^{M1}$)=C($R^{M1}$)—.
G is selected from the group consisting of
—C≡C—, —C≡C—C≡C—;
Y is phenyl;
X is selected from the group consisting of —C(=O)—, and —S(=O);
$R^{A1}$ is selected from the group consisting of
$C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl,
$R^{A2}$ is hydrogen or $C_{1-6}$alkyl
or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, $SO_2NR^{A3}R^{A4}$, —C(=O)$NR^{A3}R^{A4}$, $C_{1-6}$-alkyl substituted with hydroxy;

wherein
R$^{43}$, R$^{44}$, R$^{45}$ are independently chosen from
H, or C$_{1-6}$-alkyl.

In some embodiments of the invention and/or embodiments thereof the compound is a compound according to formula

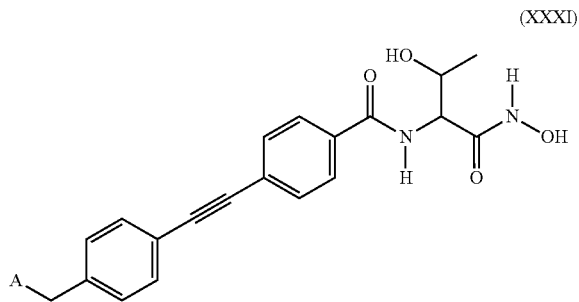

(XXXI)

or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A, is defined as in any of the embodiments described herein.

In some embodiments of the invention and/or embodiments thereof the compound is a compound according to formula (XXXI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein
A is selected from the group consisting of
H, C$_{1-6}$-alkyl, C$_{2-6}$-alkenyl, C$_{2-6}$-alkynyl, C$_{3-10}$-cycloalkyl, aryl, heterocyclyl, heteroaryl, NR$^{41}$R$^{42}$, halo-C$_{1-6}$-alkyl, amine, nitro, C$_{1-6}$-alkyloxy, C=N—OH, C$_{1-6}$-alkyloxy-C$_1$-C$_6$alkyl,
wherein
R$^{41}$, R$^{42}$ are independently selected from the group consisting of
H, C$_{1-8}$-alkyl, C$_{2-6}$-alkenyl, C$_{2-6}$-alkynyl, C$_{3-10}$-cycloalkyl, aryl, heterocyclyl, heteroaryl, C$_{1-6}$-alkyloxy-C$_1$-C$_6$-alkyl, C$_1$-C$_6$-alkyl substituted with aryl, C$_1$-C$_6$-alkyl substituted with heteroaryl, C$_1$-C$_6$-alkyl substituted with heterocyclyl, or
R$^{E1}$, R$^{E2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, alkynyl, cycloalkyl, aryl, heterocyclyl, heteroaryl, alkyloxy or the heterocyclic ring formed by R$^{41}$, R$^{42}$ together with the N atom to which they are attached is optionally substituted with a substituent selected from the group consisting of
C$_{1-6}$-alkyl, C$_{3-8}$-cycloalky, C$_{1-6}$-alkyloxy, —NR$^{43}$R$^{44}$, carbonyl, —C(=O)—OR$^{45}$, halogen atom, amino, C$_{1-6}$-alkyl substituted with halo, C$_{1-6}$-alkyloxy-C$_1$-C$_6$—, aryl, heteroaryl, C$_1$-C$_6$-alkyl substituted with aryl, cyano, hydroxy, —SR$^{45}$, —SO$_2$R$^{45}$, —C(=O)NR$^{43}$R$^{44}$, C$_{1-6}$-alkyl substituted with hydroxy;
wherein
R$^{43}$, R$^{44}$, R$^{45}$ are independently chosen from
H, or C$_{1-6}$-alkyl;

In some embodiments of the invention and/or embodiments thereof the compound is a compound according to formula (XXXI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein
A is selected from the group consisting of
H, C$_{1-6}$-alkyl, C$_{2-6}$-alkenyl, aryl, heterocyclyl, heteroaryl, NR$^{41}$R$^{42}$, halo-C$_{1-6}$-alkyl, amine, nitro, C$_{1-6}$-alkyloxy, C=N—OH, C$_{1-6}$-alkyloxy-C$_1$-C$_6$;

In some embodiments of the invention and/or embodiments thereof the compound is a compound according to formula (XXXI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein
A is NR$^{41}$R$^{42}$;
R$^{41}$, R$^{42}$ are independently selected from the group consisting of
H, C$_{1-6}$-alkyl, C$_{2-6}$-alkenyl, C$_{2-6}$-alkynyl, C$_{3-10}$-cycloalkyl, aryl, heterocyclyl, heteroaryl, C$_{1-6}$-alkyloxy-C$_1$-C$_6$-alkyl, C$_1$-C$_6$-alkyl substituted with aryl, C$_1$-C$_6$-alkyl substituted with heteroaryl, C$_1$-C$_6$-alkyl substituted with heterocyclyl, or
R$^{41}$, R$^{42}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, alkynyl, cycloalkyl, aryl, heterocyclyl, heteroaryl, alkyloxy or the heterocyclic ring formed by R$^{41}$, R$^{42}$ together with the N atom to which they are attached is optionally substituted with a substituent selected from the group consisting of
C$_{1-6}$-alkyl, C$_{3-8}$-cycloalky, C$_{1-6}$-alkyloxy, —NR$^{43}$R$^{44}$, carbonyl, —C(=O)—OR$^{45}$, halogen atom, amino, C$_{1-6}$-alkyl substituted with halo, C$_{1-6}$-alkyloxy-C$_1$-C$_6$alkyl, aryl, heteroaryl, C$_1$-C$_6$-alkyl substituted with aryl, cyano, hydroxy, —SR$^{45}$, —SO$_2$R$^{45}$, —C(=O)NR$^{43}$R$^{44}$, C$_{1-6}$-alkyl substituted with hydroxy;
wherein
R$^{43}$, R$^{44}$, R$^{45}$ are independently chosen from
H, or C$_{1-6}$-alkyl.

In some embodiments of the invention and/or embodiments thereof the compound is a compound according to formula (XXXI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein
A is NR$^{41}$R$^{42}$;
R$^{41}$, R$^{42}$ are independently selected from the group consisting of
H, C$_{1-6}$-alkyl, C$_{2-6}$-alkenyl, C$_{3-10}$-cycloalkylC$_{1-6}$-alkyloxy-C$_1$-C$_6$-alkyl, C$_1$-C$_6$-alkyl substituted with aryl, C$_1$-C$_6$-alkyl substituted with heteroaryl, or
R$^{41}$, R$^{42}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, cycloalkyl, aryl, heteroaryl, or alkyloxy or the heterocyclic ring formed by R$^{41}$, R$^{42}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(═O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(═O)$NR^{A3}R^{A4}$, $C_{1-6}$-alkyl substituted with hydroxy; wherein $R^{A3}$, $R^{A4}$, $R^{A5}$ are independently chosen from
H, or $C_{1-6}$-alkyl.

In some embodiments of the invention and/or embodiments thereof the compound is a compound according to formula (XXXI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein
A is $NR^{A1}R^{A2}$;
$R^{A1}$, $R^{A2}$ are independently selected from the group consisting of
H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(═O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(═O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXXI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein
A is $NR^{A1}R^{A2}$;
$R^{A1}$, $R^{A2}$ are independently selected from the group consisting of
H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(═O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(═O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXXI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein
A is $NR^{A1}$, $R^{A2}$;
$R^{A1}$ is selected from the group consisting of
$C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl,
$R^{A2}$ is hydrogen or $C_{1-6}$alkyl
or
$R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;
wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(═O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(═O)$NR^{A3}R^{A4}$, $C_{1-6}$-alkyl substituted with hydroxy;
wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXXI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$ and $NR^{A1}R^{A2}$ is selected from the group consisting of (a-1)-(a-143) as defined herein.

In some embodiments of the invention and/or embodiments thereof the compound is a compound according to formula (XXXI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$ and $NR^{A1}R^{A2}$ is selected from the group consisting of (a-1), (a-3), (a-5), (a-9), (a-20), (a-21), (a-22), (a-23), (a-24), (a-25), (a-26), (a-27), (a-28), (a-29), (a-30), (a-31), (a-33), (a-34), (a-35), (a-36), (a-42), (a-43), (a-46), (a-55), (a-64), (a-65), (a-82), (a-83), (a-84), (a-98), (a-99), (a-100), (a-101), (a-102), (a-103), (a-104), (a-105), (a-106), (a-107), (a-108), (a-109), (a-110), (a-111), (a-112), (a-113), (a-114), (a-115), (a-116), (a-117), (a-118), (a-119), (a-120), (a-121), (a-122), (a-123), (a-124), (a-125), (a126), (a-127), (a-128), (a-129), (a-130), and (a-131).

In some embodiments of the invention and/or embodiments thereof the compound is a compound according to formula (XXXI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$ and $NR^{A1}R^{A2}$ is selected from the group consisting of (a-1), (a-3), (a-5), (a-9), (a-20), (a-34), (a-35), (a-36), (a-42), (a-46), (a-55), (a-64), (a-65), (a-98), (a-99), (a-100), (a-103), (a-104), (a-105), (a-106), (a-107), (a-108), (a-120), (a-121), (a-125), (a126), and (a-128).

In some embodiments of the invention and/or embodiments thereof the compound is a compound according to formula (XXXI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$ and $NR^{A1}R^{A2}$ is selected from the group consisting of (a-1), (a-3), (a-5), (a-9), (a-20), (a-34), (a-35), (a-36), (a-42), (a-46), (a-55), (a-64), and (a-65).

In some embodiments of the invention and/or embodiments thereof the compound is a compound according to formula (XXXI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$ and $NR^{A1}R^{A2}$ is selected from the group consisting of (a-1), (a-3), (a-5), (a-20), (a-34), (a-35), (a-36), (a-46), (a-55), and (a-65).

In some embodiments of the invention and/or embodiments thereof the compound is a compound according to formula

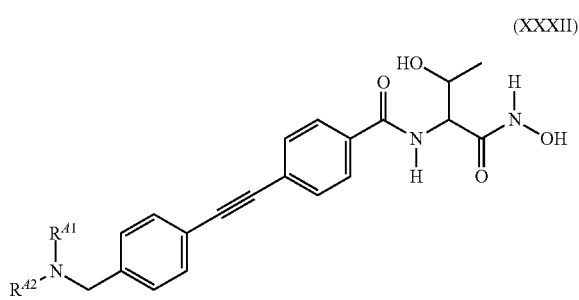

(XXXII)

or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{A1}$, $R^{A2}$, are defined as in any of the embodiments described herein.

In some embodiments of the invention and/or embodiments thereof the compound is a compound according to formula (XXXII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{A1}$, $R^{A2}$ are independently selected from the group consisting of H, $C_{1-6}$ alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{E1}$, $R^{E2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(═O)—$OR^{A5}$, halogen atom, amino, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, —$SR^{A5}$, —$SO_2R^{A5}$, —C(═O)$NR^{A3}R^{A4}$, $C_{1-6}$-alkyl substituted with hydroxy;

wherein $R^{A3}$, $R^{A4}$, $R^{A5}$ are independently chosen from H, or $C_{1-6}$-alkyl;

In some embodiments of the invention and/or embodiments thereof the compound is a compound according to formula (XXXII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{A1}$, $R^{A2}$ are independently selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —O(═O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —O(═O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXXII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{A1}$, $R^{A2}$ are independently selected from the group consisting of H, $C_{1-6}$-alkyl, $C_{2-6}$-alkenyl, $C_{3-10}$-cycloalkyl$C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —O(=O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —O(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXXII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{A1}$, $R^{A2}$ are independently selected from the group consisting of H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —O(=O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —O(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXXII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{A1}$, $R^{A2}$ are independently selected from the group consisting of H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXXII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{A1}$ is selected from the group consisting of $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, $R^{A2}$ is hydrogen or $C_{1-6}$alkyl or $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXXII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $NR^{A1}R^{A2}$ is selected from the group consisting of (a-1)-(a-143) as defined herein.

In some embodiments of the invention and/or embodiments thereof the compound is a compound according to formula (XXXII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $NR^{41}R^{42}$ is selected from the group consisting of (a-1), (a-3), (a-5), (a-9), (a-20), (a-21), (a-22), (a-23), (a-24), (a-25), (a-26), (a-27), (a-28), (a-29), (a-30), (a-31), (a-33), (a-34), (a-35), (a-36), (a-42), (a-43), (a-46), (a-55), (a-64), (a-65), (a-82), (a-83), (a-84), (a-98), (a-99), (a-100), (a-101), (a-102), (a-103), (a-104), (a-105), (a-106), (a-107), (a-108), (a-109), (a-110), (a-111), (a-112), (a-113), (a-114), (a-115), (a-116), (a-117), (a-118), (a-119), (a-120), (a-121), (a-122), (a-123), (a-124), (a-125), (a126), (a-127), (a-128), (a-129), (a-130), and (a-131).

In some embodiments of the invention and/or embodiments thereof the compound is a compound according to formula (XXXII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $NR^{41}R^{42}$ is selected from the group consisting of (a-1), (a-3), (a-5), (a-9), (a-20), (a-34), (a-35), (a-36), (a-42), (a-46), (a-55), (a-64), (a-65), (a-98), (a-99), (a-100), (a-103), (a-104), (a-105), (a-106), (a-107), (a-108), (a-120), (a-121), (a-125), (a126), and (a-128).

In some embodiments of the invention and/or embodiments thereof the compound is a compound according to formula (XXXII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $NR^{41}R^{42}$ is selected from the group consisting of (a-1), (a-3), (a-5), (a-9), (a-20), (a-34), (a-35), (a-36), (a-42), (a-46), (a-55), (a-64), and (a-65).

In some embodiments of the invention and/or embodiments thereof the compound is a compound according to formula (XXXII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $NR^{41}R^{42}$ is selected from the group consisting of (a-1), (a-3), (a-5), (a-20), (a-34), (a-35), (a-36), (a-46), (a-55), and (a-65).

In some embodiments of the invention and/or embodiments thereof the compound is a compound according to formula (XXXIII)

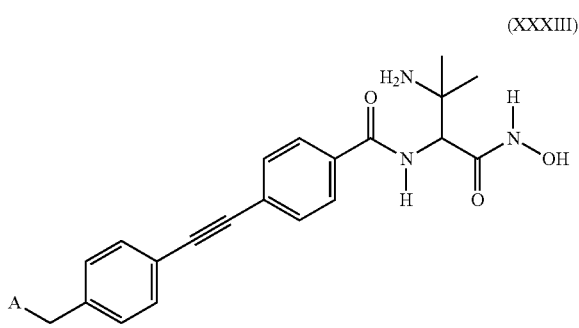

or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A, is defined as in any of the embodiments described herein.

In some embodiments of the invention and/or embodiments thereof the compound is a compound according to formula (XXXIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $NR^{41}R^{42}$, halo-$C_{1-6}$-alkyl, amine, nitro, $C_{1-6}$-alkyloxy, C=N—OH, $C_{1-6}$-alkyloxy-$C_1$-$C_6$-alkyl, wherein $R^{41}$, $R^{42}$ are independently selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{E1}$, $R^{E2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{41}$, $R^{42}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{43}R^{44}$, carbonyl, —C(=O)—$OR^{45}$, halogen atom, amino, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, —$SR^{45}$, —$SO_2R^{45}$, —C(=O)$NR^{43}R^{44}$, $C_{1-6}$-alkyl substituted with hydroxy;

wherein $R^{43}$, $R^{44}$, $R^{45}$ are independently chosen from

H, or $C_{1-6}$-alkyl;

In some embodiments of the invention and/or embodiments thereof the compound is a compound according to formula (XXXIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is selected from the group consisting of H, $C_{1-6}$-alkyl, $C_{2-6}$-alkenyl, aryl, heterocyclyl, heteroaryl, $NR^{41}R^{42}$, halo-$C_{1-6}$-alkyl, amine, nitro, $C_{1-6}$-alkyloxy, C=N—OH, $C_{1-6}$-alkyloxy-$C_1$-$C_6$;

In some embodiments of the invention and/or embodiments thereof the compound is a compound according to formula (XXXIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{41}R^{42}$;

$R^{41}$, $R^{42}$ are independently selected from the group consisting of

H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXXIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$;

$R^{A1}$, $R^{A2}$ are independently selected from the group consisting of

H, $C_{1-6}$-alkyl, $C_{2-6}$-alkenyl, $C_{3-10}$-cycloalkyl$C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXXIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$;

$R^{A1}$, $R^{A2}$ are independently selected from the group consisting of

H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXXIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$;

$R^{A1}$, $R^{A2}$ are independently selected from the group consisting of

H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl; wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —O(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXXIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$;

$R^{A1}$ is selected from the group consisting of $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, $R^{A2}$ is hydrogen or $C_{1-6}$alkyl or $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{41}$, $R^{42}$ with the N atom to which they are attached is optionally substituted with a substituent selected from the group consisting of
$C_{1-6}$-alkyl, $C_{3-8}$-cycloalky, $C_{1-6}$-alkyloxy, —$NR^{43}R^{44}$, carbonyl, —C(=O)—$OR^{45}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{45}$, —$SO_2R^{45}$, —C(=O)$NR^{43}R^{44}$, $C_{1-6}$-alkyl substituted with hydroxy;
wherein
$R^{43}$, $R^{44}$, $R^{45}$ are independently chosen from
H, or $C_{1-6}$-alkyl.

In some embodiments of the invention and/or embodiments thereof the compound is a compound according to formula (XXXIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{41}R^{42}$ and $NR^{41}R^{42}$ is selected from the group consisting of (a-1)-(a-143) as defined herein.

In some embodiments of the invention and/or embodiments thereof the compound is a compound according to formula (XXXIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{41}R^{42}$ and $NR^{41}R^{42}$ is selected from the group consisting of (a-1), (a-3), (a-5), (a-9), (a-20), (a-21), (a-22), (a-23), (a-24), (a-25), (a-26), (a-27), (a-28), (a-29), (a-30), (a-31), (a-33), (a-34), (a-35), (a-36), (a-42), (a-43), (a-46), (a-55), (a-64), (a-65), (a-82), (a-83), (a-84), (a-98), (a-99), (a-100), (a-101), (a-102), (a-103), (a-104), (a-105), (a-106), (a-107), (a-108), (a-109), (a-110), (a-111), (a-112), (a-113), (a-114), (a-115), (a-116), (a-117), (a-118), (a-119), (a-120), (a-121), (a-122), (a-123), (a-124), (a-125), (a126), (a-127), (a-128), (a-129), (a-130), and (a-131).

In some embodiments of the invention and/or embodiments thereof the compound is a compound according to formula (XXXIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{41}R^{42}$ and $NR^{41}R^{42}$ is selected from the group consisting of (a-1), (a-3), (a-5), (a-9), (a-20), (a-34), (a-35), (a-36), (a-42), (a-46), (a-55), (a-64), (a-65), (a-98), (a-99), (a-100), (a-103), (a-104), (a-105), (a-106), (a-107), (a-108), (a-120), (a-121), (a-125), (a126), and (a-128).

In some embodiments of the invention and/or embodiments thereof the compound is a compound according to formula (XXXIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{41}R^{42}$ and $NR^{41}R^{42}$ is selected from the group consisting of (a-1), (a-3), (a-5), (a-9), (a-20), (a-34), (a-35), (a-36), (a-42), (a-46), (a-55), (a-64), and (a-65).

In some embodiments of the invention and/or embodiments thereof the compound is a compound according to formula (XXXIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{41}R^{42}$ and $NR^{41}R^{42}$ is selected from the group consisting of (a-1), (a-3), (a-5), (a-20), (a-34), (a-35), (a-36), (a-46), (a-55), and (a-65).

In some embodiments of the invention and/or embodiments thereof the compound is a compound according to formula

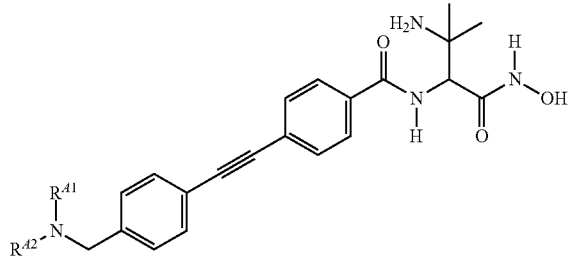

(XXXIV)

or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{41}$, K, are defined as in any of the embodiments described herein.

In some embodiments of the invention and/or embodiments thereof the compound is a compound according to formula (XXXIV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{41}$, $R^{42}$ are independently selected from the group consisting of
H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or
$R^{E1}$, $R^{E2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;
wherein the alkyl, alkenyl, alkynyl, cycloalkyl, aryl, heterocyclyl, heteroaryl, alkyloxy or the heterocyclic ring formed by $R^{41}$, $R^{42}$ together with the N atom to which they are attached is optionally substituted with a substituent selected from the group consisting of
$C_{1-6}$-alkyl, $C_{3-8}$-cycloalky, $C_{1-6}$-alkyloxy, —$NR^{43}R^{44}$, carbonyl, —C(=O)—$OR^{45}$, halogen atom, amino, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, —$SR^{45}$, —$SO_2R^{45}$, —C(=O)$NR^{43}R^{44}$, $C_{1-6}$-alkyl substituted with hydroxy; wherein
$R^{43}$, $R^{44}$, $R^{45}$ are independently chosen from H, or $C_{1-6}$-alkyl;

In some embodiments of the invention and/or embodiments thereof the compound is a compound according to formula (XXXIV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{41}$, $R^{42}$ are independently selected from the group consisting of H, $C_{1-6}$ alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{41}$, $R^{42}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{41}$, $R^{42}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{43}R^{44}$, carbonyl, —C(=O)—$OR^{45}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{45}$, —$SO_2R^{45}$, —C(=O)$NR^{43}R^{44}$, $C_{1-6}$-alkyl substituted with hydroxy;

wherein $R^{43}$, $R^{44}$, $R^{45}$ are independently chosen from

H, or $C_{1-6}$-alkyl.

In some embodiments of the invention and/or embodiments thereof the compound is a compound according to formula (XXXIV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{41}$, $R^{42}$ are independently selected from the group consisting of H, $C_{1-5}$-alkyl, $C_{2-6}$-alkenyl, $C_{3-10}$-cycloalkyl$C_{1-6}$-alkyloxy-$C_1$-$C_6$-alkyl, $C_1$-$C_6$-alkyl substituted with aryl, $C_1$-$C_6$-alkyl substituted with heteroaryl, or $R^{41}$, $R^{42}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, cycloalkyl, aryl, heteroaryl, or alkyloxy or the heterocyclic ring formed by $R^{41}$, $R^{42}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{43}R^{44}$, carbonyl, —C(=O)—$OR^{45}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{45}$, —$SO_2R^{45}$, —C(=O)$NR^{43}R^{44}$, $C_{1-6}$-alkyl substituted with hydroxy;

wherein $R^{43}$, $R^{44}$, $R^{45}$ are independently chosen from

H, or $C_{1-6}$-alkyl.

In some embodiments of the invention and/or embodiments thereof the compound is a compound according to formula (XXXIV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{41}$, $R^{42}$ are independently selected from the group consisting of H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or $R^{41}$, $R^{42}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{41}$, $R^{42}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{43}R^{44}$, carbonyl, —C(=O)—$OR^{45}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{45}$, —$SO_2R^{45}$, —C(=O)$NR^{43}R^{44}$, $C_{1-6}$-alkyl substituted with hydroxy;

wherein $R^{43}$, $R^{44}$, $R^{45}$ are independently chosen from

H, or $C_{1-6}$-alkyl.

In some embodiments of the invention and/or embodiments thereof the compound is a compound according to formula (XXXIV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{41}$, $R^{42}$ are independently selected from the group consisting of H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or $R^{41}$, $R^{42}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{41}$, $R^{42}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{43}R^{44}$, carbonyl, —C(=O)—$OR^{45}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{45}$, —$SO_2R^{45}$, —C(=O)$NR^{43}R^{44}$, $C_{1-6}$ alkyl substituted with hydroxy;

wherein $R^{43}$, $R^{44}$, $R^{45}$ are independently chosen from

H, or $C_{1-6}$-alkyl.

In some embodiments of the invention and/or embodiments thereof the compound is a compound according to formula (XXXIV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{41}$ is selected from the group consisting of $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, $R^{42}$ is hydrogen or $C_{1-6}$alkyl or $R^{41}$, $R^{42}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{41}$, $R^{42}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{43}R^{44}$, carbonyl, —C(=O)—$OR^{45}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{45}$, —$SO_2R^{45}$, —C(=O)$NR^{43}R^{44}$, $C_{1-6}$-alkyl substituted with hydroxy;

wherein $R^{43}$, $R^{44}$, $R^{45}$ are independently chosen from

H, or $C_{1-6}$-alkyl.

In some embodiments of the invention and/or embodiments thereof the compound is a compound according to formula (XXXIV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $NR^{41}R^{42}$ is selected from the group consisting of (a-1)-(a-143) as defined herein.

In some embodiments of the invention and/or embodiments thereof the compound is a compound according to formula (XXXIV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $NR^{41}R^{42}$ is selected from the group consisting of (a-1), (a-3), (a-5), (a-9), (a-20), (a-21), (a-22), (a-23), (a-24), (a-25), (a-26), (a-27), (a-28), (a-29), (a-30), (a-31), (a-33), (a-34), (a-35), (a-36), (a-42), (a-43), (a-46), (a-55), (a-64), (a-65), (a-82), (a-83), (a-84), (a-98), (a-99), (a-100), (a-101), (a-102), (a-103), (a-104), (a-105), (a-106), (a-107), (a-108), (a-109), (a-110), (a-111), (a-112), (a-113), (a-114), (a-115), (a-116), (a-117), (a-118), (a-119), (a-120), (a-121), (a-122), (a-123), (a-124), (a-125), (a126), (a-127), (a-128), (a-129), (a-130), and (a-131).

In some embodiments of the invention and/or embodiments thereof the compound is a compound according to formula (XXXIV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $NR^{41}R^{42}$ is selected from the group consisting of (a-1), (a-3), (a-5), (a-9), (a-20), (a-34), (a-35), (a-36), (a-42), (a-46), (a-55), (a-64), (a-65), (a-98), (a-99), (a-100), (a-103), (a-104), (a-105), (a-106), (a-107), (a-108), (a-120), (a-121), (a-125), (a126), and (a-128).

In some embodiments of the invention and/or embodiments thereof the compound is a compound according to formula (XXXIV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $NR^{41}R^{42}$ is selected from the group consisting of (a-1), (a-3), (a-5), (a-9), (a-20), (a-34), (a-35), (a-36), (a-42), (a-46), (a-55), (a-64), and (a-65).

In some embodiments of the invention and/or embodiments thereof the compound is a compound according to formula (XXXIV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $NR^{41}R^{42}$ is selected from the group consisting of (a-1), (a-3), (a-5), (a-20), (a-34), (a-35), (a-36), (a-46), (a-55), and (a-65).

In some embodiments of the invention and/or embodiments thereof the compound is a compound according to formula

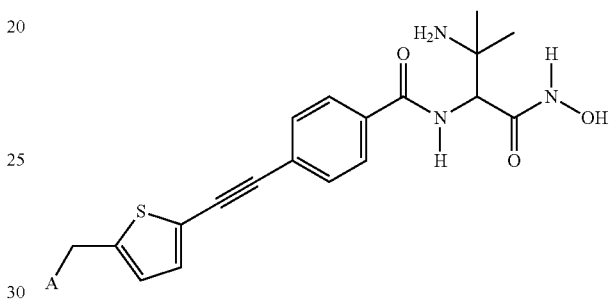

(XXXV)

or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A, is defined as in any of the embodiments described herein.

In some embodiments of the invention and/or embodiments thereof the compound is a compound according to formula (XXXV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $NR^{41}R^{42}$, halo-$C_{1-6}$-alkyl, amine, nitro, $C_{1-6}$-alkyloxy, C=N—OH, $C_{1-6}$-alkyloxy-$C_1$-$C_6$-alkyl, wherein $R^{41}$, $R^{42}$ are independently selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{E1}$, $R^{E2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{41}$, $R^{42}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, —$SR^{A5}$, —$SO_2R^{A5}$, —C(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl;

In some embodiments of the invention and/or embodiments thereof the compound is a compound according to formula (XXXV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is selected from the group consisting of H, $C_{1-6}$-alkyl, $C_{2-6}$-alkenyl, aryl, heterocyclyl, heteroaryl, $NR^{A1}R^{A2}$, halo-$C_{1-6}$-alkyl, amine, nitro, $C_{1-6}$-alkyloxy, C=N—OH, $C_{1-6}$-alkyloxy-$C_1$-$C_6$;

In some embodiments of the invention and/or embodiments thereof the compound is a compound according to formula (XXXV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$;

$R^{A1}$, $R^{A2}$ are independently selected from the group consisting of

H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXXV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$;

$R^{A1}$, $R^{A2}$ are independently selected from the group consisting of

H, $C_{1-6}$-alkyl, $C_{2-6}$-alkenyl, $C_{3-10}$-cycloalkyl$C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXXV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$;

$R^{A1}$, $R^{A2}$ are independently selected from the group consisting of

H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(=O)$NR^{A3}R^{A4}$, $C_{1-6}$-alkyl substituted with hydroxy; wherein $R^{A3}$, $R^{A4}$, $R^{A5}$ are independently chosen from H, or $C_{1-6}$-alkyl.

In some embodiments of the invention and/or embodiments thereof the compound is a compound according to formula (XXXV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$;

$R^{A1}$, $R^{A2}$ are independently selected from the group consisting of

H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXXV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$;

$R^{A1}$ is selected from the group consisting of $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, $R^{A2}$ is hydrogen or $C_{1-6}$alkyl or $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{A1}$, $R^{A2}$ with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXXV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$ and $NR^{A1}R^{A2}$ is selected from the group consisting of (a-1)-(a-143) as defined herein.

In some embodiments of the invention and/or embodiments thereof the compound is a compound according to formula (XXXV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$ and $NR^{A1}R^{A2}$ is selected from the group consisting of (a-1), (a-3), (a-5), (a-9), (a-20), (a-21), (a-22), (a-23), (a-24), (a-25), (a-26), (a-27), (a-28), (a-29), (a-30), (a-31), (a-33), (a-34), (a-35), (a-36), (a-42), (a-43), (a-46), (a-55), (a-64), (a-65), (a-82), (a-83), (a-84), (a-98), (a-99), (a-100), (a-101), (a-102), (a-103), (a-104), (a-105), (a-106), (a-107), (a-108), (a-109), (a-110), (a-111), (a-112), (a-113), (a-114), (a-115), (a-116), (a-117), (a-118), (a-119), (a-120), (a-121), (a-122), (a-123), (a-124), (a-125), (a126), (a-127), (a-128), (a-129), (a-130), and (a-131).

In some embodiments of the invention and/or embodiments thereof the compound is a compound according to formula (XXXV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$ and $NR^{A1}R^{A2}$ is selected from the group consisting of (a-1), (a-3), (a-5), (a-9), (a-20), (a-34), (a-35), (a-36), (a-42), (a-46), (a-55), (a-64), (a-65), (a-98), (a-99), (a-100), (a-103), (a-104), (a-105), (a-106), (a-107), (a-108), (a-120), (a-121), (a-125), (a126), and (a-128).

In some embodiments of the invention and/or embodiments thereof the compound is a compound according to formula (XXXV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$ and $NR^{A1}R^{A2}$ is selected from the group consisting of (a-1), (a-3), (a-5), (a-9), (a-20), (a-34), (a-35), (a-36), (a-42), (a-46), (a-55), (a-64), and (a-65).

In some embodiments of the invention and/or embodiments thereof the compound is a compound according to formula (XXXV) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$ and $NR^{A1}R^{A2}$ is selected from the group consisting of (a-1), (a-3), (a-5), (a-20), (a-34), (a-35), (a-36), (a-46), (a-55), and (a-65).

In some embodiments of the invention and/or embodiments thereof the compound is a compound according to formula

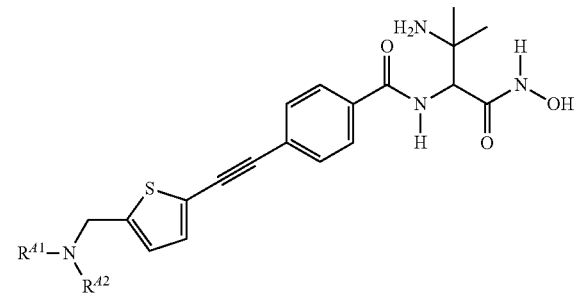

(XXXVI)

or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{A1}$, $R^{A2}$, are defined as in any of the embodiments described herein.

In some embodiments of the invention and/or embodiments thereof the compound is a compound according to formula (XXXVI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{A1}$, $R^{A2}$ are independently selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{E1}$, $R^{E2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, —$SR^{A5}$, —$SO_2R^{A5}$, —C(=O)$NR^{A3}R^{A4}$, $C_{1-6}$-alkyl substituted with hydroxy;

wherein $R^{A3}$, $R^{A4}$, $R^{A5}$ are independently chosen from H, or $C_{1-6}$-alkyl;

In some embodiments of the invention and/or embodiments thereof the compound is a compound according to formula (XXXVI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{A1}$, $R^{A2}$ are independently selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(=O)$NR^{A3}R^{A4}$, $C_{1-6}$-alkyl substituted with hydroxy;

wherein $R^{A3}$, $R^{A4}$, $R^{A5}$ are independently chosen from H, or $C_{1-6}$-alkyl.

In some embodiments of the invention and/or embodiments thereof the compound is a compound according to formula (XXXVI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{A1}$, $R^{A2}$ are independently selected from the group consisting of H, $C_{1-6}$-alkyl, $C_{2-6}$-alkenyl, $C_{3-10}$-cycloalkyl$C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(=O)$NR^{A3}R^{A4}$, $C_{1-6}$-alkyl substituted with hydroxy;

wherein $R^{A3}$, $R^{A4}$, $R^{A5}$ are independently chosen from H, or $C_{1-6}$-alkyl.

In some embodiments of the invention and/or embodiments thereof the compound is a compound according to formula (XXXVI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{A1}$, $R^{A2}$ are independently selected from the group consisting of H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(=O)$NR^{A3}R^{A4}$, $C_{1-6}$-alkyl substituted with hydroxy;

wherein $R^{A3}$, $R^{A4}$, $R^{A5}$ are independently chosen from H, or $C_{1-6}$-alkyl.

In some embodiments of the invention and/or embodiments thereof the compound is a compound according to formula (XXXVI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{41}$, $R^{42}$ are independently selected from the group consisting of H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or $R^{41}$, $R^{42}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{41}$, $R^{42}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{43}R^{44}$, carbonyl, —C(=O)—$OR^{45}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{45}$, —$SO_2R^{45}$, —C(=O)$NR^{43}R^{44}$, $C_{1-6}$-alkyl substituted with hydroxy;

wherein $R^{43}$, $R^{44}$, $R^{45}$ are independently chosen from

H, or $C_{1-6}$-alkyl.

In some embodiments of the invention and/or embodiments thereof the compound is a compound according to formula (XXXVI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{41}$ is selected from the group consisting of $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, $R^{42}$ is hydrogen or $C_{1-6}$alkyl or $R^{41}$, $R^{42}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{41}$, $R^{42}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{43}R^{44}$, carbonyl, —C(=O)—$OR^{45}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{45}$, —$SO_2R^{45}$, —C(=O)$NR^{43}R^{44}$, $C_{1-6}$-alkyl substituted with hydroxy;

wherein $R^{43}$, $R^{44}$, $R^{45}$ are independently chosen from

H, or $C_{1-6}$-alkyl.

In some embodiments of the invention and/or embodiments thereof the compound is a compound according to formula (XXXVI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $NR^{41}R^{42}$ is selected from the group consisting of (a-1)-(a-143) as defined herein.

In some embodiments of the invention and/or embodiments thereof the compound is a compound according to formula (XXXVI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $NR^{41}R^{42}$ is selected from the group consisting of (a-1), (a-3), (a-5), (a-9), (a-20), (a-21), (a-22), (a-23), (a-24), (a-25), (a-26), (a-27), (a-28), (a-29), (a-30), (a-31), (a-33), (a-34), (a-35), (a-36), (a-42), (a-43), (a-46), (a-55), (a-64), (a-65), (a-82), (a-83), (a-84), (a-98), (a-99), (a-100), (a-101), (a-102), (a-103), (a-104), (a-105), (a-106), (a-107), (a-108), (a-109), (a-110), (a-111), (a-112), (a-113), (a-114), (a-115), (a-116), (a-117), (a-118), (a-119), (a-120), (a-121), (a-122), (a-123), (a-124), (a-125), (a126), (a-127), (a-128), (a-129), (a-130), and (a-131).

In some embodiments of the invention and/or embodiments thereof the compound is a compound according to formula (XXXVI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $NR^{41}R^{42}$ is selected from the group consisting of (a-1), (a-3), (a-5), (a-9), (a-20), (a-34), (a-35), (a-36), (a-42), (a-46), (a-55), (a-64), (a-65), (a-98), (a-99), (a-100), (a-103), (a-104), (a-105), (a-106), (a-107), (a-108), (a-120), (a-121), (a-125), (a126), and (a-128).

In some embodiments of the invention and/or embodiments thereof the compound is a compound according to formula (XXXVI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $NR^{41}R^{42}$ is selected from the group consisting of (a-1), (a-3), (a-5), (a-9), (a-20), (a-34), (a-35), (a-36), (a-42), (a-46), (a-55), (a-64), and (a-65).

In some embodiments of the invention and/or embodiments thereof the compound is a compound according to formula (XXXVI) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $NR^{41}R^{42}$ is selected from the group consisting of (a-1), (a-3), (a-5), (a-20), (a-34), (a-35), (a-36), (a-46), (a-55), and (a-65).

In some embodiments of the invention and/or embodiments thereof the compound is a compound according to formula

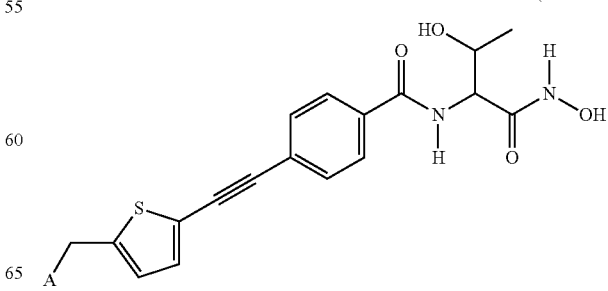

(XXXVII)

or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A, L, M, G, Y, and X, are defined as in any of the embodiments described herein.

In some embodiments of the invention and/or embodiments thereof the compound is a compound according to formula (XXXVII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $NR^{A1}R^{A2}$, halo-$C_{1-6}$-alkyl, amine, nitro, $C_{1-6}$-alkyloxy, C=N—OH, $C_{1-6}$-alkyloxy-$C_1$-$C_6$-alkyl, wherein $R^{A1}$, $R^{A2}$ are independently selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heterocyclyl, or $R^{E1}$, $R^{E2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, —$SR^{A5}$, —$SC_2R^{A5}$, —C(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl;

In some embodiments of the invention and/or embodiments thereof the compound is a compound according to formula (XXXVII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is selected from the group consisting of H, $C_{1-6}$-alkyl, $C_{2-6}$-alkenyl, aryl, heterocyclyl, heteroaryl, $NR^{A1}R^{A2}$, halo-$C_{1-6}$-alkyl, amine, nitro, $C_{1-6}$-alkyloxy, C=N—OH, $C_{1-6}$-alkyloxy-$C_1$-$C_6$;

In some embodiments of the invention and/or embodiments thereof the compound is a compound according to formula (XXXVII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$;

$R^{A1}$, $R^{A2}$ are independently selected from the group consisting of

H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXXVII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$; and $R^{A1}$, $R^{A2}$ are independently selected from the group consisting of H, $C_{1-6}$-alkyl, $C_{2-6}$-alkenyl, $C_{3-10}$-cycloalkyl$C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —C(=O)—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —C(=O)$NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXXVII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$; and $R^{A1}$, $R^{A2}$ are independently selected from the group consisting of H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —$C(=O)$—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —$C(=O)NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXXVII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$; and $R^{A1}$, $R^{A2}$ are independently selected from the group consisting of H, $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —$C(=O)$—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —$C(=O)NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXXVII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$; and $R^{A1}$ is selected from the group consisting of $C_{1-6}$-alkyl, $C_{2-6}$-alkenyl, $C_{3-10}$-cycloalkyl, $C_{1-6}$-alkyloxy-$C_1$-$C_6$-alkyl, $C_1$-$C_6$-alkyl substituted with aryl, $C_1$-$C_6$-alkyl substituted with heteroaryl, $R^{A2}$ is hydrogen or $C_{1-6}$alkyl or $R^{A1}$, $R^{A2}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, —$NR^{A3}R^{A4}$, carbonyl, —$C(=O)$—$OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —$SR^{A5}$, —$SO_2R^{A5}$, —$C(=O)NR^{A3}R^{A4}$, $C_{1-6}$-alkyl substituted with hydroxy;

wherein $R^{A3}$, $R^{A4}$, $R^{A5}$ are independently chosen from

H, or $C_{1-6}$-alkyl.

In some embodiments of the invention and/or embodiments thereof the compound is a compound according to formula (XXXVII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$ and $NR^{A1}R^{A2}$ is selected from the group consisting of (a-1)-(a-143) as defined herein.

In some embodiments of the invention and/or embodiments thereof the compound is a compound according to formula (XXXVII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$ and $NR^{A1}R^{A2}$ is selected from the group consisting of (a-1), (a-3), (a-5), (a-9), (a-20), (a-21), (a-22), (a-23), (a-24), (a-25), (a-26), (a-27), (a-28), (a-29), (a-30), (a-31), (a-33), (a-34), (a-35), (a-36), (a-42), (a-43), (a-46), (a-55), (a-64), (a-65), (a-82), (a-83), (a-84), (a-98), (a-99), (a-100), (a-101), (a-102), (a-103), (a-104), (a-105), (a-106), (a-107), (a-108), (a-109), (a-110), (a-111), (a-112), (a-113), (a-114), (a-115), (a-116), (a-117), (a-118), (a-119), (a-120), (a-121), (a-122), (a-123), (a-124), (a-125), (a126), (a-127), (a-128), (a-129), (a-130), and (a-131).

In some embodiments of the invention and/or embodiments thereof the compound is a compound according to formula (XXXVII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$ and $NR^{A1}R^{A2}$ is selected from the group consisting of (a-1), (a-3), (a-5), (a-9), (a-20), (a-34), (a-35), (a-36), (a-42), (a-46), (a-55), (a-64), (a-65), (a-98), (a-99), (a-100), (a-103), (a-104), (a-105), (a-106), (a-107), (a-108), (a-120), (a-121), (a-125), (a126), and (a-128).

In some embodiments of the invention and/or embodiments thereof the compound is a compound according to formula (XXXVIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $NR^{A1}R^{A2}$ is selected from the group consisting of (a-1), (a-3), (a-5), (a-9), (a-20), (a-34), (a-35), (a-36), (a-42), (a-46), (a-55), (a-64), and (a-65).

In some embodiments of the invention and/or embodiments thereof the compound is a compound according to formula (XXXVII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein A is $NR^{A1}R^{A2}$ and $NR^{A1}R^{A2}$ is selected from the group consisting of (a-1), (a-3), (a-5), (a-20), (a-34), (a-35), (a-36), (a-46), (a-55), and (a-65).

In some embodiments of the invention and/or embodiments thereof the compound is a compound according to formula

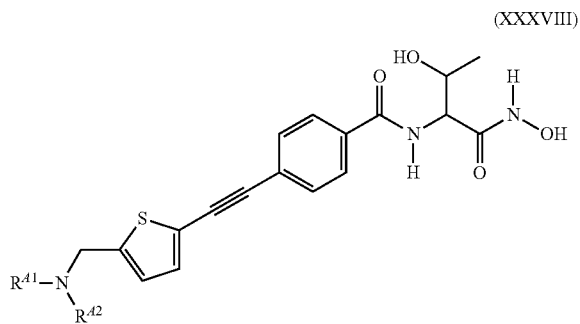

(XXXVIII)

or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{A1}$, $R^{A2}$, are defined as in any of the embodiments described herein.

In some embodiments of the invention and/or embodiments thereof the compound is a compound according to formula (XXXVIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{A1}$, $R^{A2}$ are independently selected from the group consisting of H, $C_{1-6}$-alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{E1}$, $R^{E2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, $-NR^{A3}R^{A4}$, carbonyl, $-C(=O)-OR^{A5}$, halogen atom, amino, $C_{1-6}$-alkyl substituted with halo, $C_{1-6}$-alkyloxy-$C_1$-$C_6$—, aryl, heteroaryl, $C_1$-$C_6$-alkyl substituted with aryl, cyano, hydroxy, $-SR^{A5}$, $-SO_2R^{A5}$, $-C(=O)NR^{A3}R^{A4}$, $C_{1-6}$-alkyl substituted with hydroxy; wherein $R^{A3}$, $R^{A4}$, $R^{A5}$ are independently chosen from H, or $C_{1-6}$-alkyl;

In some embodiments of the invention and/or embodiments thereof the compound is a compound according to formula (XXXVIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{A1}$, $R^{A2}$ are independently selected from the group consisting of H, $C_{1-6}$ alkyl, $C_{2-6}$-alkenyl, $C_{2-6}$-alkynyl, $C_{3-10}$-cycloalkyl, aryl, heterocyclyl, heteroaryl, $C_{1-6}$-alkyloxy-$C_1$-$C_6$-alkyl, $C_1$-$C_6$-alkyl substituted with aryl, $C_1$-$C_6$-alkyl substituted with heteroaryl, $C_1$-$C_6$-alkyl substituted with heterocyclyl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, alkynyl, cycloalkyl, aryl, heterocyclyl, heteroaryl, alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, $-NR^{A3}R^{A4}$, carbonyl, $-C(=O)-OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, $-SR^{A5}$, $-SO_2R^{A5}$, $-C(=O)NR^{A3}R^{A4}$, $C_{1-6}$-alkyl substituted with hydroxy;

wherein
$R^{A3}$, $R^{A4}$, $R^{A5}$ are independently chosen from
H, or $C_{1-6}$-alkyl.

In some embodiments of the invention and/or embodiments thereof the compound is a compound according to formula (XXXVIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $R^{A1}$, $R^{A2}$ are independently selected from the group consisting of H, $C_{1-5}$ alkyl, $C_{2-6}$-alkenyl, $C_{3-10}$-cycloalkyl$C_{1-6}$-alkyloxy-$C_1$-$C_6$-alkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring having 3 to 12 ring atoms, wherein 1 ring atom is N and wherein 0, 1, 2, or 3 further ring atoms are selected from N, S, and O;

wherein the alkyl, alkenyl, cycloalkyl, aryl, heteroaryl, or alkyloxy or the heterocyclic ring formed by $R^{A1}$, $R^{A2}$ together with the N atom to which they are attached is optionally substituted with a substituent selected from the group consisting of $C_{1-6}$-alkyl, $C_{3-8}$-cycloalky, $C_{1-6}$-alkyloxy, $-NR^{A3}R^{A4}$, carbonyl, $-C(=O)-OR^{A5}$, halogen atom, amino, $C_{1-6}$-alkyl substituted with halo, $C_{1-6}$-alkyloxy-$C_1$-$C_6$-alkyl, aryl, heteroaryl, $C_1$-$C_6$-alkyl substituted with aryl, cyano, hydroxy, —SR$^{A5}$, —SO$_2$R$^{A5}$, —C(=O)NR$^{A3}$R$^{A4}$, C$_{1-6}$-alkyl substituted with hydroxy;
wherein
R$^{A3}$, R$^{A4}$, R$^{A5}$ are independently chosen from
H, or C$_{1-6}$-alkyl.

In some embodiments of the invention and/or embodiments thereof the compound is a compound according to formula (XXXVIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein R$^{41}$, R$^{42}$ are independently selected from the group consisting of H, C$_{1-6}$-alkyl, C$_{2-6}$-alkenyl, C$_{3-10}$-cycloalkyl, C$_{1-6}$-alkyloxy-C$_1$-C$_6$-alkyl, C$_1$-C$_6$-alkyl substituted with aryl, C$_1$-C$_6$-alkyl substituted with heteroaryl, or R$^{41}$, R$^{42}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by R$^{41}$, R$^{42}$ together with the N atom to which they are attached is optionally substituted with a substituent selected from the group consisting of C$_{1-6}$-alkyl, C$_{3-8}$-cycloalky, C$_{1-6}$-alkyloxy, —NR$^{A3}$R$^{A4}$, carbonyl, —C(=O)—OR$^{A5}$, halogen atom, amino, C$_{1-6}$-alkyl substituted with halo, C$_{1-6}$-alkyloxy-C$_1$-C$_6$-alkyl, aryl, heteroaryl, C$_1$-C$_6$-alkyl substituted with aryl, cyano, hydroxy, —SR$^{A5}$, —SO$_2$R$^{A5}$, —C(=O)NR$^{A3}$R$^{A4}$, C$_{1-6}$-alkyl substituted with hydroxy;
wherein
R$^{A3}$, R$^{A4}$, R$^{A5}$ are independently chosen from
H, or C$_{1-6}$-alkyl.

In some embodiments of the invention and/or embodiments thereof the compound is a compound according to formula (XXXVIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein R$^{41}$, R$^{42}$ are independently selected from the group consisting of H, C$_{1-6}$-alkyl, C$_{2-6}$-alkenyl, C$_{3-10}$-cycloalkyl, C$_{1-6}$-alkyloxy-C$_1$-C$_6$-alkyl, C$_1$-C$_6$-alkyl substituted with aryl, C$_1$-C$_6$-alkyl substituted with heteroaryl, or R$^{41}$, R$^{42}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by R$^{41}$, R$^{42}$ together with the N atom to which they are attached is optionally substituted with a substituent selected from the group consisting of C$_{1-6}$-alkyl, C$_{3-8}$-cycloalky, C$_{1-6}$-alkyloxy, —NR$^{A3}$R$^{A4}$, carbonyl, —C(=O)—OR$^{A5}$, halogen atom, amino, C$_{1-6}$-alkyl substituted with halo, C$_{1-6}$-alkyloxy-C$_1$-C$_6$-alkyl, aryl, heteroaryl, C$_1$-C$_6$-alkyl substituted with aryl, cyano, hydroxy, —SR$^{A5}$, —SO$_2$R$^{A5}$, —C(=O)NR$^{A3}$R$^{A4}$, C$_{1-6}$ alkyl substituted with hydroxy;

wherein
R$^{A3}$, R$^{A4}$, R$^{A5}$ are independently chosen from
H, or C$_{1-6}$-alkyl.

In some embodiments of the invention and/or embodiments thereof the compound is a compound according to formula (XXXVIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein R$^{41}$ is selected from the group consisting of C$_{1-6}$-alkyl, C$_{2-6}$-alkenyl, C$_{3-10}$-cycloalkyl, C$_{1-6}$-alkyloxy-C$_1$-C$_6$-alkyl, C$_1$-C$_6$-alkyl substituted with aryl, C$_1$-C$_6$-alkyl substituted with heteroaryl, R$^{42}$ is hydrogen or C$_{1-6}$alkyl
or R$^{41}$, R$^{42}$ together with the N atom to which they are attached can form a saturated or unsaturated heterocyclic ring selected from the group consisting of morpholinyl, thiomorpholinyl dioxide, piperidinyl, piperazinyl, tetrahydroisoquinolinyl, pyrrolidinyl, azepanyl, pyrrolinyl;

wherein the alkyl, alkenyl, cycloalkyl, aryl, heteroaryl, or alkyloxy or the heterocyclic ring formed by R$^{41}$, R$^{42}$ together with the N atom to which they are attached is optionally substituted with a substituent selected from the group consisting of C$_{1-6}$-alkyl, C$_{3-8}$-cycloalkyl, C$_{1-6}$-alkyloxy, —NR$^{A3}$R$^{A4}$, carbonyl, —C(=O)—OR$^{A5}$, halogen atom, amino, C$_{1-6}$-alkyl substituted with halo, C$_{1-6}$-alkyloxy-C$_1$-C$_6$-alkyl, aryl, heteroaryl, C$_1$-C$_6$-alkyl substituted with aryl, cyano, hydroxy, —SR$^{A5}$, —SO$_2$R$^{A5}$, —C(=O)NR$^{A3}$R$^{A4}$, C$_{1-6}$-alkyl substituted with hydroxy;
wherein
R$^{A3}$, R$^{A4}$, R$^{A5}$ are independently chosen from
H, or C$_{1-6}$-alkyl.

In some embodiments of the invention and/or embodiments thereof the compound is a compound according to formula (XXXVIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein NR$^{41}$R$^{42}$ is selected from the group consisting of (a-1)-(a-143) as defined herein.

In some embodiments of the invention and/or embodiments thereof the compound is a compound according to formula (XXXVIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein NR$^{41}$R$^{42}$ is selected from the group consisting of (a-1), (a-3), (a-5), (a-9), (a-20), (a-21), (a-22), (a-23), (a-24), (a-25), (a-26), (a-27), (a-28), (a-29), (a-30), (a-31), (a-33), (a-34), (a-35), (a-36), (a-42), (a-43), (a-46), (a-55), (a-64), (a-65), (a-82), (a-83), (a-84), (a-98), (a-99), (a-100), (a-101), (a-102), (a-103), (a-104), (a-105), (a-106), (a-107), (a-108), (a-109), (a-110), (a-111), (a-112), (a-113), (a-114), (a-115), (a-116), (a-117), (a-118), (a-119), (a-120), (a-121), (a-122), (a-123), (a-124), (a-125), (a126), (a-127), (a-128), (a-129), (a-130), and (a-131).

In some embodiments of the invention and/or embodiments thereof the compound is a compound according to formula (XXXVIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein NR$^{41}$R$^{42}$ is selected from the group consisting of (a-1), (a-3), (a-5), (a-9), (a-20), (a-34), (a-35), (a-36), (a-42), (a-46), (a-55), (a-64), (a-65), (a-98), (a-99), (a-100), (a-103), (a-104), (a-105), (a-106), (a-107), (a-108), (a-120), (a-121), (a-125), (a126), and (a-128).

In some embodiments of the invention and/or embodiments thereof the compound is a compound according to formula (XXXVIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $NR^{A1}R^{A2}$ is selected from the group consisting of (a-1), (a-3), (a-5), (a-9), (a-20), (a-34), (a-35), (a-36), (a-42), (a-46), (a-55), (a-64), and (a-65).

In some embodiments of the invention and/or embodiments thereof the compound is a compound according to formula (XXXVIII) or a stereoisomer, pharmaceutically acceptable salt, ester or prodrug thereof, for use in the treatment of an infection by a bacteria in an animal wherein the bacteria is at least one of the bacteria selected from the group *Mannheimia Haemolytica* and *Histopholus Somni*, wherein $NR^{A1}R^{A2}$ is selected from the group consisting of (a-1), (a-3), (a-5), (a-20), (a-34), (a-35), (a-36), (a-46), (a-55), and (a-65).

Compound according to the formula (I):

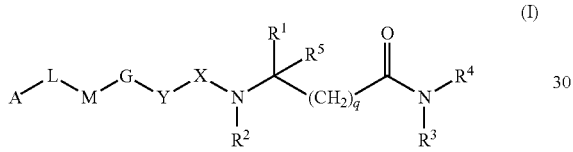

(I)

or a stereoisomer, pharmaceutically acceptable salt, ester, solvate, or prodrug thereof, for use according to the invention, wherein A is $NR^{A1}R^{A2}$ wherein $R^{A1}$, $R^{A2}$ are independently selected from
H, $C_{1-6}$-alkyl, $C_{2-6}$-alkenyl, $C_{3-10}$-cycloalkyl, $C_1$-$C_6$-alkyl substituted with aryl, $C_1$-$C_6$-alkyl substituted with heteroaryl;

L is absent or $C_{1-6}$-alkyl;

M is aryl or heteroaryl;

G is —C≡C—, or —C≡C—C≡C—;

Y is aryl;

X is —C(=O)—;

$R^1$ is selected from the group consisting of
$C_{1-6}$-alkyl optionally substituted with a substituent selected from the group consisting of
$C_{1-6}$alkyl, $NR^6R^7$, carbonyl, nitro, hydroxy, —$SR^8$, —$SO_2R^8$, $SO_2NR^6R^7$, wherein $R^6$, $R^7$, $R^8$ are independently chosen from H, or $C_{1-6}$-alkyl;

$R^2$, $R^3$ is H, or un-substituted $C_{1-6}$-alkyl;

q is 0;

$R^4$ is selected from the group consisting of H, —$OR^8$;

$R^5$ is $C_{1-6}$-alkyl or H.

Compound according to the formula (I):

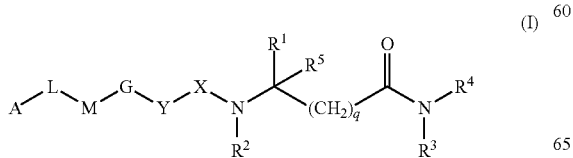

(I)

or a stereoisomer, pharmaceutically acceptable salt, ester, solvate, or prodrug thereof, for use according to the invention, wherein A is $NR^{A1}R^{A2}$ wherein $R^{A1}$, $R^{A2}$ are independently selected from
H, $C_{1-6}$-alkyl, $C_{2-6}$-alkenyl, $C_{3-10}$-cycloalkyl, $C_1$-$C_6$-alkyl substituted with phenyl, $C_1$-$C_6$-alkyl substituted with pyridine or furan;

L is —$CH_2$—;

M is phenyl or thiophene;

G is —C≡C—;

Y is phenyl;

X is —C(=O)—;

$R^1$ is selected from the group consisting of
$C_{1-6}$-alkyl optionally substituted with a substituent selected from the group consisting of
$C_{1-6}$-alkyl, $NR^6R^7$, hydroxy, —$SR^8$, —$SO_2R^8$, $SO_2NR^6R^7$, wherein $R^6$, $R^7$, $R^8$ are independently chosen from H, or $C_{1-6}$-alkyl;

$R^2$, $R^3$ is H, or un-substituted $C_{1-6}$-alkyl;

q is 0;

$R^4$ is OH;

$R^5$ is H

Compound according to the formula (I):

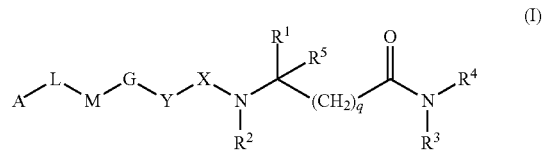

(I)

or a stereoisomer, pharmaceutically acceptable salt, ester, solvate, or prodrug thereof, for use according to the invention, wherein A is $NR^{A1}R^{A2}$, wherein $R^{A1}$, $R^{A2}$ are independently selected from
H, $C_{1-6}$-alkyl, $C_{2-6}$-alkenyl, $C_{2-6}$-alkynyl, $C_{3-10}$-cycloalkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring having 5 to 10 ring atoms, wherein 1 ring atom is N and wherein 0, 1, further ring atoms are selected from N, and O;

wherein the alkyl, alkenyl, alkynyl, cycloalkyl, aryl, heteroaryl or the heterocyclic ring formed by $R^{A1}$, $R^{A2}$ together with the N atom to which they are attached is optionally substituted with a substituent selected from the group consisting of
$C_{1-6}$-alkyl, $C_{1-6}$-alkyloxy, -halogen cyano, —$SR^{45}$;

wherein $R^{45}$ is selected from H or $C_{1-6}$-alkyl;

L is absent or $C_{1-6}$-alkyl;

M is aryl or heteroaryl;

G is selected from the group consisting of
—C≡C—, —C≡C—C≡C—;

Y is aryl;

X is —C(=O)—;

$R^1$ is selected from the group consisting of
H, $C_{1-6}$-alkyl optionally substituted with a substituent selected from the group consisting of $C_{1-6}$-alkyl, nitro, amino, —$SR^8$, —$SO_2R^8$, $SO_2NR^6R^7$;

$R^2$, $R^3$ is H, or un-substituted $C_{1-6}$-alkyl;

q is 0;

$R^4$ is selected from the group consisting of H, —$OR^8$;

$R^5$ is selected from the group consisting of H, and $C_{1-6}$-alkyl;
$R^8$ is selected from the group consisting of H,
Compound according to the formula (I):

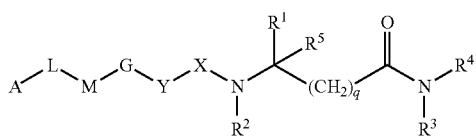

or a stereoisomer, pharmaceutically acceptable salt, ester, solvate, or prodrug thereof, for use according to the invention, wherein A is $NR^{A1}R^{A2}$, wherein
$R^{A1}$, $R^{A2}$ are independently selected from
H, $C_{1-6}$-alkyl, $C_{2-6}$-alkenyl, $C_{2-6}$-alkynyl, $C_{3-10}$-cycloalkyl, methyl substituted with phenyl, methyl substituted with heteroaryl selected from the group consisting of pyridine, oxazole, pyrimidine, thiophene, furan, and thiazol; or
$R^{A1}$, $R^{A2}$ together with the N atom to which they are attached can form a saturated or unsaturated heterocyclic ring selected from the group consisting of tetrahydro-isoquinoline, pyrroline, and morpholine;
wherein the alkyl, alkenyl, alkynyl, cycloalkyl, aryl, heteroaryl or the heterocyclic ring formed by $R^{A1}$, $R^{A2}$ together with the N atom to which they are attached is optionally substituted with a substituent selected from the group consisting of
methyl, methoxy, chloro, fluoro, cyano, $SCH_3$;
L is absent or methyl;
M is phenyl, thiophene, furan, or pyridine;
G is selected from the group consisting of
—C≡C—, —C≡C—C≡C—;
Y is phenyl;
X is —C(=O)—;
$R^1$ is selected from the group consisting of
H, $C_{1-6}$-alkyl optionally substituted with a substituent selected from the group consisting of $C_{1-6}$-alkyl, nitro, amino, —$SCH_3$, —$SO_2CH_3$;
$R^2$, $R^3$ is H, or un-substituted $C_{1-6}$-alkyl;
q is 0, 1;
$R^4$ is OH;
$R^5$ is H.
Compound according to the formula (I):

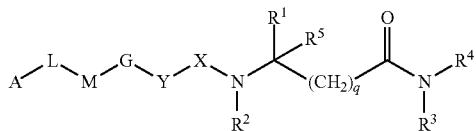

or a stereoisomer, pharmaceutically acceptable salt, ester, solvate, or prodrug thereof, for use according to the invention, wherein A is $NR^{A1}R^{A2}$, wherein
$R^{A1}$, $R^{A2}$ are independently selected from
H, $C_{1-6}$-alkyl, $C_{2-6}$-alkenyl, $C_{2-6}$-alkynyl, $C_{3-10}$-cycloalkyl, $C_1$-$C_6$-alkyl substituted with aryl, $C_1$-$C_6$-alkyl substituted with heteroaryl, or $R^{A1}$, $R^{A2}$ together with the N atom to which they are attached can form a saturated or unsaturated heterocyclic ring having 5 to 10 ring atoms, wherein 1 ring atom is N and wherein 0, or 1, further ring atoms are selected from N, and O;
wherein the alkyl, alkenyl, alkynyl, cycloalkyl, aryl, heterocyclyl, heteroaryl, alkyloxy or the heterocyclic ring formed by R together with the N atom to which they are attached is optionally substituted with a substituent selected from the group consisting of
$C_{1-6}$-alkyloxy, halogen atom, cyano, —$SR^{45}$—;
wherein $R^{45}$ is H, or $C_{1-6}$-alkyl;
L is absent or $C_{1-6}$-alkyl;
M is aryl, or heteroaryl;
G is —C≡C— or —C≡C—C≡C—;
Y is aryl;
X is —C(=O)—;
$R^1$ is selected from the group consisting of
H, $C_{1-6}$-alkyl, wherein the alkyl is optionally substituted with a substituent selected from the group consisting of $C_{1-6}$-alkyl, nitro, amino, OH, —$SR^8$, —$SO_2R^8$, $SO_2NR^6R^7$;
wherein $R^8$ is chosen from H or $C_{1-6}$-alkyl;
$R^2$, $R^3$ is H, or un-substituted $C_{1-6}$-alkyl;
q is 0;
$R^4$ is selected from the group consisting of
H, $C_{1-6}$-alkyl, —$OR^8$;
$R^5$ is selected from the group consisting of H, and $C_{1-6}$-alkyl.
Compound according to the formula (I):

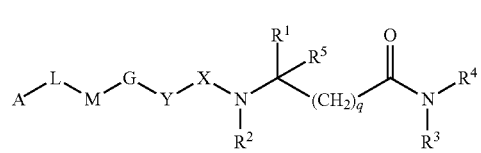

or a stereoisomer, pharmaceutically acceptable salt, ester, solvate, or prodrug thereof, for use according to the invention, wherein A is $NR^{A1}R^{A2}$, wherein
$R^{A1}$, $R^{A2}$ are independently selected from
H, $C_{1-6}$-alkyl, $C_{2-6}$-alkenyl, $C_{2-6}$-alkynyl, $C_{3-10}$-cycloalkyl, $C_1$-$C_6$-alkyl substituted with phenyl, $C_1$-$C_6$-alkyl substituted with heteroaryl selected from the group consisting of oxazole, pyridine, thiophene, thiazole, and furan, or
$R^{A1}$, $R^{A2}$ together with the N atom to which they are attached can form a saturated or unsaturated heterocyclic ring selected from the group consisting of tetrahydro-isoquinoline, and morpholine;
wherein the alkyl, alkenyl, alkynyl, cycloalkyl, aryl, heteroaryl, or the heterocyclic ring formed by $R^{A1}$, $R^{A2}$ together with the N atom to which they are attached is optionally substituted with a substituent selected from the group consisting of
methyl, methoxy, fluoro, chloro, cyano, —$SCH_3$—;
L is —$CH_2$—;
M is phenyl, pyridine, or thiophene;
G is —C≡C—;
Y is phenyl;
X is —C(=O)—;

$R^1$ is selected from the group consisting of
H, $C_{1-6}$-alkyl, wherein the alkyl is optionally substituted with a substituent selected from the group consisting of $C_{1-6}$-alkyl, nitro, amino, OH, —$SCH_3$, —$SO_2CH_3$;
$R^2$, $R^3$ is H, or un-substituted $C_{1-6}$-alkyl;
q is 0;
$R^4$ is selected from the group consisting of H, —OH;
$R^5$ is H.
Compound according to the formula (I):

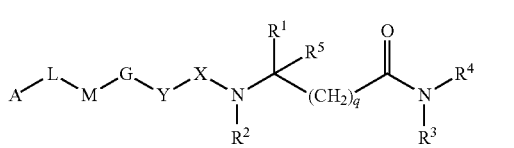

or a stereoisomer, pharmaceutically acceptable salt, ester, solvate, or prodrug thereof, for use according to the invention, wherein
A is $NR^{A1}R^{A2}$, wherein
$R^{A1}$, $R^{A2}$ are independently selected from
H, $C_{1-6}$-alkyl, $C_{2-6}$-alkenyl, $C_{2-6}$-alkynyl, $C_{3-10}$-cycloalkyl, $C_1$-$C_6$-alkyl substituted with aryl, $C_1$-$C_6$-alkyl substituted with heteroaryl; or
$R^{A1}$, $R^{A2}$ together with the N atom to which they are attached can form a saturated or unsaturated heterocyclic ring having 6 ring atoms, wherein 1 ring atom is N and wherein 0, or 1 further ring atoms are selected from N, and O;
wherein the alkyl, alkenyl, alkynyl, aryl, heteroaryl, or the heterocyclic ring formed by $R^{A1}R^{A2}$, together with the N atom to which they are attached is optionally substituted with a substituent selected from the group consisting of $C_{1-6}$-alkyl, $C_{1-6}$-alkyloxy, halogen atom;
L is absent or $C_{1-6}$-alkyl;
M is aryl, or heteroaryl;
G is —C≡C—, or —C≡C—C≡C—;
Y is aryl;
X is —C(=O)—;
$R^1$ is selected from the group consisting of
H, $C_{1-6}$-alkyl, wherein alkyl is optionally substituted with a substituent selected from the group consisting of $C_{1-6}$-alkyl, $NR^6R^7$, nitro, hydroxy, —$SR^8$, —$SO_2R^8$, $SO_2NR^6R^7$;
wherein $R^6$, $R^7$, $R^8$ are independently chosen from H, or $C_{1-6}$-alkyl;
$R^2$, $R^3$ is H, or un-substituted $C_{1-6}$-alkyl;
q is 0;
$R^4$ is H, $C_{1-6}$-alkyl or —$OR^8$;
$R^5$ is H, or $C_{1-6}$-alkyl.
Compound according to the formula (I):

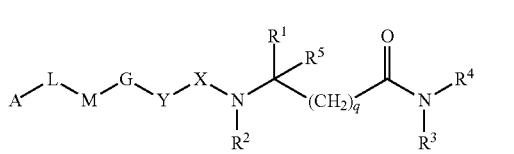

or a stereoisomer, pharmaceutically acceptable salt, ester, solvate, or prodrug thereof, for use according to the invention, wherein A is $NR^{A1}R^{A2}$, wherein
$R^{A1}$, $R^{A2}$ are independently selected from
H, $C_{1-6}$-alkyl, $C_{2-6}$-alkenyl, $C_{2-6}$-alkynyl, $C_{3-10}$-cycloalkyl, $C_1$-$C_6$-alkyl substituted with phenyl, and $C_1$-$C_6$-alkyl substituted with heteroaryl selected from the group consisting of pyridine, oxazol, pyrimidine thiophene, furan, and thiazole; or
$R^{A1}$, $R^{A2}$ together with the N atom to which they are attached can form morpholine;
wherein the alkyl, alkenyl, alkynyl, phenyl, heteroaryl, or the heterocyclic ring formed by $R^{A1}$, $R^{A2}$ together with the N atom to which they are attached is optionally substituted with a substituent selected from the group consisting of methyl, methoxy, chloro,
L is absent or —$CH_2$—;
M is phenyl, or thiophene;
G is —C≡C—, or —C≡C—C≡C—;
Y is phenyl;
X is —C(=O)—;
$R^1$ is selected from the group consisting of
H, $C_{1-6}$-alkyl, wherein alkyl is optionally substituted with a substituent selected from the group consisting of $C_{1-6}$-alkyl, amino, nitro, hydroxy, —$SCH_3$, —$SO_2CH_3$—;
$R^2$, $R^3$ is H, or un-substituted $C_{1-6}$-alkyl;
q is 0;
$R^4$ is H, $C_{1-6}$-alkyl, or —OH;
$R^5$ is H.

Types of animals that may benefit from the practice of the invention include any that are susceptible to infection by an etiological agent of Bovine respiratory Disease (BRD) or swine respiratory disease (SRD).

Exemplary animals include but are not limited to: members of the biological subfamily Bovinae which includes medium- to large-sized ungulates such as domestic dairy and beef cattle, bison, African buffalo, the water buffalo, etc. The animals may be so-called livestock raised in an agricultural setting for the production of dairy products or meat; or may be raised to perform work; or may be in another setting, e.g. in a zoo, animal reserve, etc., or raised for some other reason, e.g. as pets, show animals, for breeding purposes, etc.

Especially preferred is the use of the compounds of the current invention in beef cattle. Beef cattle are cattle raised for meat production (as distinguished from dairy cattle, used for milk production). There are three main stages in beef production: cow-calf operations, backgrounding, and feedlot operations. Especially preferred is the use of the compounds of the current invention in beef cattle in feedlot (feedyard) operations. The compounds of the invention can be used in beef (and dairy) cattle of every age, in calf, heifers, steer, or cows. The compound of the invention can be used in animals of different weight, including calves of between 80 and 150 kg as well as heavy animals of a weight higher than 350 kg.

Other exemplary animals that can be treated with the compounds and compositions of the current invention are small ruminants, such a sheep or goats or pseudoruminants, such as e.g. camels or lamas.

In one embodiment the compounds of the current invention is used to treat respiratory diseases such as enzootic pneumonia of lambs and/or adult sheep (ewes, rams) that are kept for meat or as beeding stock. Enzootic pneumonia is an acute infectious disease of sheep characterised by fever, nasal discharge, pneumonitis and pleuritis.

The compounds of the current invention can be alternatively used to treat Swine respiratory disease (SRD), hat is a disease of animals of the family Suidae, commonly called pigs or swine. The compounds of the current invention can be administered in general to all swine animals; to sucker, weaner, boars, barrows, gilts or sows. It can be used in one or more of the phases of swine farming for meat: suckling pigs, feeder pigs, grower, and finisher pigs or in backfatter pigs. Alternatively it can be used in breeding stocks, i.e. in breeding sows, gilts or boars or the offspring of such animal as replacement breeding stock.

In one embodiment, the animal that is treated is a bovine animal and the disease that is treated is BRD.

In another embodiment the animal is a suidae (porcine) animal and the disease that is treated is SRD.

The compounds of the current invention can be used to treat diseased animals that display clininal symptoms of Bovine Respiratory disease or Swine respiratory disease.

The compounds of the current invention can additionally or alternatively be used to treat animals with subclinical infections with *Pasteurella* spp., *Mannheimia* spp. and *Histophilus* spp. infections. A subclinical infection is nearly or completely asymptomatic (no disease signs or symptoms) and subclinical infections are mainly detected at the slaughterhouse when checking the lungs for lesions. However, subclinical BRD or SRD infection are commercially very relevant, because they result in lower average daily weight gains of infected animals that are additionally a source of infection for their contact animals.

In addition to treatment purposes, the compositions and methods of the invention are also suitable for metaphylactic use. For example, in case of an outbreak of Bovine Respiratory disease or Swine respiratory disease, administration of the compounds of the current invention to non-affected (or sub-clinical infected) animals, especially those which are in close contact with those showing clinical signs of disease, could prevent the spread of the infection.

In addition, prophylactic treatment might be undertaken in bovines considered to be vulnerable to infection and/or in whom infection could have grave consequences, e.g. calves, show cattle, pregnant females, prize bulls or boars, etc., whether or not an outbreak of the disease is known to have occurred. Another option is the prophylactic administration of compounds according to the current invention in animals before shipping and other stress inducing events to prevent outbreak of the disease in such animals.

The same concept of prophylactic or metaphyclactic treatment, as described in the preceeding paragraph applies to swine animals at risk for SRD.

In some embodiments, one or more, preferably one compound according to this invention is used to treat an infection by a pathogen that is resistant (not sensitive for) to one or more other antibacterial agents. In some embodiments, the compound according to this invention is active against a pathogen, that is resistant to one or more of the following antibacterials: macrolide antibiotics, aminoglycosides, fluoroquinolones, especially one or more selected from the group of tylosin, erythromycin, tildipirosin, timicosin, tulathromycin, gamithromycin, gentamicin, neomycin, enrofloxacin, ciprofloxacin, danafloxaxin, oxytetracycline, chlortetracycline, or florfenicol, sulfonamides or Beta-lactam antibiotics such as cefquinome, ceftiofur or penicillin. In one embodiment the resistant pathogen is *Mannheimia haemolytica* that is resistant against macrolide antibiotics.

The compounds according to this invention may be administered in various dosage forms. The term "dosage form" means that the compounds according to this invention are formulated into a product suitable for administering to the animal via the envisaged dosage route. Such dosage forms are sometimes referred to herein as formulations or pharmaceutical composition.

Dosage forms useful in the current invention can be liquid, semi-solid or solid dosage forms.

Liquid dosage forms of the compounds are generally solutions, suspensions or emulsions. A solution is a mixture of two or more components that form a single phase that is homogeneous down to the molecular level. A suspension consists of insoluble solid particles dispersed in a liquid medium, with the solid particles accounting for about 0.5% to about 30% of the suspension. The liquid may be aqueous, oily, or both. An emulsion is a heterogeneous dispersion of one immiscible liquid in another; it relies on an emulsifying agent for stability. A dry powder (or granule) for reconstitution is mixed and reconstituted with a diluent (e.g. water) as a solution or as a suspension immediately prior to injection. The principal advantage of this dosage form is that it overcomes the problem of instability in solution or suspension.

One dosage route (administration route) is the parenteral, especially injection administration (e.g. subcutaneous injection, intravenous injection, intramuscular injection, etc.). Parenteral formulations and delivery systems for non-oral routes comprise liquids (e.g. solutions, suspensions, emulsions, and dry powders for reconstitution), semi-solids and solids (e.g. implants). The majority of implants that are used in veterinary medicine are compressed tablets or dispersed matrix systems in which the drug is uniformly dispersed within a nondegradable polymer or alternatively extrusion products.

In one embodiment the compounds of the current invention are administered subcutaneously.

Another possible dosage route is the oral dosage route, wherein the compound according to this invention is administered via the mouth. Oral dosage forms suitable for oral administration comprise liquids (e.g. injectable, drench, in-feed or drinking water formulations), semi-solids (e.g. pastes, gels), and solids (e.g. tablets, capsules, powders, granules, chewable treats, premixes and medicated blocks).

A drench is a liquid oral formulation that is administered directly into the mouth/throat of an animal, especially a livestock animal, by means of a "drench gun" or syringe or another suitable device. When the composition is administered in the animal recipient's drinking water or as a drench, it may be convenient to use a solution or suspension formulation. This formulation can be, for example, a concentrated suspension that is mixed with water or a dry preparation that is mixed and suspended in the water.

Semi-solid oral formulations (pastes or gels) are generally administered via an applicator directly into the mouth of an animal or mixed with the feed.

Solid oral formulations are either administered directly to an animal (tablet, capsule) or mixed with the feed or via medicated feed blocks.

When the oral formulation is administered via a non-human animal's feed, especially for swine in case of SRD, it may, for example, be fed as a discrete feed. Alternatively (or additionally), it may, for example, be intimately dispersed in the animal recipient's regular feed, used as a top dressing, or in the form of solid pellets, paste or liquid that is added to the finished feed. When the oral formulation is administered as a feed additive, it may be convenient to prepare a "premix" in which the oral formulation is dispersed in a small amount of a liquid or solid carrier. This "premix" is, in turn, dispersed in the animal's regular feed using, for example, a conventional mixer.

Several modified-release delivery systems have been developed, that take advantage of the unique anatomy of the ruminant forestomach, i.e. for intra-ruminal administration.

An intraruminal bolus is a specific formulation for ruminants and pseudo-ruminants (cattle, sheep, goats, buffalos, camelids, deer etc.). It is a veterinary delayed release delivery system which remains in the rumeno-reticular sac of a ruminant animal over an extended period of time and in which the therapeutically active substance has a predictable and delayed release pattern. Such intraruminal boluses are usually administered using a balling gun or another suitable device.

It is contemplated that the compounds according to the current invention may alternatively be administered topically (e.g., transdermal via a spot-on, pour-on or spray, or alternatively as a nasal spray or by inhalation).

For instance the compounds according to this invention may be administered topically using a transdermal formulation (i.e. a formulation that passes through the skin). Alternatively the compounds according to this invention may be administered topically via the mucosa, e.g. as nasal spray.

Further aspects regarding formulation of drugs and various excipients are found in, for example, Gennaro, A. R., et al., eds., Remington: The Science and Practice of Pharmacy (Lippincott Williams & Wilkins, 20th Ed., 2000).

In carrying out the method of this invention, a specified compound according to the invention is preferably administered parenterally to an infected or susceptible animal.

In another embodiment the compound is administered orally (especially to swine in case of SRD).

When the compound according to this invention is administered orally or parenterally by subcutaneous injection, the total dose is generally greater than about 0.01 mg/kg (i.e., milligram of compound according to this invention per kilogram body weight of the treated animal).

In some such embodiments, the total dose is from about 0.01 to about 100 mg/kg, from about 0.01 to about 50 mg/kg, from about 0.1 to about 25 mg/kg, or from about 1 to about 20.

For BRD or SRD, for example, the dose is generally from about 0.5 to about 15 mg/kg, from about 1 to about 10 mg/kg. The same dose range may be suitable for other dosage routes.

The desired dose, however, may be less in some instances where the compound according to this invention is administered intravenously.

The dose used to control *Pasteurella multocida*, *Mannheimia haemolytica* or *Histophilus somni* infections or especially BRD will vary with the compound, the severity of the infection, and the age, weight, and condition of the animal. The total dose required for several days protection will generally, however, be in the range of from about 1 to about 40 mg/kg bodyweight, and preferably will be in the range of from about 2.5 to about 35 mg/kg. Similar dosages are administered to pigs to treat SRD.

Protection for up to about seven days can be provided by a single injection; the length of protection will depend upon the dose given. The total dose can also be divided into smaller doses given at intervals, such as once daily for two to seven days. Obviously, other suitable dosage regimens can be constructed.

A single administration of a composition comprising a compound according to this invention can be sufficient to treat an infection and to clinically and/or bacteriologically cure BRD or SRD, or at least diminish the clinical symptoms in diseased animals; this is called "one shot" administration.

The pharmacokinetic data that were generated for the compounds according to the invention support such beneficial behaviour of the compounds in the animal, that allow such a "one shot" administration.

Although such a "one-shot" single dose is preferred, it is contemplated that multiple doses can be used, e.g. two administrations 12-24 hours apart or alternatively, two administrations, 48-72 hours apart.

Factors affecting the preferred dosage may include, for example, infection to be treated, the type (e.g., species and breed), age, size, sex, diet, activity, and condition of the of the infected animal; the dosage route; pharmacological considerations, such as the activity, efficacy, pharmacokinetic, and toxicology profiles of the particular compound of the invention and the composition administered; and whether the compound according to this invention being administered as part of a combination of active ingredients. Thus, the preferred amount of the compound according to this invention can vary, and, therefore, can deviate from the typical dosages set forth above. Determining such dosage adjustments is generally within the skill of those in the art. The effective dosage will vary; for example for prophylactic treatment relatively low doses would be administered over an extended time.

The compounds of this invention may be formulated for parenteral administration (especially subcutaneous injection) by methods recognized in the veterinary pharmaceutical art.

Effective injectable compositions containing these compounds may be in either suspension or solution form. In the preparation of suitable formulations it will be recognized that, in general, the water solubility of the acid addition salts is greater than that of the corresponding free bases. Similarly, the free bases are more soluble in dilute acids or in acidic solutions than in neutral or basic solutions.

In the solution form a compound is dissolved in a physiologically acceptable vehicle. Such vehicles comprise a suitable solvent, preservatives such as benzyl alcohol, if needed, and buffers. Useful solvents include, for example, water and aqueous alcohols, glycols, and carbonate esters such as diethyl carbonate.

Injectable suspension compositions employ a liquid suspending medium, with or without adjuvants, as a vehicle. The suspending medium can be, aqueous or non-aqueous, e.g. water, polyethylene glycol, benzyl alcohol, N methyl pyrrolidone, 2, pyrrolidone, triacetin, inert oils such as vegetable oils or highly refined mineral oils.

Suitable physiologically acceptable adjuvants are necessary to keep the compound suspended in suspension compositions. The adjuvants may be chosen from among thickeners such as carboxymethylcellulose, polyvinylpyrrolidone, gelatin, and the alginates. Many surfactants are also useful as suspending agents. Lecithin, alkylphenol polyethylene oxide adducts, naphthalenesulfonates, alkylbenzenesulfonates, and the polyoxyethylene sorbitan esters are useful suspending agents. Many substances which affect the hydrophilicity, density, and surface tension of the liquid suspending medium can assist in making injectable suspensions in individual cases. For example, silicone antifoams, sorbitol, and sugars can be useful suspending agents. Other conventional ingredients such as preservatives, buffers, surfactants, or thickeners can be present in the injectable formulation.

The concentration of the compounds according to this invention in the applied dosage form may vary widely depending on, for example, the dosage route. In general, the concentration for injectable or oral administration is from about 1 to about 70% (by weight). In some such embodiments, for example, the concentration is from about 1 to about 50% (by weight), or from about 10 to about 50% (by weight). In other embodiments, the concentration is from about 35 to about 65% (by weight), from about 40 to about 60% (by weight), from about 45 to about 55% (by weight), or about 50% (by weight).

Preferred concentration in drinking water are from 0.01 to 0.05% weight by volume, particularly 0.01 to 0.025%, and in-feed from 100 to 400 ppm (g/metric ton), particularly 100 to 200 ppm.

In another aspect the present invention thus provides the administration of a pharmaceutical composition comprising an antibacterial effective amount of one or more, preferably one compound according to this invention and one or more pharmaceutically acceptable excipients to an animal, especially a bovine animal or alternatively a porcine animal, especially for the treatment of BRD or SRD.

The formulation type chosen for a dosage form in any instance will depend upon the particular purpose envisaged and the physical, chemical and biological properties of the compound according to this invention.

If the compound according to this invention is administered parenterally via an injection, the concentration of the compound according to this invention in the composition/formulation/dosage form preferably is sufficient to provide the desired therapeutically effective amount of the compound according to this invention in a volume that is acceptable for parenteral (subcutaneous) administration and allows an injection volume of less than 20 ml, preferably less than 10 ml per injection site.

In one embodiment the composition of a compound according to the invention is administered in a non-edible tissue of the animal that is removed at slaughter and does not enter the human food chain, e.g. in the ear or at the base of the ear (at the junction of the pinna with the cranium), or behind the ear, e.g. as described in WO1998041207 or WO2003079923, the content of which is incorporated by reference. Injection in alternative animal tissues of food producing animals, that do not enter the (human) food chain after slaughtering of the animal are also envisaged.

The methods and pharmaceutical compositions of this invention encompass methods wherein a compound according to this invention is the sole active ingredient administered to the recipient animal. It is contemplated, however, that the methods and pharmaceutical compositions also encompass combination therapies wherein a compound is administered in combination with one or more other pharmaceutically acceptable active ingredients. The other active ingredient(s) may be, for example, one or more other compounds according to this invention. Alternatively (or additionally), the other active ingredient(s) may be one or more pharmaceutically acceptable compounds that are not compounds according to this invention. The other active ingredient(s) may target the same and/or different diseases or conditions.

Contemplated active ingredient(s) that may be administered in combination with the compounds of the current invention include, for example, antibacterials, anti-inflammatories, pharmaceutically acceptable anthelmintics, insecticides and acaricides, insect growth regulators, hormones, immunostimulats, dermatological preparations (e.g. antiseptics and disinfectants), and immunobiologicals (e.g., vaccines and antisera) for disease prevention.

Therefore this invention is also directed to the use as a medicament of combinations comprising a) one or more compounds according to this invention with b) one or more pharmaceutically acceptable active compounds which differ in structure from component a). The active compounds b) are preferably anti-inflammatory compounds, more preferably selected from the group consisting of non-steroidal anti-inflammatory agents (NSAID's), such as e.g. flunixin meglumine, meloxicam, carprofen, ketoprofen, phenylbutazone, or Aspirin. In one embodiment a compound according to the invention is combined with flunixin. In another embodiment a compound of the invention is combined with meloxicam. Preferably such combination is used to treat BRD in cattle.

Combination means that a compound of the current invention is administered in a common formulation with the one or more pharmaceutically acceptable active compounds which differ in structure. Alternatively the compound according to the invention is administered to the animal in parallel (not more than approximately 30 minutes apart) from one or more pharmaceutically acceptable active compounds which differ in structure.

In another embodiment the one or more pharmaceutically acceptable active compounds which differ in structure b) are antibacterials especially one or more selected grom the group of tylosin, erythromycin, tildipirosin, timicosin, tulathromycin, gamithromycin, gentamicin, neomycin, enrofloxacin, ciprofloxacin, danafloxaxin, oxytetracycline, chlortetracycline, cefquinome, ceftiofur or florfenicol, sulfonamides or penicillin.

In one embodiment a compound of the current invention is combined with tildipirosin, tulathromycin, tilmicosin or florfenicol and (at least) does not influence negatively the antibacterial activity of such combination partner.

Veterinary formulations for use in the present invention may be prepared by mixing the ingredients in the required proportions using conventional techniques. In case of a liquid formulation for injection, especially for subcutaneous administration The formulation is then packaged into an appropriate container containing single or multiple doses ready for administration (ready to use—RTU) or alternatively, a powder or granulate that can be mixed with a diluent and reconstituted before administration.

Features of the invention have been described in embodiments in the present application; however for brevity not all combinations of the features are literally described. Combinations of features as described above are however expressly considered to be part of the invention.

The invention will now be further described by the following, non-limiting, examples.

Example 1

Synthesis Examples

Some compounds of the current invention can be synthesized by methods that are described in the prior art, e.g. in WO2004/062601 and WO2008/154642.

Example 1A

General Procedure for the Synthesis of Aldehyde Containing Resins

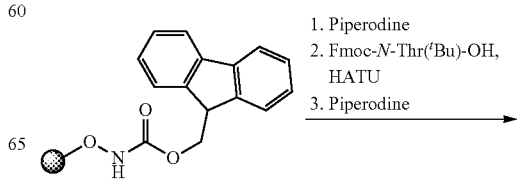

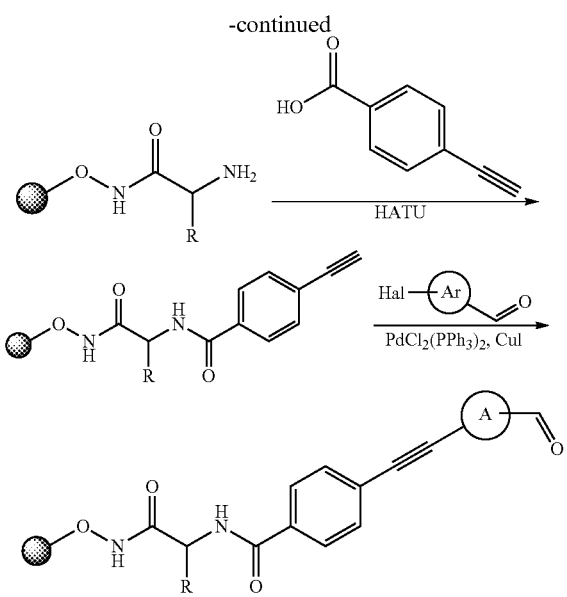

A suspension of N-Fmoc-hydroxylamine 2-chlorotrityl resin (12.0 g, 6.0 mmol) in dichloromethane (160 mL) was shaken for 2 hours and drained. The resin was treated with 20% v/v piperidine in DMF (150 mL) for 30 minutes, washed with DMF (5×80 mL) and drained completely. In a separate flask, the N-Fmoc-protected amino acid (18.0 mmol), HATU (6.5 g, 17.1 mmol) and DIEA (6.3 mL, 36.0 mmol) were dissolved in DMF (50 mL), stirred for three minutes and then added to the resin. After mixing under an atmosphere of nitrogen for 2 hours, the mixture was drained, washed with DMF (3×80 mL), and again treated with N-Fmoc-protected amino acid (18.0 mmol), HATU (6.5 g, 17.1 mmol) and DIEA (6.3 mL, 36.0 mmol). Mixing was continued for 2 hours, when the resin was drained, washed with DMF (5×80 mL) and drained again. The resin then was treated with 20% v/v piperidine in DMF (150 mL) for 30 minutes, drained and washed with DMF (5×80 mL) and drained again. A solution of 4-ethynylbenzoic acid (2.63 g, 18 mmol), HATU (6.5 g, 17.1 mmol) and DIEA (6.3 ml, 36.0 mmol) in DMF (50 mL) was then added to the resin and mixing under an atmosphere of nitrogen was continued for 2 hours. The mixture was then drained, washed with DMF (5×80 mL) and drained. A solution of the respective haloaryl- or halo-heteroarylaldehyde (24.0 mmol) and DIEA (10.5 mL, 60.0 mmol) in DMF (150 mL) was purged with a stream of nitrogen for two minutes and added to the resin. After mixing for 5 min, PdCl$_2$(PPh$_3$)$_2$ (842 mg, 1.2 mmol) and CuI (571 mg, 3.0 mmol) were added and the mixture was mixed under an atmosphere of nitrogen for 48 hours. The resin was drained, washed with DMF (4×100 mL), DCM (4×100 mL) and dried in vacuo to give the aldehyde containing resin which was used in the next steps without further purification.

Using this procedure, the corresponding amino acid-containing aldehyde resins were obtained using Fmoc-N-Thr($^t$Bu)-OH, Fmoc-N—(S)-Val-OH, Fmoc-N—(S)Ser ($^t$Bu)-OH, Fmoc-N—(S)-Ile-OH, Fmoc-N-2-amino-3-NHBoc-(2S)-butanoic acid, Fmoc-N-3-NHBoc-Val-OH, Fmoc-N-3-OTBS-(S)-Val-OH, Fmoc-N-3-MeS—(S)-Val-OH, Fmoc-N-2-amino-3-methoxyimino-(2S)-butanoic acid and Fmoc-N-2-amino-2-(2-methyl-1,3-dioxolan-2-yl)acetic acid.

Using this procedure, all aldehyde-containing resins were obtained using 4-iodobenzaldehyde, 3-iodobenzaldehyde, 5-bromopicolinaldehyde, 2-bromothiazole-5-carbaldehyde, 5-bromofuran-2-carbaldehyde and 5-bromothiophene-2-carbaldehyde.

Example 1B

Synthesis of 4-[2-[4-[[[4-(dimethylamino)phenyl]methylamino]methyl]phenyl]ethynyl]-N-[(1S,2R)-2-hydroxy-1-(hydroxycarbamoyl)propyl]benzamide [122]

The respective aldehyde containing resin (105 mg, 0.25 mmol) was treated successively with TFA/DCM 1% v/v (2×10 mL) for 20 minutes. The cleavage fractions were collected by filtration, combined and treated with 4-(dimethylamino)benzylamine dihydrochloride (314 mg, 1.5 mmol) dissolved in dichloromethane (3 mL) and with DIEA (2.0 mmol) and trimethyl orthoformate (180 µL, 1.625 mmol). After stirring for 5 minutes, acetic acid (176 µL, 3.08 mmol) and a solution of NaBH$_3$CN (71 mg, 1.125 mmol) in methanol (1 mL) were added to the reaction mixture which was shaken overnight and then concentrated in vacuo to give a crude residue which was purified by column chromatography as described in the general procedure for the reductive amination of the aldehyde-containing resins with primary and secondary amines.

Example 1C

General Procedure for the Oxidation of Methyl-sulfon-Containing Resins Prepared from Fmoc-N-3-MeS-(S)-Val-OH and N-Fmoc-hydroxylamine 2-chlorotrityl Resin A suspension of N-Fmoc-hydroxylamine 2-chlorotrityl resin (20.0 g, 10 mmol) in dichloromethane (200 mL) was shaken for 2 hours and drained. The resin was treated with 20% piperidine in DMF (320 mL) for 30 minutes, washed with DMF (5×200 mL) and drained completely. In a separate flask, a solution of (R)-2-((((9H-fluoren-9-yl)methoxy)carbonyl)amino)-3-methyl-3-(methylthio)butanoic acid (7.71 g, 20 mmol), HATU (72 g, 19 mmol) and DIEA (10.5 mL, 60 mmol) in DMF (40 mL) was stirred for three minutes and then added to the resin and mixing under an atmosphere of nitrogen was continued for 2 hours. The resin was drained, washed with DMF (3×200 mL) and drained again. The resin was then treated with 3-chlorobenzoperoxoic acid (6.9 g, 40 mmol) in DCM (200 mL) for 3 hours. The resin was washed with DMF (3×200 mL), drained and was then treated with 20% piperidine v/v in DMF (320 mL) for 30 minutes. After draining again and washing with DMF (5×200 mL), the resin was drained completely and 4-ethynylbenzoic acid (4.38 g, 30 mmol), HATU (10.5 g, 28.5 mmol) and DIEA (10.5 ml, 60 mmol) dissolved in DMF (40 mL) were added to the resin. Mixing under an atmosphere of nitrogen was continued for 2 hours after which the resin was drained, washed with DMF (5×200 mL) and drained again. A solution of the respective halo-aryl- or halo-heteroarylaldehyde (40 mmol) and DIEA (17.5 ml, 100 mmol) in DMF (400 mL) was purged with a stream of nitrogen for two minutes and then added to the resin. After mixing for 5 minutes, PdCl$_2$(PPh$_3$)$_2$ (1.40 g, 2.0 mmol) and CuI (950 mg, 5.0 mmol) were added and the mixture was mixing was continued under an atmosphere of nitrogen for 48 hours. The resin was drained, washed with DMF (4×200 mL) and MeOH (3×200 mL) and dried in vacuo.

Using this procedure, all aldehyde resins were obtained using 4-iodobenzaldehyde, 5-bromopicolinaldehyde and 5-bromothiophene-2-carbaldehyde Example 1D General Procedure for the Reductive Amination of the Aldehyde-Containing Resins with Primary and Secondary Amines A solution of the amine (1.5 mmol) and trimethyl orthoformate (180 µL, 1.625 mmol) in THF (20 mL) was added to the aldehyde-containing resin (105 mg, 0.25 mmol). An atmosphere of nitrogen was established and after mixing for 5 minutes, acetic acid (180 µL, 3.08 mmol) followed by a solution of NaBH$_3$CN (71 mg, 1.125 mmol) in methanol (1 mL) was added. Mixing was continued for 44 hours after which the resin was filtered, drained and washed with DMF (2×10 mL) and methanol (3×10 mL), drained again and dried in vacuo. Cleavage from the resin was achieved by treatment with trifluoroacetic acid (10 mL) for 30 minutes. The solution was collected and concentrated to dryness to give a crude residue which was purified by preparative HPLC using a e.g. Gilson GX-281 semi-preparative HPLC system equipped with a Luna 200×25 mm (C18, 10µ) or a Gemini 150×30 mm (C18, 5µ) column applying a gradient consisting of 0.1% TFA/water and acetonitrile.

The product containing fractions were collected and concentrated by freeze-drying. By this method, compounds 769-787 were obtained as the TFA salts whereas all other compounds were submitted to another reverse-phase chromatography using a gradient consisting of aqueous ammonium hydrogencarbonate (7.5 mmol/L) and acetonitrile to remove any residual trifluoroacetic acid.

Using this procedure, the following compounds can be synthesized:

Compound No. 1-100
Compound No. 103-121
Compound No. 123-241
Compound No. 247-364
Compound No. 366
Compound No. 381-435
Compound No. 467-511
Compound No. 513-551
Compound No. 555-651
Compound No. 666-788

Example 1E

Synthesis of (2S)-3-(tert-butoxycarbonylamino)-2-(9H-fluoren-9-ylmethoxycarbonylamino)butanoic Acid

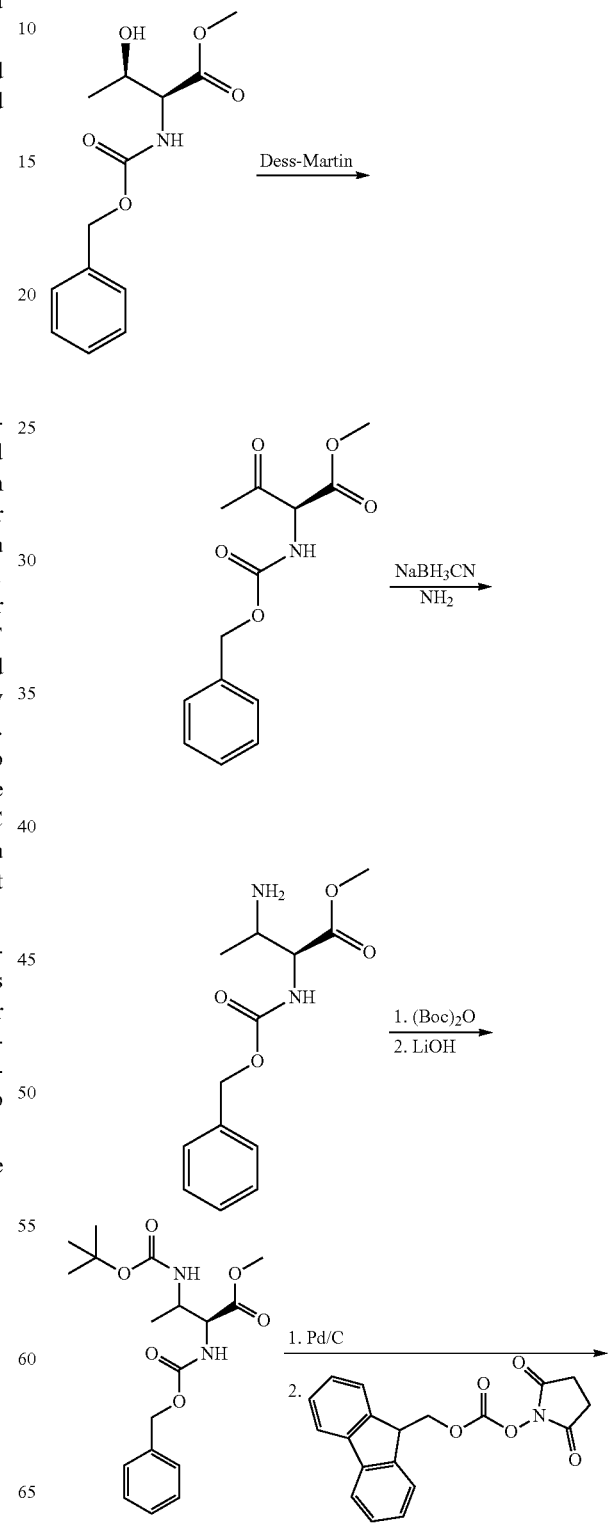

171
-continued

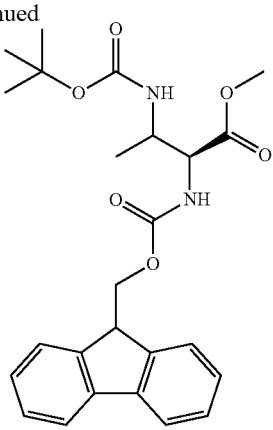

Step 1: (S)-Methyl 2-(((benzyloxy)carbonyl)amino)-3-oxobutanoate

To a solution of (2S,3R)-methyl 2-(((benzyloxy)carbonyl)amino)-3-hydroxybutanoate (89 g, 333 mmol) and sodium hydrogencarbonate (84 g, 999 mmol) in dichloromethane (2000 mL) was added Des-Martin periodinane (155 g, 366 mmol) at 0° C. The mixture was then allowed to attain room temperature and stirring was continued for 5 hours. The reaction mixture was quenched by addition saturated $Na_2S_2O_3$ (4000 mL) at 0° C. The organic phase was then washed with sat. $Na_2S_2O_3$ (2×500 mL and 1×800 mL), $NaHCO_3$ (800 mL), dried over $Na_2SO_4$ and concentrate in vacuo. The residue was purified by column chromatography on silica gel (ethyl acetate/petroleum ether) to provide the title compound.

Step 2: (2S)-Methyl 2-((benzyloxy)carbonyl)amino)-3-aminobutanoate (S)-methyl 2-(((benzyloxy)carbonyl)amino)-3-oxobutanoate (60 g, 226 mmol), ammonium acetate (349 g, 4524 mmol) and acetic acid (1.295 ml, 22.62 mmol) were dissolved in MeOH (1000 mL). After stirring at room temperature for 390 minutes, sodium cyanoborohydride (42.6 g, 679 mmol) was added. The mixture was allowed to stir at 50° C. for 16 hours. The reaction mixture was then cooled to 0° C. and water (10 mL) was added. After removal of some volatiles in vacuo, the residual mixture was extracted with ethyl acetate (3×500 mL). The combined organic layers were washed with brine (500 mL), dried over $Na_2SO_4$, filtered and concentrated under reduced pressure to provide the crude title compound which was used in the next step without further purification.

Step 3: (2S)-Methyl 2-(((benzyloxy)carbonyl)amino)-3-((tert-butoxycarbonyl)amino)butanoate To a solution of (2S)-methyl 2-((benzyloxy)carbonyl) amino)-3-aminobutanoate (25 g, 68.2 mmol) in dichloromethane (20 mL) was added DIEA (79 mL, 451 mmol) and $(Boc)_2O$ (105 mL, 451 mmol). The mixture was stirred at 20° C. for 16 hours and then concentrated in vacuo. The resulting residue was purified by column chromatography on silica gel (ethyl acetate/petroleum ether) to provide the title compound.

172

Step 4: (2S)-2-(((Benzyloxy)carbonyl)amino)-3-((tert-butoxycarbonyl)amino)butanoic acid To a solution of (2S)-methyl 2-(((benzyloxy)carbonyl) amino)-3-((tert-butoxycarbonyl)amino)butanoate (13 g, 36.9 mmol) in THF (120 mL) and water (30 mL) was added LiOH (4.90 g, 205 mmol). The mixture was stirred at 20° C. for 16 hours. The reaction mixture was adjust to pH=4-5 and extracted with ethyl acetate (2×200 mL). The combined organic layers were washed with brine (100 mL), dried over $Na_2SO_4$, filtered and concentrated under reduced pressure to give a residue which was purified by column chromatography on silica gel (MeOH/DCM) to provide the title compound.

Step 5: (2S)-2-Amino-3-((tert-butoxycarbonyl)amino)butanoic Acid

To a solution of (2S)-2-(((benzyloxy)carbonyl)amino)-3-((tert-butoxycarbonyl)amino)butanoic acid (13 g, 36.9 mmol) in THF (200 mL) was added Palladium on carbon (10%, 3.93 g) under an atmosphere of nitrogen. The mixture was degassed under vacuum and purged with hydrogen several times. The mixture was then stirred at 20° C. under atmosphere of hydrogen (45 psi) for 16 hours. The reaction mixture was filtered, the liquid collected and concentrated in vacuo. The resulting crude title compound was used in next step without further purification.

Step 6: (2S)-3-(tert-Butoxycarbonylamino)-2-(9H-fluoren-9-ylmethoxycarbonylamino)butanoic acid To a solution of (2S)-2-amino-3-((tert-butoxycarbonyl) amino)butanoic acid (8.2 g, 37.6 mmol) and sodium bicarbonate (3.16 g, 37.6 mmol) in water (300 mL) was added a solution of (9H-fluoren-9-yl)methyl (2,5-dioxopyrrolidin-1-yl) carbonate (12.67 g, 37.6 mmol) in acetone (100 mL) at 0° C. over a period of 30 minutes. The reaction mixture was then allowed to stir at 20° C. for 6 hours. All volatiles were then removed in vacuo and to the resulting mixture was added critic acid until pH 5 was reached. After extraction with ethyl acetate (3×200 mL), the combined organic layers were washed with brine (200 mL), dried ($Na_2SO_4$) and concentrated under reduced pressure. The resulting residue was purified by column chromatography on silica gel (ethyl acetate/petroleum ether) to provide the title compound. MS: 341 (M+1-Boc).

Example 1F: Synthesis of 3-(tert-butoxycarbonylamino)-2-(9H-fluoren-9-ylmethoxycarbonylamino)-3-methyl-butanoic Acid

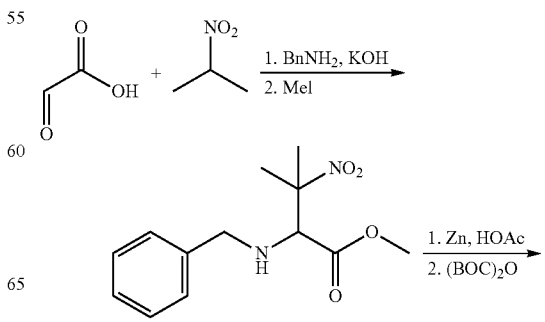

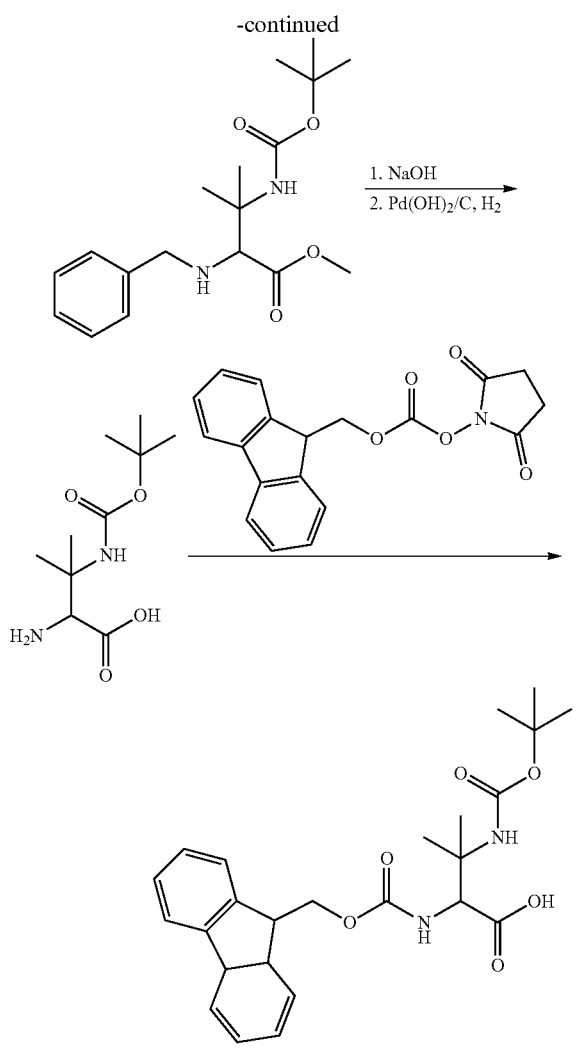

Step 1: 2-(Benzylamino)-3-methyl-3-nitrobutanoic Acid

2-Nitropropane (292 mL, 3250 mmol) was added to a cooled (10° C.) solution of potassium hydroxide (219 g, 3900 mmol) in water (750 mL). The reaction mixture was kept between 0-10° C. and benzylamine (355 ml, 3250 mmol) was added dropwise. To this mixture a solution of 2-oxoacetic acid in water (370 ml, 3250 mmol) in water (1.1 L) was added over a period of 90 minutes and stirring at room temperature was continued for 20 hours. The reaction mixture was diluted with 8 L water and concentrated hydrochloric acid was added until pH 2 was reached. The resulting precipitate was collected by filtration, washed with 10 L water and dried at 40° C. under reduced pressure to give the desired compound.

Step 2: Methyl 2-(benzylamino)-3-methyl-3-nitrobutanoate

Two identical batches were prepared in parallel in which iodomethane (34.8 ml, 556 mmol) was added dropwise to a mixture of 2-(benzylamino)-3-methyl-3-nitrobutanoic acid (146 g, 506 mmol) and cesium carbonate (181 g, 556 mmol) in DMF (1530 ml) at −78° C. After the addition was complete, the mixture was allowed to stir without further cooling for 2.5 hours. Both batches were combined, diluted with ethyl acetate (2.1 L) and 556 ml 1M hydrochloric acid (556 mmol). The layers were separated and the organic phase extracted with water (900 mL) and the aqueous phase with ethyl acetate (300 mL). The combined organics were extracted with 500 mL of saturated aqueous NaHCO$_3$ and dried (Na$_2$SO$_4$). After filtration and evaporation of all volatiles, the desired compound was obtained as an oil.

Step 3: Methyl 3-amino-2-(benzylamino)-3-methylbutanoate

Acetic acid (654 mL) was added to a mixture of zinc (187 g, 2854 mmol), ethanol (1.1 L) and water (100 mL) stirred at −20° C. Methyl 2-(benzylamino)-3-methyl-3-nitrobutanoate (152 g, 571 mmol) dissolved in ethanol (1.1 L) was added dropwise over a period of 60 minutes. The mixture was stirred without further cooling overnight, filtered over celite and concentrated in vacuo. The residue was taken up in a mixture of 1000 mL ethyl acetate and 1000 mL water. Under ice cooling, 5 M NaOH was added until the mixture reached pH 9. The mixture was then filtered through celite, the layers were separated and the aqueous phase extracted with 300 mL ethyl acetate. The combined organic layers were dried (Na$_2$SO$_4$), filtered and the solvent was evaporated under reduced pressure to give the desired compound as an oil.

Step 4: Methyl 2-(benzylamino)-3-((tert-butoxycarbonyl)amino)-3-methylbutanoate Di-tert-butyl dicarbonate (230 g, 1054 mmol) was added to a stirred mixture of methyl 3-amino-2-(benzylamino)-3-methylbutanoate (83 g, 351 mmol) and Na$_2$CO$_3$ (112 g, 1054 mmol) in dioxane (830 mL). Stirring at room temperature was continued for 18 hours. The reaction mixture was diluted with water (800 mL) and dichloromethane (800 mL) and the layers separated. The aqueous phase was extracted with dichloromethane (500 mL) and the combined organic fractions were dried (Na$_2$SO$_4$), filtered and concentration to dryness provided 250 g of a yellow oil. This was taken up in n-pentane (500 mL) and stirred at room temperature overnight. The mixture was then stirred at 0° C. for 1 hour and the precipitate was collected by filtration and washed with cold n-pentane (200 mL). The liquid fraction was concentrated in vacuo and purified by column chromatography using n-pentane/ethyl acetate as the eluent. The product containing fractions were combined and concentrated to dryness. All solids were combined to yield the desired compound.

Step 5: 2-(Benzylamino)-3-((tert-butoxycarbonyl)amino)-3-methylbutanoic Acid Methyl 2-(benzylamino)-3-((tert-butoxycarbonyl)amino)-3-methylbutanoate (145 g, 431 mmol) was added to a mixture of NaOH (138 g, 3448 mmol) in methanol (150 mL) and water (150 mL) at room temperature. The reaction mixture was heated at 70° C. for 2 hours. After cooling to room temperature, the reaction mixture was concentrated under reduced pressure. The resulting mixture was cooled with an ice bath and acidified with 1.0 M HCl until pH 5.4 was reached. The resulting white precipitate was collected by filtration, washed with cold water and dried in vacuo to give 120 g of the crude product which was used in the next step without further purification.

Step 6: 2-Amino-3-((tert-butoxycarbonyl)amino)-3-methylbutanoic Acid 2-(Benzylamino)-3-((tert-butoxycarbonyl)amino)-3-methylbutanoic acid (120 g, 372 mmol) was added to a suspension of palladium hydroxide on carbon (25 g, 35.6 mmol) in methanol (500 mL) and the mixture was stirred for 16 hours at 25° C. under an atmosphere of hydrogen (P=48 psi). The reaction mixture was filtered, washed with methanol several times and the combined organic phases were evaporated under reduced pressure to give the desired product.

Step 7: 3-(tert-Butoxycarbonylamino)-2-(9H-fluoren-9-ylmethoxycarbonylamino)-3-methyl-butanoic acid (9H-Fluoren-9-yl)-methyl-(2,5-dioxopyrrolidin-1-yl) carbonate (142 g, 420 mmol) was added to a stirred mixture of 2-amino-3-((tert-butoxycarbonyl)amino)-3-methylbutanoic acid (65 g, 280 mmol) and NaHCO$_3$ (47 g, 560 mmol) in acetone (780 mL) and water (520 mL) and stirred at room temperature for 3 hours. The reaction mixture was concentrated under reduced pressure and the resulting mixture was cooled with an ice bath. Hydrochloric acid (1 M) was added until pH 6 was reached and the mixture was then extracted with ethyl acetate (3×500 mL). The combined organic fractions were dried, evaporated to dryness and submitted to column chromatography on silica gel (ethyl acetate/petroleum ether) to provide a solid. MS: 355 (M-Boc+1). $^1$H NMR (400 MHz, CDCl$_3$): δ7.76 (d, J=7.6 Hz, 2H), 7.5-7.6 (m, 2H), 7.3-7.4 (m, 4H), 4.59 (b, 1H), 4.4-4.5 (m, 2H), 4.24 (t, J=6.8 Hz, 1H), 1.3-1.5 (b, 15H).

Example 1G

Synthesis of (2S)-3-[tert-butyl(dimethyl)silyl]oxy-2-(9H-fluoren-9-ylmethoxycarbonylamino)-3-methyl-butanoic Acid

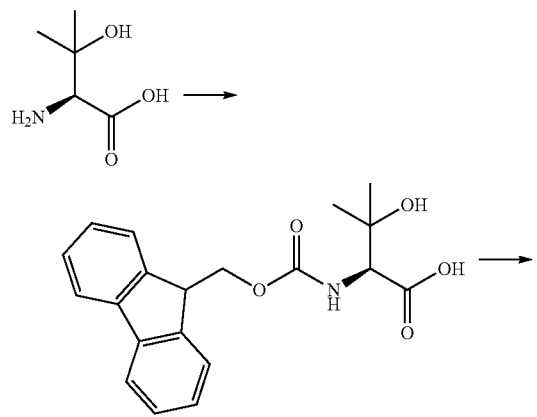

Step 1: (S)-2-((((9H-Fluoren-9-yl)methoxy)carbonyl)amino)-3-hydroxy-3-methylbutanoic Acid

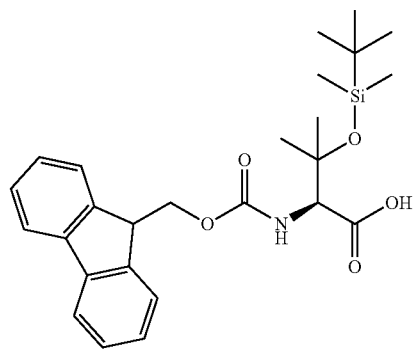

To a solution of (S)-2-amino-3-hydroxy-3-methylbutanoic acid hydrochloride (30.1 g, 177 mmol) in a mixture of dioxane (500 mL) and water (250 mL) was added an aqueous NaHCO$_3$ solution (44.7 g in 500 mL water) at 20° C. The reaction mixture was stirred at this temperature for 30 minutes. Then a solution of (9H-fluoren-9-yl)methyl (2,5-dioxopyrrolidin-1-yl) carbonate (59.9 g, 177 mmol) in dioxane (625 mL) was added. The resulting mixture was then stirred at room temperature for 3 hours. The dioxane was removed in vacuo and the remaining solution washed with methyl-tert-butylether (3×1000 mL). The aqueous phase was then acidified with 1.0 M hydrochloric acid until the pH 2-3 was reached and was then extracted with ethyl acetate (4×800 mL). The organic phases were combined, washed with brine, dried, filtered and concentrated to give the title compound.

Step 2: (2S)-3-[tert-Butyl(dimethypsilyl]oxy-2-(9H-fluoren-9-ylmethoxycarbonylamino)-3-methyl-butanoic Acid N,N-Diisopropylethylamine (36.4 g, 281 mmol) was added to a solution of (S)-2-((((9H-fluoren-9-yl)methoxy)carbonyl)amino)-3-hydroxy-3-methylbutanoic acid (20 g, 56.3 mmol) in dichloromethane (500 mL) at 0° C. over a period of 20 minutes. Then, tert-butyldimethylsilyl trifluoromethanesulfonate (59.5 g, 225 mmol) was added dropwise to the mixture and after stirring for 4 hours at 0° C. All volatiles were removed in vacuo and to the residue ethyl acetate (400 mL) was added. 1.0 M hydrochloric acid was added until pH 2-3 was reached and the aqueous layer was extracted with ethyl acetate (4×300 mL). The combined organic phases were washed with brine, dried, filtered and concentrated to give the crude product which was purified by column chromatography on silica gel (petroleum ether/ethyl acetate) to provide the title compound as a solid. $^1$H NMR (400 MHz, CDCl$_3$): δ7.77 (d, J=7.6 Hz, 2H), 7.61 (dd, J=6.8 Hz, J=6.4 Hz, 2H), 7.30-7.41 (m, 4H), 5.56 (d, J=9.2 Hz, 1H), 4.2 (d, J=6.8 Hz, 2H), 4.23-4.30 (m, 2H), 1.45 (s, 3H), 1.30 (s, 3H), 0.92 (s, 9H), 0.19 (s, 3H), 0.18 (s, 3H).

Example 1H

Synthesis of (2R)-2-(9H-fluoren-9-ylmethoxycarbonylamino)-3-methyl-3-methylsulfanyl-butanoic Acid

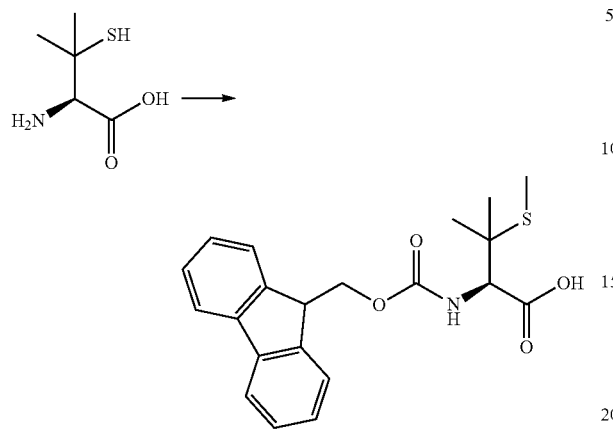

To a solution of (R)-2-amino-3-mercapto-3-methylbutanoic acid in methanol was added sodium (3.08 g, 134 mmol) followed by iodomethane (5 g, 35.2 mmol). The reaction mixture was stirred for 3 hours at 25° C. and then concentrated in vacuo. The residue was treated with 1 M hydrochloric acid until pH 7 was reached and the mixture was then diluted with water (50 mL). NaHCO₃ (5.6 g, 67 mmol) and a solution of (9H-fluoren-9-yl)methyl (2,5-dioxopyrrolidin-1-yl)carbonate in acetone was added. After stirring at 25° C. for 3 hours, the solution was concentrated in vacuo and treated with 1 M hydrochloric acid until pH 4 was reached. The mixture was then extracted with ethyl acetate (4×50 mL) and the combined organic layers were evaporated to dryness and the residue submitted to column chromatography on silica gel (ethyl acetate/petroleum ether 1:100 to 1:10) to provide the title compound as a solid. MS: 385.8 (M+1). NMR (400 MHz, CDCl₃): δ7.77 (d, J=7.6 Hz, 2H), 7.61 (d, J=7.2 Hz, 2H), 7.32-7.43 (m, 4H), 5.57 (d, J=7.6 Hz, 1H), 4.3-4.5 (m, 3H), 4.25 (t, J=6.8 Hz, 1H), 2.10 (s, 3H), 1.43 (s, 3H), 1.39 (s, 3H).

Example 1I

Synthesis of (2S)-2-(9H-fluoren-9-ylmethoxycarbonylamino)-2-(2-methyl-1,3-dioxolan-2-yl) Acetic Acid

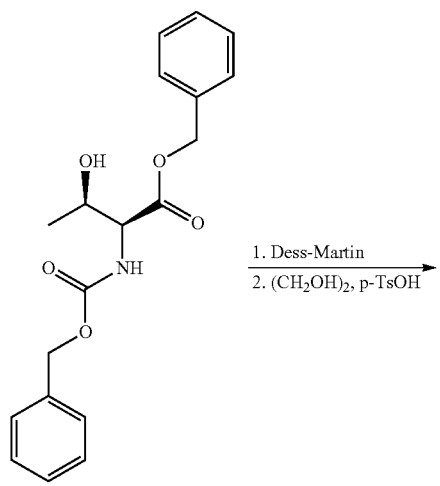

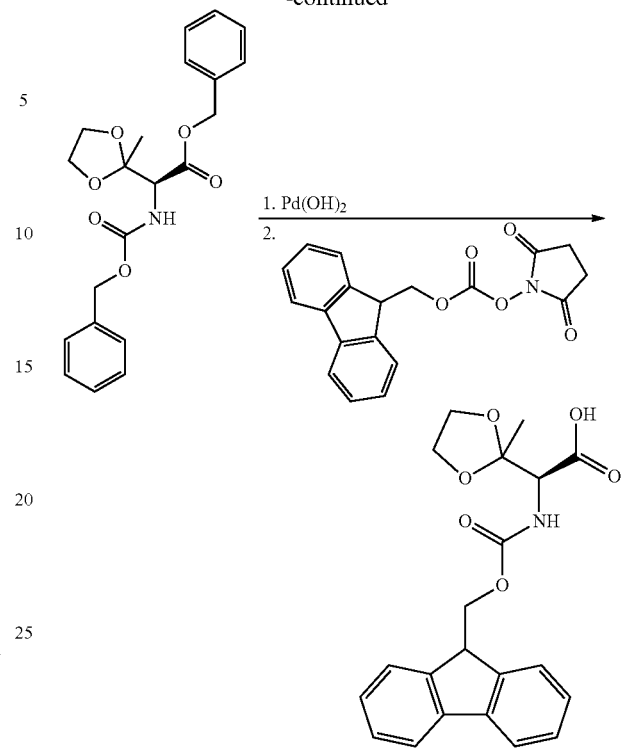

Step 1: Synthesis of benzyl (2S)-2-(benzyloxycarbonylamino)-3-oxo-butanoate

To a mixture of (benzyl (2S,3R)-2-(benzyloxycarbonylamino)-3-hydroxy-butanoate (20 g, 58.2 mmol) in dichloromethane (300 mL) was added Dess-Martin Periodinane (37.1 g, 87 mmol) and NaHCO₃ (0.489 g, 5.82 mmol) at 0° C. The mixture was then stirred at room temperature for 16 hours and concentrated under reduced pressure to remove all volatiles. To the mixture was then added saturated Na₂SO₃ (400 mL) and ethyl acetate (400 mL) and both layers shaken vigorously. The aqueous phase was separated and extracted with ethyl acetate (1×400 mL). The combined organic layers were washed with brine (3×400 mL), dried over Na₂SO₄, filtered and concentrated under reduced pressure to provide the crude title compound which was used in the next step without further purification.

Step 2: Synthesis of benzyl (2S)-2-(benzyloxycarbonylamino)-2(2-methyl-1,3-dioxolan-2-yl) acetate A solution of benzyl (2S)-2-(benzyloxycarbonylamino)-3-oxo-butanoate (40 g, 117 mmol), 4-methylbenzenesulfonic acid hydrate (22.29 g, 117 mmol) in ethane-1,2-diol (400 mL) and tetrahydrofuran (50 mL) was stirred at ambient temperature for 16 hours. The reaction mixture was then concentrated under reduced pressure and the residue was purified by reverse phase preparative HPLC applying a water/acetonitrile gradient without additives to provide the title compound.

Step 3: (2S)-2-amino-2-(2-methyl-1,3-dioxolan-2-yl) Acetic Acid

A mixture of benzyl (2S)-2-(benzyloxycarbonylamino)-2-(2-methyl-1,3-dioxolan-2-yl) acetate (8 g, 20.76 mmol)

and Pd(OH)$_2$ on carbon (1 g, 20% purity) in methanol (200 mL) was stirred at ambient temperature under an atmosphere of hydrogen (50 psi) for 16 hours. The mixture was filtered and concentrated under reduced pressure to provide the crude title compound which was used in the next step without further purification.

Step 4: (2S)-2-(9H-fluoren-9-ylmethoxycarbonylamino)-2-(2-methyl-1,3-dioxolan-2-yl) Acetic Acid To a mixture of (S)-2-amino-2-(2-methyl-1,3-dioxolan-2-yl) acetic acid (4 g, 24.82 mmol) and NaHCO$_3$ (6.26 g, 74.5 mmol) in acetone (50 mL) and water (50 mL) was added a solution of (9H-fluoren-9-yl)methyl (2,5-dioxopyrrolidin-1-yl) carbonate (9.21 g, 27.3 mmol) in acetone (20 mL) under stirring at ambient temperature and stirring was continued for 2 hours. All volatiles were then removed under reduced pressure and the residue was combined with water (20 mL). The resulting mixture was washed with ethyl acetate (50 mL), the aqueous layer was acidified with 3 M HCl to pH=4. The precipitate was collected by filtration and washed with water (30 mL) and dried under freeze-drying condition to provide the title compound. $^1$H NMR (400 MHz, DMSO-d$_6$): δ7.89 (d, J=7.6 Hz, 2H), 7.78 (d, J=7.6 Hz, 2H), 7.69 (m, 2H), 7.42 (dd, J=7.6 Hz, 2H), 7.33 (dd, J=7.6 Hz, 2H) 4.1-4.4 (m, 4H), 3.7-4.0 (m, 4H), 1.38 (s, 3H).

Example 1J

Synthesis of (2S)-2-(9H-fluoren-9-ylmethoxycarbonylamino)-3-methoxyimino-butanoic Acid

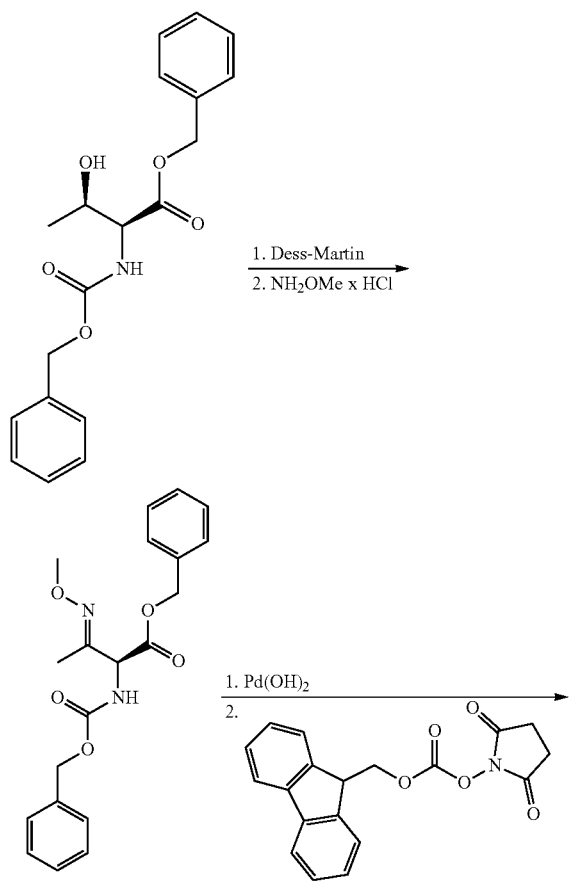

Step 1: Synthesis of benzyl (2S)-2-(benzyloxycarbonylamino)-3-oxo-butanoate

To a mixture of (benzyl (2S,3R)-2-(benzyloxycarbonylamino)-3-hydroxy-butanoate (20 g, 58.2 mmol) in dichloromethane (300 mL) was added Dess-Martin Periodinane (37.1 g, 87 mmol) and NaHCO$_3$ (0.489 g, 5.82 mmol) at 0° C. The mixture was then stirred at room temperature for 16 hours and concentrated under reduced pressure to remove all volatiles. To the mixture was then added saturated Na$_2$SO$_3$ (400 mL) and ethyl acetate (400 mL) and both layers shaken vigorously. The aqueous phase was separated and extracted with ethyl acetate (1×400 mL). The combined organic layers were washed with brine (3×400 mL), dried over Na$_2$SO$_4$, filtered and concentrated under reduced pressure to provide the crude title compound which was used in the next step without further purification.

Step 2: Synthesis of benzyl (2S)-2-(benzyloxycarbonylamino)-3-methoxyimino-butanoate Benzyl (2S)-2-(benzyloxycarbonylamino)-3-oxo-butanoate (0.5 g, 1.46 mmol) was added to a solution of methoxylamine hydrochloride (183 mg, 2.197 mmol) and titanium (IV) isopropoxide (83 mg, 0.29 mmol) in DIEA (0.767 mL) and tetrahydrofuran (10 mL) at 20° C. The reaction mixture was heated at 72° C. for 12 hours and then diluted with water (10 mL). The aqueous layer was extracted with dichloromethane and the combined organic extracts were washed with 10% aqueous HCl (50 mL), saturated NaHCO$_3$ (50 mL) and brine (50 mL) and then dried over Na$_2$SO$_4$. It was then filtered and concentrated under reduced pressure to give a residue which was purified by column chromatography on silica gel (petroleum ether/ethyl acetate) to provide the title compound.

Step 3: (2S)-2-Amino-3-methoxyimino-butanoic Acid

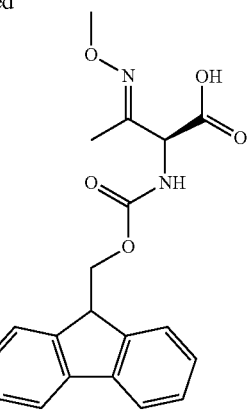

To a solution of benzyl (2S)-2-(benzyloxycarbonylamino)-3-methoxyimino-butanoate (50 g, 135 mmol) in methanol (1000 mL) was added palladium on carbon (15%, 10 g) and an atmosphere of nitrogen (15 psi) was established. The reaction mixture was then stirred at 20° C. for 90 minutes and all solids removed by filtration. The solution was collected and concentrated to provide the title compound.

Step 4: Synthesis of (2S)-2-(9H-fluoren-9-yl-methoxycarbonylamino)-3-methoxyimino-butanoic Acid (9H-Fluoren-9-yl)methyl (2,5-dioxopyrrolidin-1-yl) carbonate (69.2 g, 205 mmol) was added to a solution of (S)-2-amino-3-(methoxyimino)-butanoic acid (20 g, 137 mmol) in a mixture of acetone (400 mL) and saturated aqueous NaHCO$_3$ (400 mL). The solution was stirred ambient temperature for 10 hours. Water was then added to the reaction mixture and the formed precipitate collected by filtration. The filter cake was then purified by flash C18 reverse phase chromatography applying a water/acetonitrile gradient to provide the title compound. $^1$H NMR (400 MHz, CDCl$_3$): δ7.89 (d, J=7.6 Hz, 2H), 7.68 (d, J=7.6 Hz, 2H), 7.42 (dd, J=7.6 Hz, 2H), 7.33 (dd, J=7.6 Hz, 2H), 6.7 (b, 1H), 4.1-4.4 (m, 4H), 3.72 (s, 3H), 1.62 (s, 3H).

Example 1K

General Procedure for the Synthesis of Crotonaldehyde-Containing Resin

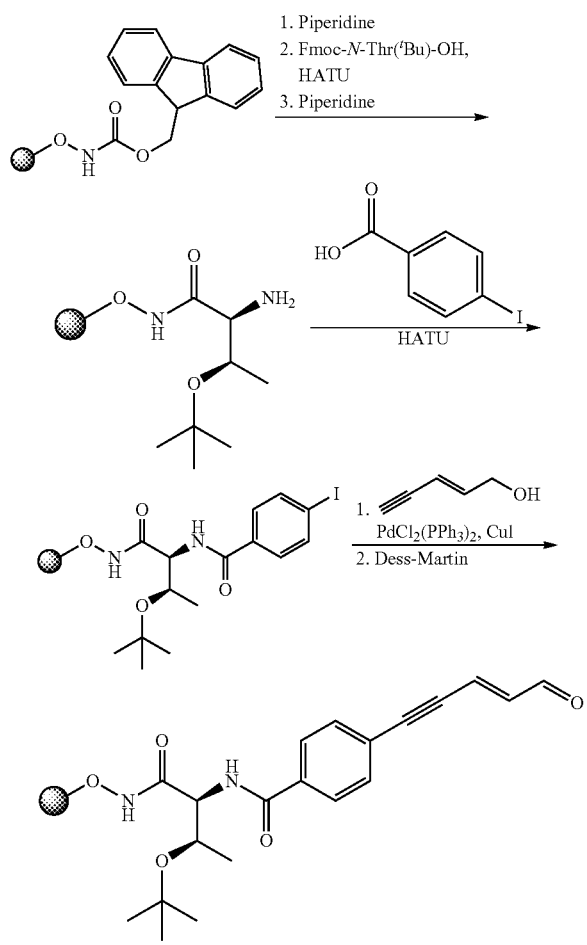

A suspension of N-Fmoc-hydroxylamine 2-chlorotrityl resin (50.0 g, 25 mmol) in dichloromethane (500 mL) was shaken for 2 hours and drained. The resin was then treated with 20% piperidine in DMF (500 mL) for 30 minutes, washed with DMF (5×200 mL) and drained completely. In a separate flask, Fmoc-N-Thr($^t$Bu)-OH (30 g, 75 mmol), HATU (27 g, 71.3 mmol) and DIEA (26.0 mL, 150 mmol) were dissolved in DMF (100 mL), stirred for three minutes and then added to the resin. After mixing under an atmosphere of nitrogen for 2 hours, the mixture was drained, washed with DMF (3×200 mL), treated a second time with the DMF solution of Fmoc-N-Thr($^t$Bu)-OH (30 g, 75 mmol), HATU (27 g, 71.3 mmol) and DIEA (26.0 mL, 150 mmol). The mixture was left shaking for another 2 hours, washed with DMF (5×200 mL) and drained. The resin was then treated with 20% piperidine in DMF (500 mL) for 30 minutes, washed with DMF (5×200 mL) and drained completely. 4-iodobenzoic acid (19 g, 75 mmol), HATU (27 g, 71.3 mmol) and DIEA (26 mL, 150 mmol) dissolved in DMF (100 mL) were then added to the resin and the mixture was mixed under an atmosphere of nitrogen for 1 hour. The mixture was drained, washed with DMF (3×200 mL), MeOH (3×200 mL) and drained, dried in vacuo.

A solution of (E)-pent-2-en-4-yn-1-ol (8.21 g, 100 mmol) and DIEA (44 mL, 250 mmol) in DMF (250 mL) was purged with a stream of nitrogen for two minutes and then added to the resin. After mixing for 5 minutes, PdCl$_2$(PPh$_3$)$_2$ (3.51 g, 5.0 mmol) and CuI (2.38 g, 12.5 mmol) were added and the mixture was shaken under an atmosphere of nitrogen for 48 hours. The resin was drained, washed with DMF (4×150 mL), dichloromethane (4×100 mL) and drained again. The resin was then treated with Dess-Martin periodinane (21.2 g, 50 mmol) and Na$_2$CO$_3$ (10.6 g, 100 mmol) in dichloromethane for 1 hour, and drained completely. The resin was washed with DMF (3×150 mL) and MeOH (3×150 mL) and dried in vacuo.

Using this procedure, the corresponding amino acid-containing aldehyde resin was obtained using Fmoc-N-(S)-Val-OH.

Example 1L

General Procedure for the Reductive Amination of the Crotonaldehyde-Containing Resins with Primary and Secondary Amines A solution of the amine (2.4 mmol) and trimethyl orthoformate (287 μL, 2.6 mmol) in THF (20 mL) was added to a vial containing the resin (186 mg). After purging the vessel with nitrogen for 5 minutes, it was treated with acetic acid (282 μL, 4.92 mmol) followed by a solution of NaBH$_3$CN (113 mg, 1.8 mmol) in MeOH (1.0 mL) and mixing under an atmosphere of nitrogen was continued for 48 hours. The resin was drained, washed with DMF (2×10 mL) and MeOH (3×10 mL) and drained again and dried under reduced pressure. Cleavage from the resin was achieved by treatment with 30% v/v TFA/DCM (20 mL) and for 30 minutes. The solution was collected and concentrated to dryness to give a crude residue which was purified by preparative HPLC using a Gilson GX-281 semi-preparative HPLC system equipped with a Luna 200×25 mm (C18, 10μ, 100 A) or a Gemini 150×30 mm (C18, 5 um, 110 A) column applying a gradient consisting of 0.1% TFA/water and acetonitrile. The product containing fractions were collected, concentrated by freeze-drying and the residual trifluoroacetic acid was removed by another reverse-phase chromatography using a gradient consisting of aqueous ammonium hydrogencarbonate (7.5 mmol/L) and acetonitrile.

Using this procedure, the following compounds can be synthesized:
Compound No. 101-102
Compound No. 365
Compound No. 367-380
Compound No. 436-443

Example 1M

General Procedure for the Synthesis of Crotonaldehyde-Containing Resins Bearing a Bisacetylene Linker

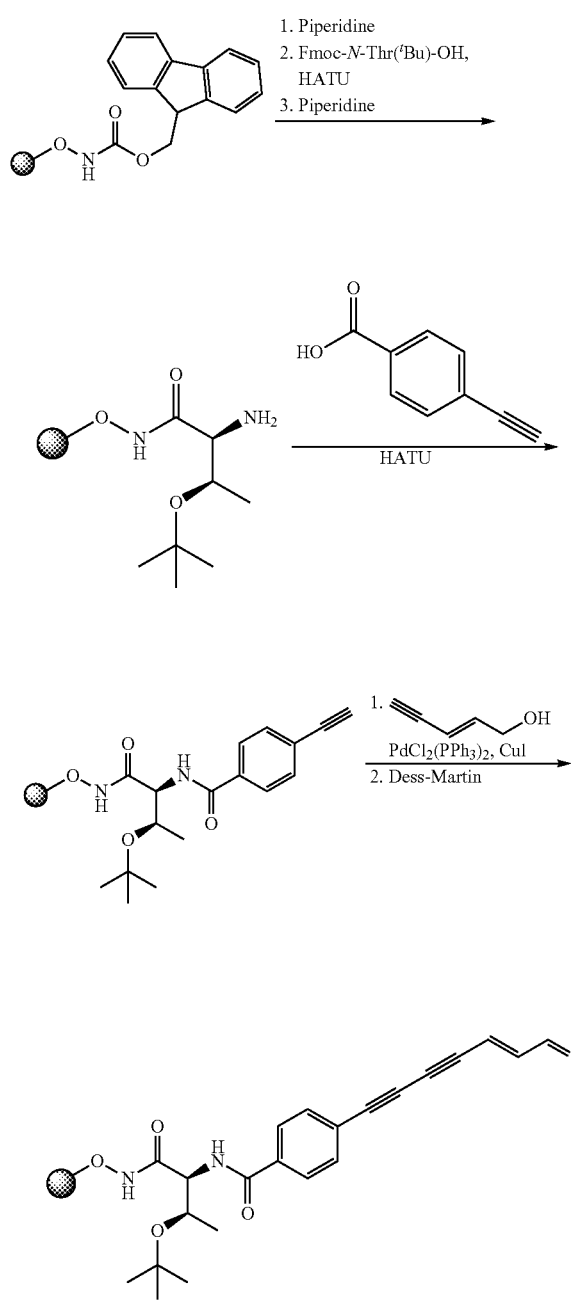

A suspension of N-Fmoc-hydroxylamine 2-chlorotrityl resin (50.0 g, 25.0 mmol) in DCM (500 mL) was shaken for 2 hours and drained. The resin was treated with 20% piperidine in DMF (500 mL) for 30 minutes, washed with DMF (5×200 mL) and drained completely. In a separate flask, Fmoc-N-Thr($^t$Bu)-OH (30 g, 75 mmol), HATU (27 g, 71.3 mmol) and DIEA (26 mL, 150 mmol) were dissolved in DMF (100 mL), stirred for 3 minutes and added to the resin. After mixing under an atmosphere of nitrogen for 2 hours, the mixture was drained, washed with DMF (3×200 mL), treated a second time with Fmoc-N-Thr($^t$Bu)-OH (30 g, 75 mmol), HATU (27 g, 71.3 mmol) and DIEA (26 mL, 150 mmol) for another 2 hours, washed with DMF (5×200 mL) and drained. The resin then was treated with 20% piperidine in DMF (500 mL) for 30 minutes, washed with DMF (5×200 mL) and drained completely. 4-ethynylbenzoic acid (10.96 g, 75 mmol), HATU (27 g, 71.3 mmol) and DIEA (26 mL, 150 mmol) dissolved in DMF (100 mL) were then added to the resin, and mixing under an atmosphere of nitrogen was continued for 1 hour. The mixture was drained, washed with DMF (3×200 mL), MeOH (3×200 mL) and dried in vacuo. (E)-pent-2-en-4-yn-1-ol (20.53 g, 250 mmol) was added to a flame dried vial containing a mixture of the propargyl alcohol functionalized trityl resin (25 mmol) and tetrahydrofuran (750 mL). To CuI (2.4 g, 12.5 mmol.), PdCl$_2$(PPh$_3$)$_2$ (3.51 g, 5.0 mmol) and DIEA (32.3 g, 250 mmol) placed in a separate flame-dried vial, THF (7.5 mL) was added. The catalyst mixture was then transferred to the resin in one portion and allowed to mix at 60° C. for 16 hours. The resin was then collected and washed with DCM and MeOH (5 alternating rinses with 200 mL each). The resin was treated with Dess-Martin periodinane (21.2 g, 50 mmol) and Na$_2$CO$_3$ (10.6 g, 100 mmol) in dichloromethane for 1 hour. The resin was collected, drained, washed with DMF (3×150 mL) and MeOH (3×150 mL) and dried in vacuo.

Example 1N

General Procedure for the Reductive Amination of the Crotonaldehyde-Containing Resins Bearing a Bisacetylene Linker with Primary and Secondary Amines A solution of the amine (3.0 mmol) and trimethyl orthoformate (359 µL, 3.25 mmol) in THF (20 mL) was added to a vial containing the resin. Mixing under an atmosphere of nitrogen was continued for 5 minutes when acetic acid (352 µL, 6.15 mmol) followed by a solution of NaBH$_3$CN (141.0 mg, 2.25 mmol) in MeOH (1 mL) was added. Mixing under an atmosphere of nitrogen was continued for 44 hours. The raisin was drained, washed with DMF (2× 10 mL) and MeOH (3×10 mL) and dried under reduced pressure. Cleavage from the resin was achieved by treatment with TFA (10 mL) for 30 minutes. The solution was collected and concentrated to dryness to give a crude residue which was purified by preparative HPLC using a Gilson GX-281 semi-preparative HPLC system equipped with a Luna 200×25 mm (C18, 10µ, 100 A) or a Gemini 150×30 mm (C18, 5 um, 110 A) column applying a gradient consisting of 0.1% TFA/water and acetonitrile. The product containing fractions were collected, concentrated by freeze-drying and the residual trifluoroacetic acid was removed by another reverse-phase chromatography using a gradient consisting of aqueous ammonium hydrogencarbonate (7.5 mmol/L) and acetonitrile.

Using this procedure, the following compounds can be synthesized:

Compounds No. 444-466

Example 1O

Synthesis of N-[(1S)-2-(hydroxyamino)-1-(hydroxymethyl)-2-oxo-ethyl]-4-[2-(4-nitrophenyl)ethynyl]benzamide [242] and 4-[2-(4-aminophenyl)ethynyl]-N-[(1S)-2-(hydroxyamino)-1-(hydroxymethyl)-2-oxo-ethyl]benzamide [244]

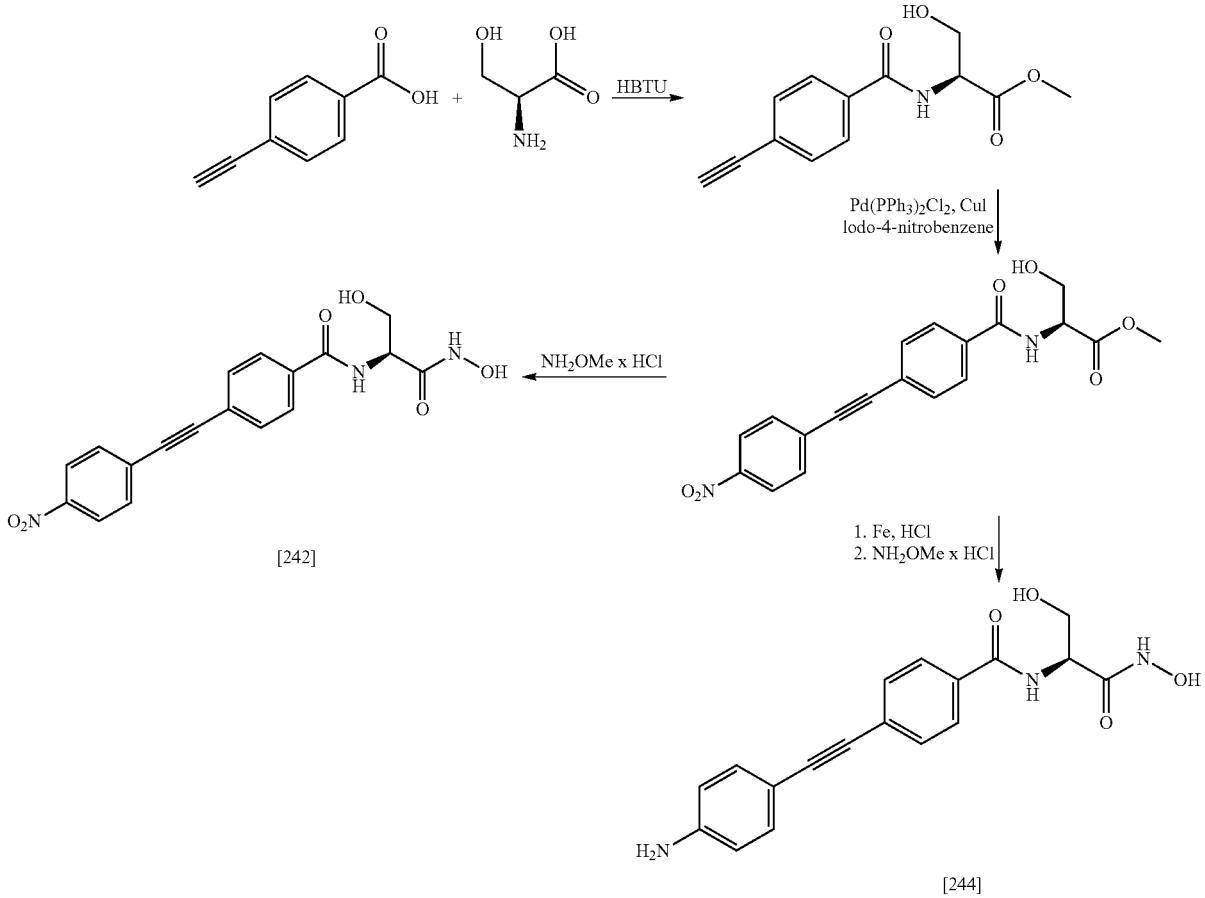

Step 1: Synthesis of methyl (2S)-2-[(4-ethynylbenzoyl)amino]-3-hydroxy-propanoate 4-Ethynylbenzoic acid (300 mg, 2.05 mmol) and HBTU (779 mg, 2.0 mmol) were dissolved in DMF (1 mL) and stirred at ambient temperature. After 5 minutes, (S)-methyl 2-amino-3-hydroxypropanoate hydrochloride (351 mg, 2.26 mmol), tetrahydrofuran (4 mL) and triethylamine (0.658 ml, 4.7 mmol) were added and stirring was continued for 1 hour at ambient temperature. The reaction mixture was diluted with ethyl acetate and washed twice with NaHCO$_3$ solution. The organic layer was washed with brine, dried over MgSO$_4$ and concentrated under reduced pressure. The residue was purified by column chromatography (silica, pentane/ethyl acetate) to provide the title compound.

Step 2: Synthesis of methyl (2S)-3-hydroxy-2-[[4-[2-(4-nitrophenyl)ethynyl]benzoyl]amino]propanoate Iodo-4-nitrobenzene (528 mg, 2.12 mmol) and triethylamine (0.34 ml, 2.44 mmol) were added to a solution of Pd(PPh$_3$)$_2$Cl$_2$ (29.8 mg, 0.042 mmol) and CuI (12.1 mg, 0.064 mmol) in tetrahydrofuran (5 mL) under an atmosphere of nitrogen. To this mixture was then added dropwise a solution of (S)-methyl 2-(4-ethynylbenzamido)-3-hydroxypropanoate (262 mg, 1.06 mmol) in tetrahydrofuran (2 mL). The reaction mixture was taken up on silica gel and purified by column chromatography on silica gel (pentane/ethyl acetate) to provide the title compound.

Step 3: Synthesis of N-[(1S)-2-(hydroxyamino)-1-(hydroxymethyl)-2-oxo-ethyl]-4-[2-(4-nitrophenyl)ethynyl]benzamide [242]

Sodium (14 mg, 0.61 mmol) was added to dry methanol (1 mL) and the mixture was stirred for 20 minutes. Hydroxylamine hydrochloride (40.6 mg, 0.58 mmol) was then added and stirring at ambient temperature was continued for 45 minutes. Then, a solution of methyl (2S)-3-hydroxy-2-[[4-[2-(4-nitrophenyl)ethynyl]benzoyl]amino]propanoate (50 mg, 0.14 mmol) in methanol/tetrahydrofuran 1:1 (1 mL) was added and the reaction mixture stirred overnight. All volatiles were then removed under reduced pressure and the resulting residue was purified by reverse phase preparative HPLC using an Atlantis® C18 column applying a gradient consisting of 0.1% aqueous formic acid and acetonitrile to provide the title compound. $^1$H NMR (300 MHz, DMSO-d$_6$): δ10.71 (b, 1H), 8.86 (b, 1H), 8.45 (d, J=7.96 Hz, 1H), 8.30 (m, 2H), 7.99 (d, J=8.4 Hz, 2H), 7.87 (m, 2H), 7.74 (d, J=8.4 Hz, 2H), 4.98 (t, J=5.8 Hz, 1H), 4.43 (m, 1H), 3.69 (m, 2H).

Step 4: Synthesis of methyl (2S)-2-[[4-[2-(4-aminophenyl)ethynyl]benzoyl]amino]-3-hydroxy-propanoate Methyl (2S)-3-hydroxy-2-[[4-[2-(4-nitrophenyl)ethynyl]benzoyl]amino]propanoate (100 mg, 0.27 mmol), 2 M hydrochloric acid (0.54 ml, 1.1 mmol) and iron (106 mg, 1.9 mmol) were stirred in ethanol (2.5 mL) at 80° C. for 3.5 hours. The reaction mixture was then concentrated under reduced pressure and the resulting residue taken up in water and extracted with dichloromethane (2×). The organic layers were combined, washed with brine, dried over MgSO$_4$ and concentrated under reduced pressure to provide the title compound which was used in the next step without further purification.

Step 5: Synthesis of 4-[2-(4-aminophenyl)ethynyl]-N-[(1S)-2-(hydroxyamino)-1-(hydroxymethyl)-2-oxo-ethyl]benzamide [244]

Sodium (11.6 mg, 0.5 mmol) was added to dry methanol (1 mL) and stirred for 20 minutes. Hydroxylamine hydrochloride (33.6 mg, 0.48 mmol) was then added and stirring at ambient temperature was continued for 45 minutes. Then, a solution of methyl (2S)-2-[[4-[2-(4-aminophenyl)ethynyl]benzoyl]amino]-3-hydroxy-propanoate (38 mg, 0.11 mmol) in methanol/tetrahydrofuran 1:1 (1 mL) was added and the reaction mixture stirred for 2 hours. Then, another methanolic solution of hydroxylamine prepared from sodium (11.6 mg, 0.5 mmol), hydroxylamine hydrochloride (33.6 mg, 0.48 mmol) and methanol (1 mL) was added to the reaction mixture and heated at 40° C. overnight. The reaction mixture was allowed to attain room temperature and all volatiles were then removed under reduced pressure and the resulting residue was purified by reverse phase preparative HPLC using an Atlantis® C18 column applying a gradient consisting of 0.1% $^1$H NMR (300 MHz, DMSO-d$_6$) δ10.69 (s, 1H), 8.85 (s, 1H), 8.34 (d, J=8.0 Hz, 1H), 7.90 (d, J=8.5 Hz, 2H), 7.54 (d, J=8.4 Hz, 2H), 7.23 (d, J=8.5 Hz, 2H), 6.57 (d, J=8.6 Hz, 2H), 5.64 (s, 2H), 4.98 (t, J=5.6 Hz, 1H), 4.42 (q, J=6.2 Hz, 1H), 3.68 (s, 2H).

Example 1P

Synthesis of N-[(1S,2R)-2-hydroxy-1-(hydroxycarbamoyl)propyl]-4-[2-(4-nitrophenyl)ethynyl]benzamide [243] and 4-[2-(4-aminophenyl)ethynyl]-N-[(1S,2R)-2-hydroxy-1-(hydroxycarbamoyl) propyl] benzamide [245]

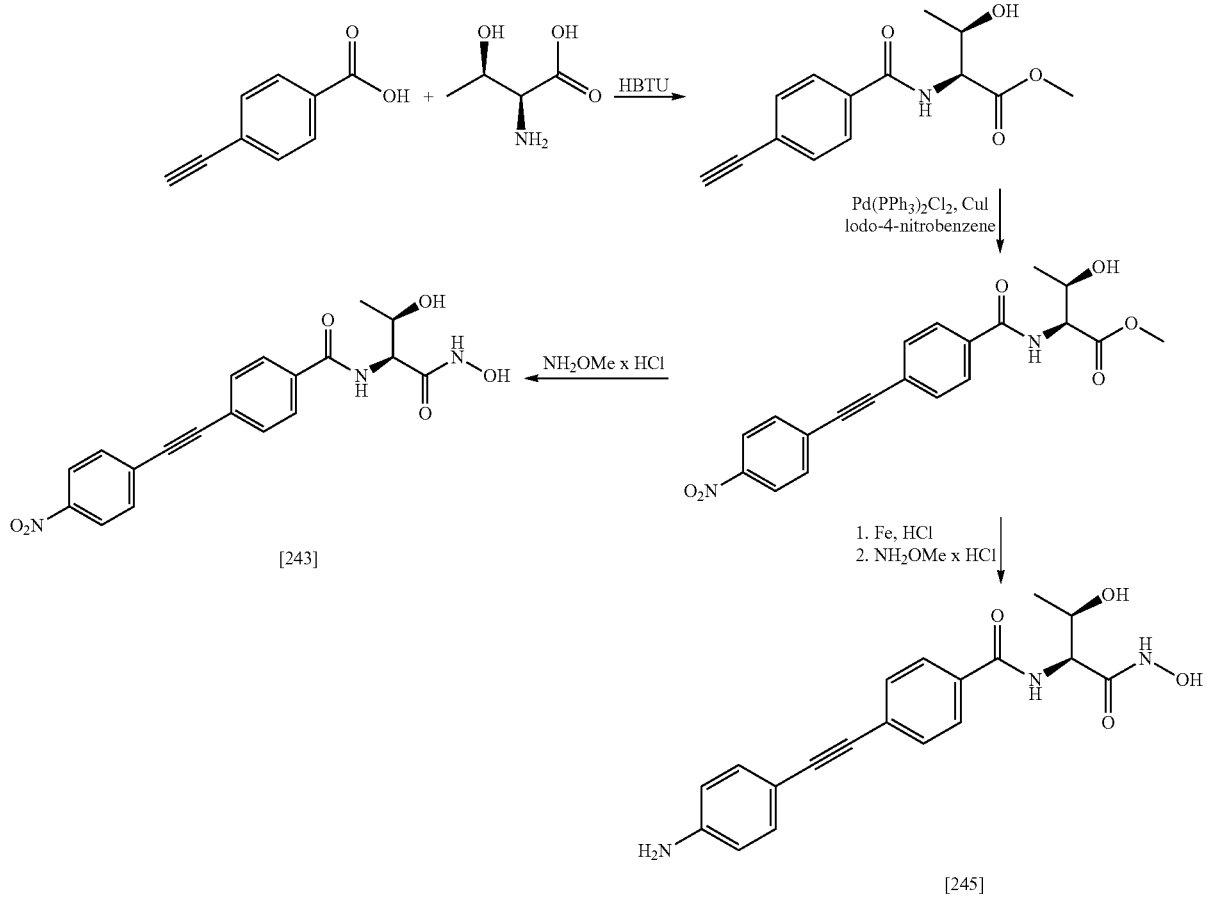

Step 1: Synthesis of methyl (2S,3R)-2-[(4-ethynylbenzoyl)amino]-3-hydroxy-butanoate 4-Ethynylbenzoic acid (200 mg, 1.37 mmol) and HBTU (519 mg, 1.37 mmol) were dissolved in DMF (1 mL) and stirred at ambient temperature for 5 minutes. Then, (2S,3R)- methyl 2-amino-3-hydroxybutanoate hydrochloride (255 mg, 1.5 mmol), tetrahydrofuran (4 mL) and triethylamine (0.439 ml, 3.15 mmol) were added. The mixture was stirred for 30 minutes and was then diluted with ethyl acetate and extracted with NaHCO$_3$ solution. The organic layer was washed with brine, dried over MgSO$_4$ and concentrated under reduced pressure. The residue was purified by column chromatography (silica, pentane/ethyl acetate) to provide the title compound.

Step 2: Synthesis of methyl (2S,3R)-3-hydroxy-2 [[4-[2-(4-nitrophenyl)ethynyl]benzoyl]amino]butanoate A solution of iodo-4-nitrobenzene (396 mg, 1.6 mmol), Pd(PPh$_3$)$_2$Cl$_2$ (22 mg, 0.032 mmol), CuI (9 mg, 0.048 mmol) in tetrahydrofuran (3 mL) and trimethylamine (0.255 mL, 1.83 mmol) was placed under an atmosphere of argon. After 3 minutes of stirring at ambient temperature, a solution of methyl (2S,3R)-2-[(4-ethynylbenzoyl)amino]-3-hydroxy-butanoate (208 mg, 0.8 mmol) in tetrahydrofuran (2 mL) was added dropwise and the mixture was left stirring for another 40 minutes. The reaction mixture was concentrated under reduced pressure and the residue was purified by column chromatography on silica gel (pentane/ethyl acetate) to provide the title compound.

Step 3: Synthesis of N-[(1S,2R)-2-hydroxy-1-(hydroxycarbamoyl)propyl]-4-[2-(4-nitrophenyl)ethynyl]benzamide [243]

Sodium (13.5 mg, 0.59 mmol) was added to dry methanol (1 mL) and the mixture was stirred for 20 minutes. Hydroxylamine hydrochloride (39 mg, 0.56 mmol) was then added and stirring at ambient temperature was continued for 45 minutes. Then, a solution of methyl (2S)-3-hydroxy-2-[[4-[2-(4-nitrophenyl)ethynyl]benzoyl]amino]propanoate (50 mg, 0.13 mmol) in methanol/tetrahydrofuran 1:1 (1 mL) was added and the reaction mixture stirred overnight. Then, another methanolic solution of hydroxylamine prepared from sodium (13.5 mg, 0.59 mmol), hydroxylamine hydrochloride (39.1 mg, 0.56 mmol) and methanol (1 mL) was added to the reaction mixture and stirring was continued for 1 hour. All volatiles were then removed under reduced pressure and the resulting residue was purified by reverse phase preparative HPLC using an Atlantis® C18 column applying a gradient consisting of 0.1% aqueous formic acid and acetonitrile to provide the title compound. $^1$H NMR (300 MHz, DMSO-d$_6$) δ10.70 (s, 1H), 8.88 (d, J=1.3 Hz, 1H), 8.30 (q, J=3.0 Hz, 2H), 8.20 (d, J=8.4 Hz, 1H), 7.99 (d, J=8.4 Hz, 2H), 7.88 (q, J=3.0 Hz, 2H), 7.75 (d, J=8.4 Hz, 2H), 4.92 (d, J=6.3 Hz, 1H), 4.27 (dd, J=5.6, 8.4 Hz, 1H), 4.04 (q, J=6.1 Hz, 1H), 1.11 (d, J=6.3 Hz, 3H).

Step 4: Synthesis of methyl (2S,3R)-2-[[4-[2-(4-aminophenyl)ethynyl]benzoyl]amino]-3-hydroxy-butanoate Methyl (2S,3R)-3-hydroxy-2-[[4-[2-(4-nitrophenyl)ethynyl]benzoyl]amino]butanoate (150 mg, 0.39 mmol), 2 M hydrochloric acid (0.785 mL, 1.6 mmol) and iron (153 mg, 2.75 mmol) were stirred together with ethanol (3 mL) at 80° C. After 2.5 hours the reaction mixture was allowed to attain room temperature and concentrated under reduced pressure. The residue was then taken up in water and extracted with dichloromethane (2×). The organic layers were combined, washed with brine, dried over MgSO$_4$ and concentrated to provide the title compound.

Step 5: Synthesis of 4-[2-(4-aminophenyl)ethynyl]-N-[(1S,2R)-2-hydroxy-1-(hydroxycarbamoyl) propyl]benzamide [245]

Sodium (23.19 mg, 1.0 mmol) was added to dry methanol (1 mL) and stirred for 20 minutes. Hydroxylamine hydrochloride (67 mg, 0.96 mmol) was then added and stirring at ambient temperature was continued for 45 minutes. Then, a solution of methyl (2S, 3R)-2-[[4-[2-(4-aminophenyl)ethynyl]benzoyl]amino]-3-hydroxy-butanoate (79 mg, 0.22 mmol) in methanol/tetrahydrofuran 1:1 (2 mL) was added and the reaction mixture stirred for 2 hours. Then another methanolic solution of hydroxylamine prepared from sodium (23.2 mg, 1.01 mmol), hydroxylamine hydrochloride (67 mg, 0.96 mmol) and methanol (1 mL) was added to the reaction mixture and stirred at ambient temperature for 1 hour. All volatiles were then removed under reduced pressure and the resulting residue was purified by reverse phase preparative HPLC using an Atlantis® C18 column from Waters applying a gradient consisting of 0.1% aqueous formic acid and acetonitrile to provide the title compound. $^1$H NMR (300 MHz, DMSO-d$_6$) δ10.68 (s, 1H), 8.87 (s, 1H), 8.10 (d, J=8.5 Hz, 1H), 7.91 (d, J=8.5 Hz, 2H), 7.55 (d, J=8.4 Hz, 2H), 7.23 (d, J=8.6 Hz, 2H), 6.57 (d, J=8.6 Hz, 2H), 5.64 (s, 2H), 4.94 (s, 1H), 4.27 (dd, J=5.5, 8.4 Hz, 1H), 4.03 (d, J=4.4 Hz, 1H), 1.10 (d, J=6.3 Hz, 3H).

Example 1Q

Synthesis of N-[(1S,2R)-2-hydroxy-1-(hydroxycarbamoyl)propyl]-4-[2-(4-nitrophenyl) ethynyl]benzamide [246]

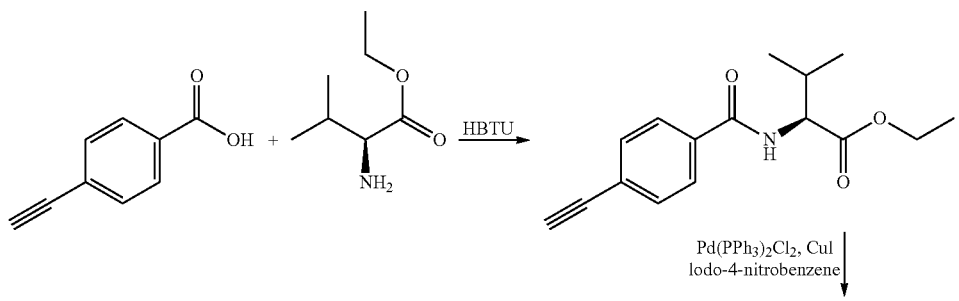

-continued

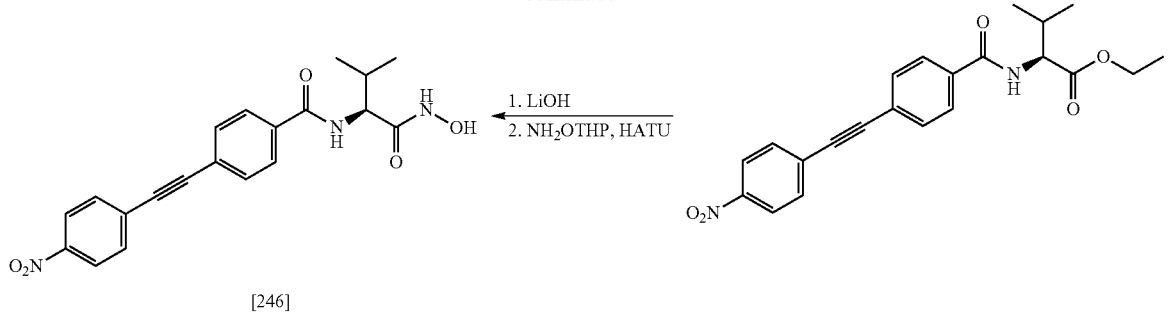

[246]

Step 1: Synthesis of (2S)-ethyl-2-[(4-ethynyl benzoyl)amino]-3-methyl-butanoate 4-Ethynylbenzoic acid (600 mg, 4.11 mmol) and HBTU (1557 mg, 4.11 mmol) were dissolved in DMF (3 mL) and stirred at ambient temperature for 5 minutes. (S)-ethyl 2-amino-3-methylbutanoate hydrochloride (820 mg, 4.52 mmol), tetrahydrofuran (7 mL) and triethylamine (1.316 ml, 9.44 mmol) were then added and the resulting reaction mixture was stirred at ambient temperature for 1 hour. The mixture was then diluted with ethyl acetate and washed twice with NaHCO₃ solution. The organic layer was washed with brine and dried over MgSO4 and concentrated. The resulting residue was purified by column chromatography on silica gel (pentane/ethyl acetate) to provide the title compound.

Step 2: Synthesis of ethyl (2S)-3-methyl-2-[[4-[2-(4-nitrophenyl)ethynyl]benzoyl]amino]butanoate A solution of triethylamine (0.235 ml, 1.683 mmol) in tetrahydrofuran (5 mL) was added to Pd(PPh$_3$)$_2$Cl$_2$ (20.54 mg, 0.029 mmol), CuI (8.36 mg, 0.044 mmol), (2S)-ethyl-2-[(4-ethynylbenzoyl)amino]-3-methyl-butanoate (200 mg, 0.732 mmol) and iodo-4-nitrobenzene (364 mg, 1.463 mmol) under argon and the resulting reaction mixture was stirred for 30 minutes. The reaction mixture was concentrated and the residue was purified by column chromatography on silica gel (pentane/ethyl acetate) to provide the title compound.

Step 3: Synthesis of (2S)-3-methyl-2-[[4-[2-(4-nitrophenyl)ethynyl]benzoyl]amino]butanoic Acid To a solution of ethyl (2S)-3-methyl-2-[[4-[2-(4-nitrophenyl)ethynyl]benzoyl]amino]butanoate (133 mg, 0.337 mmol) in tetrahydrofuran (4 mL) was added LiOH (48.5 mg, 2.023 mmol) and the mixture was stirred at ambient temperature for 1 hour. Water (1 drop) was added and the mixture was allowed to stir overnight. The reaction mixture was acidified and extracted with ethyl acetate. The organic layer was washed with brine, dried over MgSO₄ and concentrated under reduced pressure to provide the title compound with was used in the next step without further purification.

Step 4: Synthesis of N-[(1S)-1-(hydroxycarbamoyl)-2-methyl-propyl]-4-[2-(4-nitrophenyl)ethynyl] benzamide [246]

(2S)-3-methyl-2-[[4-[2-(4-nitrophenyl)ethynyl]benzoyl]amino]butanoic acid (33 mg, 0.09 mmol) and HATU (37.7 mg, 0.1 mmol) were stirred for 3 minutes in a 1:1 mixture of tetrahydrofuran and DMF at ambient temperature. O-(tetrahydro-2H-pyran-2-yl)hydroxylamine (11.6 mg, 0.1 mmol) and triethylamine (0.025 ml, 0.18 mmol) were added and the mixture was left stirring for another hour. All volatiles were then removed under reduced pressure and the resulting residue was purified by reverse phase preparative HPLC using an Atlantis® C18 column applying a gradient consisting of 0.1% aqueous formic acid and acetonitrile to provide the title compound. ¹H NMR (600 MHz, DMSO-d$_6$) δ11.25 (s, 1H), 8.51 (d, J=8.6 Hz, 1H), 8.23 (d, J=8.9 Hz, 2H), 7.91 (d, J=8.9 Hz, 2H), 7.80 (d, J=8.9 Hz, 2H), 7.66 (d, J=8.5 Hz, 2H), 4.08 (td, J=8.0, 17.3 Hz, 1H), 2.03 (m, J=5.9 Hz, 1H), 0.86 (m, J=3.5 Hz, 3H).

Example 1R

Synthesis of N-[(1S,2R)-2-hydroxy-1-(hydroxycarbamoyl)propyl]-4-[2-(4-morpholinophenyl)ethynyl] benzamide

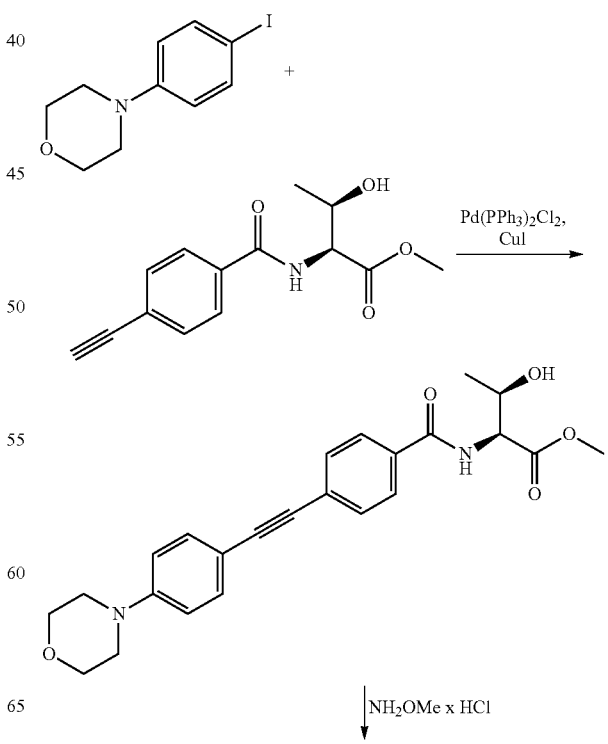

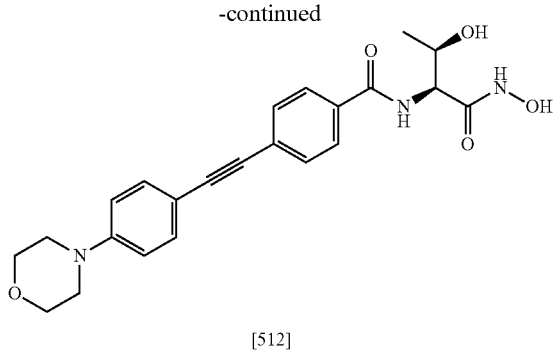

[512]

Step 1: Synthesis of 4-(4-iodophenyl)morpholine 1,4-Diiodobenzene (330 mg, 1.0 mmol), KOH (112 mg, 2.0 mmol) and CuI (38.1 mg, 0.2 mmol) were placed in a flask and an atmosphere of nitrogen was established. A solution of morpholine (0.096 mL, 1.1 mmol) in N-methyl-2-pyrrolidinone (2 mL) was then added and the mixture was stirred at 100° C. for 6 hours and then at ambient temperature overnight. More morpholine (0.096 ml, 1.1 mmol) was added and heating was continued at 100° C. for 7 hours. The reaction mixture was allowed to attain room temperature and was then diluted with ethyl acetate and washed with aqueous NaHCO$_3$ solution. The aqueous layer was extracted with ethyl acetate and the combined organic layers were washed with brine, dried over MgSO$_4$ and concentrated under reduced pressure. All volatiles were then removed under reduced pressure and the resulting residue was purified by reverse phase preparative HPLC using an XBridge® C18 column applying a gradient consisting of 0.2% aqueous ammonia and acetonitrile to provide the title compound.

Step 2: Synthesis of methyl (2S,3R)-3-hydroxy-2-[[4-[2-(4-morpholinophenyl)ethynyl]benzoyl]amino]butanoate CuI (3.6 mg, 0.02 mmol), PdCl$_2$(PPh$_3$)$_2$ (8.74 mg, 0.012 mmol) and (2S,3R)-methyl 2-(4-ethynylbenzamido)-3-hydroxybutanoate (81 mg, 0.311 mmol) were placed in a flask and an atmosphere of nitrogen was established. A solution of 4-(4-iodophenyl)morpholine (90 mg, 0.31 mmol) and triethylamine (0.1 mL, 0.716 mmol) in tetrahydrofuran (3 mL) was then added and the mixture was stirred for 2 hours at ambient temperature. The reaction mixture was absorbed on silica gel and purified by column chromatography on silica gel (pentane/ethyl acetate) to provide the title compound.

Step 3: Synthesis of N-[(1S,2R)-2-hydroxy-1-(hydroxycarbamoyl)propyl]-4-[2-(4-morpholinophenyl)ethynyl]benzamide [512]

Sodium (16 mg, 0.71 mmol) was dissolved in dry methanol (1 mL). After stirring for 5 minutes hydroxylamine hydrochloride (44 mg, 0.64 mmol) was added and the mixture was stirred 40 minutes at ambient temperature. A solution of methyl (2S,3R)-3-hydroxy-2-[[4-[2-(4-morpholinophenyl)ethynyl]benzoyl]amino]butanoate (60 mg, 0.142 mmol) in tetrahydrofuran (2 mL) was added and stirring was continued for 2 hours. The reaction mixture was concentrated under reduced pressure and purified by reverse-phase preparative HPLC using a Sunfire C18® column applying a gradient consisting of 0.1% aqueous formic acid and acetonitrile to provide the title compound. $^1$H NMR (300 MHz, DMSO-d$_6$) δ10.68 (s, 1H), 8.87 (s, 1H), 8.15 (d, J=8.5 Hz, 1H), 7.95 (d, J=8.3 Hz, 2H), 7.66 (d, J=8.4 Hz, 2H), 7.30 (t, J=8.0 Hz, 1H), 7.12 (m, 1H), 7.02 (m, J=6.9 Hz, 2H), 4.92 (d, J=6.3 Hz, 1H), 4.27 (m, 1H), 4.04 (m, 1H), 3.75 (m, 4H), 3.16 (m, 4H), 1.10 (d, J=6.3 Hz, 3H).

Example 1S

Synthesis of N-(3-amino-1-(hydroxyamino)-3-methyl-1-oxobutan-2-yl)-4-((4-nitrophenyl)ethynyl)benzamide [552] and N-(3-amino-1-(hydroxyamino)-3-methyl-1-oxobutan-2-yl)-4-((4-aminophenyl) ethynyl)benzamide [553]

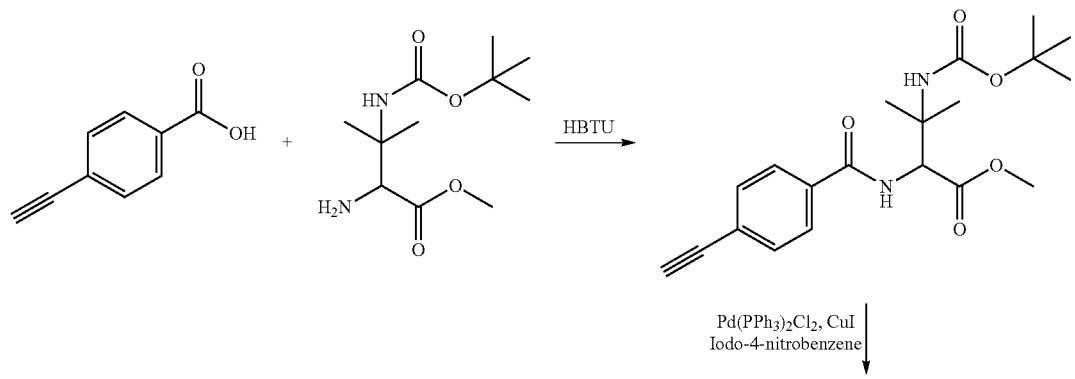

Pd(PPh$_3$)$_2$Cl$_2$, CuI
Iodo-4-nitrobenzene

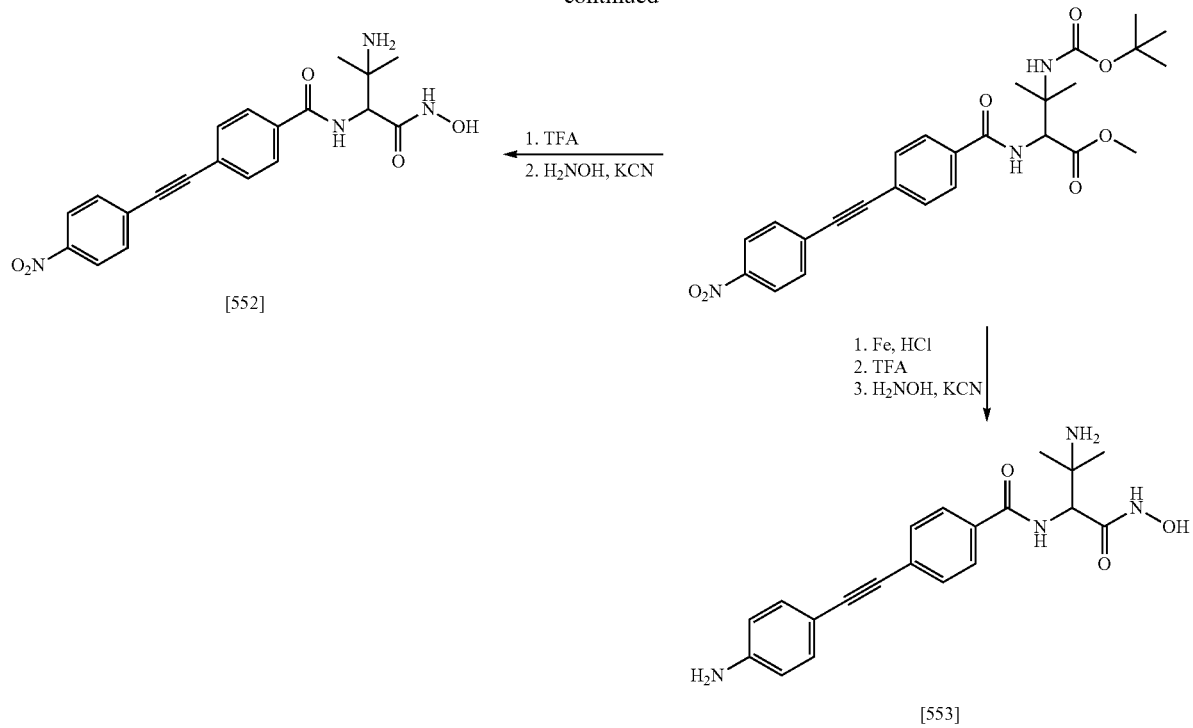

[552]

[553]

Step 1: Synthesis of methyl 3-(tert-butoxycarbonylamino)-2-[(4-ethynylbenzoyl)amino]-3-methyl-butanoate 4-Ethynylbenzoic acid (146 mg, 1.0 mmol) and HBTU (379 mg, 1.0 mmol) were dissolved in DMF (1.5 mL) and stirred at ambient temperature. After 5 minutes methyl 3-(tert-butoxycarbonylamino)-2-[(4-ethynylbenzoyl)amino]-3-methyl-butanoate (280 mg, 1.14 mmol), tetrahydrofuran (3 mL) and triethylamine (0.321 ml, 2.3 mmol) were added. The reaction mixture was allowed to stir for 1 more hour at ambient temperature and was then diluted with ethyl acetate and extracted twice with NaHCO₃ solution. The organic layer was washed with brine, dried over MgSO₄ and concentrated under reduced pressure. Column chromatography on silica gel (pentane/ethyl acetate) provided the title compound.

Step 2: Synthesis of methyl 3-(tert-butoxycarbonylamino)-3-methyl-2-[[4-[2-(4-nitrophenyl)ethynyl]benzoyl]amino]butanoate A solution of triethylamine (230 μl, 1.65 mmol) and methyl 3-((tert-butoxycarbonyl)amino)-2-(4-ethynylbenzamido)-3-methylbutanoate (269 mg, 0.72 mmol) in tetrahydrofuran was added to PdCl₂(PPh₃)₂ (20.17 mg, 0.03 mmol), CuI (8.21 mg, 0.043 mmol) and 1-iodo-4-nitrobenzene (358 mg, 1.44 mmol) under an atmosphere of argon. The reaction mixture was allowed to stir at ambient temperature for 30 minutes, concentrated and purified by column chromatography on silica gel (pentane/ethyl acetate) to provide the title compound.

Step 3: Synthesis of methyl 3-amino-3-methyl-2-[[4-[2-(4-nitrophenyl)ethynyl]benzoyl]amino]butanoate A mixture of dichloromethane (4 mL) and trifluoroacetic acid (1 mL, 13 mmol) was added to methyl 3-(tert-butoxycarbonylamino)-3-methyl-2-[[4-[2-(4-nitrophenyl)ethynyl]benzoyl]amino]butanoate (90 mg, 0.18 mmol) and stirred at ambient temperature for 1 hour. The reaction mixture was then concentrated under reduced pressure and the residue was dissolved in ethyl acetate. The organic layer was washed with NaHCO₃ solution and brine, dried over Na₂SO₄ and concentrated under reduced pressure to provide the title compound which was used in the next step without further purification.

Step 4: Synthesis of N-[2-amino-1-(hydroxycarbamoyl)-2-methyl-propyl]-4-[2-(4-nitrophenyl)ethynyl]benzamide [552]

Hydroxylamine (50% in water, 0.5 mL, 8.1 mmol) was added to a solution of methyl 3-(tert-butoxycarbonylamino)-3-methyl-2-[[4-[2-(4-nitrophenyl)ethynyl]benzoyl]amino] butanoate (66 mg, 0.167 mmol) in methanol/tetrahydrofuran 1:1 (2 mL) followed by a catalytic amount of potassium cyanide. The reaction mixture was stirred at ambient temperature overnight and then centrifuged. The supernatant was discarded and the solid was washed twice with water and dried at 40° C. under reduced pressure to provide the title compound. ¹H NMR (300 MHz, DMSO-d₆) δ8.30 (d, J=8.7 Hz, 2H), 7.95 (d, J=8.2 Hz, 2H), 7.88 (d, J=8.7 Hz, 2H), 7.74 (d, J=8.2 Hz, 2H), 4.31 (s, 1H), 1.11 (s, 3H), 1.03 (s, 3H).

Step 5: Synthesis of methyl 2-[[4-[2-(4-aminophenyl)ethynyl]benzoyl]amino]-3-(tert-butoxycarbonylamino)-3-methyl-butanoate A mixture of methyl 3-(tert-butoxycarbonylamino)-3-methyl-2-[[4-[2-(4-nitrophenyl)ethynyl]benzoyl]amino]butanoate (238 mg, 0.48 mmol), hydrochloric acid (480 μl, 1.92 mmol) and iron (188 mg, 3.4 mmol) were stirred in ethanol (4 mL) at 80° C. for 1 hour. The reaction mixture was filtered and the filtrate concentrated under reduced pressure. The residue was taken up in a small amount of water and extracted twice with dichloromethane. The organic layers were combined, washed with brine, dried over MgSO$_4$ and concentrated under reduced pressure to provide the title compound which was used in the next step without further purification.

Step 6: Synthesis of methyl 3-amino-2-[[4-[2-(4-aminophenyl)ethynyl]benzoyl]amino]-3-methyl-butanoate Trifluoroacetic acid (0.5 mL, 6.5 mmol) was added to a solution of methyl 2-[[4-[2-(4-aminophenyl)ethynyl]benzoyl]amino]-3-(tert-butoxycarbonylamino)-3-methyl-butanoate (90 mg, 0.19 mmol) in dichloromethane (1 mL) and the reaction mixture was stirred at ambient temperature for 1 hour. The reaction mixture was then concentrated under reduced pressure and the residue was dissolved in ethyl acetate. The organic phase was washed twice with NaHCO$_3$ solution, brine, dried over Na$_2$SO$_4$ and concentrated under reduced pressure. Purification of the residue by reverse-phase preparative HPLC using a SUNFIRE® C18 column applying a gradient consisting of 0.1% aqueous formic acid and acetonitrile provided the title compound.

Step 7: Synthesis of N-(3-amino-1-(hydroxyamino)-3-methyl-1-oxobutan-2-yl)-4-((4-aminophenyl)ethynyl)benzamide [553]

Hydroxylamine (50% in water, 0.5 mL, 8.1 mmol) was added to a solution of methyl 3-amino-2-[[4-[2-(4-aminophenyl)ethynyl]benzoyl]amino]-3-methyl-butanoate (20 mg, 0.055 mmol) in methanol/tetrahydrofuran 1:1 (1 mL) followed by a catalytic amount of potassium cyanide. The reaction mixture was stirred at ambient temperature for 3 days and concentrated under reduced pressure. Purification of the residue by reverse-phase preparative HPLC using a SUNFIRE® C18 column applying a gradient consisting of 0.1% aqueous formic acid and acetonitrile provided the title compound. $^1$H NMR (300 MHz, DMSO-d$_6$) δ8.34 (s, 1H), 8.28 (s, 1H), 7.90 (d, J=8.0 Hz, 2H), 7.55 (d, J=8.0 Hz, 2H), 7.23 (d, J=8.3 Hz, 2H), 6.57 (d, J=8.4 Hz, 2H), 5.65 (s, 1H), 4.47 (s, 1H), 1.21 (s, 3H), 1.14 (s, 3H).

Example 1T

Synthesis of methyl 2-[[4-[2-(4-formylphenyl)ethynyl]benzoyl]amino]-3-methyl-3-nitro-butanoate

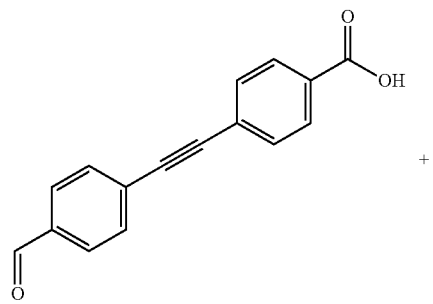

+

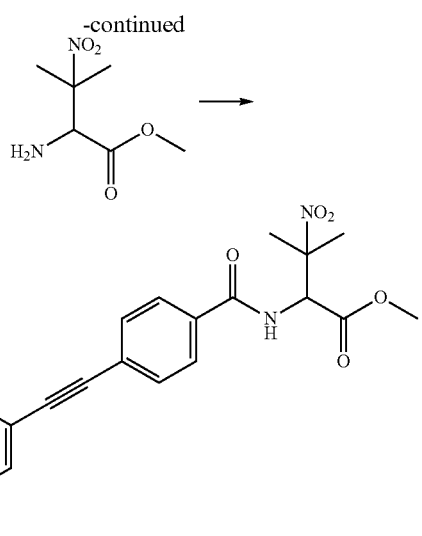

4-((4-formylphenyl)ethynyl)benzoic acid (1316 mg, 5.26 mmol) was mixed with tetrahydrofuran (20 mL) and 2 drops of DMF. Oxalyl chloride (0.506 mL, 5.8 mmol) was then added dropwise and the reaction mixture stirred at room temperature for 4 hours. More tetrahydrofuran (100 mL) was added to the slurry and after 1 hour, methyl 2-amino-3-methyl-3-nitrobutanoate (927 mg, 5.26 mmol) was added to the yellow solution. The reaction mixture was allowed to stir at ambient temperature overnight, was then diluted with ethyl acetate and washed with saturated aqueous sodium hydrogen carbonate. The organic phase was separated, dried over MgSO$_4$, filtered and evaporated under reduced pressure to provide the title compound which was used in the next steps without further purification. MS: 409.1 (M+1).

Example 1U

General Procedure for the Synthesis of Compounds in Solution Phase Containing a Nitro-Valine as the Amino Acid To a mixture of methyl 2-[[4-[2-(4-formylphenyl)ethynyl]benzoyl]amino]-3-methyl-3-nitro-butanoate (65 mg, 0.16 mmol) in tetrahydrofuran (1 mL) was added the respective amine (0.16 mmol) and the solution was stirred for 30 min at room temperature. Then, sodium triacetoxyborohydride (135 mg, 0.64 mmol) was added and the reaction mixture stirred at room temperature until all of the methyl 2-[[4-[2-(4-formylphenyl)ethynyl]benzoyl]amino]-3-methyl-3-nitro-butanoate was consumed. Dichloromethane was then added and the mixture washed with 0.1 N HCl. The organic phase was separated, dried over with MgSO$_4$, filtered and evaporated to dryness under reduced pressure. The resulting residue was dissolved in a 1:1 mixture of methanol and tetrahydrofuran (1 mL) and hydroxylamine (50% in water, 0.3 mL, 4.9 mmol) and KCN (1.8 mg, 0.028 mmol) were added. The resulting reaction mixture was stirred until all the starting material was consumed or until the reaction did not progress any further. The mixture was then purified by preparative reverse-phase HPLC using an XBridge® column and a gradient consisting of acetonitrile/water+0.1% formic acid or for the more basic compounds a gradient consisting of acetonitrile/water+0.1% ammonia to provide the title compounds.

Using this procedure, the following compounds can be synthesized:
Compound No. 554
Compound No. 652-665

Example 2

Analytics—HPLC Methods

Method 1
Chromatographic System:
Column: Chromolith FastGradient RP-18e from Merck, 2*50 mm
Oven: 35° C.
Eluents: Solvent A: water/HCO$_2$H (0.1%); Solvent B: acetonitrile/HCO$_2$H (0.1%)
Flow: 1.2 ml/min
Gradient:

| Time [min] | Solvent A [%] | Solvent B [%] |
|---|---|---|
| 0.0 | 90 | 10 |
| 2.0 | 0 | 100 |
| 2.7 | 0 | 100 |

Run time: 3.5 min (equilibration included)
Method 2
Chromatographic System:
Column: Chromolith FastGradient RP-18e from Merck, 2*50 mm
Oven: 30° C.
Eluents: Solvent A: water/HCO$_2$H (0.1%); Solvent B: acetonitrile/HCO$_2$H (0.1%)
Flow: 1.2 ml/min
Gradient:

| Time [min] | Solvent A [%] | Solvent B [%] |
|---|---|---|
| 0.0 | 98 | 2 |
| 0.2 | 98 | 2 |
| 2.2 | 2 | 98 |
| 2.7 | 2 | 98 |

Run time: 3.5 min (equilibration included)
Method—3
Chromatographic System:
Column: Atlantis dC18 Waters, 4.6×50 mm, 3μ
Oven: 30° C.
Eluents: Solvent A: water/HCO$_2$H (0.1%); Solvent B: acetonitrile/HCO$_2$H (0.1%)
Flow: 1.2 ml/min
Gradient:

| Time [min] | Solvent A [%] | Solvent B [%] |
|---|---|---|
| 0.0 | 95 | 5 |
| 1.0 | 95 | 5 |
| 5.0 | 2 | 98 |
| 7.0 | 2 | 98 |
| 8.0 | 95 | 5 |

Run time: 10 min (equilibration included)
Method—4
Chromatographic System:
Column: Xbridge BEH C18 Waters, 2.1×50 mm, 2.5μ
Oven: 40° C.
Eluents: Solvent A: water/HCO$_2$H (0.05%); Solvent B: acetonitrile/HCO$_2$H (0.05%)
Flow: 0.8 ml/min
Gradient:

| Time [min] | Solvent A [%] | Solvent B [%] |
|---|---|---|
| 0.0 | 98 | 2 |
| 1.2 | 0 | 100 |
| 1.7 | 0 | 100 |
| 1.8 | 98 | 2 |

Run time: 2.2 min+0.5 min equilibration time
Method—5
Chromatographic System:
Column: Phenomenex Jupiter Proteo C18 90 A, 4.6×50 mm, 4μ
Oven: 30° C.
Eluents: Solvent A: water/TFA (0.1%); Solvent B: acetonitrile/TFA (0.1%)
Flow: 1.0 ml/min
Gradient:

| Time [min] | Solvent A [%] | Solvent B [%] |
|---|---|---|
| 0.0 | 98 | 2 |
| 3.0 | 0 | 100 |
| 4.0 | 0 | 100 |
| 4.5 | 98 | 2 |
| 5 | 98 | 2 |

Run time: 5 min
Specific Compounds
Table A provides for each of the exemplified compounds the structure according to Formula 1 below.C.No. means compound ID or Compound number. The same numbering is used in the biological examples.
Compounds of Formula 1:

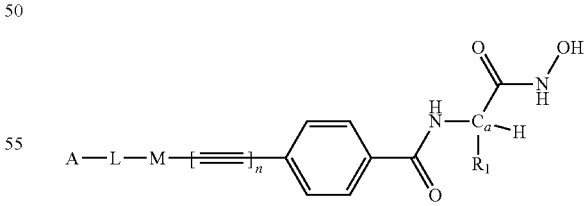

Formula 1
The residue A in Table A is described either in form of a molecular formula or in form of a chemical name, in this latter case A is an amine which is inked with its nitrogen atom to residue L.
In the column $C_a$ the stereochemistry of the atom $C_a$ is denoted. If there is no entry in column $C_a$ then both stereoisomers regarding $C_a$ are present.

The values for M in Table A have the following meaning:

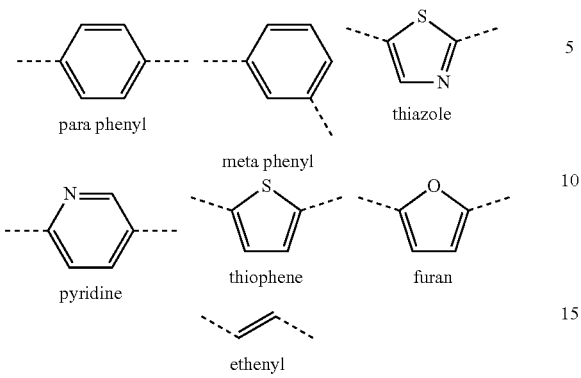

- para phenyl
- meta phenyl
- thiazole — 5
- pyridine
- thiophene
- furan — 10
- ethenyl — 15

The orientation of the residues with regard to Formula 1 is as drawn.

TABLE A

| C. No | A | L | M | n | $R_1$ | Ca |
|---|---|---|---|---|---|---|
| 1 | morpholine | —$CH_2$— | para phenyl | 1 | (R)—CH($CH_3$)OH | (S) |
| 2 | benzylamine | —$CH_2$— | para phenyl | 1 | (R)—CH($CH_3$)OH | (S) |
| 3 | piperazine | —$CH_2$— | para phenyl | 1 | (R)—CH($CH_3$)OH | (S) |
| 4 | N-methylpiperazine | —$CH_2$— | para phenyl | 1 | (R)—CH($CH_3$)OH | (S) |
| 5 | pyrrolidine | —$CH_2$— | para phenyl | 1 | (R)—CH($CH_3$)OH | (S) |
| 6 | piperidine | —$CH_2$— | para phenyl | 1 | (R)—CH($CH_3$)OH | (S) |
| 7 | $(CH_3)_2CHNH$— | —$CH_2$— | meta phenyl | 1 | (R)—CH($CH_3$)OH | (S) |
| 8 | $CH_2CHCH_2NH$— | —$CH_2$— | meta phenyl | 1 | (R)—CH($CH_3$)OH | (S) |
| 9 | $(CH_3)_3CCH_2NH$— | —$CH_2$— | meta phenyl | 1 | (R)—CH($CH_3$)OH | (S) |
| 10 | $CH_3O(CH_2)_2NH$— | —$CH_2$— | meta phenyl | 1 | (R)—CH($CH_3$)OH | (S) |
| 11 | $(CH_3)_2N(CH_2)_2NH$— | —$CH_2$— | meta phenyl | 1 | (R)—CH($CH_3$)OH | (S) |
| 12 | $CO_2HCH_2NH$— | —$CH_2$— | meta phenyl | 1 | (R)—CH($CH_3$)OH | (S) |
| 13 | $(C_2H_5)_2N$— | —$CH_2$— | meta phenyl | 1 | (R)—CH($CH_3$)OH | (S) |
| 14 | morpholine | —$CH_2$— | meta phenyl | 1 | (R)—CH($CH_3$)OH | (S) |
| 15 | 1,1-dioxo-thiomorpholine | —$CH_2$— | meta phenyl | 1 | (R)—CH($CH_3$)OH | (S) |
| 16 | 4-tert-butyl-piperidine | —$CH_2$— | meta phenyl | 1 | (R)—CH($CH_3$)OH | (S) |
| 17 | 4-phenyl-piperidine | —$CH_2$— | meta phenyl | 1 | (R)—CH($CH_3$)OH | (S) |
| 18 | 4-phenyl-piperazine | —$CH_2$— | meta phenyl | 1 | (R)—CH($CH_3$)OH | (S) |
| 19 | 1-(pyridin-2-yl)-piperazine | —$CH_2$— | meta phenyl | 1 | (R)—CH($CH_3$)OH | (S) |
| 20 | 1,2,3,4-tetrahydro-isoquinoline | —$CH_2$— | meta phenyl | 1 | (R)—CH($CH_3$)OH | (S) |
| 21 | heliamine | —$CH_2$— | meta phenyl | 1 | (R)—CH($CH_3$)OH | (S) |
| 22 | benzylamine | —$CH_2$— | meta phenyl | 1 | (R)—CH($CH_3$)OH | (S) |
| 23 | N-methylbenzylamine | —$CH_2$— | meta phenyl | 1 | (R)—CH($CH_3$)OH | (S) |
| 24 | 4-chlorobenzylamine | —$CH_2$— | meta phenyl | 1 | (R)—CH($CH_3$)OH | (S) |
| 25 | 4-methoxybenzylamine | —$CH_2$— | meta phenyl | 1 | (R)—CH($CH_3$)OH | (S) |
| 26 | 4-dimethylaminobenzylamine | —$CH_2$— | meta phenyl | 1 | (R)—CH($CH_3$)OH | (S) |
| 27 | 4-trifluoromethylbenzylamine | —$CH_2$— | meta phenyl | 1 | (R)—CH($CH_3$)OH | (S) |
| 28 | 4-pyridylmethanamine | —$CH_2$— | meta phenyl | 1 | (R)—CH($CH_3$)OH | (S) |
| 29 | 3,4-dimethylbenzylamine | —$CH_2$— | meta phenyl | 1 | (R)—CH($CH_3$)OH | (S) |
| 30 | cyclopropylamine | —$CH_2$— | meta phenyl | 1 | —$CH_2OH$ | (S) |
| 31 | $(CH_3)_2CHNH$— | —$CH_2$— | meta phenyl | 1 | —$CH_2OH$ | (S) |
| 32 | $CH_2CHCH_2NH$— | —$CH_2$— | meta phenyl | 1 | —$CH_2OH$ | (S) |
| 33 | $(CH_3)_3CCH_2NH$— | —$CH_2$— | meta phenyl | 1 | —$CH_2OH$ | (S) |
| 34 | $CH_3O(CH_2)_2NH$— | —$CH_2$— | meta phenyl | 1 | —$CH_2OH$ | (S) |
| 35 | $(CH_3)_2N(CH_2)_2NH$— | —$CH_2$— | meta phenyl | 1 | —$CH_2OH$ | (S) |
| 36 | $CO_2HCH_2NH$— | —$CH_2$— | meta phenyl | 1 | —$CH_2OH$ | (S) |
| 37 | $(C_2H_5)_2N$— | —$CH_2$— | meta phenyl | 1 | —$CH_2OH$ | (S) |
| 38 | morpholine | —$CH_2$— | meta phenyl | 1 | —$CH_2OH$ | (S) |
| 39 | 4-tert-butyl-piperidine | —$CH_2$— | meta phenyl | 1 | —$CH_2OH$ | (S) |
| 40 | 4-phenyl-piperidine | —$CH_2$— | meta phenyl | 1 | —$CH_2OH$ | (S) |
| 41 | 4-phenyl-piperazine | —$CH_2$— | meta phenyl | 1 | —$CH_2OH$ | (S) |
| 42 | 1-(pyridin-2-yl)-piperazine | —$CH_2$— | meta phenyl | 1 | —$CH_2OH$ | (S) |
| 43 | 1,2,3,4-tetrahydro-isoquinoline | —$CH_2$— | meta phenyl | 1 | —$CH_2OH$ | (S) |
| 44 | heliamine | —$CH_2$— | meta phenyl | 1 | —$CH_2OH$ | (S) |
| 45 | benzylamine | —$CH_2$— | meta phenyl | 1 | —$CH_2OH$ | (S) |
| 46 | N-methylbenzylamine | —$CH_2$— | meta phenyl | 1 | —$CH_2OH$ | (S) |
| 47 | 4-chlorobenzylamine | —$CH_2$— | meta phenyl | 1 | —$CH_2OH$ | (S) |
| 48 | 4-methoxybenzylamine | —$CH_2$— | meta phenyl | 1 | —$CH_2OH$ | (S) |
| 49 | 4-dimethylaminobenzylamine | —$CH_2$— | meta phenyl | 1 | —$CH_2OH$ | (S) |
| 50 | 4-trifluoromethylbenzylamine | —$CH_2$— | meta phenyl | 1 | —$CH_2OH$ | (S) |
| 51 | 4-pyridylmethanamine | —$CH_2$— | meta phenyl | 1 | —$CH_2OH$ | (S) |
| 52 | 3,4-dimethylbenzylamine | —$CH_2$— | meta phenyl | 1 | —$CH_2OH$ | (S) |

TABLE A-continued

| C. No | A | L | M | n | R₁ | Ca |
|---|---|---|---|---|---|---|
| 53 | cyclopropylamine | —CH₂— | meta phenyl | 1 | —CH(CH₃)₂ | (S) |
| 54 | (CH₃)₂CHNH— | —CH₂— | meta phenyl | 1 | —CH(CH₃)₂ | (S) |
| 55 | CH₂CHCH₂NH— | —CH₂— | meta phenyl | 1 | —CH(CH₃)₂ | (S) |
| 56 | (CH₃)₃CCH₂NH— | —CH₂— | meta phenyl | 1 | —CH(CH₃)₂ | (S) |
| 57 | CH₃O(CH₂)₂NH— | —CH₂— | meta phenyl | 1 | —CH(CH₃)₂ | (S) |
| 58 | (CH₃)₂N(CH₂)₂NH— | —CH₂— | meta phenyl | 1 | —CH(CH₃)₂ | (S) |
| 59 | CO₂HCH₂NH— | —CH₂— | meta phenyl | 1 | —CH(CH₃)₂ | (S) |
| 60 | (C₂H₅)₂N— | —CH₂— | meta phenyl | 1 | —CH(CH₃)₂ | (S) |
| 61 | morpholine | —CH₂— | meta phenyl | 1 | —CH(CH₃)₂ | (S) |
| 62 | 1,1-dioxo-thiomorpholine | —CH₂— | meta phenyl | 1 | —CH(CH₃)₂ | (S) |
| 63 | 4-tert-butyl-piperidine | —CH₂— | meta phenyl | 1 | —CH(CH₃)₂ | (S) |
| 64 | 4-phenyl-piperidine | —CH₂— | meta phenyl | 1 | —CH(CH₃)₂ | (S) |
| 65 | 4-phenyl-piperazine | —CH₂— | meta phenyl | 1 | —CH(CH₃)₂ | (S) |
| 66 | 1-(pyridin-2-yl)-piperazine | —CH₂— | meta phenyl | 1 | —CH(CH₃)₂ | (S) |
| 67 | 1,2,3,4-tetrahydro-isoquinoline | —CH₂— | meta phenyl | 1 | —CH(CH₃)₂ | (S) |
| 68 | heliamine | —CH₂— | meta phenyl | 1 | —CH(CH₃)₂ | (S) |
| 69 | benzylamine | —CH₂— | meta phenyl | 1 | —CH(CH₃)₂ | (S) |
| 70 | N-methylbenzylamine | —CH₂— | meta phenyl | 1 | —CH(CH₃)₂ | (S) |
| 71 | 4-chlorobenzylamine | —CH₂— | meta phenyl | 1 | —CH(CH₃)₂ | (S) |
| 72 | 4-methoxybenzylamine | —CH₂— | meta phenyl | 1 | —CH(CH₃)₂ | (S) |
| 73 | 4-dimethylaminobenzylamine | —CH₂— | meta phenyl | 1 | —CH(CH₃)₂ | (S) |
| 74 | 4-trifluoromethylbenzylamine | —CH₂— | meta phenyl | 1 | —CH(CH₃)₂ | (S) |
| 75 | 4-pyridylmethanamine | —CH₂— | meta phenyl | 1 | —CH(CH₃)₂ | (S) |
| 76 | 3,4-dimethylbenzylamine | —CH₂— | meta phenyl | 1 | —CH(CH₃)₂ | (S) |
| 77 | (CH₃)₂CHNH— | —CH₂— | meta phenyl | 1 | (S)—CH(CH₃)C₂H₅ | (S) |
| 78 | CH₂CHCH₂NH— | —CH₂— | meta phenyl | 1 | (S)—CH(CH₃)C₂H₅ | (S) |
| 79 | (CH₃)₃CCH₂NH— | —CH₂— | meta phenyl | 1 | (S)—CH(CH₃)C₂H₅ | (S) |
| 80 | CH₃O(CH₂)₂NH— | —CH₂— | meta phenyl | 1 | (S)—CH(CH₃)C₂H₅ | (S) |
| 81 | (CH₃)₂N(CH₂)₂NH— | —CH₂— | meta phenyl | 1 | (S)—CH(CH₃)C₂H₅ | (S) |
| 82 | CO₂HCH₂NH— | —CH₂— | meta phenyl | 1 | (S)—CH(CH₃)C₂H₅ | (S) |
| 83 | (C₂H₅)₂N— | —CH₂— | meta phenyl | 1 | (S)—CH(CH₃)C₂H₅ | (S) |
| 84 | morpholine | —CH₂— | meta phenyl | 1 | (S)—CH(CH₃)C₂H₅ | (S) |
| 85 | 1,1-dioxo-thiomorpholine | —CH₂— | meta phenyl | 1 | (S)—CH(CH₃)C₂H₅ | (S) |
| 86 | 4-tert-butyl-piperidine | —CH₂— | meta phenyl | 1 | (S)—CH(CH₃)C₂H₅ | (S) |
| 87 | 4-phenyl-piperidine | —CH₂— | meta phenyl | 1 | (S)—CH(CH₃)C₂H₅ | (S) |
| 88 | 4-phenyl-piperazine | —CH₂— | meta phenyl | 1 | (S)—CH(CH₃)C₂H₅ | (S) |
| 89 | 1-(pyridin-2-yl)-piperazine | —CH₂— | meta phenyl | 1 | (S)—CH(CH₃)C₂H₅ | (S) |
| 90 | 1,2,3,4-tetrahydro-isoquinoline | —CH₂— | meta phenyl | 1 | (S)—CH(CH₃)C₂H₅ | (S) |
| 91 | heliamine | —CH₂— | meta phenyl | 1 | (S)—CH(CH₃)C₂H₅ | (S) |
| 92 | benzylamine | —CH₂— | meta phenyl | 1 | (S)—CH(CH₃)C₂H₅ | (S) |
| 93 | N-methylbenzylamine | —CH₂— | meta phenyl | 1 | (S)—CH(CH₃)C₂H₅ | (S) |
| 94 | 4-chlorobenzylamine | —CH₂— | meta phenyl | 1 | (S)—CH(CH₃)C₂H₅ | (S) |
| 95 | 4-methoxybenzylamine | —CH₂— | meta phenyl | 1 | (S)—CH(CH₃)C₂H₅ | (S) |
| 96 | 4-dimethylaminobenzylamine | —CH₂— | meta phenyl | 1 | (S)—CH(CH₃)C₂H₅ | (S) |
| 97 | 4-trifluoromethylbenzylamine | —CH₂— | meta phenyl | 1 | (S)—CH(CH₃)C₂H₅ | (S) |
| 98 | 4-pyridylmethanamine | —CH₂— | meta phenyl | 1 | (S)—CH(CH₃)C₂H₅ | (S) |
| 99 | 3,4-dimethylbenzylamine | —CH₂— | meta phenyl | 1 | (S)—CH(CH₃)C₂H₅ | (S) |
| 100 | cyclopropylamine | —CH₂— | meta phenyl | 1 | (R)—CH(CH₃)OH | (S) |
| 101 | pyrrolidine | —CH₂— | ethenyl | 1 | (R)—CH(CH₃)OH | (S) |
| 102 | piperidine | —CH₂— | ethenyl | 1 | (R)—CH(CH₃)OH | (S) |
| 103 | cyclopropylamine | —CH₂— | para phenyl | 1 | (R)—CH(CH₃)OH | (S) |
| 104 | (CH₃)₂CHNH— | —CH₂— | para phenyl | 1 | (R)—CH(CH₃)OH | (S) |
| 105 | CH₂CHCH₂NH— | —CH₂— | para phenyl | 1 | (R)—CH(CH₃)OH | (S) |
| 106 | (CH₃)₃CCH₂NH— | —CH₂— | para phenyl | 1 | (R)—CH(CH₃)OH | (S) |
| 107 | (CH₃)₂N(CH₂)₂NH— | —CH₂— | para phenyl | 1 | (R)—CH(CH₃)OH | (S) |
| 108 | CO₂HCH₂NH— | —CH₂— | para phenyl | 1 | (R)—CH(CH₃)OH | (S) |
| 109 | (C₂H₅)₂N— | —CH₂— | para phenyl | 1 | (R)—CH(CH₃)OH | (S) |
| 110 | 1,1-dioxo-thiomorpholine | —CH₂— | para phenyl | 1 | (R)—CH(CH₃)OH | (S) |
| 111 | 4-tert-butyl-piperidine | —CH₂— | para phenyl | 1 | (R)—CH(CH₃)OH | (S) |
| 112 | 4-phenyl-piperidine | —CH₂— | para phenyl | 1 | (R)—CH(CH₃)OH | (S) |
| 113 | 4-phenyl-piperazine | —CH₂— | para phenyl | 1 | (R)—CH(CH₃)OH | (S) |
| 114 | 1-(pyridin-2-yl)-piperazine | —CH₂— | para phenyl | 1 | (R)—CH(CH₃)OH | (S) |
| 115 | 1,2,3,4-tetrahydro-isoquinoline | —CH₂— | para phenyl | 1 | (R)—CH(CH₃)OH | (S) |
| 116 | heliamine | —CH₂— | para phenyl | 1 | (R)—CH(CH₃)OH | (S) |
| 117 | N-methylbenzylamine | —CH₂— | para phenyl | 1 | (R)—CH(CH₃)OH | (S) |
| 118 | 4-chlorobenzylamine | —CH₂— | para phenyl | 1 | (R)—CH(CH₃)OH | (S) |
| 119 | 4-methoxybenzylamine | —CH₂— | para phenyl | 1 | (R)—CH(CH₃)OH | (S) |
| 120 | 4-trifluoromethylbenzylamine | —CH₂— | para phenyl | 1 | (R)—CH(CH₃)OH | (S) |
| 121 | 4-pyridylmethanamine | —CH₂— | para phenyl | 1 | (R)—CH(CH₃)OH | (S) |
| 122 | 4-dimethylaminobenzylamine | —CH₂— | para phenyl | 1 | (R)—CH(CH₃)OH | (S) |
| 123 | cyclopropylamine | —CH₂— | para phenyl | 1 | —CH₂OH | (S) |
| 124 | (CH₃)₂CHNH— | —CH₂— | para phenyl | 1 | —CH₂OH | (S) |
| 125 | CH₂CHCH₂NH— | —CH₂— | para phenyl | 1 | —CH₂OH | (S) |
| 126 | CH₃O(CH₂)₂NH— | —CH₂— | para phenyl | 1 | —CH₂OH | (S) |
| 127 | (CH₃)₂N(CH₂)₂NH— | —CH₂— | para phenyl | 1 | —CH₂OH | (S) |
| 128 | (C₂H₅)₂N— | —CH₂— | para phenyl | 1 | —CH₂OH | (S) |
| 129 | morpholine | —CH₂— | para phenyl | 1 | —CH₂OH | (S) |
| 130 | 1,1-dioxo-thiomorpholine | —CH₂— | para phenyl | 1 | —CH₂OH | (S) |

TABLE A-continued

| C. No | A | L | M | n | R₁ | Ca |
|---|---|---|---|---|---|---|
| 131 | 4-tert-butyl-piperidine | —CH₂— | para phenyl | 1 | —CH₂OH | (S) |
| 132 | 4-phenyl-piperidine | —CH₂— | para phenyl | 1 | —CH₂OH | (S) |
| 133 | 4-phenyl-piperazine | —CH₂— | para phenyl | 1 | —CH₂OH | (S) |
| 134 | 1-(pyridin-2-yl)-piperazine | —CH₂— | para phenyl | 1 | —CH₂OH | (S) |
| 135 | 1,2,3,4-tetrahydro-isoquinoline | —CH₂— | para phenyl | 1 | —CH₂OH | (S) |
| 136 | heliamine | —CH₂— | para phenyl | 1 | —CH₂OH | (S) |
| 137 | benzylamine | —CH₂— | para phenyl | 1 | —CH₂OH | (S) |
| 138 | N-methylbenzylamine | —CH₂— | para phenyl | 1 | —CH₂OH | (S) |
| 139 | 4-chlorobenzylamine | —CH₂— | para phenyl | 1 | —CH₂OH | (S) |
| 140 | 4-methoxybenzylamine | —CH₂— | para phenyl | 1 | —CH₂OH | (S) |
| 141 | 4-trifluoromethylbenzylamine | —CH₂— | para phenyl | 1 | —CH₂OH | (S) |
| 142 | 4-pyridylmethanamine | —CH₂— | para phenyl | 1 | —CH₂OH | (S) |
| 143 | 3,4-dimethylbenzylamine | —CH₂— | para phenyl | 1 | —CH₂OH | (S) |
| 144 | cyclopropylamine | —CH₂— | para phenyl | 1 | —CH(CH₃)₂ | (S) |
| 145 | (CH₃)₂CHNH— | —CH₂— | para phenyl | 1 | —CH(CH₃)₂ | (S) |
| 146 | CH₂CHCH₂NH— | —CH₂— | para phenyl | 1 | —CH(CH₃)₂ | (S) |
| 147 | (CH₃)₃CCH₂NH | —CH₂— | para phenyl | 1 | —CH(CH₃)₂ | (S) |
| 148 | CH₃O(CH₂)₂NH— | —CH₂— | para phenyl | 1 | —CH(CH₃)₂ | (S) |
| 149 | (C₂H₅)₂N— | —CH₂— | para phenyl | 1 | —CH(CH₃)₂ | (S) |
| 150 | morpholine | —CH₂— | para phenyl | 1 | —CH(CH₃)₂ | (S) |
| 151 | 1,1-dioxo-thiomorpholine | —CH₂— | para phenyl | 1 | —CH(CH₃)₂ | (S) |
| 152 | 4-phenyl-piperidine | —CH₂— | para phenyl | 1 | —CH(CH₃)₂ | (S) |
| 153 | 1-(pyridin-2-yl)-piperazine | —CH₂— | para phenyl | 1 | —CH(CH₃)₂ | (S) |
| 154 | 1,2,3,4-tetrahydro-isoquinoline | —CH₂— | para phenyl | 1 | —CH(CH₃)₂ | (S) |
| 155 | heliamine | —CH₂— | para phenyl | 1 | —CH(CH₃)₂ | (S) |
| 156 | benzylamine | —CH₂— | para phenyl | 1 | —CH(CH₃)₂ | (S) |
| 157 | N-methylbenzylamine | —CH₂— | para phenyl | 1 | —CH(CH₃)₂ | (S) |
| 158 | 4-chlorobenzylamine | —CH₂— | para phenyl | 1 | —CH(CH₃)₂ | (S) |
| 159 | 4-methoxybenzylamine | —CH₂— | para phenyl | 1 | —CH(CH₃)₂ | (S) |
| 160 | 4-dimethylaminobenzylamine | —CH₂— | para phenyl | 1 | —CH(CH₃)₂ | (S) |
| 161 | 4-trifluoromethylbenzylamine | —CH₂— | para phenyl | 1 | —CH(CH₃)₂ | (S) |
| 162 | 4-pyridylmethanamine | —CH₂— | para phenyl | 1 | —CH(CH₃)₂ | (S) |
| 163 | 3,4-dimethylbenzylamine | —CH₂— | para phenyl | 1 | —CH(CH₃)₂ | (S) |
| 164 | cyclopropylamine | —CH₂— | para phenyl | 1 | (S)—CH(CH₃)C₂H₅ | (S) |
| 165 | CH₂CHCH₂NH— | —CH₂— | para phenyl | 1 | (S)—CH(CH₃)C₂H₅ | (S) |
| 166 | (CH₃)₃CCH₂NH— | —CH₂— | para phenyl | 1 | (S)—CH(CH₃)C₂H₅ | (S) |
| 167 | CH₃O(CH₂)₂NH— | —CH₂— | para phenyl | 1 | (S)—CH(CH₃)C₂H₅ | (S) |
| 168 | (CH₃)₂N(CH₂)₂NH— | —CH₂— | para phenyl | 1 | (S)—CH(CH₃)C₂H₅ | (S) |
| 169 | CO₂HCH₂NH— | —CH₂— | para phenyl | 1 | (S)—CH(CH₃)C₂H₅ | (S) |
| 170 | (C₂H₅)₂N— | —CH₂— | para phenyl | 1 | (S)—CH(CH₃)C₂H₅ | (S) |
| 171 | morpholine | —CH₂— | para phenyl | 1 | (S)—CH(CH₃)C₂H₅ | (S) |
| 172 | 4-tert-butyl-piperidine | —CH₂— | para phenyl | 1 | (S)—CH(CH₃)C₂H₅ | (S) |
| 173 | 4-phenyl-piperidine | —CH₂— | para phenyl | 1 | (S)—CH(CH₃)C₂H₅ | (S) |
| 174 | 4-phenyl-piperazine | —CH₂— | para phenyl | 1 | (S)—CH(CH₃)C₂H₅ | (S) |
| 175 | 1-(pyridin-2-yl)-piperazine | —CH₂— | para phenyl | 1 | (S)—CH(CH₃)C₂H₅ | (S) |
| 176 | 1,2,3,4-tetrahydro-isoquinoline | —CH₂— | para phenyl | 1 | (S)—CH(CH₃)C₂H₅ | (S) |
| 177 | heliamine | —CH₂— | para phenyl | 1 | (S)—CH(CH₃)C₂H₅ | (S) |
| 178 | benzylamine | —CH₂— | para phenyl | 1 | (S)—CH(CH₃)C₂H₅ | (S) |
| 179 | N-methylbenzylamine | —CH₂— | para phenyl | 1 | (S)—CH(CH₃)C₂H₅ | (S) |
| 180 | 4-chlorobenzylamine | —CH₂— | para phenyl | 1 | (S)—CH(CH₃)C₂H₅ | (S) |
| 181 | 4-methoxybenzylamine | —CH₂— | para phenyl | 1 | (S)—CH(CH₃)C₂H₅ | (S) |
| 182 | 4-dimethylaminobenzylamine | —CH₂— | para phenyl | 1 | (S)—CH(CH₃)C₂H₅ | (S) |
| 183 | 4-trifluoromethylbenzylamine | —CH₂— | para phenyl | 1 | (S)—CH(CH₃)C₂H₅ | (S) |
| 184 | 4-pyridylmethanamine | —CH₂— | para phenyl | 1 | (S)—CH(CH₃)C₂H₅ | (S) |
| 185 | 3,4-dimethylbenzylamine | —CH₂— | para phenyl | 1 | (S)—CH(CH₃)C₂H₅ | (S) |
| 186 | 4-dimethylaminobenzylamine | —CH₂— | para phenyl | 1 | —CH₂OH | (S) |
| 187 | 4-phenyl-piperazine | —CH₂— | para phenyl | 1 | —CH(CH₃)₂ | (S) |
| 188 | 3,4-dimethylbenzylamine | —CH₂— | para phenyl | 1 | (R)—CH(CH₃)OH | (S) |
| 189 | CH₃O(CH₂)₂NH— | —CH₂— | thiophene | 1 | (R)—CH(CH₃)OH | (S) |
| 190 | (CH₃)₂N(CH₂)₂NH— | —CH₂— | thiophene | 1 | (R)—CH(CH₃)OH | (S) |
| 191 | CO₂HCH₂NH— | —CH₂— | thiophene | 1 | (R)—CH(CH₃)OH | (S) |
| 192 | morpholine | —CH₂— | thiophene | 1 | (R)—CH(CH₃)OH | (S) |
| 193 | 4-phenyl-piperazine | —CH₂— | thiophene | 1 | (R)—CH(CH₃)OH | (S) |
| 194 | 1,2,3,4-tetrahydro-isoquinoline | —CH₂— | thiophene | 1 | (R)—CH(CH₃)OH | (S) |
| 195 | benzylamine | —CH₂— | thiophene | 1 | (R)—CH(CH₃)OH | (S) |
| 196 | N-methylbenzylamine | —CH₂— | thiophene | 1 | (R)—CH(CH₃)OH | (S) |
| 197 | pyrrolidine | —CH₂— | thiophene | 1 | (R)—CH(CH₃)OH | (S) |
| 198 | piperazine | —CH₂— | thiophene | 1 | (R)—CH(CH₃)OH | (S) |
| 199 | N-methylpiperazine | —CH₂— | thiophene | 1 | (R)—CH(CH₃)OH | (S) |
| 200 | CH₃O(CH₂)₂NH— | —CH₂— | furan | 1 | (R)—CH(CH₃)OH | (S) |
| 201 | (CH₃)₂N(CH₂)₂NH— | —CH₂— | furan | 1 | (R)—CH(CH₃)OH | (S) |
| 202 | morpholine | —CH₂— | furan | 1 | (R)—CH(CH₃)OH | (S) |
| 203 | 1,2,3,4-tetrahydro-isoquinoline | —CH₂— | furan | 1 | (R)—CH(CH₃)OH | (S) |
| 204 | benzylamine | —CH₂— | furan | 1 | (R)—CH(CH₃)OH | (S) |
| 205 | N-methylbenzylamine | —CH₂— | furan | 1 | (R)—CH(CH₃)OH | (S) |
| 206 | 4-methoxybenzylamine | —CH₂— | furan | 1 | (R)—CH(CH₃)OH | (S) |
| 207 | pyrrolidine | —CH₂— | furan | 1 | (R)—CH(CH₃)OH | (S) |
| 208 | CH₃O(CH₂)₂NH— | —CH₂— | thiazole | 1 | (R)—CH(CH₃)OH | (S) |

TABLE A-continued

| C. No | A | L | M | n | R$_1$ | Ca |
|---|---|---|---|---|---|---|
| 209 | (CH$_3$)$_2$N(CH$_2$)$_2$NH— | —CH$_2$— | thiazole | 1 | (R)—CH(CH$_3$)OH | (S) |
| 210 | CO$_2$HCH$_2$NH— | —CH$_2$— | thiazole | 1 | (R)—CH(CH$_3$)OH | (S) |
| 211 | morpholine | —CH$_2$— | thiazole | 1 | (R)—CH(CH$_3$)OH | (S) |
| 212 | 4-phenyl-piperazine | —CH$_2$— | thiazole | 1 | (R)—CH(CH$_3$)OH | (S) |
| 213 | 1,2,3,4-tetrahydro-isoquinoline | —CH$_2$— | thiazole | 1 | (R)—CH(CH$_3$)OH | (S) |
| 214 | benzylamine | —CH$_2$— | thiazole | 1 | (R)—CH(CH$_3$)OH | (S) |
| 215 | N-methylbenzylamine | —CH$_2$— | thiazole | 1 | (R)—CH(CH$_3$)OH | (S) |
| 216 | 4-methoxybenzylamine | —CH$_2$— | thiazole | 1 | (R)—CH(CH$_3$)OH | (S) |
| 217 | pyrrolidine | —CH$_2$— | thiazole | 1 | (R)—CH(CH$_3$)OH | (S) |
| 218 | piperazine | —CH$_2$— | thiazole | 1 | (R)—CH(CH$_3$)OH | (S) |
| 219 | N-methylpiperazine | —CH$_2$— | thiazole | 1 | (R)—CH(CH$_3$)OH | (S) |
| 220 | CH$_3$O(CH$_2$)$_2$NH— | —CH$_2$— | pyridine | 1 | (R)—CH(CH$_3$)OH | (S) |
| 221 | CO$_2$HCH$_2$NH— | —CH$_2$— | pyridine | 1 | (R)—CH(CH$_3$)OH | (S) |
| 222 | morpholine | —CH$_2$— | pyridine | 1 | (R)—CH(CH$_3$)OH | (S) |
| 223 | 4-phenyl-piperazine | —CH$_2$— | pyridine | 1 | (R)—CH(CH$_3$)OH | (S) |
| 224 | 1,2,3,4-tetrahydro-isoquinoline | —CH$_2$— | pyridine | 1 | (R)—CH(CH$_3$)OH | (S) |
| 225 | benzylamine | —CH$_2$— | pyridine | 1 | (R)—CH(CH$_3$)OH | (S) |
| 226 | N-methylbenzylamine | —CH$_2$— | pyridine | 1 | (R)—CH(CH$_3$)OH | (S) |
| 227 | 4-methoxybenzylamine | —CH$_2$— | pyridine | 1 | (R)—CH(CH$_3$)OH | (S) |
| 228 | pyrrolidine | —CH$_2$— | pyridine | 1 | (R)—CH(CH$_3$)OH | (S) |
| 229 | piperazine | —CH$_2$— | pyridine | 1 | (R)—CH(CH$_3$)OH | (S) |
| 230 | N-methylpiperazine | —CH$_2$— | pyridine | 1 | (R)—CH(CH$_3$)OH | (S) |
| 231 | CH$_3$O(CH$_2$)$_2$NH— | —CH$_2$— | para phenyl | 1 | (R)—CH(CH$_3$)OH | (S) |
| 232 | (CH$_3$)$_3$CCH$_2$NH— | —CH$_2$— | para phenyl | 1 | —CH$_2$OH | (S) |
| 233 | CO$_2$HCH$_2$NH— | —CH$_2$— | para phenyl | 1 | —CH$_2$OH | (S) |
| 234 | (CH$_3$)$_2$N(CH$_2$)$_2$NH— | —CH$_2$— | para phenyl | 1 | —CH(CH$_3$)$_2$ | (S) |
| 235 | CO$_2$HCH$_2$NH— | —CH$_2$— | para phenyl | 1 | —CH(CH$_3$)$_2$ | (S) |
| 236 | 4-tert-butyl-piperidine | —CH$_2$— | para phenyl | 1 | —CH(CH$_3$)$_2$ | (S) |
| 237 | (CH$_3$)$_2$CHNH— | —CH$_2$— | para phenyl | 1 | (S)—CH(CH$_3$)C$_2$H$_5$ | (S) |
| 238 | 1,1-dioxo-thiomorpholine | —CH$_2$— | para phenyl | 1 | (S)—CH(CH$_3$)C$_2$H$_5$ | (S) |
| 239 | 1,1-dioxo-thiomorpholine | —CH$_2$— | meta phenyl | 1 | —CH$_2$OH | (S) |
| 240 | cyclopropylamine | —CH$_2$— | meta phenyl | 1 | (S)—CH(CH$_3$)C$_2$H$_5$ | (S) |
| 241 | (CH$_3$)$_2$N(CH$_2$)$_2$NH— | —CH$_2$— | pyridine | 1 | (R)—CH(CH$_3$)OH | (S) |
| 242 | NO$_2$ | — | para phenyl | 1 | —CH$_2$OH | (S) |
| 243 | NO$_2$ | — | para phenyl | 1 | (R)—CH(CH$_3$)OH | (S) |
| 244 | NH$_2$ | — | para phenyl | 1 | —CH$_2$OH | (S) |
| 245 | NH$_2$ | — | para phenyl | 1 | (R)—CH(CH$_3$)OH | (S) |
| 246 | NO$_2$ | — | para phenyl | 1 | —CH(CH$_3$)$_2$ | (S) |
| 247 | cyclobutylamine | —CH$_2$— | para phenyl | 1 | (R)—CH(CH$_3$)OH | (S) |
| 248 | cyclopentylamine | —CH$_2$— | para phenyl | 1 | (R)—CH(CH$_3$)OH | (S) |
| 249 | cyclohexylamine | —CH$_2$— | para phenyl | 1 | (R)—CH(CH$_3$)OH | (S) |
| 250 | C$_2$H$_5$NH | —CH$_2$— | para phenyl | 1 | (R)—CH(CH$_3$)OH | (S) |
| 251 | CH$_3$(CH$_2$)$_2$NH— | —CH$_2$— | para phenyl | 1 | (R)—CH(CH$_3$)OH | (S) |
| 252 | CH$_3$O(CH$_2$)$_3$NH— | —CH$_2$— | para phenyl | 1 | (R)—CH(CH$_3$)OH | (S) |
| 253 | CH$_3$O(CH$_2$)$_2$N(CH$_3$)— | —CH$_2$— | para phenyl | 1 | (R)—CH(CH$_3$)OH | (S) |
| 254 | 1,4-oxazepane | —CH$_2$— | para phenyl | 1 | (R)—CH(CH$_3$)OH | (S) |
| 255 | 2,6-dimethylmorpholine | —CH$_2$— | para phenyl | 1 | (R)—CH(CH$_3$)OH | (S) |
| 256 | 3-pyridylmethanamine | —CH$_2$— | para phenyl | 1 | (R)—CH(CH$_3$)OH | (S) |
| 257 | (2-chloro-4-pyridyl)methanamine | —CH$_2$— | para phenyl | 1 | (R)—CH(CH$_3$)OH | (S) |
| 258 | 2-pyridylmethanamine | —CH$_2$— | para phenyl | 1 | (R)—CH(CH$_3$)OH | (S) |
| 259 | furfurylamine | —CH$_2$— | para phenyl | 1 | (R)—CH(CH$_3$)OH | (S) |
| 260 | 2-thienylmethanamine | —CH$_2$— | para phenyl | 1 | (R)—CH(CH$_3$)OH | (S) |
| 261 | 4-methylbenzylamine | —CH$_2$— | para phenyl | 1 | (R)—CH(CH$_3$)OH | (S) |
| 262 | tetrahydrofurfurylamine | —CH$_2$— | para phenyl | 1 | (R)—CH(CH$_3$)OH | (S) |
| 263 | imidazol-$_2$-ylmethanamine | —CH$_2$— | para phenyl | 1 | (R)—CH(CH$_3$)OH | (S) |
| 264 | CH$_3$CCH$_2$CH(CH$_3$)NH— | —CH$_2$— | para phenyl | 1 | (R)—CH(CH$_3$)OH | (S) |
| 265 | pyrrolidine | —CH$_2$— | para phenyl | 1 | —CH$_2$OH | (S) |
| 266 | N-methylpiperazine | —CH$_2$— | para phenyl | 1 | —CH$_2$OH | (S) |
| 267 | cyclobutylamine | —CH$_2$— | para phenyl | 1 | —CH$_2$OH | (S) |
| 268 | cyclopentylamine | —CH$_2$— | para phenyl | 1 | —CH$_2$OH | (S) |
| 269 | cyclohexylamine | —CH$_2$— | para phenyl | 1 | —CH$_2$OH | (S) |
| 270 | CH$_3$NH— | —CH$_2$— | para phenyl | 1 | —CH$_2$OH | (S) |
| 271 | C$_2$H$_5$NH— | —CH$_2$— | para phenyl | 1 | —CH$_2$OH | (S) |
| 272 | CH$_3$(CH$_2$)$_2$NH— | —CH$_2$— | para phenyl | 1 | —CH$_2$OH | (S) |
| 273 | CH$_3$O(CH$_2$)$_3$NH— | —CH$_2$— | para phenyl | 1 | —CH$_2$OH | (S) |
| 274 | CH$_3$O(CH$_2$)$_2$N(CH$_3$)— | —CH$_2$— | para phenyl | 1 | —CH$_2$OH | (S) |
| 275 | 2,6-dimethylmorpholine | —CH$_2$— | para phenyl | 1 | —CH$_2$OH | (S) |
| 276 | piperidine | —CH$_2$— | para phenyl | 1 | —CH$_2$OH | (S) |
| 277 | 3-pyridylmethanamine | —CH$_2$— | para phenyl | 1 | —CH$_2$OH | (S) |
| 278 | 2-pyridylmethanamine | —CH$_2$— | para phenyl | 1 | —CH$_2$OH | (S) |
| 279 | furfurylamine | —CH$_2$— | para phenyl | 1 | —CH$_2$OH | (S) |
| 280 | 2-thienylmethanamine | —CH$_2$— | para phenyl | 1 | —CH$_2$OH | (S) |
| 281 | 4-methylbenzylamine | —CH$_2$— | para phenyl | 1 | —CH$_2$OH | (S) |
| 282 | tetrahydrofurfurylamine | —CH$_2$— | para phenyl | 1 | —CH$_2$OH | (S) |
| 283 | imidazol-$_2$-ylmethanamine | —CH$_2$— | para phenyl | 1 | —CH$_2$OH | (S) |
| 284 | CH$_3$OCH$_2$CH(CH$_3$)NH— | —CH$_2$— | para phenyl | 1 | —CH$_2$OH | (S) |
| 285 | 2,6-dimethylmorpholine | —CH$_2$— | para phenyl | 1 | —CH(CH$_3$)$_2$ | (S) |

TABLE A-continued

| C. No | A | L | M | n | R$_1$ | Ca |
|---|---|---|---|---|---|---|
| 286 | piperidine | —CH$_2$— | para phenyl | 1 | —CH(CH$_3$)$_2$ | (S) |
| 287 | 3-pyridylmethanamine | —CH$_2$— | para phenyl | 1 | —CH(CH$_3$)$_2$ | (S) |
| 288 | (2-chloro-4-pyridyl)methanamine | —CH$_2$— | para phenyl | 1 | —CH(CH$_3$)$_2$ | (S) |
| 289 | 2-pyridylmethanamine | —CH$_2$— | para phenyl | 1 | —CH(CH$_3$)$_2$ | (S) |
| 290 | furfurylamine | —CH$_2$— | para phenyl | 1 | —CH(CH$_3$)$_2$ | (S) |
| 291 | 2-thienylmethanamine | —CH$_2$— | para phenyl | 1 | —CH(CH$_3$)$_2$ | (S) |
| 292 | 4-methylbenzylamine | —CH$_2$— | para phenyl | 1 | —CH(CH$_3$)$_2$ | (S) |
| 293 | imidazol-2-ylmethanamine | —CH$_2$— | para phenyl | 1 | —CH(CH$_3$)$_2$ | (S) |
| 294 | pyrrolidine | —CH$_2$— | para phenyl | 1 | (S)—CH(CH$_3$)C$_2$H$_5$ | (S) |
| 295 | N-methylpiperazine | —CH$_2$— | para phenyl | 1 | (S)—CH(CH$_3$)C$_2$H$_5$ | (S) |
| 296 | C$_2$H$_5$NH— | —CH$_2$— | para phenyl | 1 | (S)—CH(CH$_3$)C$_2$H$_5$ | (S) |
| 297 | CH$_3$O(CH$_2$)$_3$NH— | —CH$_2$— | para phenyl | 1 | (S)—CH(CH$_3$)C$_2$H$_5$ | (S) |
| 298 | CH$_3$O(CH$_2$)$_2$N(CH$_3$)— | —CH$_2$— | para phenyl | 1 | (S)—CH(CH$_3$)C$_2$H$_5$ | (S) |
| 299 | 3-pyridylmethanamine | —CH$_2$— | para phenyl | 1 | (S)—CH(CH$_3$)C$_2$H$_5$ | (S) |
| 300 | 2-pyridylmethanamine | —CH$_2$— | para phenyl | 1 | (S)—CH(CH$_3$)C$_2$H$_5$ | (S) |
| 301 | furfurylamine | —CH$_2$— | para phenyl | 1 | (S)—CH(CH$_3$)C$_2$H$_5$ | (S) |
| 302 | 2-thienylmethanamine | —CH$_2$— | para phenyl | 1 | (S)—CH(CH$_3$)C$_2$H$_5$ | (S) |
| 303 | tetrahydrofurfurylamine | —CH$_2$— | para phenyl | 1 | (S)—CH(CH$_3$)C$_2$H$_5$ | (S) |
| 304 | imidazol-2-ylmethanamine | —CH$_2$— | para phenyl | 1 | (S)—CH(CH$_3$)C$_2$H$_5$ | (S) |
| 305 | CH$_3$OCH$_2$CH(CH$_3$)NH— | —CH$_2$— | para phenyl | 1 | (S)—CH(CH$_3$)C$_2$H$_5$ | (S) |
| 306 | 4-methoxybenzylamine | —CH$_2$— | thiophene | 1 | (R)—CH(CH$_3$)OH | (S) |
| 307 | CO$_2$HCH$_2$NH | —CH$_2$— | furan | 1 | (R)—CH(CH$_3$)OH | (S) |
| 308 | 4-phenyl-piperazine | —CH$_2$— | furan | 1 | (R)—CH(CH$_3$)OH | (S) |
| 309 | piperazine | —CH$_2$— | furan | 1 | (R)—CH(CH$_3$)OH | (S) |
| 310 | N-methylpiperazine | —CH$_2$— | furan | 1 | (R)—CH(CH$_3$)OH | (S) |
| 311 | 1,4-oxazepane | —CH$_2$— | para phenyl | 1 | (S)—CH(CH$_3$)C$_2$H$_5$ | (S) |
| 312 | piperidine | —CH$_2$— | para phenyl | 1 | (S)—CH(CH$_3$)C$_2$H$_5$ | (S) |
| 313 | (2-chloro-4-pyridyl)methanamine | —CH$_2$— | para phenyl | 1 | —C(CH$_3$)$_2$NH$_2$ | |
| 314 | piperidine | —CH$_2$— | para phenyl | 1 | —C(CH$_3$)$_2$NH$_2$ | |
| 315 | 1,4-oxazepane | —CH$_2$— | para phenyl | 1 | —C(CH$_3$)$_2$NH$_2$ | |
| 316 | CH$_3$O(CH$_2$)$_2$N(CH$_3$)— | —CH$_2$— | para phenyl | 1 | —C(CH$_3$)$_2$NH$_2$ | |
| 317 | CH$_3$O(CH$_2$)$_3$NH— | —CH$_2$— | para phenyl | 1 | —C(CH$_3$)$_2$NH$_2$ | |
| 318 | CH$_3$NH— | —CH$_2$— | para phenyl | 1 | —C(CH$_3$)$_2$NH$_2$ | |
| 319 | pyrrolidine | —CH$_2$— | para phenyl | 1 | —C(CH$_3$)$_2$NH$_2$ | |
| 320 | 4-pyridylmethanamine | —CH$_2$— | para phenyl | 1 | —C(CH$_3$)$_2$NH$_2$ | |
| 321 | benzylamine | —CH$_2$— | para phenyl | 1 | —C(CH$_3$)$_2$NH$_2$ | |
| 322 | 4-phenyl-piperazine | —CH$_2$— | para phenyl | 1 | —C(CH$_3$)$_2$NH$_2$ | |
| 323 | 4-phenyl-piperidine | —CH$_2$— | para phenyl | 1 | —C(CH$_3$)$_2$NH$_2$ | |
| 324 | 1,1-dioxo-thiomorpholine | —CH$_2$— | para phenyl | 1 | —C(CH$_3$)$_2$NH$_2$ | |
| 325 | morpholine | —CH$_2$— | para phenyl | 1 | —C(CH$_3$)$_2$NH$_2$ | |
| 326 | CH$_3$O(CH$_2$)$_2$NH— | —CH$_2$— | para phenyl | 1 | —C(CH$_3$)$_2$NH$_2$ | |
| 327 | CH$_2$CHCH$_2$NH— | —CH$_2$— | para phenyl | 1 | —C(CH$_3$)$_2$NH$_2$ | |
| 328 | (CH$_3$)$_2$CHNH— | —CH$_2$— | para phenyl | 1 | —C(CH$_3$)$_2$NH$_2$ | |
| 329 | cyclopropylamine | —CH$_2$— | para phenyl | 1 | —C(CH$_3$)$_2$NH$_2$ | |
| 330 | thiazol-2-ylmethanamine | —CH$_2$— | para phenyl | 1 | (S)—CH(CH$_3$)C$_2$H$_5$ | (S) |
| 331 | 4-methylbenzylamine | —CH$_2$— | para phenyl | 1 | (S)—CH(CH$_3$)C$_2$H$_5$ | (S) |
| 332 | (2-chloro-4-pyridyl)methanamine | —CH$_2$— | para phenyl | 1 | (S)—CH(CH$_3$)C$_2$H$_5$ | (S) |
| 333 | 2,6-dimethylmorpholine | —CH$_2$— | para phenyl | 1 | (S)—CH(CH$_3$)C$_2$H$_5$ | (S) |
| 334 | NCCH$_2$NH— | —CH$_2$— | para phenyl | 1 | (S)—CH(CH$_3$)C$_2$H$_5$ | (S) |
| 335 | CH$_3$(CH$_2$)$_2$NH— | —CH$_2$— | para phenyl | 1 | (S)—CH(CH$_3$)C$_2$H$_5$ | (S) |
| 336 | CH$_3$NH— | —CH$_2$— | para phenyl | 1 | (S)—CH(CH$_3$)C$_2$H$_5$ | (S) |
| 337 | cyclohexylamine | —CH$_2$— | para phenyl | 1 | (S)—CH(CH$_3$)C$_2$H$_5$ | (S) |
| 338 | cyclopentylamine | —CH$_2$— | para phenyl | 1 | (S)—CH(CH$_3$)C$_2$H$_5$ | (S) |
| 339 | cyclobutylamine | —CH$_2$— | para phenyl | 1 | (S)—CH(CH$_3$)C$_2$H$_5$ | (S) |
| 340 | CH$_3$OCH$_2$CH(CH$_3$)NH— | —CH$_2$— | para phenyl | 1 | —CH(CH$_3$)$_2$ | (S) |
| 341 | thiazol-2-ylmethanamine | —CH$_2$— | para phenyl | 1 | —CH(CH$_3$)$_2$ | (S) |
| 342 | tetrahydrofurfurylamine | —CH$_2$— | para phenyl | 1 | —CH(CH$_3$)$_2$ | (S) |
| 343 | C$_2$H$_5$NH— | —CH$_2$— | para phenyl | 1 | —CH(CH$_3$)$_2$ | (S) |
| 344 | 1,4-oxazepane | —CH$_2$— | para phenyl | 1 | —CH(CH$_3$)$_2$ | (S) |
| 345 | CH$_3$O(CH$_2$)$_2$N(CH$_3$)— | —CH$_2$— | para phenyl | 1 | —CH(CH$_3$)$_2$ | (S) |
| 346 | NCCH$_2$NH— | —CH$_2$— | para phenyl | 1 | —CH(CH$_3$)$_2$ | (S) |
| 347 | CH$_3$O(CH$_2$)$_3$NH— | —CH$_2$— | para phenyl | 1 | —CH(CH$_3$)$_2$ | (S) |
| 348 | CH$_3$(CH$_2$)$_2$NH— | —CH$_2$— | para phenyl | 1 | —CH(CH$_3$)$_2$ | (S) |
| 349 | CH$_3$NH— | —CH$_2$— | para phenyl | 1 | —CH(CH$_3$)$_2$ | (S) |
| 350 | cyclohexylamine | —CH$_2$— | para phenyl | 1 | —CH(CH$_3$)$_2$ | (S) |
| 351 | cyclopentylamine | —CH$_2$— | para phenyl | 1 | —CH(CH$_3$)$_2$ | (S) |
| 352 | cyclobutylamine | —CH$_2$— | para phenyl | 1 | —CH(CH$_3$)$_2$ | (S) |
| 353 | N-methylpiperazine | —CH$_2$— | para phenyl | 1 | —CH(CH$_3$)$_2$ | (S) |
| 354 | pyrrolidine | —CH$_2$— | para phenyl | 1 | —CH(CH$_3$)$_2$ | (S) |
| 355 | thiazol-2-ylmethanamine | —CH$_2$— | para phenyl | 1 | —CH$_2$OH | (S) |
| 356 | (2-chloro-4-pyridyl)methanamine | —CH$_2$— | para phenyl | 1 | —CH$_2$OH | (S) |
| 357 | 1,4-oxazepane | —CH$_2$— | para phenyl | 1 | —CH$_2$OH | (S) |
| 358 | NCCH$_2$NH— | —CH$_2$— | para phenyl | 1 | —CH$_2$OH | (S) |
| 359 | thiazol-2-ylmethanamine | —CH$_2$— | para phenyl | 1 | (R)—CH(CH$_3$)OH | (S) |

TABLE A-continued

| C. No | A | L | M | n | R₁ | Ca |
|---|---|---|---|---|---|---|
| 360 | NCCH₂NH— | —CH₂— | para phenyl | 1 | (R)—CH(CH₃)OH | (S) |
| 361 | CH₃NH— | —CH₂— | para phenyl | 1 | (R)—CH(CH₃)OH | (S) |
| 362 | CH₃OCH₂CH(CH₃)NH— | —CH₂— | para phenyl | 1 | —C(CH₃)₂NH₂ | |
| 363 | tetrahydrofurfurylamine | —CH₂— | para phenyl | 1 | —C(CH₃)₂NH₂ | |
| 364 | 3-pyridylmethanamine | —CH₂— | para phenyl | 1 | —C(CH₃)₂NH₂ | |
| 365 | morpholine | —CH₂— | ethenyl | 1 | —CH(CH₃)₂ | (S) |
| 366 | HO(CH₂)₃NH— | —CH₂— | para phenyl | 1 | (R)—CH(CH₃)OH | (S) |
| 367 | morpholine | —CH₂— | ethenyl | 1 | (R)—CH(CH₃)OH | (S) |
| 368 | cyclopropylamine | —CH₂— | ethenyl | 1 | (R)—CH(CH₃)OH | (S) |
| 369 | CH₂CHCH₂NH— | —CH₂— | ethenyl | 1 | (R)—CH(CH₃)OH | (S) |
| 370 | 4-phenyl-piperidine | —CH₂— | ethenyl | 1 | (R)—CH(CH₃)OH | (S) |
| 371 | 4-phenyl-piperazine | —CH₂— | ethenyl | 1 | (R)—CH(CH₃)OH | (S) |
| 372 | 1,2,3,4-tetrahydro-isoquinoline | —CH₂— | ethenyl | 1 | (R)—CH(CH₃)OH | (S) |
| 373 | 4-pyridylmethanamine | —CH₂— | ethenyl | 1 | (R)—CH(CH₃)OH | (S) |
| 374 | CH₃O(CH₂)₃NH— | —CH₂— | ethenyl | 1 | (R)—CH(CH₃)OH | (S) |
| 375 | 1,4-oxazepane | —CH₂— | ethenyl | 1 | (R)—CH(CH₃)OH | (S) |
| 376 | 3-pyridylmethanamine | —CH₂— | ethenyl | 1 | (R)—CH(CH₃)OH | (S) |
| 377 | 2-pyridylmethanamine | —CH₂— | ethenyl | 1 | (R)—CH(CH₃)OH | (S) |
| 378 | 2-thienylmethanamine | —CH₂— | ethenyl | 1 | (R)—CH(CH₃)OH | (S) |
| 379 | 4-methylbenzylamine | —CH₂— | ethenyl | 1 | (R)—CH(CH₃)OH | (S) |
| 380 | tetrahydrofurfurylamine | —CH₂— | ethenyl | 1 | (R)—CH(CH₃)OH | (S) |
| 381 | cyclopropylamine | —CH₂— | para phenyl | 1 | —CH(CH₃)NH₂ | (S) |
| 382 | (CH₃)₂CHNH— | —CH₂— | para phenyl | 1 | —CH(CH₃)NH₂ | (S) |
| 383 | CH₃O(CH₂)₂NH— | —CH₂— | para phenyl | 1 | —CH(CH₃)NH₂ | (S) |
| 384 | morpholine | —CH₂— | para phenyl | 1 | —CH(CH₃)NH₂ | (S) |
| 385 | 1,1-dioxo-thiomorpholine | —CH₂— | para phenyl | 1 | —CH(CH₃)NH₂ | (S) |
| 386 | 4-phenyl-piperidine | —CH₂— | para phenyl | 1 | —CH(CH₃)NH₂ | (S) |
| 387 | 4-phenyl-piperazine | —CH₂— | para phenyl | 1 | —CH(CH₃)NH₂ | (S) |
| 388 | benzylamine | —CH₂— | para phenyl | 1 | —CH(CH₃)NH₂ | (S) |
| 389 | 4-pyridylmethanamine | —CH₂— | para phenyl | 1 | —CH(CH₃)NH₂ | (S) |
| 390 | pyrrolidine | —CH₂— | para phenyl | 1 | —CH(CH₃)NH₂ | (S) |
| 391 | CH₃O(CH₂)₃NH— | —CH₂— | para phenyl | 1 | —CH(CH₃)NH₂ | (S) |
| 392 | CH₃O(CH₂)₂N(CH₃)— | —CH₂— | para phenyl | 1 | —CH(CH₃)NH₂ | (S) |
| 393 | piperidine | —CH₂— | para phenyl | 1 | —CH(CH₃)NH₂ | (S) |
| 394 | 3-pyridylmethanamine | —CH₂— | para phenyl | 1 | —CH(CH₃)NH₂ | (S) |
| 395 | (2-chloro-4-pyridyl)methanamine | —CH₂— | para phenyl | 1 | —CH(CH₃)NH₂ | (S) |
| 396 | tetrahydrofurfurylamine | —CH₂— | para phenyl | 1 | —CH(CH₃)NH₂ | (S) |
| 397 | CH₃OCH₂CH(CH₃)NH— | —CH₂— | para phenyl | 1 | —CH(CH₃)NH₂ | (S) |
| 398 | cyclopropylamine | —CH₂— | thiophene | 1 | (R)—CH(CH₃)OH | (S) |
| 399 | (CH₃)₂CHNH— | —CH₂— | thiophene | 1 | (R)—CH(CH₃)OH | (S) |
| 400 | CH₂CHCH₂NH— | —CH₂— | thiophene | 1 | (R)—CH(CH₃)OH | (S) |
| 401 | 4-pyridylmethanamine | —CH₂— | thiophene | 1 | (R)—CH(CH₃)OH | (S) |
| 402 | cyclobutylamine | —CH₂— | thiophene | 1 | (R)—CH(CH₃)OH | (S) |
| 403 | cyclopentylamine | —CH₂— | thiophene | 1 | (R)—CH(CH₃)OH | (S) |
| 404 | CH₃(CH₂)₂NH— | —CH₂— | thiophene | 1 | (R)—CH(CH₃)OH | (S) |
| 405 | CH₃O(CH₂)₃NH— | —CH₂— | thiophene | 1 | (R)—CH(CH₃)OH | (S) |
| 406 | NCCH₂NH— | —CH₂— | thiophene | 1 | (R)—CH(CH₃)OH | (S) |
| 407 | 3-pyridylmethanamine | —CH₂— | thiophene | 1 | (R)—CH(CH₃)OH | (S) |
| 408 | 2-pyridylmethanamine | —CH₂— | thiophene | 1 | (R)—CH(CH₃)OH | (S) |
| 409 | furfurylamine | —CH₂— | thiophene | 1 | (R)—CH(CH₃)OH | (S) |
| 410 | 2-thienylmethanamine | —CH₂— | thiophene | 1 | (R)—CH(CH₃)OH | (S) |
| 411 | 4-methylbenzylamine | —CH₂— | thiophene | 1 | (R)—CH(CH₃)OH | (S) |
| 412 | tetrahydrofurfurylamine | —CH₂— | thiophene | 1 | (R)—CH(CH₃)OH | (S) |
| 413 | cyclopropylamine | —CH₂— | pyridine | 1 | (R)—CH(CH₃)OH | (S) |
| 414 | (CH₃)₂CHNH— | —CH₂— | pyridine | 1 | (R)—CH(CH₃)OH | (S) |
| 415 | CH₂CHCH₂NH— | —CH₂— | pyridine | 1 | (R)—CH(CH₃)OH | (S) |
| 416 | 4-pyridylmethanamine | —CH₂— | pyridine | 1 | (R)—CH(CH₃)OH | (S) |
| 417 | cyclobutylamine | —CH₂— | pyridine | 1 | (R)—CH(CH₃)OH | (S) |
| 418 | cyclopentylamine | —CH₂— | pyridine | 1 | (R)—CH(CH₃)OH | (S) |
| 419 | CH₃(CH₂)₂NH— | —CH₂— | pyridine | 1 | (R)—CH(CH₃)OH | (S) |
| 420 | CH₃O(CH₂)₃NH— | —CH₂— | pyridine | 1 | (R)—CH(CH₃)OH | (S) |
| 421 | NCCH₂NH— | —CH₂— | pyridine | 1 | (R)—CH(CH₃)OH | (S) |
| 422 | 3-pyridylmethanamine | —CH₂— | pyridine | 1 | (R)—CH(CH₃)OH | (S) |
| 423 | 2-pyridylmethanamine | —CH₂— | pyridine | 1 | (R)—CH(CH₃)OH | (S) |
| 424 | furfurylamine | —CH₂— | pyridine | 1 | (R)—CH(CH₃)OH | (S) |
| 425 | 2-thienylmethanamine | —CH₂— | pyridine | 1 | (R)—CH(CH₃)OH | (S) |
| 426 | 4-methylbenzylamine | —CH₂— | pyridine | 1 | (R)—CH(CH₃)OH | (S) |
| 427 | tetrahydrofurfurylamine | —CH₂— | pyridine | 1 | (R)—CH(CH₃)OH | (S) |
| 428 | 4-hydroxypiperidine | —CH₂— | para phenyl | 1 | (R)—CH(CH₃)OH | (S) |
| 429 | trans 4-hydroxycyclohexylamine | —CH₂— | para phenyl | 1 | (R)—CH(CH₃)OH | (S) |
| 430 | (S)-2-hydroxymethylpyrrolidine | —CH₂— | para phenyl | 1 | (R)—CH(CH₃)OH | (S) |
| 431 | (S)-3-hydroxypyrrolidine | —CH₂— | para phenyl | 1 | (R)—CH(CH₃)OH | (S) |
| 432 | HO(CH₂)₂NH— | —CH₂— | para phenyl | 1 | (R)—CH(CH₃)OH | (S) |
| 433 | CH₂CHCH₂NH— | —CH₂— | para phenyl | 1 | —CH(CH₃)NH₂ | (S) |
| 434 | CH₃NH— | —CH₂— | para phenyl | 1 | —CH(CH₃)NH₂ | (S) |
| 435 | 1,4-oxazepane | —CH₂— | para phenyl | 1 | —CH(CH₃)NH₂ | (S) |

TABLE A-continued

| C. No | A | L | M | n | R₁ | Ca |
|---|---|---|---|---|---|---|
| 436 | CH₃O(CH₂)₂NH— | —CH₂— | ethenyl | 1 | (R)—CH(CH₃)OH | (S) |
| 437 | benzylamine | —CH₂— | ethenyl | 1 | (R)—CH(CH₃)OH | (S) |
| 438 | N-methylbenzylamine | —CH₂— | ethenyl | 1 | (R)—CH(CH₃)OH | (S) |
| 439 | 4-chlorobenzylamine | —CH₂— | ethenyl | 1 | (R)—CH(CH₃)OH | (S) |
| 440 | 4-methoxybenzylamine | —CH₂— | ethenyl | 1 | (R)—CH(CH₃)OH | (S) |
| 441 | CH₃O(CH₂)₂N(CH₃)— | —CH₂— | ethenyl | 1 | (R)—CH(CH₃)OH | (S) |
| 442 | (2-chloro-4-pyridyl)methanamine | —CH₂— | ethenyl | 1 | (R)—CH(CH₃)OH | (S) |
| 443 | furfurylamine | —CH₂— | ethenyl | 1 | (R)—CH(CH₃)OH | (S) |
| 444 | cyclopropylamine | —CH₂— | ethenyl | 2 | (R)—CH(CH₃)OH | (S) |
| 445 | CH₂CHCH₂NH— | —CH₂— | ethenyl | 2 | (R)—CH(CH₃)OH | (S) |
| 446 | CH₃O(CH₂)₂NH— | —CH₂— | ethenyl | 2 | (R)—CH(CH₃)OH | (S) |
| 447 | morpholine | —CH₂— | ethenyl | 2 | (R)—CH(CH₃)OH | (S) |
| 448 | 4-phenyl-piperidine | —CH₂— | ethenyl | 2 | (R)—CH(CH₃)OH | (S) |
| 449 | 4-phenyl-piperazine | —CH₂— | ethenyl | 2 | (R)—CH(CH₃)OH | (S) |
| 450 | 1,2,3,4-tetrahydro-isoquinoline | —CH₂— | ethenyl | 2 | (R)—CH(CH₃)OH | (S) |
| 451 | benzylamine | —CH₂— | ethenyl | 2 | (R)—CH(CH₃)OH | (S) |
| 452 | N-methylbenzylamine | —CH₂— | ethenyl | 2 | (R)—CH(CH₃)OH | (S) |
| 453 | 4-chlorobenzylamine | —CH₂— | ethenyl | 2 | (R)—CH(CH₃)OH | (S) |
| 454 | 4-methoxybenzylamine | —CH₂— | ethenyl | 2 | (R)—CH(CH₃)OH | (S) |
| 455 | 4-pyridylmethanamine | —CH₂— | ethenyl | 2 | (R)—CH(CH₃)OH | (S) |
| 456 | CH₃O(CH₂)₃NH— | —CH₂— | ethenyl | 2 | (R)—CH(CH₃)OH | (S) |
| 457 | CH₃O(CH₂)₂N(CH₃)— | —CH₂— | ethenyl | 2 | (R)—CH(CH₃)OH | (S) |
| 458 | 1,4-oxazepane | —CH₂— | ethenyl | 2 | (R)—CH(CH₃)OH | (S) |
| 459 | piperidine | —CH₂— | ethenyl | 2 | (R)—CH(CH₃)OH | (S) |
| 460 | 3-pyridylmethanamine | —CH₂— | ethenyl | 2 | (R)—CH(CH₃)OH | (S) |
| 461 | (2-chloro-4-pyridyl)methanamine | —CH₂— | ethenyl | 2 | (R)—CH(CH₃)OH | (S) |
| 462 | 2-pyridylmethanamine | —CH₂— | ethenyl | 2 | (R)—CH(CH₃)OH | (S) |
| 463 | furfurylamine | —CH₂— | ethenyl | 2 | (R)—CH(CH₃)OH | (S) |
| 464 | 2-thienylmethanamine | —CH₂— | ethenyl | 2 | (R)—CH(CH₃)OH | (S) |
| 465 | 4-methylbenzylamine | —CH₂— | ethenyl | 2 | (R)—CH(CH₃)OH | (S) |
| 466 | tetrahydrofurfurylamine | —CH₂— | ethenyl | 2 | (R)—CH(CH₃)OH | (S) |
| 467 | CF₃CH₂NH— | —CH₂— | para phenyl | 1 | (R)—CH(CH₃)OH | (S) |
| 468 | 3-pyrroline | —CH₂— | para phenyl | 1 | (R)—CH(CH₃)OH | (S) |
| 469 | HCCCH₂NH— | —CH₂— | para phenyl | 1 | (R)—CH(CH₃)OH | (S) |
| 470 | HOC(CH₃)₂CH₂NH— | —CH₂— | para phenyl | 1 | (R)—CH(CH₃)OH | (S) |
| 471 | cyclopropylmethanamine | —CH₂— | para phenyl | 1 | (R)—CH(CH₃)OH | (S) |
| 472 | CH₃S(CH₂)₂NH— | —CH₂— | para phenyl | 1 | (R)—CH(CH₃)OH | (S) |
| 473 | CH₃SO₂(CH₂)₂NH— | —CH₂— | para phenyl | 1 | (R)—CH(CH₃)OH | (S) |
| 474 | (5-methyloxazol-2-yl)methanamine | —CH₂— | para phenyl | 1 | (R)—CH(CH₃)OH | (S) |
| 475 | 4-fluorobenzylamine | —CH₂— | para phenyl | 1 | (R)—CH(CH₃)OH | (S) |
| 476 | CH₂C(CH₃)CH₂NH— | —CH₂— | thiophene | 1 | (R)—CH(CH₃)OH | (S) |
| 477 | CF₃CH₂NH— | —CH₂— | thiophene | 1 | (R)—CH(CH₃)OH | (S) |
| 478 | 3-pyrroline | —CH₂— | thiophene | 1 | (R)—CH(CH₃)OH | (S) |
| 479 | HCCCH₂NH— | —CH₂— | thiophene | 1 | (R)—CH(CH₃)OH | (S) |
| 480 | HOC(CH₃)₂CH₂NH— | —CH₂— | thiophene | 1 | (R)—CH(CH₃)OH | (S) |
| 481 | cyclopropylmethanamine | —CH₂— | thiophene | 1 | (R)—CH(CH₃)OH | (S) |
| 482 | CH₃S(CH₂)₂NH— | —CH₂— | thiophene | 1 | (R)—CH(CH₃)OH | (S) |
| 483 | CH₃SO₂(CH₂)₂NH— | —CH₂— | thiophene | 1 | (R)—CH(CH₃)OH | (S) |
| 484 | (5-methyloxazol-2-yl)methanamine | —CH₂— | thiophene | 1 | (R)—CH(CH₃)OH | (S) |
| 485 | 4-fluorobenzylamine | —CH₂— | thiophene | 1 | (R)—CH(CH₃)OH | (S) |
| 486 | CH₂C(CH₃)CH₂NH— | —CH₂— | pyridine | 1 | (R)—CH(CH₃)OH | (S) |
| 487 | CF₃CH₂NH— | —CH₂— | pyridine | 1 | (R)—CH(CH₃)OH | (S) |
| 488 | 3-pyrroline | —CH₂— | pyridine | 1 | (R)—CH(CH₃)OH | (S) |
| 489 | (1-cyanocyclopropyl)amine | —CH₂— | pyridine | 1 | (R)—CH(CH₃)OH | (S) |
| 490 | HCCCH₂NH— | —CH₂— | pyridine | 1 | (R)—CH(CH₃)OH | (S) |
| 491 | HOC(CH₃)₂CH₂NH— | —CH₂— | pyridine | 1 | (R)—CH(CH₃)OH | (S) |
| 492 | cyclopropylmethanamine | —CH₂— | pyridine | 1 | (R)—CH(CH₃)OH | (S) |
| 493 | CH₃S(CH₂)₂NH— | —CH₂— | pyridine | 1 | (R)—CH(CH₃)OH | (S) |
| 494 | CH₃SO₂(CH₂)₂NH— | —CH₂— | pyridine | 1 | (R)—CH(CH₃)OH | (S) |
| 495 | (5-methyloxazol-2-yl)methanamine | —CH₂— | pyridine | 1 | (R)—CH(CH₃)OH | (S) |
| 496 | 4-fluorobenzylamine | —CH₂— | pyridine | 1 | (R)—CH(CH₃)OH | (S) |
| 497 | CH₂C(CH₃)CH₂NH— | —CH₂— | para phenyl | 1 | (R)—CH(CH₃)OH | (S) |
| 498 | (1-cyanocyclopropyl)amine | —CH₂— | para phenyl | 1 | (R)—CH(CH₃)OH | (S) |
| 499 | H₂NCOCH₂NH— | —CH₂— | para phenyl | 1 | (R)—CH(CH₃)OH | (S) |
| 500 | 2-pyrimidinylmethanamine | —CH₂— | para phenyl | 1 | (R)—CH(CH₃)OH | (S) |
| 501 | ethylpyrrol-2-yl)methanamine | —CH₂— | para phenyl | 1 | (R)—CH(CH₃)OH | (S) |
| 502 | CH₂CH(CH₂)₂NH— | —CH₂— | para phenyl | 1 | (R)—CH(CH₃)OH | (S) |
| 503 | (1-cyanocyclopropyamine | —CH₂— | thiophene | 1 | (R)—CH(CH₃)OH | (S) |
| 504 | H₂NCOCH₂NH— | —CH₂— | thiophene | 1 | (R)—CH(CH₃)OH | (S) |
| 505 | 2-pyrimidinylmethanamine | —CH₂— | thiophene | 1 | (R)—CH(CH₃)OH | (S) |
| 506 | (1-methylpyrrol-2-yl)methanamine | —CH₂— | thiophene | 1 | (R)—CH(CH₃)OH | (S) |

TABLE A-continued

| C. No | A | L | M | n | R₁ | Ca |
|---|---|---|---|---|---|---|
| 507 | CH₂CH(CH₂)₂NH— | —CH₂— | thiophene | 1 | (R)—CH(CH₃)OH | (S) |
| 508 | H₂NCOCH₂NH— | —CH₂— | pyridine | 1 | (R)—CH(CH₃)OH | (S) |
| 509 | 2-pyrimidinylmethanamine | —CH₂— | pyridine | 1 | (R)—CH(CH₃)OH | (S) |
| 510 | (1-methylpyrrol-2-yl)methanamine | —CH₂— | pyridine | 1 | (R)—CH(CH₃)OH | (S) |
| 511 | CH₂CH(CH₂)₂NH— | —CH₂— | pyridine | 1 | (R)—CH(CH₃)OH | (S) |
| 512 | morpholine | | para phenyl | 1 | (R)—CH(CH₃)OH | (S) |
| 513 | 4-methoxybenzylamine | —CH₂— | para phenyl | 1 | —C(CH₃)₂NH₂ | |
| 514 | cyclobutylamine | —CH₂— | para phenyl | 1 | —C(CH₃)₂NH₂ | |
| 515 | cyclopentylamine | —CH₂— | para phenyl | 1 | —C(CH₃)₂NH₂ | |
| 516 | CH₃(CH₂)₂NH— | —CH₂— | para phenyl | 1 | —C(CH₃)₂NH₂ | |
| 517 | 2-pyridylmethanamine | —CH₂— | para phenyl | 1 | —C(CH₃)₂NH₂ | |
| 518 | furfurylamine | —CH₂— | para phenyl | 1 | —C(CH₃)₂NH₂ | |
| 519 | 2-thienylmethanamine | —CH₂— | para phenyl | 1 | —C(CH₃)₂NH₂ | |
| 520 | 4-methylbenzylamine | —CH₂— | para phenyl | 1 | —C(CH₃)₂NH₂ | |
| 521 | cyclopropylamine | —CH₂— | thiophene | 1 | —C(CH₃)₂NH₂ | |
| 522 | CH₂CHCH₂NH— | —CH₂— | thiophene | 1 | —C(CH₃)₂NH₂ | |
| 523 | CH₃O(CH₂)₂NH— | —CH₂— | thiophene | 1 | —C(CH₃)₂NH₂ | |
| 524 | morpholine | —CH₂— | thiophene | 1 | —C(CH₃)₂NH₂ | |
| 525 | benzylamine | —CH₂— | thiophene | 1 | —C(CH₃)₂NH₂ | |
| 526 | 4-methoxybenzylamine | —CH₂— | thiophene | 1 | —C(CH₃)₂NH₂ | |
| 527 | 4-pyridylmethanamine | —CH₂— | thiophene | 1 | —C(CH₃)₂NH₂ | |
| 528 | pyrrolidine | —CH₂— | thiophene | 1 | —C(CH₃)₂NH₂ | |
| 529 | cyclobutylamine | —CH₂— | thiophene | 1 | —C(CH₃)₂NH₂ | |
| 530 | cyclopentylamine | —CH₂— | thiophene | 1 | —C(CH₃)₂NH₂ | |
| 531 | CH₃(CH₂)₂NH— | —CH₂— | thiophene | 1 | —C(CH₃)₂NH₂ | |
| 532 | 3-pyridylmethanamine | —CH₂— | thiophene | 1 | —C(CH₃)₂NH₂ | |
| 533 | (2-chloro-4-pyridyl)methanamine | —CH₂— | thiophene | 1 | —C(CH₃)₂NH₂ | |
| 534 | 2-pyridylmethanamine | —CH₂— | thiophene | 1 | —C(CH₃)₂NH₂ | |
| 535 | furfurylamine | —CH₂— | thiophene | 1 | —C(CH₃)₂NH₂ | |
| 536 | 2-thienylmethanamine | —CH₂— | thiophene | 1 | —C(CH₃)₂NH₂ | |
| 537 | 4-methylbenzylamine | —CH₂— | thiophene | 1 | —C(CH₃)₂NH₂ | |
| 538 | tetrahydrofurfurylamine | —CH₂— | thiophene | 1 | —C(CH₃)₂NH₂ | |
| 539 | cyclopropylamine | —CH₂— | pyridine | 1 | —C(CH₃)₂NH₂ | |
| 540 | CH₃O(CH₂)₂NH— | —CH₂— | pyridine | 1 | —C(CH₃)₂NH₂ | |
| 541 | benzylamine | —CH₂— | pyridine | 1 | —C(CH₃)₂NH₂ | |
| 542 | 4-methoxybenzylamine | —CH₂— | pyridine | 1 | —C(CH₃)₂NH₂ | |
| 543 | pyrrolidine | —CH₂— | pyridine | 1 | —C(CH₃)₂NH₂ | |
| 544 | cyclobutylamine | —CH₂— | pyridine | 1 | —C(CH₃)₂NH₂ | |
| 545 | CH₃(CH₂)₂NH— | —CH₂— | pyridine | 1 | —C(CH₃)₂NH₂ | |
| 546 | 3-pyridylmethanamine | —CH₂— | pyridine | 1 | —C(CH₃)₂NH₂ | |
| 547 | (2-chloro-4-pyridyl)methanamine | —CH₂— | pyridine | 1 | —C(CH₃)₂NH₂ | |
| 548 | furfurylamine | —CH₂— | pyridine | 1 | —C(CH₃)₂NH₂ | |
| 549 | 2-thienylmethanamine | —CH₂— | pyridine | 1 | —C(CH₃)₂NH₂ | |
| 550 | 4-methylbenzylamine | —CH₂— | pyridine | 1 | —C(CH₃)₂NH₂ | |
| 551 | tetrahydrofurfurylamine | —CH₂— | pyridine | 1 | —C(CH₃)₂NH₂ | |
| 552 | NO₂ | — | para phenyl | 1 | —C(CH₃)₂NH₂ | |
| 553 | NH₂ | — | para phenyl | 1 | —C(CH₃)₂NH₂ | |
| 554 | cyclopropylamine | —CH₂— | para phenyl | 1 | —C(CH₃)₂NO₂ | |
| 555 | CH₂CHCH₂NH— | —CH₂— | pyridine | 1 | —C(CH₃)₂NH₂ | |
| 556 | morpholine | —CH₂— | pyridine | 1 | —C(CH₃)₂NH₂ | |
| 557 | 4-pyridylmethanamine | —CH₂— | pyridine | 1 | —C(CH₃)₂NH₂ | |
| 558 | cyclopentylamine | —CH₂— | pyridine | 1 | —C(CH₃)₂NH₂ | |
| 559 | 2-pyridylmethanamine | —CH₂— | pyridine | 1 | —C(CH₃)₂NH₂ | |
| 560 | thiazol-2-ylmethanamine | —CH₂— | pyridine | 1 | —C(CH₃)₂NH₂ | |
| 561 | NCCH₂NH— | —CH₂— | para phenyl | 1 | —C(CH₃)₂NH₂ | |
| 562 | thiazol-2-ylmethanamine | —CH₂— | para phenyl | 1 | —C(CH₃)₂NH₂ | |
| 563 | NCCH₂NH— | —CH₂— | thiophene | 1 | —C(CH₃)₂NH₂ | |
| 564 | thiazol-2-ylmethanamine | —CH₂— | thiophene | 1 | —C(CH₃)₂NH₂ | |
| 565 | cyclopropylamine | —CH₂— | para phenyl | 1 | —C(CH₃)₂OH | (S) |
| 566 | CH₂CHCH₂NH— | —CH₂— | para phenyl | 1 | —C(CH₃)₂OH | (S) |
| 567 | CH₃O(CH₂)₂NH— | —CH₂— | para phenyl | 1 | —C(CH₃)₂OH | (S) |
| 568 | morpholine | —CH₂— | para phenyl | 1 | —C(CH₃)₂OH | (S) |
| 569 | benzylamine | —CH₂— | para phenyl | 1 | —C(CH₃)₂OH | (S) |
| 570 | 4-methoxybenzylamine | —CH₂— | para phenyl | 1 | —C(CH₃)₂OH | (S) |
| 571 | pyrrolidine | —CH₂— | para phenyl | 1 | —C(CH₃)₂OH | (S) |
| 572 | cyclobutylamine | —CH₂— | para phenyl | 1 | —C(CH₃)₂OH | (S) |
| 573 | cyclopentylamine | —CH₂— | para phenyl | 1 | —C(CH₃)₂OH | (S) |
| 574 | 3-pyridylmethanamine | —CH₂— | para phenyl | 1 | —C(CH₃)₂OH | (S) |
| 575 | (2-chloro-4-pyridyl)methanamine | —CH₂— | para phenyl | 1 | —C(CH₃)₂OH | (S) |
| 576 | 2-pyridylmethanamine | —CH₂— | para phenyl | 1 | —C(CH₃)₂OH | (S) |
| 577 | furfurylamine | —CH₂— | para phenyl | 1 | —C(CH₃)₂OH | (S) |
| 578 | 2-thienylmethanamine | —CH₂— | para phenyl | 1 | —C(CH₃)₂OH | (S) |
| 579 | 4-methylbenzylamine | —CH₂— | para phenyl | 1 | —C(CH₃)₂OH | (S) |
| 580 | tetrahydrofurfurylamine | —CH₂— | para phenyl | 1 | —C(CH₃)₂OH | (S) |

TABLE A-continued

| C. No | A | L | M | n | R₁ | Ca |
|---|---|---|---|---|---|---|
| 581 | cyclopropylamine | —CH₂— | para phenyl | 1 | —C(CH₃)₂SCH₃ | (R) |
| 582 | CH₂CHCH₂NH— | —CH₂— | para phenyl | 1 | —C(CH₃)₂SCH₃ | (R) |
| 583 | CH₃O(CH₂)₂NH— | —CH₂— | para phenyl | 1 | —C(CH₃)₂SCH₃ | (R) |
| 584 | morpholine | —CH₂— | para phenyl | 1 | —C(CH₃)₂SCH₃ | (R) |
| 585 | benzylamine | —CH₂— | para phenyl | 1 | —C(CH₃)₂SCH₃ | (R) |
| 586 | 4-methoxybenzylamine | —CH₂— | para phenyl | 1 | —C(CH₃)₂SCH₃ | (R) |
| 587 | 4-pyridylmethanamine | —CH₂— | para phenyl | 1 | —C(CH₃)₂SCH₃ | (R) |
| 588 | pyrrolidine | —CH₂— | para phenyl | 1 | —C(CH₃)₂SCH₃ | (R) |
| 589 | cyclobutylamine | —CH₂— | para phenyl | 1 | —C(CH₃)₂SCH₃ | (R) |
| 590 | cyclopentylamine | —CH₂— | para phenyl | 1 | —C(CH₃)₂SCH₃ | (R) |
| 591 | CH₃(CH₂)₂NH— | —CH₂— | para phenyl | 1 | —C(CH₃)₂SCH₃ | (R) |
| 592 | NCCH₂NH— | —CH₂— | para phenyl | 1 | —C(CH₃)₂SCH₃ | (R) |
| 593 | 3-pyridylmethanamine | —CH₂— | para phenyl | 1 | —C(CH₃)₂SCH₃ | (R) |
| 594 | (2-chloro-4-pyridyl)methanamine | —CH₂— | para phenyl | 1 | —C(CH₃)₂SCH₃ | (R) |
| 595 | 2-pyridylmethanamine | —CH₂— | para phenyl | 1 | —C(CH₃)₂SCH₃ | (R) |
| 596 | furfurylamine | —CH₂— | para phenyl | 1 | —C(CH₃)₂SCH₃ | (R) |
| 597 | 2-thienylmethanamine | —CH₂— | para phenyl | 1 | —C(CH₃)₂SCH₃ | (R) |
| 598 | 4-methylbenzylamine | —CH₂— | para phenyl | 1 | —C(CH₃)₂SCH₃ | (R) |
| 599 | tetrahydrofurfurylamine | —CH₂— | para phenyl | 1 | —C(CH₃)₂SCH₃ | (R) |
| 600 | thiazol-2-ylmethanamine | —CH₂— | para phenyl | 1 | —C(CH₃)₂SCH₃ | (R) |
| 601 | cyclopropylamine | —CH₂— | para phenyl | 1 | —C(CH₃)₂SO₂CH₃ | (R) |
| 602 | CH₂CHCH₂NH— | —CH₂— | para phenyl | 1 | —C(CH₃)₂SO₂CH₃ | (R) |
| 603 | CH₃O(CH₂)₂NH— | —CH₂— | para phenyl | 1 | —C(CH₃)₂SO₂CH₃ | (R) |
| 604 | morpholine | —CH₂— | para phenyl | 1 | —C(CH₃)₂SO₂CH₃ | (R) |
| 605 | benzylamine | —CH₂— | para phenyl | 1 | —C(CH₃)₂SO₂CH₃ | (R) |
| 606 | 4-methoxybenzylamine | —CH₂— | para phenyl | 1 | —C(CH₃)₂SO₂CH₃ | (R) |
| 607 | 4-pyridylmethanamine | —CH₂— | para phenyl | 1 | —C(CH₃)₂SO₂CH₃ | (R) |
| 608 | pyrrolidine | —CH₂— | para phenyl | 1 | —C(CH₃)₂SO₂CH₃ | (R) |
| 609 | cyclobutylamine | —CH₂— | para phenyl | 1 | —C(CH₃)₂SO₂CH₃ | (R) |
| 610 | cyclopentylamine | —CH₂— | para phenyl | 1 | —C(CH₃)₂SO₂CH₃ | (R) |
| 611 | CH₃(CH₂)₂NH— | —CH₂— | para phenyl | 1 | —C(CH₃)₂SO₂CH₃ | (R) |
| 612 | NCCH₂NH— | —CH₂— | para phenyl | 1 | —C(CH₃)₂SO₂CH₃ | (R) |
| 613 | 3-pyridylmethanamine | —CH₂— | para phenyl | 1 | —C(CH₃)₂SO₂CH₃ | (R) |
| 614 | (2-chloro-4-pyridyl)methanamine | —CH₂— | para phenyl | 1 | —C(CH₃)₂SO₂CH₃ | (R) |
| 615 | 2-pyridylmethanamine | —CH₂— | para phenyl | 1 | —C(CH₃)₂SO₂CH₃ | (R) |
| 616 | furfurylamine | —CH₂— | para phenyl | 1 | —C(CH₃)₂SO₂CH₃ | (R) |
| 617 | 2-thienylmethanamine | —CH₂— | para phenyl | 1 | —C(CH₃)₂SO₂CH₃ | (R) |
| 618 | 4-methylbenzylamine | —CH₂— | para phenyl | 1 | —C(CH₃)₂SO₂CH₃ | (R) |
| 619 | tetrahydrofurfurylamine | —CH₂— | para phenyl | 1 | —C(CH₃)₂SO₂CH₃ | (R) |
| 620 | thiazol-2-ylmethanamine | —CH₂— | para phenyl | 1 | —C(CH₃)₂SO₂CH₃ | (R) |
| 621 | C₂H₅NH— | —CH₂— | para phenyl | 1 | —C(CH₃)₂NH₂ | |
| 622 | CH₂C(CH₃)CH₂NH— | —CH₂— | para phenyl | 1 | —C(CH₃)₂NH₂ | |
| 623 | CF₃CH₂NH— | —CH₂— | para phenyl | 1 | —C(CH₃)₂NH₂ | |
| 624 | 3-pyrroline | —CH₂— | para phenyl | 1 | —C(CH₃)₂NH₂ | |
| 625 | (1-cyanocyclopropyl)amine | —CH₂— | para phenyl | 1 | —C(CH₃)₂NH₂ | |
| 626 | HCCCH₂NH— | —CH₂— | para phenyl | 1 | —C(CH₃)₂NH₂ | |
| 627 | cyclopropylmethanamine | —CH₂— | para phenyl | 1 | —C(CH₃)₂NH₂ | |
| 628 | CH₃S(CH₂)₂NH— | —CH₂— | para phenyl | 1 | —C(CH₃)₂NH₂ | |
| 629 | (5-methyloxazol-2-yl)methanamine | —CH₂— | para phenyl | 1 | —C(CH₃)₂NH₂ | |
| 630 | 4-fluorobenzylamine | —CH₂— | para phenyl | 1 | —C(CH₃)₂NH₂ | |
| 631 | C₂H₅NH— | —CH₂— | thiophene | 1 | —C(CH₃)₂NH₂ | |
| 632 | CH₂C(CH₃)CH₂NH— | —CH₂— | thiophene | 1 | —C(CH₃)₂NH₂ | |
| 633 | HCCCH₂NH— | —CH₂— | thiophene | 1 | —C(CH₃)₂NH₂ | |
| 634 | cyclopropylmethanamine | —CH₂— | thiophene | 1 | —C(CH₃)₂NH₂ | |
| 635 | CH₃S(CH₂)₂NH— | —CH₂— | thiophene | 1 | —C(CH₃)₂NH₂ | |
| 636 | (5-methyloxazol-2-yl)methanamine | —CH₂— | thiophene | 1 | —C(CH₃)₂NH₂ | |
| 637 | 4-fluorobenzylamine | —CH₂— | thiophene | 1 | —C(CH₃)₂NH₂ | |
| 638 | CH₂C(CH₃)CH₂NH— | —CH₂— | pyridine | 1 | —C(CH₃)₂NH₂ | |
| 639 | CF₃CH₂NH— | —CH₂— | pyridine | 1 | —C(CH₃)₂NH₂ | |
| 640 | 3-pyrroline | —CH₂— | pyridine | 1 | —C(CH₃)₂NH₂ | |
| 641 | (1-cyanocyclopropyl)amine | —CH₂— | pyridine | 1 | —C(CH₃)₂NH₂ | |
| 642 | cyclopropylmethanamine | —CH₂— | pyridine | 1 | —C(CH₃)₂NH₂ | |
| 643 | CH₃S(CH₂)₂NH— | —CH₂— | pyridine | 1 | —C(CH₃)₂NH₂ | |
| 644 | (5-methyloxazol-2-yl)methanamine | —CH₂— | pyridine | 1 | —C(CH₃)₂NH₂ | |
| 645 | 4-fluorobenzylamine | —CH₂— | pyridine | 1 | —C(CH₃)₂NH₂ | |
| 646 | C₂H₅NH— | —CH₂— | pyridine | 1 | —C(CH₃)₂NH₂ | |
| 647 | HCCCH₂NH— | —CH₂— | pyridine | 1 | —C(CH₃)₂NH₂ | |
| 648 | CF₃CH₂NH— | —CH₂— | thiophene | 1 | —C(CH₃)₂NH₂ | |
| 649 | 3-pyrroline | —CH₂— | thiophene | 1 | —C(CH₃)₂NH₂ | |
| 650 | (1-cyanocyclopropyl)amine | —CH₂— | thiophene | 1 | —C(CH₃)₂NH₂ | |
| 651 | 4-pyridylmethanamine | —CH₂— | para phenyl | 1 | —C(CH₃)₂OH | (S) |
| 652 | benzylamine | —CH₂— | para phenyl | 1 | —C(CH₃)₂NO₂ | |
| 653 | 4-chlorobenzylamine | —CH₂— | para phenyl | 1 | —C(CH₃)₂NO₂ | |

TABLE A-continued

| C. No | A | L | M | n | R₁ | Ca |
|---|---|---|---|---|---|---|
| 654 | 4-pyridylmethanamine | —CH₂— | para phenyl | 1 | —C(CH₃)₂NO₂ | |
| 655 | 4-trifluoromethylbenzylamine | —CH₂— | para phenyl | 1 | —C(CH₃)₂NO₂ | |
| 656 | CH₂CHCH₂NH— | —CH₂— | para phenyl | 1 | —C(CH₃)₂NO₂ | |
| 657 | (CH₃)₂CHNH— | —CH₂— | para phenyl | 1 | —C(CH₃)₂NO₂ | |
| 658 | 2-pyridylmethanamine | —CH₂— | para phenyl | 1 | —C(CH₃)₂NO₂ | |
| 659 | 4-methylbenzylamine | —CH₂— | para phenyl | 1 | —C(CH₃)₂NO₂ | |
| 660 | 4-fluorobenzylamine | —CH₂— | para phenyl | 1 | —C(CH₃)₂NO₂ | |
| 661 | CH₃O(CH₂)₃NH— | —CH₂— | para phenyl | 1 | —C(CH₃)₂NO₂ | |
| 662 | 3-pyridylmethanamine | —CH₂— | para phenyl | 1 | —C(CH₃)₂NO₂ | |
| 663 | furfurylamine | —CH₂— | para phenyl | 1 | —C(CH₃)₂NO₂ | |
| 664 | CF₃CH₂NH— | —CH₂— | para phenyl | 1 | —C(CH₃)₂NO₂ | |
| 665 | 2-thienylmethanamine | —CH₂— | para phenyl | 1 | —C(CH₃)₂NO₂ | |
| 666 | cyclopropylamine | —CH₂— | thiophene | 1 | —C(CH₃)₂OH | (S) |
| 667 | CH₂CHCH₂NH— | —CH₂— | thiophene | 1 | —C(CH₃)₂OH | (S) |
| 668 | CH₃O(CH₂)₂NH— | —CH₂— | thiophene | 1 | —C(CH₃)₂OH | (S) |
| 669 | morpholine | —CH₂— | thiophene | 1 | —C(CH₃)₂OH | (S) |
| 670 | benzylamine | —CH₂— | thiophene | 1 | —C(CH₃)₂OH | (S) |
| 671 | 4-methoxybenzylamine | —CH₂— | thiophene | 1 | —C(CH₃)₂OH | (S) |
| 672 | 3-pyridylmethanamine | —CH₂— | thiophene | 1 | —C(CH₃)₂OH | (S) |
| 673 | 2-pyridylmethanamine | —CH₂— | thiophene | 1 | —C(CH₃)₂OH | (S) |
| 674 | furfurylamine | —CH₂— | thiophene | 1 | —C(CH₃)₂OH | (S) |
| 675 | (5-methyloxazol-2-yl)methanamine | —CH₂— | thiophene | 1 | —C(CH₃)₂OH | (S) |
| 676 | cyclopropylamine | —CH₂— | thiophene | 1 | —C(CH₃)₂SCH₃ | (R) |
| 677 | CH₂CHCH₂NH— | —CH₂— | thiophene | 1 | —C(CH₃)₂SCH₃ | (R) |
| 678 | CH₃O(CH₂)₂NH— | —CH₂— | thiophene | 1 | —C(CH₃)₂SCH₃ | (R) |
| 679 | morpholine | —CH₂— | thiophene | 1 | —C(CH₃)₂SCH₃ | (R) |
| 680 | benzylamine | —CH₂— | thiophene | 1 | —C(CH₃)₂SCH₃ | (R) |
| 681 | 4-methoxybenzylamine | —CH₂— | thiophene | 1 | —C(CH₃)₂SCH₃ | (R) |
| 682 | 3-pyridylmethanamine | —CH₂— | thiophene | 1 | —C(CH₃)₂SCH₃ | (R) |
| 683 | 2-pyridylmethanamine | —CH₂— | thiophene | 1 | —C(CH₃)₂SCH₃ | (R) |
| 684 | furfurylamine | —CH₂— | thiophene | 1 | —C(CH₃)₂SCH₃ | (R) |
| 685 | CF₃CH₂NH— | —CH₂— | thiophene | 1 | —C(CH₃)₂SCH₃ | (R) |
| 686 | (5-methyloxazol-2-yl)methanamine | —CH₂— | thiophene | 1 | —C(CH₃)₂SCH₃ | (R) |
| 687 | cyclopropylamine | —CH₂— | thiophene | 1 | —C(CH₃)₂SO₂CH₃ | (R) |
| 688 | CH₂CHCH₂NH— | —CH₂— | thiophene | 1 | —C(CH₃)₂SO₂CH₃ | (R) |
| 689 | CH₃O(CH₂)₂NH— | —CH₂— | thiophene | 1 | —C(CH₃)₂SO₂CH₃ | (R) |
| 690 | morpholine | —CH₂— | thiophene | 1 | —C(CH₃)₂SO₂CH₃ | (R) |
| 691 | benzylamine | —CH₂— | thiophene | 1 | —C(CH₃)₂SO₂CH₃ | (R) |
| 692 | 4-methoxybenzylamine | —CH₂— | thiophene | 1 | —C(CH₃)₂SO₂CH₃ | (R) |
| 693 | 4-pyridylmethanamine | —CH₂— | thiophene | 1 | —C(CH₃)₂SO₂CH₃ | (R) |
| 694 | NCCH₂NH— | —CH₂— | thiophene | 1 | —C(CH₃)₂SO₂CH₃ | (R) |
| 695 | 3-pyridylmethanamine | —CH₂— | thiophene | 1 | —C(CH₃)₂SO₂CH₃ | (R) |
| 696 | 2-pyridylmethanamine | —CH₂— | thiophene | 1 | —C(CH₃)₂SO₂CH₃ | (R) |
| 697 | furfurylamine | —CH₂— | thiophene | 1 | —C(CH₃)₂SO₂CH₃ | (R) |
| 698 | 2-pyrimidinylmethanamine | —CH₂— | thiophene | 1 | —C(CH₃)₂SO₂CH₃ | (R) |
| 699 | (5-methyloxazol-2-yl)methanamine | —CH₂— | thiophene | 1 | —C(CH₃)₂SO₂CH₃ | (R) |
| 700 | cyclopropylamine | —CH₂— | pyridine | 1 | —C(CH₃)₂OH | (S) |
| 701 | CH₃O(CH₂)₂NH— | —CH₂— | pyridine | 1 | —C(CH₃)₂OH | (S) |
| 702 | morpholine | —CH₂— | pyridine | 1 | —C(CH₃)₂OH | (S) |
| 703 | benzylamine | —CH₂— | pyridine | 1 | —C(CH₃)₂OH | (S) |
| 704 | 4-methoxybenzylamine | —CH₂— | pyridine | 1 | —C(CH₃)₂OH | (S) |
| 705 | 4-pyridylmethanamine | —CH₂— | pyridine | 1 | —C(CH₃)₂OH | (S) |
| 706 | 3-pyridylmethanamine | —CH₂— | pyridine | 1 | —C(CH₃)₂OH | (S) |
| 707 | 2-pyridylmethanamine | —CH₂— | pyridine | 1 | —C(CH₃)₂OH | (S) |
| 708 | furfurylamine | —CH₂— | pyridine | 1 | —C(CH₃)₂OH | (S) |
| 709 | CF₃CH₂NH— | —CH₂— | pyridine | 1 | —C(CH₃)₂OH | (S) |
| 710 | (5-methyloxazol-2-yl)methanamine | —CH₂— | pyridine | 1 | —C(CH₃)₂OH | (S) |
| 711 | cyclopropylamine | —CH₂— | pyridine | 1 | —C(CH₃)₂SCH₃ | (R) |
| 712 | CH₂CHCH₂NH— | —CH₂— | pyridine | 1 | —C(CH₃)₂SCH₃ | (R) |
| 713 | CH₃O(CH₂)₂NH— | —CH₂— | pyridine | 1 | —C(CH₃)₂SCH₃ | (R) |
| 714 | morpholine | —CH₂— | pyridine | 1 | —C(CH₃)₂SCH₃ | (R) |
| 715 | benzylamine | —CH₂— | pyridine | 1 | —C(CH₃)₂SCH₃ | (R) |
| 716 | 4-methoxybenzylamine | —CH₂— | pyridine | 1 | —C(CH₃)₂SCH₃ | (R) |
| 717 | 4-pyridylmethanamine | —CH₂— | pyridine | 1 | —C(CH₃)₂SCH₃ | (R) |
| 718 | NCCH₂NH— | —CH₂— | pyridine | 1 | —C(CH₃)₂SCH₃ | (R) |
| 719 | 2-pyridylmethanamine | —CH₂— | pyridine | 1 | —C(CH₃)₂SCH₃ | (R) |
| 720 | furfurylamine | —CH₂— | pyridine | 1 | —C(CH₃)₂SCH₃ | (R) |
| 721 | CF₃CH₂NH— | —CH₂— | pyridine | 1 | —C(CH₃)₂SCH₃ | (R) |
| 722 | 2-pyrimidinylmethanamine | —CH₂— | pyridine | 1 | —C(CH₃)₂SCH₃ | (R) |
| 723 | (5-methyloxazol-2-yl)methanamine | —CH₂— | pyridine | 1 | —C(CH₃)₂SCH₃ | (R) |
| 724 | cyclopropylamine | —CH₂— | pyridine | 1 | —C(CH₃)₂SO₂CH₃ | (R) |
| 725 | CH₃O(CH₂)₂NH— | —CH₂— | pyridine | 1 | —C(CH₃)₂SO₂CH₃ | (R) |
| 726 | morpholine | —CH₂— | pyridine | 1 | —C(CH₃)₂SO₂CH₃ | (R) |

TABLE A-continued

| C. No | A | L | M | n | R₁ | Ca |
|---|---|---|---|---|---|---|
| 727 | benzylamine | —CH₂— | pyridine | 1 | —C(CH₃)₂SO₂CH₃ | (R) |
| 728 | 4-methoxybenzylamine | —CH₂— | pyridine | 1 | —C(CH₃)₂SO₂CH₃ | (R) |
| 729 | 2-pyridylmethanamine | —CH₂— | pyridine | 1 | —C(CH₃)₂SO₂CH₃ | (R) |
| 730 | furfurylamine | —CH₂— | pyridine | 1 | —C(CH₃)₂SO₂CH₃ | (R) |
| 731 | CF₃CH₂NH— | —CH₂— | pyridine | 1 | —C(CH₃)₂SO₂CH₃ | (R) |
| 732 | 2-pyrimidinylmethanamine | —CH₂— | pyridine | 1 | —C(CH₃)₂SO₂CH₃ | (R) |
| 733 | (5-methyloxazol-2-yl)methanamine | —CH₂— | pyridine | 1 | —C(CH₃)₂SO₂CH₃ | (R) |
| 734 | NCCH₂NH— | —CH₂— | thiophene | 1 | —C(CH₃)₂OH | (S) |
| 735 | thiazol-2-ylmethanamine | —CH₂— | thiophene | 1 | —C(CH₃)₂OH | (S) |
| 736 | 2-pyrimidinylmethanamine | —CH₂— | thiophene | 1 | —C(CH₃)₂OH | (S) |
| 737 | CH₂CHCH₂NH— | —CH₂— | pyridine | 1 | —C(CH₃)₂OH | (S) |
| 738 | thiazol-2-ylmethanamine | —CH₂— | pyridine | 1 | —C(CH₃)₂OH | (S) |
| 739 | 2-pyrimidinylmethanamine | —CH₂— | pyridine | 1 | —C(CH₃)₂OH | (S) |
| 740 | 4-pyridylmethanamine | —CH₂— | thiophene | 1 | —C(CH₃)₂SCH₃ | (R) |
| 741 | thiazol-2-ylmethanamine | —CH₂— | thiophene | 1 | —C(CH₃)₂SCH₃ | (R) |
| 742 | 2-pyrimidinylmethanamine | —CH₂— | thiophene | 1 | —C(CH₃)₂SCH₃ | (R) |
| 743 | 3-pyridylmethanamine | —CH₂— | pyridine | 1 | —C(CH₃)₂SCH₃ | (R) |
| 744 | thiazol-2-ylmethanamine | —CH₂— | pyridine | 1 | —C(CH₃)₂SCH₃ | (R) |
| 745 | thiazol-2-ylmethanamine | —CH₂— | thiophene | 1 | —C(CH₃)₂SO₂CH₃ | (R) |
| 746 | CH₂CHCH₂NH— | —CH₂— | pyridine | 1 | —C(CH₃)₂SO₂CH₃ | (R) |
| 747 | 4-pyridylmethanamine | —CH₂— | pyridine | 1 | —C(CH₃)₂SO₂CH₃ | (R) |
| 748 | NCCH₂NH— | —CH₂— | pyridine | 1 | —C(CH₃)₂SO₂CH₃ | (R) |
| 749 | 3-pyridylmethanamine | —CH₂— | pyridine | 1 | —C(CH₃)₂SO₂CH₃ | (R) |
| 750 | thiazol-2-ylmethanamine | —CH₂— | pyridine | 1 | —C(CH₃)₂SO₂CH₃ | (R) |
| 751 | cyclopropylamine | —CH₂— | para phenyl | 1 | C=N—OCH₃ | (S) |
| 752 | CH2CHCH2NH— | —CH₂— | para phenyl | 1 | C=N—OCH₃ | (S) |
| 753 | CH3O(CH2)2NH— | —CH₂— | para phenyl | 1 | C=N—OCH₃ | (S) |
| 754 | morpholine | —CH₂— | para phenyl | 1 | C=N—OCH₃ | (S) |
| 755 | benzylamine | —CH₂— | para phenyl | 1 | C=N—OCH₃ | (S) |
| 756 | 4-methoxybenzylamine | —CH₂— | para phenyl | 1 | C=N—OCH₃ | (S) |
| 757 | pyrrolidine | —CH₂— | para phenyl | 1 | C=N—OCH₃ | (S) |
| 758 | cyclobutylamine | —CH₂— | para phenyl | 1 | C=N—OCH₃ | (S) |
| 759 | cyclopentylamine | —CH₂— | para phenyl | 1 | C=N—OCH₃ | (S) |
| 760 | CH3(CH2)2NH— | —CH₂— | para phenyl | 1 | C=N—OCH₃ | (S) |
| 761 | 3-pyridylmethanamine | —CH₂— | para phenyl | 1 | C=N—OCH₃ | (S) |
| 762 | (2-chloro-4-pyridyl)methanamine | —CH₂— | para phenyl | 1 | C=N—OCH₃ | (S) |
| 763 | 2-pyridylmethanamine | —CH₂— | para phenyl | 1 | C=N—OCH₃ | (S) |
| 764 | furfurylamine | —CH₂— | para phenyl | 1 | C=N—OCH₃ | (S) |
| 765 | 2-thienylmethanamine | —CH₂— | para phenyl | 1 | C=N—OCH₃ | (S) |
| 766 | 4-methylbenzylamine | —CH₂— | para phenyl | 1 | C=N—OCH₃ | (S) |
| 767 | tetrahydrofurfurylamine | —CH₂— | para phenyl | 1 | C=N—OCH₃ | (S) |
| 768 | thiazol-2-ylmethanamine | —CH₂— | para phenyl | 1 | C=N—OCH₃ | (S) |
| 769 | cyclopropylamine | —CH₂— | para phenyl | 1 | —COCH₃ | (S) |
| 770 | CH2CHCH2NH— | —CH₂— | para phenyl | 1 | —COCH₃ | (S) |
| 771 | CH3O(CH2)2NH— | —CH₂— | para phenyl | 1 | —COCH₃ | (S) |
| 772 | morpholine | —CH₂— | para phenyl | 1 | —COCH₃ | (S) |
| 773 | benzylamine | —CH₂— | para phenyl | 1 | —COCH₃ | (S) |
| 774 | 4-methoxybenzylamine | —CH₂— | para phenyl | 1 | —COCH₃ | (S) |
| 775 | 4-pyridylmethanamine | —CH₂— | para phenyl | 1 | —COCH₃ | (S) |
| 776 | pyrrolidine | —CH₂— | para phenyl | 1 | —COCH₃ | (S) |
| 777 | cyclobutylamine | —CH₂— | para phenyl | 1 | —COCH₃ | (S) |
| 778 | cyclopentylamine | —CH₂— | para phenyl | 1 | —COCH₃ | (S) |
| 779 | CH₃(CH₂)₂NH— | —CH₂— | para phenyl | 1 | —COCH₃ | (S) |
| 780 | 3-pyridylmethanamine | —CH₂— | para phenyl | 1 | —COCH₃ | (S) |
| 781 | (2-chloro-4-pyridyl)methanamine | —CH₂— | para phenyl | 1 | —COCH₃ | (S) |
| 782 | 2-pyridylmethanamine | —CH₂— | para phenyl | 1 | —COCH₃ | (S) |
| 783 | furfurylamine | —CH₂— | para phenyl | 1 | —COCH₃ | (S) |
| 784 | 2-thienylmethanamine | —CH₂— | para phenyl | 1 | —COCH₃ | (S) |
| 785 | 4-methylbenzylamine | —CH₂— | para phenyl | 1 | —COCH₃ | (S) |
| 786 | tetrahydrofurfurylamine | —CH₂— | para phenyl | 1 | —COCH₃ | (S) |
| 787 | thiazol-2-ylmethanamine | —CH₂— | para phenyl | 1 | —COCH₃ | (S) |
| 788 | 4-pyridylmethanamine | —CH₂— | para phenyl | 1 | C=N—OCH₃ | (S) |

Table B provides for each of the exemplified compounds of Table A the calculated molecular weight (MW), the observed mass signal (m/z), the HPLC retention time (Rt) in minutes and the number of the HPLC method as described above ("HPLC methods").

TABLE B

| C. No | HPLC RT | m/z | MW | HPLC method |
|---|---|---|---|---|
| 1 | 2.10 | 438.1 | 437.5 | 5 |
| 2 | 2.39 | 458.2 | 457.5 | 5 |
| 3 | 0.56 | 437.2 | 436.5 | 4 |
| 4 | 2.19 | 451.1 | 450.5 | 5 |
| 5 | 2.30 | 422.1 | 421.5 | 5 |
| 6 | 2.36 | 436.1 | 435.5 | 5 |
| 7 | 2.22 | 410.2 | 409.5 | 5 |
| 8 | 2.22 | 408.1 | 407.5 | 5 |
| 9 | 2.41 | 438.3 | 437.5 | 5 |
| 10 | 2.18 | 426.2 | 425.5 | 5 |
| 11 | 2.03 | 439.2 | 438.5 | 5 |
| 12 | 2.10 | 426.1 | 425.4 | 5 |
| 13 | 2.23 | 424.2 | 423.5 | 5 |
| 14 | 2.15 | 438.1 | 437.5 | 5 |
| 15 | 2.25 | 486.0 | 485.6 | 5 |
| 16 | 2.69 | 493.3 | 491.6 | 5 |
| 17 | 2.63 | 512.2 | 511.6 | 5 |
| 18 | 2.56 | 513.2 | 512.6 | 5 |
| 19 | 2.09 | 514.2 | 513.6 | 5 |
| 20 | 2.48 | 484.3 | 483.6 | 5 |
| 21 | 2.41 | 544.2 | 543.6 | 5 |
| 22 | 2.43 | 458.2 | 457.5 | 5 |
| 23 | 2.45 | 472.1 | 471.6 | 5 |
| 24 | 2.56 | 492.1 | 492.0 | 5 |
| 25 | 2.47 | 488.1 | 487.6 | 5 |
| 26 | 2.16 | 501.2 | 500.6 | 5 |
| 27 | 2.65 | 526.2 | 525.5 | 5 |
| 28 | 2.03 | 459.1 | 458.5 | 5 |
| 29 | 2.62 | 486.3 | 485.6 | 5 |
| 30 | 2.15 | 394.1 | 393.4 | 5 |
| 31 | 2.17 | 396.2 | 395.5 | 5 |
| 32 | 2.17 | 394.1 | 393.4 | 5 |
| 33 | 2.37 | 424.2 | 423.5 | 5 |
| 34 | 2.14 | 412.3 | 411.5 | 5 |
| 35 | 1.99 | 425.2 | 424.5 | 5 |
| 36 | 2.04 | 412.0 | 411.4 | 5 |
| 37 | 2.18 | 410.2 | 409.5 | 5 |
| 38 | 2.10 | 424.2 | 423.5 | 5 |
| 39 | 2.63 | 478.3 | 477.6 | 5 |
| 40 | 2.60 | 498.2 | 497.6 | 5 |
| 41 | 2.53 | 499.3 | 498.6 | 5 |
| 42 | 2.04 | 500.3 | 499.6 | 5 |
| 43 | 2.42 | 470.2 | 469.5 | 5 |
| 44 | 2.37 | 530.2 | 529.6 | 5 |
| 45 | 2.39 | 444.1 | 443.5 | 5 |
| 46 | 2.42 | 458.2 | 457.5 | 5 |
| 47 | 2.52 | 478.2 | 477.9 | 5 |
| 48 | 2.43 | 474.1 | 473.5 | 5 |
| 49 | 2.12 | 487.2 | 486.6 | 5 |
| 50 | 2.62 | 512.2 | 511.5 | 5 |
| 51 | 1.99 | 445.2 | 444.5 | 5 |
| 52 | 2.58 | 472.2 | 471.6 | 5 |
| 53 | 2.41 | 406.2 | 405.5 | 5 |
| 54 | 2.43 | 408.3 | 407.5 | 5 |
| 55 | 2.43 | 407.2 | 405.5 | 5 |
| 56 | 2.60 | 436.3 | 435.6 | 5 |
| 57 | 2.40 | 424.3 | 423.5 | 5 |
| 58 | 2.21 | 437.2 | 436.6 | 5 |
| 59 | 2.31 | 424.2 | 423.5 | 5 |
| 60 | 2.44 | 422.3 | 421.5 | 5 |
| 61 | 2.36 | 436.3 | 435.5 | 5 |
| 62 | 2.47 | 484.1 | 483.6 | 5 |
| 63 | 2.84 | 490.4 | 489.7 | 5 |
| 64 | 2.81 | 510.2 | 509.6 | 5 |
| 65 | 2.72 | 511.3 | 510.6 | 5 |
| 66 | 2.27 | 512.3 | 511.6 | 5 |
| 67 | 2.65 | 482.2 | 481.6 | 5 |
| 68 | 2.60 | 542.2 | 541.6 | 5 |
| 69 | 2.61 | 456.3 | 455.6 | 5 |
| 70 | 2.65 | 470.2 | 469.6 | 5 |
| 71 | 2.74 | 490.1 | 490.0 | 5 |
| 72 | 2.66 | 486.2 | 485.6 | 5 |
| 73 | 2.34 | 499.2 | 498.6 | 5 |
| 74 | 2.81 | 524.3 | 523.6 | 5 |
| 75 | 2.22 | 457.2 | 456.5 | 5 |
| 76 | 2.79 | 484.3 | 483.6 | 5 |
| 77 | 2.53 | 422.3 | 421.5 | 5 |
| 78 | 2.53 | 420.2 | 419.5 | 5 |
| 79 | 2.70 | 450.3 | 449.6 | 5 |
| 80 | 2.50 | 438.3 | 437.5 | 5 |
| 81 | 2.31 | 451.2 | 450.6 | 5 |
| 82 | 2.42 | 438.2 | 437.5 | 5 |
| 83 | 2.56 | 436.2 | 435.6 | 5 |
| 84 | 2.48 | 450.2 | 449.5 | 5 |
| 85 | 2.58 | 498.1 | 497.6 | 5 |
| 86 | 2.94 | 504.4 | 503.7 | 5 |
| 87 | 2.88 | 524.4 | 523.7 | 5 |
| 88 | 2.83 | 525.3 | 524.7 | 5 |
| 89 | 2.38 | 526.3 | 525.6 | 5 |
| 90 | 2.75 | 496.3 | 495.6 | 5 |
| 91 | 2.69 | 556.2 | 555.7 | 5 |
| 92 | 2.71 | 470.3 | 469.6 | 5 |
| 93 | 2.74 | 484.3 | 483.6 | 5 |
| 94 | 2.82 | 504.2 | 504.0 | 5 |
| 95 | 2.74 | 500.3 | 499.6 | 5 |
| 96 | 2.44 | 513.2 | 512.7 | 5 |
| 97 | 2.89 | 538.2 | 537.6 | 5 |
| 98 | 2.32 | 471.2 | 470.6 | 5 |
| 99 | 2.88 | 499.3 | 497.6 | 5 |
| 100 | 2.22 | 408.1 | 407.5 | 5 |
| 101 | 1.93 | 372.2 | 371.4 | 5 |
| 102 | 2.00 | 386.2 | 385.5 | 5 |
| 103 | 2.15 | 408.1 | 407.5 | 5 |
| 104 | 2.18 | 410.2 | 409.5 | 5 |
| 105 | 2.17 | 408.2 | 407.5 | 5 |
| 106 | 2.35 | 438.3 | 437.5 | 5 |
| 107 | 1.97 | 439.2 | 438.5 | 5 |
| 108 | 2.04 | 426.1 | 425.4 | 5 |
| 109 | 2.18 | 424.3 | 423.5 | 5 |
| 110 | 2.18 | 486.1 | 485.6 | 5 |
| 111 | 2.66 | 492.2 | 491.6 | 5 |
| 112 | 2.62 | 512.2 | 511.6 | 5 |
| 113 | 2.53 | 513.2 | 512.6 | 5 |
| 114 | 2.03 | 514.4 | 513.6 | 5 |
| 115 | 2.44 | 484.3 | 483.6 | 5 |
| 116 | 2.38 | 544.2 | 543.6 | 5 |
| 117 | 2.43 | 472.2 | 471.6 | 5 |
| 118 | 2.54 | 492.1 | 492.0 | 5 |
| 119 | 2.44 | 488.2 | 487.6 | 5 |
| 120 | 2.64 | 526.1 | 525.5 | 5 |
| 121 | 1.98 | 459.2 | 458.5 | 5 |
| 122 | 2.12 | 501.2 | 500.6 | 5 |
| 123 | 2.10 | 394.2 | 393.4 | 5 |
| 124 | 2.13 | 396.2 | 395.5 | 5 |
| 125 | 2.13 | 394.1 | 393.4 | 5 |
| 126 | 2.08 | 412.2 | 411.5 | 5 |
| 127 | 1.93 | 425.2 | 424.5 | 5 |
| 128 | 2.13 | 410.2 | 409.5 | 5 |
| 129 | 2.04 | 424.2 | 423.5 | 5 |
| 130 | 2.13 | 472.1 | 471.5 | 5 |
| 131 | 2.62 | 478.2 | 477.6 | 5 |
| 132 | 2.57 | 498.2 | 497.6 | 5 |
| 133 | 2.50 | 499.7 | 498.6 | 5 |
| 134 | 1.98 | 500.2 | 499.6 | 5 |
| 135 | 2.40 | 470.2 | 469.5 | 5 |
| 136 | 2.34 | 530.2 | 529.6 | 5 |
| 137 | 2.36 | 444.1 | 443.5 | 5 |
| 138 | 2.39 | 458.2 | 457.5 | 5 |
| 139 | 2.51 | 478.1 | 477.9 | 5 |
| 140 | 2.41 | 474.1 | 473.5 | 5 |
| 141 | 2.61 | 512.2 | 511.5 | 5 |
| 142 | 1.93 | 445.1 | 444.5 | 5 |
| 143 | 2.57 | 472.3 | 471.6 | 5 |
| 144 | 2.37 | 406.1 | 405.5 | 5 |
| 145 | 2.40 | 408.1 | 407.5 | 5 |
| 146 | 2.40 | 406.1 | 405.5 | 5 |
| 147 | 2.57 | 436.1 | 435.6 | 5 |
| 148 | 2.35 | 424.1 | 423.5 | 5 |
| 149 | 2.41 | 422.1 | 421.5 | 5 |

TABLE B-continued

| C. No | HPLC RT | m/z | MW | HPLC method |
|---|---|---|---|---|
| 150 | 2.32 | 436.2 | 435.5 | 5 |
| 151 | 2.41 | 484.1 | 483.6 | 5 |
| 152 | 2.77 | 510.2 | 509.6 | 5 |
| 153 | 2.23 | 512.2 | 511.6 | 5 |
| 154 | 2.61 | 482.2 | 481.6 | 5 |
| 155 | 2.57 | 542.2 | 541.6 | 5 |
| 156 | 2.59 | 456.2 | 455.6 | 5 |
| 157 | 2.63 | 470.2 | 469.6 | 5 |
| 158 | 2.72 | 490.1 | 490.0 | 5 |
| 159 | 2.63 | 486.1 | 485.6 | 5 |
| 160 | 2.31 | 499.2 | 498.6 | 5 |
| 161 | 2.79 | 524.3 | 523.6 | 5 |
| 162 | 2.18 | 457.1 | 456.5 | 5 |
| 163 | 2.80 | 484.2 | 483.6 | 5 |
| 164 | 2.48 | 420.2 | 419.5 | 5 |
| 165 | 2.49 | 420.2 | 419.5 | 5 |
| 166 | 2.66 | 450.3 | 449.6 | 5 |
| 167 | 2.46 | 438.2 | 437.5 | 5 |
| 168 | 2.27 | 451.2 | 450.6 | 5 |
| 169 | 2.37 | 438.1 | 437.5 | 5 |
| 170 | 2.51 | 436.3 | 435.6 | 5 |
| 171 | 2.43 | 450.3 | 449.5 | 5 |
| 172 | 2.91 | 504.4 | 503.7 | 5 |
| 173 | 2.85 | 524.3 | 523.7 | 5 |
| 174 | 2.82 | 525.4 | 524.7 | 5 |
| 175 | 2.33 | 526.3 | 525.6 | 5 |
| 176 | 2.71 | 496.2 | 495.6 | 5 |
| 177 | 2.66 | 556.2 | 555.7 | 5 |
| 178 | 2.66 | 470.2 | 469.6 | 5 |
| 179 | 2.71 | 484.3 | 483.6 | 5 |
| 180 | 2.80 | 504.1 | 504.0 | 5 |
| 181 | 2.71 | 500.2 | 499.6 | 5 |
| 182 | 2.39 | 513.2 | 512.7 | 5 |
| 183 | 2.88 | 538.3 | 537.6 | 5 |
| 184 | 2.29 | 471.2 | 470.6 | 5 |
| 185 | 2.87 | 498.2 | 497.6 | 5 |
| 186 | 2.08 | 487.2 | 486.6 | 5 |
| 187 | 2.72 | 511.2 | 510.6 | 5 |
| 188 | 2.61 | 486.2 | 485.6 | 5 |
| 189 | 2.15 | 432.2 | 431.5 | 5 |
| 190 | 2.01 | 445.2 | 444.6 | 5 |
| 191 | 2.02 | 432.1 | 431.5 | 5 |
| 192 | 2.12 | 444.2 | 443.5 | 5 |
| 193 | 2.56 | 519.2 | 518.6 | 5 |
| 194 | 2.46 | 490.2 | 489.6 | 5 |
| 195 | 2.39 | 464.1 | 463.6 | 5 |
| 196 | 2.45 | 478.2 | 477.6 | 5 |
| 197 | 2.18 | 428.2 | 427.5 | 5 |
| 198 | 2.04 | 443.1 | 442.5 | 5 |
| 199 | 2.10 | 457.2 | 456.6 | 5 |
| 200 | 2.12 | 416.2 | 415.4 | 5 |
| 201 | 1.98 | 429.2 | 428.5 | 5 |
| 202 | 2.06 | 428.1 | 427.5 | 5 |
| 203 | 2.41 | 474.2 | 473.5 | 5 |
| 204 | 2.37 | 448.1 | 447.5 | 5 |
| 205 | 2.40 | 462.2 | 461.5 | 5 |
| 206 | 2.41 | 478.1 | 477.5 | 5 |
| 207 | 2.15 | 412.2 | 411.5 | 5 |
| 208 | 2.00 | 433.2 | 432.5 | 5 |
| 209 | 1.90 | 446.2 | 445.5 | 5 |
| 210 | 1.91 | 433.1 | 432.5 | 5 |
| 211 | 1.97 | 445.1 | 444.5 | 5 |
| 212 | 2.43 | 520.2 | 519.6 | 5 |
| 213 | 2.30 | 491.2 | 490.6 | 5 |
| 214 | 2.27 | 465.1 | 464.5 | 5 |
| 215 | 2.29 | 479.2 | 478.6 | 5 |
| 216 | 2.31 | 495.2 | 494.6 | 5 |
| 217 | 2.01 | 429.1 | 428.5 | 5 |
| 218 | 1.96 | 444.1 | 443.5 | 5 |
| 219 | 2.00 | 458.1 | 457.6 | 5 |
| 220 | 2.06 | 427.2 | 426.5 | 5 |
| 221 | 1.96 | 427.1 | 426.4 | 5 |
| 222 | 2.02 | 439.2 | 438.5 | 5 |
| 223 | 2.48 | 514.3 | 513.6 | 5 |
| 224 | 2.38 | 485.2 | 484.6 | 5 |
| 225 | 2.34 | 459.2 | 458.5 | 5 |
| 226 | 2.37 | 473.3 | 472.5 | 5 |
| 227 | 2.39 | 489.2 | 488.5 | 5 |
| 228 | 2.09 | 423.3 | 422.5 | 5 |
| 229 | 1.92 | 438.2 | 437.5 | 5 |
| 230 | 1.93 | 452.2 | 451.5 | 5 |
| 231 | 2.14 | 426.1 | 425.5 | 5 |
| 232 | 2.32 | 424.2 | 423.5 | 5 |
| 233 | 1.94 | 412.1 | 411.4 | 5 |
| 234 | 2.20 | 438.2 | 436.6 | 5 |
| 235 | 2.26 | 424.1 | 423.5 | 5 |
| 236 | 2.84 | 490.3 | 489.7 | 5 |
| 237 | 2.50 | 422.2 | 421.5 | 5 |
| 238 | 2.57 | 498.2 | 497.6 | 5 |
| 239 | 2.21 | 472.1 | 471.5 | 5 |
| 240 | 2.51 | 420.2 | 419.5 | 5 |
| 241 | 1.93 | 440.2 | 439.5 | 5 |
| 242 | 1.44 | 370.1 | 369.3 | 1 |
| 243 | 1.47 | 384.0 | 383.4 | 1 |
| 244 | 1.39 | 340.0 | 339.3 | 2 |
| 245 | 1.43 | 354.0 | 353.4 | 2 |
| 246 | 1.86 | 382.1 | 381.4 | 1 |
| 247 | 2.37 | 422.1 | 421.5 | 5 |
| 248 | 2.44 | 436.1 | 435.5 | 5 |
| 249 | 2.54 | 450.1 | 449.5 | 5 |
| 250 | 2.27 | 396.0 | 395.5 | 5 |
| 251 | 2.35 | 410.0 | 409.5 | 5 |
| 252 | 2.33 | 440.1 | 439.5 | 5 |
| 253 | 2.31 | 440.0 | 439.5 | 5 |
| 254 | 2.27 | 452.1 | 451.5 | 5 |
| 255 | 2.39 | 466.1 | 465.6 | 5 |
| 256 | 2.16 | 459.1 | 458.5 | 5 |
| 257 | 2.41 | 493.0 | 493.0 | 5 |
| 258 | 2.37 | 459.0 | 458.5 | 5 |
| 259 | 2.41 | 448.0 | 447.5 | 5 |
| 260 | 2.48 | 464.0 | 463.6 | 5 |
| 261 | 2.63 | 472.1 | 471.6 | 5 |
| 262 | 2.36 | 452.1 | 451.5 | 5 |
| 263 | 2.13 | 448.1 | 447.5 | 5 |
| 264 | 2.35 | 440.1 | 439.5 | 5 |
| 265 | 2.25 | 408.0 | 407.5 | 5 |
| 266 | 2.14 | 437.1 | 436.5 | 5 |
| 267 | 2.33 | 408.0 | 407.5 | 5 |
| 268 | 2.41 | 422.1 | 421.5 | 5 |
| 269 | 2.51 | 436.1 | 435.5 | 5 |
| 270 | 2.16 | 368.1 | 367.4 | 5 |
| 271 | 2.21 | 382.0 | 381.4 | 5 |
| 272 | 2.30 | 396.0 | 395.5 | 5 |
| 273 | 2.29 | 426.0 | 425.5 | 5 |
| 274 | 2.26 | 426.1 | 425.5 | 5 |
| 275 | 2.35 | 452.1 | 451.5 | 5 |
| 276 | 2.31 | 422.1 | 421.5 | 5 |
| 277 | 2.11 | 445.0 | 444.5 | 5 |
| 278 | 2.32 | 445.0 | 444.5 | 5 |
| 279 | 2.35 | 434.0 | 433.5 | 5 |
| 280 | 2.43 | 450.0 | 449.5 | 5 |
| 281 | 2.61 | 458.0 | 457.5 | 5 |
| 282 | 2.31 | 438.1 | 437.5 | 5 |
| 283 | 2.08 | 434.0 | 433.5 | 5 |
| 284 | 2.30 | 426.1 | 425.5 | 5 |
| 285 | 2.60 | 464.1 | 463.6 | 5 |
| 286 | 2.58 | 434.1 | 433.5 | 5 |
| 287 | 2.36 | 457.1 | 456.5 | 5 |
| 288 | 2.61 | 491.1 | 491.0 | 5 |
| 289 | 2.58 | 457.1 | 456.5 | 5 |
| 290 | 2.61 | 446.1 | 445.5 | 5 |
| 291 | 2.66 | 462.0 | 461.6 | 5 |
| 292 | 2.80 | 470.1 | 469.6 | 5 |
| 293 | 2.33 | 446.0 | 445.5 | 5 |
| 294 | 2.63 | 434.1 | 433.5 | 5 |
| 295 | 2.50 | 463.1 | 462.6 | 5 |
| 296 | 2.59 | 408.1 | 407.5 | 5 |
| 297 | 2.65 | 452.1 | 451.6 | 5 |
| 298 | 2.64 | 452.1 | 451.6 | 5 |
| 299 | 2.47 | 471.1 | 470.6 | 5 |
| 300 | 2.67 | 471.1 | 470.6 | 5 |
| 301 | 2.69 | 460.1 | 459.5 | 5 |
| 302 | 2.76 | 476.0 | 475.6 | 5 |
| 303 | 2.66 | 464.0 | 463.6 | 5 |
| 304 | 2.43 | 460.0 | 459.6 | 5 |
| 305 | 2.66 | 452.1 | 451.6 | 5 |

TABLE B-continued

| C. No | HPLC RT | m/z | MW | HPLC method |
|---|---|---|---|---|
| 306 | 2.38 | 494.2 | 493.6 | 5 |
| 307 | 2.00 | 416.1 | 415.4 | 5 |
| 308 | 2.47 | 503.2 | 502.6 | 5 |
| 309 | 1.96 | 427.2 | 426.5 | 5 |
| 310 | 2.01 | 441.2 | 440.5 | 5 |
| 311 | 2.60 | 464.1 | 463.6 | 5 |
| 312 | 2.68 | 448.1 | 447.6 | 5 |
| 313 | 2.19 | 506.1 | 506.0 | 5 |
| 314 | 2.18 | 449.2 | 448.6 | 5 |
| 315 | 2.10 | 465.2 | 464.6 | 5 |
| 316 | 2.17 | 453.2 | 452.5 | 5 |
| 317 | 2.23 | 453.2 | 452.5 | 5 |
| 318 | 2.14 | 395.2 | 394.5 | 5 |
| 319 | 2.20 | 435.2 | 434.5 | 5 |
| 320 | 2.10 | 472.2 | 471.6 | 5 |
| 321 | 2.49 | 471.2 | 470.6 | 5 |
| 322 | 2.59 | 526.3 | 525.6 | 5 |
| 323 | 2.71 | 525.3 | 524.7 | 5 |
| 324 | 2.12 | 499.2 | 498.6 | 5 |
| 325 | 2.10 | 451.2 | 450.5 | 5 |
| 326 | 2.13 | 439.2 | 438.5 | 5 |
| 327 | 2.20 | 421.2 | 420.5 | 5 |
| 328 | 2.21 | 423.2 | 422.5 | 5 |
| 329 | 2.17 | 421.2 | 420.5 | 5 |
| 330 | 2.49 | 477.2 | 476.6 | 5 |
| 331 | 2.78 | 484.2 | 483.6 | 5 |
| 332 | 2.57 | 505.2 | 505.0 | 5 |
| 333 | 2.56 | 478.2 | 477.6 | 5 |
| 334 | 2.46 | 419.2 | 418.5 | 5 |
| 335 | 2.51 | 422.2 | 421.5 | 5 |
| 336 | 2.40 | 394.2 | 393.5 | 5 |
| 337 | 2.67 | 462.2 | 461.6 | 5 |
| 338 | 2.60 | 448.2 | 447.6 | 5 |
| 339 | 2.53 | 434.2 | 433.5 | 5 |
| 340 | 2.41 | 438.2 | 437.5 | 5 |
| 341 | 2.38 | 463.1 | 462.6 | 5 |
| 342 | 2.40 | 450.2 | 449.5 | 5 |
| 343 | 2.32 | 394.2 | 393.5 | 5 |
| 344 | 2.34 | 450.2 | 449.5 | 5 |
| 345 | 2.37 | 438.2 | 437.5 | 5 |
| 346 | 2.35 | 405.2 | 404.5 | 5 |
| 347 | 2.40 | 438.2 | 437.5 | 5 |
| 348 | 2.42 | 408.2 | 407.5 | 5 |
| 349 | 2.28 | 380.2 | 379.5 | 5 |
| 350 | 2.59 | 448.2 | 447.6 | 5 |
| 351 | 2.49 | 434.2 | 433.5 | 5 |
| 352 | 2.41 | 420.2 | 419.5 | 5 |
| 353 | 2.19 | 449.2 | 448.6 | 5 |
| 354 | 2.37 | 420.2 | 419.5 | 5 |
| 355 | 2.13 | 451.1 | 450.5 | 5 |
| 356 | 2.22 | 479.1 | 478.9 | 5 |
| 357 | 2.06 | 438.2 | 437.5 | 5 |
| 358 | 2.06 | 393.1 | 392.4 | 5 |
| 359 | 2.17 | 465.1 | 464.5 | 5 |
| 360 | 2.10 | 407.1 | 406.4 | 5 |
| 361 | 2.05 | 382.1 | 381.4 | 5 |
| 362 | 2.68 | 453.2 | 452.5 | 5 |
| 363 | 2.61 | 465.2 | 464.6 | 5 |
| 364 | 2.15 | 472.2 | 471.6 | 5 |
| 365 | 1.32 | 386.0 | 385.5 | 2 |
| 366 | 1.32 | 426.0 | 425.5 | 2 |
| 367 | 1.87 | 388.2 | 387.4 | 5 |
| 368 | 1.93 | 358.2 | 357.4 | 5 |
| 369 | 1.95 | 358.2 | 357.4 | 5 |
| 370 | 2.45 | 462.2 | 461.6 | 5 |
| 371 | 2.37 | 463.2 | 462.5 | 5 |
| 372 | 2.26 | 434.2 | 433.5 | 5 |
| 373 | 1.79 | 409.2 | 408.5 | 5 |
| 374 | 1.97 | 390.2 | 389.4 | 5 |
| 375 | 1.91 | 402.2 | 401.5 | 5 |
| 376 | 1.79 | 409.2 | 408.5 | 5 |
| 377 | 1.99 | 409.2 | 408.5 | 5 |
| 378 | 2.14 | 414.2 | 413.5 | 5 |
| 379 | 2.35 | 422.2 | 421.5 | 5 |
| 380 | 1.99 | 402.2 | 401.5 | 5 |
| 381 | 1.98 | 407.2 | 406.5 | 5 |
| 382 | 2.00 | 409.2 | 408.5 | 5 |
| 383 | 1.96 | 425.2 | 424.5 | 5 |
| 384 | 1.93 | 437.2 | 436.5 | 5 |
| 385 | 2.03 | 485.2 | 484.6 | 5 |
| 386 | 2.42 | 511.2 | 510.6 | 5 |
| 387 | 2.35 | 512.3 | 511.6 | 5 |
| 388 | 2.22 | 457.2 | 456.5 | 5 |
| 389 | 1.84 | 458.2 | 457.5 | 5 |
| 390 | 1.98 | 421.2 | 420.5 | 5 |
| 391 | 2.01 | 439.2 | 438.5 | 5 |
| 392 | 1.98 | 439.2 | 438.5 | 5 |
| 393 | 2.03 | 435.2 | 434.5 | 5 |
| 394 | 1.84 | 458.2 | 457.5 | 5 |
| 395 | 2.10 | 492.2 | 492.0 | 5 |
| 396 | 2.03 | 451.2 | 450.5 | 5 |
| 397 | 2.03 | 439.2 | 438.5 | 5 |
| 398 | 2.08 | 414.1 | 413.5 | 5 |
| 399 | 2.11 | 416.2 | 415.5 | 5 |
| 400 | 2.10 | 414.1 | 413.5 | 5 |
| 401 | 1.92 | 465.1 | 464.5 | 5 |
| 402 | 2.16 | 428.2 | 427.5 | 5 |
| 403 | 2.24 | 442.2 | 441.5 | 5 |
| 404 | 2.14 | 416.2 | 415.5 | 5 |
| 405 | 2.12 | 446.2 | 445.5 | 5 |
| 406 | 2.14 | 413.1 | 412.5 | 5 |
| 407 | 1.93 | 465.2 | 464.5 | 5 |
| 408 | 2.15 | 465.1 | 464.5 | 5 |
| 409 | 2.20 | 454.2 | 453.5 | 5 |
| 410 | 2.27 | 470.1 | 469.6 | 5 |
| 411 | 2.45 | 478.2 | 477.6 | 5 |
| 412 | 2.14 | 458.2 | 457.5 | 5 |
| 413 | 1.99 | 409.3 | 408.5 | 5 |
| 414 | 2.01 | 411.2 | 410.5 | 5 |
| 415 | 2.02 | 409.2 | 408.5 | 5 |
| 416 | 1.85 | 460.2 | 459.5 | 5 |
| 417 | 2.06 | 423.2 | 422.5 | 5 |
| 418 | 2.14 | 437.3 | 436.5 | 5 |
| 419 | 2.05 | 411.3 | 410.5 | 5 |
| 420 | 2.04 | 441.3 | 440.5 | 5 |
| 421 | 1.96 | 408.2 | 407.4 | 5 |
| 422 | 1.86 | 460.2 | 459.5 | 5 |
| 423 | 2.05 | 460.2 | 459.5 | 5 |
| 424 | 2.13 | 449.2 | 448.5 | 5 |
| 425 | 2.20 | 465.2 | 464.5 | 5 |
| 426 | 2.39 | 473.2 | 472.5 | 5 |
| 427 | 2.06 | 453.2 | 452.5 | 5 |
| 428 | 3.57 | 452.0 | 451.5 | 3 |
| 429 | 3.58 | 466.0 | 465.5 | 3 |
| 430 | 3.59 | 452.0 | 451.5 | 3 |
| 431 | 3.54 | 438.0 | 437.5 | 3 |
| 432 | 3.49 | 412.0 | 411.5 | 3 |
| 433 | 2.00 | 407.2 | 406.5 | 5 |
| 434 | 1.91 | 381.2 | 380.4 | 5 |
| 435 | 1.95 | 451.2 | 450.5 | 5 |
| 436 | 1.87 | 376.1 | 375.4 | 5 |
| 437 | 2.19 | 408.1 | 407.5 | 5 |
| 438 | 2.23 | 422.0 | 421.5 | 5 |
| 439 | 2.38 | 442.1 | 441.9 | 5 |
| 440 | 2.26 | 438.2 | 437.5 | 5 |
| 441 | 1.93 | 390.2 | 389.4 | 5 |
| 442 | 2.06 | 443.1 | 442.9 | 5 |
| 443 | 2.06 | 398.2 | 397.4 | 5 |
| 444 | 2.09 | 382.2 | 381.4 | 5 |
| 445 | 2.11 | 382.1 | 381.4 | 5 |
| 446 | 2.06 | 400.1 | 399.4 | 5 |
| 447 | 2.03 | 412.2 | 411.5 | 5 |
| 448 | 2.57 | 486.2 | 485.6 | 5 |
| 449 | 2.49 | 487.2 | 486.6 | 5 |
| 450 | 2.18 | 458.2 | 457.5 | 5 |
| 451 | 2.34 | 432.1 | 431.5 | 5 |
| 452 | 2.37 | 446.2 | 445.5 | 5 |
| 453 | 2.50 | 466.1 | 465.9 | 5 |
| 454 | 2.38 | 462.1 | 461.5 | 5 |
| 455 | 1.91 | 433.2 | 432.5 | 5 |
| 456 | 2.11 | 414.2 | 413.5 | 5 |
| 457 | 2.08 | 414.1 | 413.5 | 5 |
| 458 | 2.05 | 426.2 | 425.5 | 5 |
| 459 | 2.15 | 410.2 | 409.5 | 5 |
| 460 | 1.93 | 433.1 | 432.5 | 5 |
| 461 | 2.21 | 467.1 | 466.9 | 5 |

TABLE B-continued

| C. No | HPLC RT | m/z | MW | HPLC method |
|---|---|---|---|---|
| 462 | 2.13 | 433.2 | 432.5 | 5 |
| 463 | 2.21 | 422.1 | 421.4 | 5 |
| 464 | 2.29 | 438.1 | 437.5 | 5 |
| 465 | 2.46 | 446.2 | 445.5 | 5 |
| 466 | 2.13 | 426.1 | 425.5 | 5 |
| 467 | 2.20 | 450.2 | 449.4 | 5 |
| 468 | 2.09 | 420.2 | 419.5 | 5 |
| 469 | 2.09 | 406.2 | 405.4 | 5 |
| 470 | 2.06 | 440.2 | 439.5 | 5 |
| 471 | 2.20 | 422.2 | 421.5 | 5 |
| 472 | 2.20 | 442.1 | 441.5 | 5 |
| 473 | 2.06 | 474.2 | 473.5 | 5 |
| 474 | 2.34 | 462.2 | 461.5 | 5 |
| 475 | 2.41 | 476.2 | 475.5 | 5 |
| 476 | 2.19 | 428.2 | 427.5 | 5 |
| 477 | 2.34 | 456.1 | 455.5 | 5 |
| 478 | 2.07 | 426.1 | 425.5 | 5 |
| 479 | 2.07 | 434.1 | 411.5 | 5 |
| 480 | 2.05 | 446.1 | 445.5 | 5 |
| 481 | 2.17 | 428.1 | 427.5 | 5 |
| 482 | 2.17 | 448.1 | 447.6 | 5 |
| 483 | 2.04 | 480.1 | 479.6 | 5 |
| 484 | 2.32 | 468.1 | 467.5 | 5 |
| 485 | 2.39 | 482.1 | 481.5 | 5 |
| 486 | 2.11 | 423.2 | 422.5 | 5 |
| 487 | 2.11 | 451.1 | 450.4 | 5 |
| 488 | 1.98 | 421.2 | 420.5 | 5 |
| 489 | 2.20 | 434.1 | 433.5 | 5 |
| 490 | 1.98 | 407.1 | 406.4 | 5 |
| 491 | 1.96 | 441.2 | 440.5 | 5 |
| 492 | 2.09 | 423.2 | 422.5 | 5 |
| 493 | 2.09 | 443.1 | 442.5 | 5 |
| 494 | 1.95 | 475.1 | 474.5 | 5 |
| 495 | 2.24 | 463.2 | 462.5 | 5 |
| 496 | 2.31 | 477.1 | 476.5 | 5 |
| 497 | 2.21 | 422.2 | 421.5 | 5 |
| 498 | 2.60 | 433.2 | 432.5 | 5 |
| 499 | 1.95 | 425.2 | 424.4 | 5 |
| 500 | 2.06 | 460.2 | 459.5 | 5 |
| 501 | 2.26 | 461.2 | 460.5 | 5 |
| 502 | 2.22 | 422.2 | 421.5 | 5 |
| 503 | 2.66 | 439.1 | 438.5 | 5 |
| 504 | 1.94 | 431.1 | 430.5 | 5 |
| 505 | 2.04 | 466.1 | 465.5 | 5 |
| 506 | 2.27 | 467.2 | 466.6 | 5 |
| 507 | 2.19 | 428.2 | 427.5 | 5 |
| 508 | 1.86 | 426.1 | 425.4 | 5 |
| 509 | 1.95 | 461.2 | 460.5 | 5 |
| 510 | 2.21 | 462.2 | 461.5 | 5 |
| 511 | 2.11 | 423.2 | 422.5 | 5 |
| 512 | 4.43 | 424.2 | 423.5 | 3 |
| 513 | 2.29 | 501.3 | 500.6 | 5 |
| 514 | 2.08 | 435.3 | 434.5 | 5 |
| 515 | 2.16 | 449.3 | 448.6 | 5 |
| 516 | 2.06 | 423.3 | 422.5 | 5 |
| 517 | 2.07 | 472.3 | 471.6 | 5 |
| 518 | 2.12 | 461.3 | 460.5 | 5 |
| 519 | 2.20 | 477.2 | 476.6 | 5 |
| 520 | 2.37 | 485.3 | 484.6 | 5 |
| 521 | 2.00 | 427.2 | 426.5 | 5 |
| 522 | 2.02 | 427.2 | 426.5 | 5 |
| 523 | 1.99 | 445.2 | 444.5 | 5 |
| 524 | 1.95 | 457.2 | 456.6 | 5 |
| 525 | 2.23 | 477.2 | 476.6 | 5 |
| 526 | 2.27 | 507.2 | 506.6 | 5 |
| 527 | 1.86 | 478.2 | 477.6 | 5 |
| 528 | 2.00 | 441.2 | 440.6 | 5 |
| 529 | 2.06 | 441.2 | 440.6 | 5 |
| 530 | 2.14 | 455.2 | 454.6 | 5 |
| 531 | 2.04 | 429.2 | 428.5 | 5 |
| 532 | 1.87 | 478.2 | 477.6 | 5 |
| 533 | 2.11 | 512.2 | 512.0 | 5 |
| 534 | 2.06 | 478.2 | 477.6 | 5 |
| 535 | 2.11 | 467.2 | 466.6 | 5 |
| 536 | 2.17 | 483.1 | 482.6 | 5 |
| 537 | 2.34 | 491.2 | 490.6 | 5 |
| 538 | 2.05 | 471.2 | 470.6 | 5 |
| 539 | 1.92 | 422.2 | 421.5 | 5 |
| 540 | 1.91 | 440.2 | 439.5 | 5 |
| 541 | 2.17 | 472.3 | 471.6 | 5 |
| 542 | 2.21 | 502.3 | 501.6 | 5 |
| 543 | 1.92 | 436.2 | 435.5 | 5 |
| 544 | 1.98 | 436.2 | 435.5 | 5 |
| 545 | 1.96 | 424.2 | 423.5 | 5 |
| 546 | 1.80 | 473.2 | 472.5 | 5 |
| 547 | 2.05 | 507.2 | 507.0 | 5 |
| 548 | 2.03 | 462.2 | 461.5 | 5 |
| 549 | 2.11 | 478.2 | 477.6 | 5 |
| 550 | 2.29 | 486.2 | 485.6 | 5 |
| 551 | 1.98 | 466.2 | 465.5 | 5 |
| 552 | 1.33 | 397.2 | 396.4 | 4 |
| 553 | 1.16 | 367.4 | 366.4 | 4 |
| 554 | 0.75 | 451.0 | 450.5 | 4 |
| 555 | 1.93 | 422.2 | 421.5 | 5 |
| 556 | 1.86 | 452.2 | 451.5 | 5 |
| 557 | 1.78 | 473.3 | 472.5 | 5 |
| 558 | 2.05 | 450.3 | 449.5 | 5 |
| 559 | 1.97 | 473.3 | 472.5 | 5 |
| 560 | 1.91 | 479.2 | 478.6 | 5 |
| 561 | 1.99 | 420.2 | 419.5 | 5 |
| 562 | 2.04 | 478.2 | 477.6 | 5 |
| 563 | 2.05 | 426.2 | 425.5 | 5 |
| 564 | 1.99 | 484.2 | 483.6 | 5 |
| 565 | 2.15 | 422.2 | 421.5 | 5 |
| 566 | 2.17 | 422.2 | 421.5 | 5 |
| 567 | 2.14 | 440.2 | 439.5 | 5 |
| 568 | 2.10 | 452.2 | 451.5 | 5 |
| 569 | 2.40 | 472.2 | 471.5 | 5 |
| 570 | 2.44 | 502.2 | 501.6 | 5 |
| 571 | 2.15 | 436.2 | 435.5 | 5 |
| 572 | 2.22 | 436.2 | 435.5 | 5 |
| 573 | 2.31 | 450.2 | 449.5 | 5 |
| 574 | 1.99 | 473.2 | 472.5 | 5 |
| 575 | 2.27 | 507.1 | 507.0 | 5 |
| 576 | 2.20 | 473.2 | 472.5 | 5 |
| 577 | 2.27 | 462.1 | 461.5 | 5 |
| 578 | 2.34 | 478.2 | 477.6 | 5 |
| 579 | 2.51 | 486.2 | 485.6 | 5 |
| 580 | 2.21 | 466.2 | 465.5 | 5 |
| 581 | 2.44 | 452.2 | 451.6 | 5 |
| 582 | 2.46 | 452.2 | 451.6 | 5 |
| 583 | 2.42 | 470.2 | 469.6 | 5 |
| 584 | 2.39 | 482.2 | 481.6 | 5 |
| 585 | 2.64 | 502.2 | 501.6 | 5 |
| 586 | 2.68 | 532.2 | 531.7 | 5 |
| 587 | 2.22 | 503.2 | 502.6 | 5 |
| 588 | 2.45 | 466.2 | 465.6 | 5 |
| 589 | 2.50 | 466.2 | 465.6 | 5 |
| 590 | 2.57 | 480.2 | 479.6 | 5 |
| 591 | 2.48 | 454.2 | 453.6 | 5 |
| 592 | 2.42 | 473.1 | 450.6 | 5 |
| 593 | 2.24 | 503.2 | 502.6 | 5 |
| 594 | 2.52 | 537.2 | 537.1 | 5 |
| 595 | 2.48 | 503.2 | 502.6 | 5 |
| 596 | 2.53 | 492.2 | 491.6 | 5 |
| 597 | 2.59 | 508.2 | 507.7 | 5 |
| 598 | 2.74 | 516.2 | 515.7 | 5 |
| 599 | 2.48 | 496.2 | 495.6 | 5 |
| 600 | 2.46 | 509.2 | 508.7 | 5 |
| 601 | 2.21 | 484.2 | 483.6 | 5 |
| 602 | 2.24 | 484.1 | 483.6 | 5 |
| 603 | 2.19 | 502.2 | 501.6 | 5 |
| 604 | 2.16 | 514.2 | 513.6 | 5 |
| 605 | 2.46 | 534.2 | 533.6 | 5 |
| 606 | 2.50 | 564.2 | 563.7 | 5 |
| 607 | 2.02 | 535.2 | 534.6 | 5 |
| 608 | 2.22 | 498.2 | 497.6 | 5 |
| 609 | 2.29 | 498.2 | 497.6 | 5 |
| 610 | 2.38 | 512.2 | 511.6 | 5 |
| 611 | 2.26 | 486.2 | 485.6 | 5 |
| 612 | 2.19 | 483.1 | 482.6 | 5 |
| 613 | 2.04 | 535.2 | 534.6 | 5 |
| 614 | 2.33 | 569.1 | 569.1 | 5 |
| 615 | 2.27 | 535.2 | 534.6 | 5 |
| 616 | 2.33 | 524.2 | 523.6 | 5 |
| 617 | 2.41 | 540.1 | 539.7 | 5 |

TABLE B-continued

| C. No | HPLC RT | m/z | MW | HPLC method |
|---|---|---|---|---|
| 618 | 2.57 | 548.2 | 547.7 | 5 |
| 619 | 2.27 | 528.2 | 527.6 | 5 |
| 620 | 2.24 | 541.1 | 540.7 | 5 |
| 621 | 1.97 | 409.2 | 408.5 | 5 |
| 622 | 2.11 | 435.2 | 434.5 | 5 |
| 623 | 2.11 | 463.2 | 462.5 | 5 |
| 624 | 1.99 | 433.2 | 432.5 | 5 |
| 625 | 2.48 | 446.2 | 445.5 | 5 |
| 626 | 1.99 | 419.2 | 418.5 | 5 |
| 627 | 2.10 | 435.2 | 434.5 | 5 |
| 628 | 2.09 | 455.2 | 454.6 | 5 |
| 629 | 2.22 | 475.2 | 474.6 | 5 |
| 630 | 2.29 | 489.2 | 488.6 | 5 |
| 631 | 1.95 | 415.1 | 414.5 | 5 |
| 632 | 2.09 | 441.2 | 440.6 | 5 |
| 633 | 1.98 | 425.2 | 424.5 | 5 |
| 634 | 2.07 | 441.2 | 440.6 | 5 |
| 635 | 2.08 | 461.1 | 460.6 | 5 |
| 636 | 2.22 | 481.2 | 480.6 | 5 |
| 637 | 2.27 | 495.1 | 494.6 | 5 |
| 638 | 2.03 | 436.2 | 435.5 | 5 |
| 639 | 2.03 | 464.2 | 463.5 | 5 |
| 640 | 1.91 | 434.2 | 433.5 | 5 |
| 641 | 2.14 | 447.2 | 446.5 | 5 |
| 642 | 2.00 | 436.2 | 435.5 | 5 |
| 643 | 2.00 | 456.2 | 455.6 | 5 |
| 644 | 2.14 | 476.2 | 475.5 | 5 |
| 645 | 2.21 | 490.2 | 489.5 | 5 |
| 646 | 1.89 | 410.1 | 409.5 | 5 |
| 647 | 1.92 | 420.2 | 419.5 | 5 |
| 648 | 2.26 | 469.1 | 468.5 | 5 |
| 649 | 2.01 | 439.1 | 438.5 | 5 |
| 650 | 2.56 | 452.1 | 451.5 | 5 |
| 651 | 2.00 | 473.2 | 472.5 | 5 |
| 652 | 0.77 | 501.0 | 500.5 | 4 |
| 653 | 0.82 | 535.0 | 535.0 | 4 |
| 654 | 0.67 | 502.0 | 501.5 | 4 |
| 655 | 0.87 | 569.0 | 568.5 | 4 |
| 656 | 0.71 | 451.0 | 450.5 | 4 |
| 657 | 0.72 | 453.0 | 452.5 | 4 |
| 658 | 0.75 | 502.0 | 501.5 | 4 |
| 659 | 0.84 | 515.0 | 514.6 | 4 |
| 660 | 0.81 | 519.0 | 518.5 | 4 |
| 661 | 0.72 | 483.0 | 482.5 | 4 |
| 662 | 0.75 | 502.0 | 501.5 | 4 |
| 663 | 0.76 | 491.0 | 490.5 | 4 |
| 664 | 0.99 | 491.0 | 492.4 | 4 |
| 665 | 0.79 | 507.0 | 506.6 | 4 |
| 666 | 2.24 | 450.1 | 427.5 | 5 |
| 667 | 2.19 | 428.1 | 427.5 | 5 |
| 668 | 2.15 | 446.1 | 445.5 | 5 |
| 669 | 2.20 | 458.2 | 457.5 | 5 |
| 670 | 2.42 | 478.2 | 477.6 | 5 |
| 671 | 2.45 | 508.1 | 507.6 | 5 |
| 672 | 2.09 | 479.1 | 478.6 | 5 |
| 673 | 2.22 | 479.1 | 478.6 | 5 |
| 674 | 2.28 | 468.1 | 467.5 | 5 |
| 675 | 2.39 | 482.1 | 481.6 | 5 |
| 676 | 2.45 | 458.2 | 457.6 | 5 |
| 677 | 2.47 | 458.2 | 457.6 | 5 |
| 678 | 2.43 | 476.2 | 475.6 | 5 |
| 679 | 2.40 | 488.1 | 487.6 | 5 |
| 680 | 2.65 | 508.2 | 507.7 | 5 |
| 681 | 2.67 | 538.2 | 537.7 | 5 |
| 682 | 2.26 | 509.1 | 508.7 | 5 |
| 683 | 2.49 | 509.1 | 508.7 | 5 |
| 684 | 2.53 | 498.2 | 497.6 | 5 |
| 685 | 2.73 | 500.1 | 499.6 | 5 |
| 686 | 2.62 | 512.2 | 511.7 | 5 |
| 687 | 2.23 | 490.2 | 489.6 | 5 |
| 688 | 2.25 | 490.2 | 489.6 | 5 |
| 689 | 2.21 | 508.1 | 507.6 | 5 |
| 690 | 2.17 | 520.1 | 519.6 | 5 |
| 691 | 2.45 | 540.2 | 539.7 | 5 |
| 692 | 2.50 | 570.1 | 569.7 | 5 |
| 693 | 2.04 | 541.1 | 540.7 | 5 |
| 694 | 2.28 | 489.1 | 488.6 | 5 |
| 695 | 2.05 | 541.2 | 540.7 | 5 |
| 696 | 2.28 | 541.1 | 540.7 | 5 |
| 697 | 2.33 | 530.2 | 529.6 | 5 |
| 698 | 2.18 | 542.1 | 541.6 | 5 |
| 699 | 2.43 | 544.2 | 543.7 | 5 |
| 700 | 2.09 | 423.2 | 422.5 | 5 |
| 701 | 2.06 | 441.2 | 440.5 | 5 |
| 702 | 2.03 | 453.2 | 452.5 | 5 |
| 703 | 2.34 | 473.2 | 472.5 | 5 |
| 704 | 2.37 | 503.2 | 502.6 | 5 |
| 705 | 1.92 | 474.2 | 473.5 | 5 |
| 706 | 1.94 | 474.2 | 473.5 | 5 |
| 707 | 2.14 | 474.2 | 473.5 | 5 |
| 708 | 2.20 | 463.2 | 462.5 | 5 |
| 709 | 2.20 | 465.2 | 464.4 | 5 |
| 710 | 2.30 | 477.3 | 476.5 | 5 |
| 711 | 2.35 | 453.2 | 452.6 | 5 |
| 712 | 2.38 | 453.2 | 452.6 | 5 |
| 713 | 2.36 | 471.1 | 470.6 | 5 |
| 714 | 2.31 | 483.3 | 482.6 | 5 |
| 715 | 2.58 | 503.2 | 502.6 | 5 |
| 716 | 2.61 | 533.2 | 532.7 | 5 |
| 717 | 2.18 | 504.2 | 503.6 | 5 |
| 718 | 2.35 | 452.1 | 451.5 | 5 |
| 719 | 2.41 | 504.2 | 503.6 | 5 |
| 720 | 2.46 | 493.2 | 492.6 | 5 |
| 721 | 2.48 | 495.2 | 494.5 | 5 |
| 722 | 2.33 | 505.2 | 504.6 | 5 |
| 723 | 2.56 | 507.2 | 506.6 | 5 |
| 724 | 2.13 | 485.2 | 484.6 | 5 |
| 725 | 2.12 | 503.2 | 502.6 | 5 |
| 726 | 2.08 | 515.2 | 514.6 | 5 |
| 727 | 2.39 | 535.2 | 534.6 | 5 |
| 728 | 2.43 | 565.2 | 564.7 | 5 |
| 729 | 2.19 | 536.2 | 535.6 | 5 |
| 730 | 2.25 | 525.2 | 524.6 | 5 |
| 731 | 2.26 | 527.1 | 526.5 | 5 |
| 732 | 2.10 | 537.2 | 536.6 | 5 |
| 733 | 2.36 | 539.2 | 538.6 | 5 |
| 734 | 2.03 | 427.2 | 426.5 | 5 |
| 735 | 2.19 | 485.2 | 484.6 | 5 |
| 736 | 2.13 | 480.2 | 479.6 | 5 |
| 737 | 2.10 | 423.3 | 422.5 | 5 |
| 738 | 2.11 | 480.2 | 479.6 | 5 |
| 739 | 2.06 | 475.2 | 474.5 | 5 |
| 740 | 2.24 | 509.2 | 508.7 | 5 |
| 741 | 2.47 | 515.2 | 514.7 | 5 |
| 742 | 2.40 | 510.2 | 509.6 | 5 |
| 743 | 2.19 | 504.2 | 503.6 | 5 |
| 744 | 2.39 | 510.2 | 509.6 | 5 |
| 745 | 2.25 | 547.2 | 546.7 | 5 |
| 746 | 2.16 | 485.2 | 484.6 | 5 |
| 747 | 1.98 | 536.3 | 535.6 | 5 |
| 748 | 2.10 | 484.1 | 483.5 | 5 |
| 749 | 1.99 | 536.3 | 535.6 | 5 |
| 750 | 2.16 | 542.2 | 541.6 | 5 |
| 751 | 2.38 | 435.2 | 434.5 | 5 |
| 752 | 2.40 | 435.2 | 434.5 | 5 |
| 753 | 2.37 | 453.2 | 452.5 | 5 |
| 754 | 2.34 | 465.2 | 464.5 | 5 |
| 755 | 2.60 | 485.2 | 484.5 | 5 |
| 756 | 2.63 | 515.2 | 514.6 | 5 |
| 757 | 2.39 | 449.2 | 448.5 | 5 |
| 758 | 2.44 | 449.2 | 448.5 | 5 |
| 759 | 2.52 | 463.2 | 462.5 | 5 |
| 760 | 2.43 | 437.2 | 436.5 | 5 |
| 761 | 2.20 | 486.2 | 485.5 | 5 |
| 762 | 2.48 | 520.2 | 520.0 | 5 |
| 763 | 2.42 | 486.2 | 485.5 | 5 |
| 764 | 2.48 | 475.2 | 474.5 | 5 |
| 765 | 2.55 | 491.2 | 490.6 | 5 |
| 766 | 2.70 | 499.3 | 498.6 | 5 |
| 767 | 2.43 | 479.2 | 478.5 | 5 |
| 768 | 2.40 | 492.2 | 491.6 | 5 |
| 769 | 2.24 | 406.2 | 405.4 | 5 |
| 770 | 2.26 | 406.2 | 405.4 | 5 |
| 771 | 2.22 | 424.2 | 423.5 | 5 |
| 772 | 2.20 | 436.2 | 435.5 | 5 |
| 773 | 2.49 | 456.2 | 455.5 | 5 |

TABLE B-continued

| C. No | HPLC RT | m/z | MW | HPLC method |
|---|---|---|---|---|
| 774 | 2.53 | 486.2 | 485.5 | 5 |
| 775 | 2.05 | 457.2 | 456.5 | 5 |
| 776 | 2.25 | 420.3 | 419.5 | 5 |
| 777 | 2.31 | 420.3 | 419.5 | 5 |
| 778 | 2.41 | 434.2 | 433.5 | 5 |
| 779 | 2.30 | 408.1 | 407.5 | 5 |
| 780 | 2.07 | 457.1 | 456.5 | 5 |
| 781 | 2.36 | 491.1 | 490.9 | 5 |
| 782 | 2.29 | 457.2 | 456.5 | 5 |
| 783 | 2.35 | 446.2 | 445.5 | 5 |
| 784 | 2.43 | 462.2 | 461.5 | 5 |
| 785 | 2.59 | 470.2 | 469.5 | 5 |
| 786 | 2.29 | 450.3 | 449.5 | 5 |
| 787 | 2.27 | 463.2 | 462.5 | 5 |
| 788 | 2.18 | 486.1 | 485.5 | 5 |

BIOLOGICAL EXAMPLES

Example 3

In-Vitro Susceptibility Testing of Representative Compounds

The Minimum inhibitory concentrations (MIC) of compounds according to the invention for a number of veterinary bacterial pathogens were determined by the broth-microdilution method according to CLSI document VET01-A4.

Microdilution trays containing a doubling dilution series of the test compound were used for the tests. The MIC results were interpreted according to the CLSI documents VET01-S3. The lowest concentration of compound at which no visible growth (i.e. no turbidity) detected by the unaided eye was recorded as the MIC.

Results

MIC Data for representative compounds is shown in Table C below.

The following pathogens/strains were tested:

| ID | Species | Ext. RefNo. | Remarks |
|---|---|---|---|
| MH 6357 | Mannheimia haemolytica | M7/2 | Reference strain (cattle infection strain) |
| MH 6374 | Mannheimia haemolytica | ATCC 33396 | Reference strain |
| MH 10720 | Mannheimia haemolytica | 154 | BRD field isolate |
| MH 13065 | Mannheimia haemolytica | XB0446-6003.9 | BRD field isolate |
| MH 13093 | Mannheimia haemolytica | XB0472-6014.1 | BRD field isolate |
| MH 12587 | Mannheimia haemolytica | 1071 | BRD field isolate, macrolide-resistance: erm+, E+ |
| PM 6267 | Pasteurella multocida | P 2225 (L386) | Reference strain (mouse infection strain) |
| PM 6391 | Pasteurella multocida | ATCC 43137 | Reference strain |
| PM 10775 | Pasteurella multocida | 080130003051 | BRD field isolate |
| PM 12080 | Pasteurella multocida | IV102277-0093 | BRD field isolate |

TABLE C

MICs in μM of representative compounds

| C. No | MH 6357 | MH 6374 | PM 6391 | MH 10720 | MH 13065 | MH 13093 | MH 12587 | PM 10775 | PM 12080 | PM 6267 |
|---|---|---|---|---|---|---|---|---|---|---|
| 2 | 0.2 | 0.2 | <=0.1 | <=0.1 | 1 | 0.8 | 0.8 | <=0.1 | <=0.1 | <=0.1 |
| 103 | 0.391 | 0.195 | 0.195 | 0.2 | 0.4 | 1.6 | 0.8 | <=0.1 | <=0.1 | <=0.1 |
| 144 | 1.563 | 0.195 | 0.098 | <=0.1 | <=0.1 | 0.2 | 0.2 | <=0.1 | <=0.1 | <=0.1 |
| 164 | 0.391 | 0.781 | 0.391 | <=0.1 | 0.4 | 0.4 | 0.8 | <=0.1 | 0.2 | <=0.1 |
| 192 | 0.8 | 0.8 | 0.2 | 0.2 | 0.8 | 0.8 | 1.6 | <=0.1 | <=0.1 | <=0.1 |
| 194 | 0.2 | 0.8 | <=0.1 | <=0.1 | 0.4 | 0.8 | 0.8 | <=0.1 | <=0.1 | <=0.1 |
| 195 | 0.2 | 0.2 | <=0.1 | <=0.1 | 0.4 | 0.4 | 0.8 | <=0.1 | <=0.1 | <=0.1 |
| 196 | 0.4 | 0.8 | <=0.1 | <=0.1 | 0.8 | 0.8 | 1.6 | <=0.1 | <=0.1 | <=0.1 |
| 203 | 0.8 | 0.8 | 0.4 | <=0.1 | 0.8 | 0.8 | 1.6 | <=0.1 | 0.2 | <=0.1 |
| 205 | 0.8 | 0.8 | 0.4 | <=0.1 | 0.8 | 1.6 | 1.6 | <=0.1 | 0.2 | <=0.1 |
| 243 | 0.2 | 0.4 | 0.2 | <=0.1 | 0.4 | 1.6 | 0.8 | <=0.1 | 0.2 | <=0.1 |
| 245 | 0.2 | 0.4 | 0.2 | <=0.1 | 0.4 | 0.4 | 0.8 | <=0.1 | <=0.1 | <=0.1 |
| 256 | 0.4 | 0.4 | <=0.1 | <=0.1 | 0.8 | 0.8 | 1.6 | <=0.1 | <=0.1 | <=0.1 |
| 257 | 0.2 | 0.2 | <=0.1 | <=0.1 | 0.4 | 0.4 | 0.8 | <=0.1 | <=0.1 | <=0.1 |
| 258 | 0.4 | 0.8 | 0.2 | 0.2 | 0.8 | 0.8 | 1.6 | <=0.1 | <=0.1 | <=0.1 |
| 259 | 0.2 | 0.2 | <=0.1 | <=0.1 | 0.4 | 0.4 | 0.4 | <=0.1 | <=0.1 | <=0.1 |
| 260 | <=0.1 | <=0.1 | <=0.1 | <=0.1 | 0.4 | 0.4 | 0.4 | <=0.1 | <=0.1 | <=0.1 |
| 261 | 0.2 | 0.2 | <=0.1 | <=0.1 | 0.4 | 0.8 | 0.8 | <=0.1 | <=0.1 | <=0.1 |
| 287 | 0.4 | 0.4 | 0.4 | <=0.1 | 0.8 | 0.8 | 0.8 | <=0.1 | 0.2 | <=0.1 |
| 288 | 0.4 | 0.8 | 0.4 | 0.2 | 0.8 | 0.8 | 1.6 | <=0.1 | 0.2 | <=0.1 |
| 289 | 0.4 | 0.8 | 0.4 | 0.2 | 0.8 | 0.8 | 1.6 | <=0.1 | 0.4 | <=0.1 |
| 290 | 0.2 | 0.4 | 0.4 | <=0.1 | 0.4 | 0.4 | 0.4 | <=0.1 | 0.2 | <=0.1 |
| 291 | 0.2 | 0.4 | 0.2 | <=0.1 | 0.2 | 0.4 | 0.8 | <=0.1 | <=0.1 | <=0.1 |
| 292 | 0.4 | 0.8 | 0.4 | 0.4 | 0.8 | 0.8 | 1.6 | <=0.1 | 0.4 | 0.2 |
| 299 | 0.4 | 0.8 | 1.6 | <=0.1 | 0.8 | 0.8 | 1.6 | <=0.1 | 0.4 | 0.2 |
| 301 | 0.4 | 0.8 | 0.8 | <=0.1 | 0.8 | 0.8 | 1.6 | <=0.1 | 0.4 | 0.4 |
| 302 | 0.4 | 1.6 | 0.8 | 0.2 | 0.8 | 0.8 | 1.6 | <=0.1 | 0.2 | 0.2 |
| 306 | 0.4 | 0.4 | 0.2 | <=0.1 | 0.4 | 0.8 | 0.8 | <=0.1 | 0.2 | <=0.1 |
| 313 | 0.8 | 0.8 | <=0.1 | 0.4 | 1.6 | 1.6 | 1.6 | 0.2 | <=0.1 | <=0.1 |
| 320 | 0.8 | 0.8 | NT | 0.4 | 0.8 | 1.6 | 1.6 | <=0.1 | <=0.1 | <=0.1 |
| 321 | 1.6 | 0.8 | <=0.1 | 0.4 | 0.8 | 1.6 | 1.6 | <=0.1 | 0.2 | 0.4 |

TABLE C-continued

MICs in μM of representative compounds

| C. No | MH 6357 | MH 6374 | PM 6391 | MH 10720 | MH 13065 | MH 13093 | MH 12587 | PM 10775 | PM 12080 | PM 6267 |
|---|---|---|---|---|---|---|---|---|---|---|
| 329 | 1.6 | 0.8 | <=0.1 | 0.4 | 0.8 | 1.6 | 1.6 | <=0.1 | <=0.1 | <=0.1 |
| 341 | 0.2 | 0.4 | <=0.1 | <=0.1 | 0.2 | 0.4 | 0.4 | <=0.1 | <=0.1 | <=0.1 |
| 346 | 0.4 | 0.4 | NT | <=0.1 | 0.2 | 0.4 | 0.8 | <=0.1 | <=0.1 | <=0.1 |
| 359 | 0.2 | 0.2 | <=0.1 | <=0.1 | 0.2 | 0.4 | 0.4 | <=0.1 | <=0.1 | <=0.1 |
| 360 | 0.4 | 0.4 | <=0.1 | 0.2 | 0.4 | 0.8 | 0.8 | <=0.1 | <=0.1 | <=0.1 |
| 364 | 1.6 | 1.6 | 0.2 | 0.8 | 0.8 | 1.6 | 1.6 | <=0.1 | <=0.1 | <=0.1 |
| 398 | 0.4 | 0.8 | <=0.1 | NT | 0.2 | 0.2 | 0.4 | <=0.1 | <=0.1 | <=0.1 |
| 401 | 0.4 | 0.8 | 0.2 | NT | 0.4 | 0.8 | 0.8 | <=0.1 | 0.2 | <=0.1 |
| 402 | 0.8 | 0.8 | 0.2 | NT | 0.4 | 0.8 | 1.6 | <=0.1 | 0.4 | <=0.1 |
| 404 | 1.6 | 1.6 | 0.4 | NT | 0.8 | 1.6 | 1.6 | <=0.1 | 0.8 | 0.4 |
| 406 | 1.6 | 1.6 | 0.2 | NT | 0.8 | 1.6 | 1.6 | <=0.1 | 0.4 | <=0.1 |
| 407 | 0.4 | 0.4 | <=0.1 | NT | 0.2 | 0.4 | 0.4 | <=0.1 | <=0.1 | <=0.1 |
| 408 | 0.4 | 0.4 | <=0.1 | NT | 0.4 | 0.4 | 0.8 | <=0.1 | <=0.1 | <=0.1 |
| 409 | 0.2 | <=0.1 | <=0.1 | NT | <=0.1 | 0.2 | 0.4 | <=0.1 | <=0.1 | <=0.1 |
| 410 | <=0.1 | <=0.1 | <=0.1 | NT | <=0.1 | <=0.1 | 0.2 | <=0.1 | <=0.1 | <=0.1 |
| 411 | 0.2 | <=0.1 | <=0.1 | NT | <=0.1 | 0.2 | 0.4 | <=0.1 | <=0.1 | <=0.1 |
| 412 | 0.8 | 0.8 | 0.2 | NT | 0.8 | 1.6 | 1.6 | <=0.1 | 0.4 | <=0.1 |
| 413 | 0.4 | 0.8 | <=0.1 | NT | 0.4 | 0.4 | 0.8 | <=0.1 | <=0.1 | <=0.1 |
| 415 | 0.8 | 1.6 | 0.2 | NT | 0.4 | 1.6 | 1.6 | <=0.1 | 0.4 | 0.2 |
| 424 | 0.8 | 1.6 | <=0.1 | NT | 0.4 | 0.8 | 1.6 | <=0.1 | <=0.1 | <=0.1 |
| 425 | 0.8 | 0.8 | <=0.1 | NT | 0.4 | 0.8 | 0.8 | <=0.1 | <=0.1 | <=0.1 |
| 444 | 0.4 | 0.8 | <=0.1 | <=0.1 | NT | 1.6 | 1.6 | NT | <=0.1 | <=0.1 |
| 448 | 0.8 | 0.4 | <=0.1 | <=0.1 | NT | 1.6 | 1.6 | NT | <=0.1 | <=0.1 |
| 452 | 0.2 | 0.4 | <=0.1 | <=0.1 | NT | 0.8 | 0.8 | NT | <=0.1 | <=0.1 |
| 453 | 1.6 | 0.4 | <=0.1 | <=0.1 | NT | 1.6 | 1.6 | NT | <=0.1 | <=0.1 |
| 460 | 0.8 | 0.8 | <=0.1 | NT | NT | 1.6 | 1.6 | NT | <=0.1 | <=0.1 |
| 461 | 0.4 | 0.4 | <=0.1 | <=0.1 | NT | 1.6 | 1.6 | NT | <=0.1 | <=0.1 |
| 464 | 0.4 | 0.2 | <=0.1 | <=0.1 | NT | 0.8 | 0.8 | NT | <=0.1 | <=0.1 |
| 467 | <=0.1 | 0.2 | <=0.1 | NT | NT | 0.4 | 0.4 | NT | <=0.1 | <=0.1 |
| 468 | <=0.1 | <=0.1 | <=0.1 | <=0.1 | NT | 0.4 | 0.4 | NT | <=0.1 | <=0.1 |
| 469 | 0.2 | <=0.1 | <=0.1 | <=0.1 | NT | 0.4 | 0.4 | NT | <=0.1 | <=0.1 |
| 472 | 0.4 | 0.8 | <=0.1 | <=0.1 | NT | 1.6 | 1.6 | NT | <=0.1 | <=0.1 |
| 474 | 0.2 | 0.4 | <=0.1 | <=0.1 | NT | 0.8 | 0.8 | NT | <=0.1 | <=0.1 |
| 475 | 0.2 | 0.4 | <=0.1 | NT | NT | 0.8 | 0.8 | NT | <=0.1 | <=0.1 |
| 476 | 0.2 | <=0.1 | <=0.1 | <=0.1 | NT | 0.4 | 0.8 | NT | <=0.1 | <=0.1 |
| 477 | <=0.1 | 0.2 | <=0.1 | <=0.1 | NT | 0.4 | 0.4 | NT | <=0.1 | <=0.1 |
| 478 | <=0.1 | <=0.1 | <=0.1 | <=0.1 | NT | 0.2 | 0.4 | NT | <=0.1 | <=0.1 |
| 479 | <=0.1 | 0.2 | <=0.1 | <=0.1 | NT | 0.8 | 0.8 | NT | <=0.1 | <=0.1 |
| 482 | 0.2 | 0.4 | <=0.1 | <=0.1 | NT | 0.8 | 0.8 | NT | <=0.1 | <=0.1 |
| 484 | 0.2 | 0.4 | <=0.1 | <=0.1 | NT | 0.8 | 0.8 | NT | <=0.1 | <=0.1 |
| 485 | <=0.1 | <=0.1 | <=0.1 | <=0.1 | NT | 0.2 | 0.4 | NT | <=0.1 | <=0.1 |
| 486 | 0.8 | 1.6 | <=0.1 | 0.2 | NT | 1.6 | 1.6 | NT | <=0.1 | <=0.1 |
| 487 | 0.4 | 1.6 | <=0.1 | <=0.1 | NT | 1.6 | 1.6 | NT | <=0.1 | <=0.1 |
| 490 | 0.4 | 0.8 | <=0.1 | <=0.1 | NT | 1.6 | 1.6 | NT | <=0.1 | NT |
| 495 | 0.4 | 1.6 | <=0.1 | <=0.1 | NT | 1.6 | 1.6 | NT | <=0.1 | <=0.1 |
| 513 | 1.6 | 0.8 | 0.2 | 0.2 | 1.6 | 1.6 | 1.6 | NT | 0.2 | 1.6 |
| 518 | 0.8 | 0.4 | NT | <=0.1 | 0.8 | 0.8 | 0.8 | NT | <=0.1 | 0.8 |
| 521 | 0.8 | 0.4 | <=0.1 | <=0.1 | 1.6 | 0.8 | 0.8 | NT | <=0.1 | 0.8 |
| 522 | 1.6 | 0.4 | 0.2 | 0.2 | 0.8 | 1.6 | 1.6 | NT | <=0.1 | 1.6 |
| 523 | 1.6 | 0.8 | 0.2 | 0.4 | 1.6 | 1.6 | 1.6 | NT | <=0.1 | NT |
| 525 | 0.8 | 0.4 | 0.2 | 0.2 | 0.8 | 0.8 | 1.6 | NT | <=0.1 | 1.6 |
| 526 | 0.8 | 0.4 | 0.2 | 0.2 | 0.8 | 1.6 | 1.6 | NT | 0.2 | 1.6 |
| 527 | 0.8 | 0.8 | <=0.1 | 0.2 | 0.8 | 1.6 | 0.8 | NT | <=0.1 | 1.6 |
| 532 | 1.6 | 0.8 | <=0.1 | 0.2 | 1.6 | 1.6 | 1.6 | NT | <=0.1 | 1.6 |
| 533 | 0.8 | 0.8 | 0.2 | 0.2 | 0.8 | 0.8 | 1.6 | NT | <=0.1 | 1.6 |
| 534 | 0.8 | 0.8 | <=0.1 | 0.2 | 0.8 | 1.6 | 1.6 | NT | <=0.1 | 1.6 |
| 535 | 0.8 | 0.2 | <=0.1 | <=0.1 | 0.4 | 0.8 | 0.8 | NT | <=0.1 | 0.8 |
| 536 | 0.8 | 0.2 | <=0.1 | <=0.1 | 0.4 | 0.8 | 0.8 | NT | <=0.1 | 0.8 |
| 537 | 0.8 | 0.8 | 0.2 | 0.2 | 0.8 | 1.6 | 1.6 | NT | <=0.1 | 1.6 |
| 548 | 1.6 | 0.8 | 0.2 | 0.2 | 0.8 | 1.6 | 1.6 | NT | <=0.1 | 1.6 |
| 549 | 0.8 | 0.4 | <=0.1 | 0.4 | 0.8 | 1.6 | 1.6 | NT | <=0.1 | 0.8 |
| 552 | 0.8 | 0.2 | <=0.1 | 0.2 | 0.8 | 0.8 | 0.8 | NT | <=0.1 | 0.8 |
| 553 | 0.8 | 0.4 | <=0.1 | 0.2 | 1.6 | 0.8 | 0.8 | NT | <=0.1 | 0.8 |
| 554 | 0.4 | 0.4 | NT | <=0.1 | 0.4 | 0.4 | 0.8 | NT | <=0.1 | 0.4 |
| 562 | 0.8 | 0.8 | <=0.1 | <=0.1 | 0.8 | 0.8 | 1.6 | <=0.1 | <=0.1 | <=0.1 |
| 564 | 0.8 | 0.4 | <=0.1 | <=0.1 | 0.8 | 0.8 | 0.8 | <=0.1 | <=0.1 | <=0.1 |
| 565 | 1.6 | 0.4 | <=0.1 | <=0.1 | 0.4 | 0.8 | 1.6 | <=0.1 | <=0.1 | <=0.1 |
| 569 | 0.8 | 0.4 | <=0.1 | <=0.1 | 0.4 | 0.4 | 0.8 | <=0.1 | <=0.1 | <=0.1 |
| 570 | 0.8 | 0.8 | 0.4 | <=0.1 | 0.8 | 0.8 | 1.6 | <=0.1 | <=0.1 | <=0.1 |
| 574 | 0.8 | 0.4 | <=0.1 | <=0.1 | 0.4 | 0.8 | 1.6 | <=0.1 | <=0.1 | <=0.1 |
| 575 | 0.4 | 0.4 | <=0.1 | <=0.1 | 0.2 | 0.4 | 0.4 | <=0.1 | <=0.1 | <=0.1 |
| 576 | 0.8 | 0.4 | <=0.1 | <=0.1 | 0.8 | 0.8 | 1.6 | <=0.1 | <=0.1 | <=0.1 |
| 577 | 0.4 | 0.2 | <=0.1 | <=0.1 | 0.2 | 0.4 | 0.8 | <=0.1 | <=0.1 | <=0.1 |
| 578 | 0.4 | <=0.1 | <=0.1 | <=0.1 | <=0.1 | 0.2 | 0.4 | <=0.1 | <=0.1 | <=0.1 |
| 579 | 0.8 | 0.4 | 0.2 | <=0.1 | 0.4 | 0.8 | 1.6 | <=0.1 | <=0.1 | <=0.1 |

TABLE C-continued

MICs in μM of representative compounds

| C. No | MH 6357 | MH 6374 | PM 6391 | MH 10720 | MH 13065 | MH 13093 | MH 12587 | PM 10775 | PM 12080 | PM 6267 |
|---|---|---|---|---|---|---|---|---|---|---|
| 581 | 0.4 | 0.8 | <=0.1 | <=0.1 | 0.4 | 0.4 | 1.6 | <=0.1 | <=0.1 | <=0.1 |
| 582 | 0.8 | 0.8 | 0.4 | <=0.1 | 0.8 | 0.8 | 1.6 | <=0.1 | 0.4 | <=0.1 |
| 585 | 0.8 | 1.6 | 0.4 | 0.2 | 0.8 | 0.8 | 1.6 | <=0.1 | 0.4 | 0.2 |
| 586 | 1.6 | 1.6 | 0.8 | 0.4 | 1.6 | 1.6 | 1.6 | 0.2 | 0.4 | 0.2 |
| 587 | 0.4 | 0.8 | <=0.1 | <=0.1 | 0.4 | 0.4 | 0.8 | <=0.1 | <=0.1 | <=0.1 |
| 592 | 0.4 | 0.8 | 0.2 | <=0.1 | 0.8 | 0.4 | 0.8 | <=0.1 | 0.2 | <=0.1 |
| 593 | 0.4 | 0.8 | 0.8 | 0.2 | 0.4 | 0.8 | 0.8 | <=0.1 | 0.2 | <=0.1 |
| 594 | 1.6 | 1.6 | 0.8 | 0.4 | 1.6 | 1.6 | 1.6 | 0.2 | 0.8 | 0.4 |
| 595 | 0.8 | 1.6 | 0.8 | 0.2 | 0.8 | 0.8 | 1.6 | <=0.1 | 0.4 | 0.2 |
| 596 | 0.4 | 0.8 | 0.2 | <=0.1 | 0.4 | 0.4 | 0.8 | <=0.1 | <=0.1 | <=0.1 |
| 597 | 0.8 | 0.8 | 0.2 | <=0.1 | 0.8 | 0.8 | 1.6 | <=0.1 | <=0.1 | <=0.1 |
| 600 | 0.8 | 1.6 | 0.4 | 0.2 | 0.8 | 0.8 | 1.6 | <=0.1 | <=0.1 | <=0.1 |
| 602 | 1.6 | 0.8 | <=0.1 | <=0.1 | 0.8 | 0.8 | 1.6 | <=0.1 | <=0.1 | <=0.1 |
| 604 | 1.6 | 1.6 | <=0.1 | 0.2 | 0.8 | 1.6 | 1.6 | <=0.1 | <=0.1 | <=0.1 |
| 607 | 0.4 | 0.4 | <=0.1 | <=0.1 | 0.4 | 0.4 | 0.8 | <=0.1 | <=0.1 | <=0.1 |
| 612 | 0.8 | 0.4 | <=0.1 | <=0.1 | 0.8 | 0.8 | 1.6 | <=0.1 | <=0.1 | <=0.1 |
| 613 | 0.8 | 0.4 | <=0.1 | <=0.1 | 0.8 | 0.8 | 1.6 | <=0.1 | <=0.1 | <=0.1 |
| 614 | 0.4 | 0.4 | <=0.1 | <=0.1 | 0.2 | 0.4 | 0.8 | <=0.1 | <=0.1 | <=0.1 |
| 615 | 1.6 | 0.4 | <=0.1 | <=0.1 | 1.6 | 0.8 | 1.6 | <=0.1 | <=0.1 | <=0.1 |
| 616 | 0.8 | 0.2 | <=0.1 | <=0.1 | 0.2 | 0.4 | 0.8 | <=0.1 | <=0.1 | <=0.1 |
| 617 | 0.4 | 0.2 | <=0.1 | <=0.1 | 0.2 | 0.4 | 0.8 | <=0.1 | <=0.1 | <=0.1 |
| 620 | 0.2 | 0.2 | <=0.1 | <=0.1 | 0.2 | 0.2 | 0.4 | <=0.1 | <=0.1 | <=0.1 |
| 623 | 0.8 | 0.4 | 0.2 | <=0.1 | 0.8 | 0.8 | 1.6 | <=0.1 | <=0.1 | <=0.1 |
| 626 | 0.8 | 0.4 | NT | <=0.1 | 0.4 | 0.8 | 0.8 | <=0.1 | <=0.1 | <=0.1 |
| 633 | 0.8 | 0.4 | 0.2 | <=0.1 | 0.8 | 0.8 | 0.8 | <=0.1 | 0.2 | <=0.1 |
| 635 | 1.6 | 0.4 | 0.4 | <=0.1 | 0.8 | 0.8 | 1.6 | <=0.1 | <=0.1 | <=0.1 |
| 636 | 0.8 | 0.4 | 0.4 | <=0.1 | 1.6 | 0.8 | 1.6 | <=0.1 | 0.4 | <=0.1 |
| 637 | 0.8 | 0.4 | 0.4 | <=0.1 | 1.6 | 0.8 | 1.6 | 0.2 | 0.2 | <=0.1 |
| 647 | 1.6 | 0.8 | 0.4 | 0.4 | 0.8 | 0.8 | 1.6 | <=0.1 | 0.4 | <=0.1 |
| 648 | 0.8 | 0.4 | 0.4 | <=0.1 | 0.4 | 1.6 | 0.8 | <=0.1 | 0.2 | <=0.1 |
| 649 | 0.8 | 0.4 | 0.2 | <=0.1 | 0.4 | 0.8 | 0.8 | <=0.1 | 0.2 | <=0.1 |
| 651 | 0.4 | 0.2 | <=0.1 | <=0.1 | 0.2 | 0.4 | 0.4 | <=0.1 | <=0.1 | <=0.1 |
| 652 | 0.8 | 0.8 | 0.4 | <=0.1 | 0.4 | 0.8 | 0.8 | <=0.1 | <=0.1 | <=0.1 |
| 654 | 0.4 | 0.4 | <=0.1 | <=0.1 | 0.4 | 0.4 | 0.8 | <=0.1 | <=0.1 | <=0.1 |
| 735 | 0.4 | 0.2 | <=0.1 | <=0.1 | 0.2 | 0.4 | 0.4 | 0.2 | <=0.1 | <=0.1 |
| 740 | 0.8 | 0.8 | 0.4 | 0.2 | 0.8 | 0.8 | 1.6 | <=0.1 | <=0.1 | 0.4 |
| 742 | 0.8 | 0.8 | 0.4 | 0.2 | 0.8 | 1.6 | 1.6 | <=0.1 | 0.2 | 0.4 |
| 744 | 0.8 | 0.8 | 0.4 | 0.4 | 0.8 | 1.6 | 1.6 | <=0.1 | 0.2 | 0.4 |
| 745 | 0.4 | 0.2 | <=0.1 | <=0.1 | 0.4 | 0.4 | 0.4 | <=0.1 | <=0.1 | <=0.1 |
| 751 | 0.8 | 0.8 | 0.4 | 0.2 | 0.8 | 0.8 | 1.6 | <=0.1 | 0.4 | 0.2 |
| 755 | 0.8 | 1.6 | 0.8 | 0.2 | 0.8 | 0.8 | 0.8 | <=0.1 | 0.4 | 0.4 |
| 764 | 0.4 | 0.4 | 0.4 | <=0.1 | 0.4 | 0.4 | 1.6 | <=0.1 | 0.4 | <=0.1 |
| 765 | 0.4 | 0.4 | 0.4 | <=0.1 | 0.4 | 0.4 | 1.6 | <=0.1 | 0.4 | <=0.1 |
| 788 | 0.4 | 0.8 | 0.4 | 0.2 | 0.4 | 0.4 | 1.6 | <=0.1 | <=0.1 | <=0.1 |

NT: not tested

Example 4

In-Vitro Susceptibility Testing of Representative Compounds

The in vitro activity of representative compounds of the current invention (Compound 189, Compound 251, Compound 326, Compound 467, Compound 105, compound 231, Compound 320, Compound 329) was tested against bacterial isolates of different species:

The Minimum inhibitory concentrations (MIC) of compounds according to the invention were determined by the broth-microdilution method according to CLSI document VET01-A4.

Microdilution trays containing a doubling dilution series of the test compound were used for the tests.

The MIC results were interpreted according to the CLSI documents VET01-S3. The lowest concentration of compound at which no visible growth (i.e. no turbidity) detected by the unaided eye was recorded as the MIC. Results are shown in Table 2.

The following pathogens/strains were tested:

| ID | Species | Ext. RefNo. | Remarks |
|---|---|---|---|
| MH 6357 | Mannheimia haemolytica | M7/2 | Reference strain (cattle infection strain) |
| MH 6374 | Mannheimia haemolytica | ATCC 33396 | Reference strain |
| PM 6267 | Pasteurella multocida | P 2225 (L386) | Reference strain (mouse infection strain) |
| PM 6391 | Pasteurella multocida | ATCC 43137 | Reference strain |
| SA 5816 | Staphylococcus aureus | 2139 | Mastitis field isolate |
| SA 6114 | Staphylococcus aureus | ATCC 29213 | Reference strain |
| MH 10720 | Mannheimia haemolytica | 154 | BRD field isolate |
| MH 12180 | Mannheimia haemolytica | KLI-02944 | BRD field isolate |
| MH 12587 | Mannheimia haemolytica | 1071 | BRD field isolate, macrolide-resistance: erm+, E+ |
| PM 10775 | Pasteurella multocida | 080130003051 | BRD field isolate |
| PM 12080 | Pasteurella multocida | IV102277-0093 | BRD field isolate |
| PM 14426 | Pasteurella multocida | 0006-439 | BRD field isolate macrolide-resistant |
| AB 15919 | Acinetobacter baumanii | IV369-2012 | Dermatitis field isolate |
| AB 16496 | Acinetobacter baumanii | ATCC 19606 | Reference strain |

TABLE 2

MICs in μg/mL of the compounds

| Strain ID | C.189 | C.251 | C.326 | C.467 | C.105 | C.231 | C.320 | C.329 |
|---|---|---|---|---|---|---|---|---|
| MH 6357 | 0.5 | 2 | 2 | 0.125 | 0.5 | 0.5 | 0.5 | 0.5 |
| MH 6374 | 0.25 | 8 | 1 | 0.063 | 0.25 | 0.25 | 0.25 | 0.25 |
| PM 6267 | 0.5 | 1 | 2 | 0.032 | ≤0.016 | ≤0.016 | ≤0.016 | ≤0.016 |
| PM 6391 | 0.25 | 8 | 0.5 | 0.032 | 0.063 | 0.063 | 0.032 | 0.063 |
| SA 5816 | >16 | >16 | >16 | >16 | >16 | >16 | >16 | >16 |
| SA 6114 | >16 | >16 | >16 | >16 | >16 | >16 | >16 | >16 |
| MH 10720 | 0.125 | 0.25 | 0.5 | ≤0.016 | 0.25 | 0.5 | 0.25 | 0.5 |
| MH 12180 | 0.25 | 8 | 0.5 | 0.032 | 0.5 | 0.5 | 0.5 | 0.5 |
| MH 12587 | 1 | 2 | 8 | 0.125 | 0.5 | 0.5 | 0.5 | 0.5 |
| PM 10775 | ≤0.016 | 8 | 0.25 | ≤0.016 | ≤0.016 | ≤0.016 | ≤0.016 | ≤0.016 |
| PM 12080 | 0.063 | 0.063 | 0.125 | ≤0.016 | 0.032 | 0.063 | ≤0.016 | 0.032 |
| PM 14426 | 0.032 | 8 | 0.063 | ≤0.016 | ≤0.016 | 0.032 | ≤0.016 | ≤0.016 |
| AB 15919 | >16 | >16 | >16 | >16 | >16 | >16 | 16 | 16 |
| AB 16496 | >16 | >16 | >16 | >16 | >16 | >16 | >16 | >16 |

Example 5

In vitro Activity Against Bacteria Isolated from Respiratory Tract of Swine and Cattle Suffering from Respiratory Disease Collected In Different European Countries The in vitro activity of compounds against 20 isolates of *Actinobacillus (A.) pleuropneumoniae*, 20 of *Bordetella (B.) bronchiseptica*, 20 of *Histophilus (H.) somni*, 40 of *Mannheimia (M.) haemolytica* and 40 of *Pasteurella (P.) multocida* collected in different European countries were determined. All bacteria were isolated from the respiratory tract of swine and cattle suffering from respiratory disease. All isolates were epidemiologically unrelated as specified by the different suppliers.

The minimum inhibitory concentrations (MIC) of compounds according to the invention were determined by the broth-microdilution method according to CLSI document VET01-A4.

Microdilution trays containing a doubling dilution series of the test compounds were used for the tests.

The MIC results were interpreted according to the CLSI documents VET01-S3. The lowest concentration of compound at which no visible growth (i.e. no turbidity) detected by the unaided eye was recorded as the MIC. The $MIC_{50}$ and $MIC_{90}$ represent the concentration at which minimum 50% or 90% of the isolates are inhibited.

Test items of the study were the following compounds: 105, 231, 320 and 329 (in the table C.105, C.231, C.320 and C.329) and 189, 251, 326 and 467 (in the table C.189, C.251, C.326 and C.467). Results are shown in Table 3.

Results

TABLE 3

| | $MIC_{50}$ and $MIC_{90}$ in µg/mL of the compounds tested | | | | | | | |
|---|---|---|---|---|---|---|---|---|
| Compund Species | C.105 | C.231 | C.320 | C.329 | C.189 | C.251 | C.326 | C.467 |
| *A. pleuropneumoniae* | | | | | | | | |
| $MIC_{50}$ | 0.125 | 0.25 | 0.5 | 0.5 | 0.25 | 0.25 | 1 | 0.032 |
| $MIC_{90}$ | 0.25 | 0.5 | 0.5 | 0.5 | 0.25 | 0.5 | 2 | 0.063 |
| *B. bronchiseptica* | | | | | | | | |
| $MIC_{50}$ | 16 | >16 | 2 | 2 | >16 | >16 | >16 | 2 |
| $MIC_{90}$ | 16 | >16 | 2 | 4 | >16 | >16 | >16 | 2 |
| *H. somni* | | | | | | | | |
| $MIC_{50}$ | 0.063 | 0.125 | 0.063 | 0.25 | 0.032 | 0.125 | 0.25 | ≤0.016 |
| $MIC_{90}$ | 0.125 | 0.25 | 0.125 | 0.25 | 0.063 | 0.25 | 0.5 | ≤0.016 |
| *M. haemolytica* | | | | | | | | |
| $MIC_{50}$ | 0.25 | 0.5 | 0.5 | 0.5 | 0.25 | 1 | 1 | 0.032 |
| $MIC_{90}$ | 0.5 | 1 | 0.5 | 1 | 0.5 | 1 | 2 | 0.063 |
| *P. multocida* | | | | | | | | |
| $MIC_{50}$ | ≤0.016 | ≤0.016 | ≤0.016 | 0.032 | 0.032 | 0.063 | 0.063 | ≤0.016 |
| $MIC_{90}$ | 0.032 | 0.063 | 0.032 | 0.032 | 0.063 | 0.125 | 0.125 | ≤0.016 |

Example 6

In Vitro Activity *Haemophilus parasuis* Isolated from the Respiratory Tract of Swine Suffering from Respiratory Disease The in vitro activity of 3 representative compounds of this invention against 15 isolates of *H. parasuis* was determined. All strains were isolated from the respiratory tract of swine in different European countries The MICs for all isolates were determined by using the agar-dilution method according to CLSI document VET01-A4 [1] with the following modification: GC agar base was used instead of Mueller-Hinton agar base for the preparation of the agar-dilution plates.

Results were interpreted according to the CLSI document VET01-S3. The MIC is the lowest concentration of antimicrobial agent that completely inhibits colony formation, disregarding a single colony or a faint haze caused by inoculum. Results are shown in Table 4.

Results:

TABLE 4

| $MIC_{50}$ and $MIC_{90}$ in µg/mL of the compounds tested | | | |
|---|---|---|---|
| | Compound | | |
| Species | C.320 | C.329 | C.467 |
| *Haemophilus parasuis* | | | |
| $MIC_{50}$ | 2 | 2 | 0.125 |
| $MIC_{90}$ | 4 | 4 | 0.25 |

Example 7

Determination of the In-Vivo Efficacy In a Mouse Septicemia Model with *Pasteurella multocida*

The objective of this study was to determine the in-vivo efficacy of antibiotic compounds after subcutaneous (SC) administration in a septicemia mouse model with *Pasteurella (P.) multocida*.

Materials and Methods

BALB/c mice were allocated to groups consisting of 6 mice. The mice of all groups (excluding the uninfected control group) were infected intraperitoneally (IP) with $3.2 \times 10^2$ CFU (colony forming units) *P. multocida* L386, Serotype A:14, per animal in 0.2 mL PBS.

Mice of the uninfected control group received 0.2 mL of sterile Phosphate Buffered Saline (PBS) intraperitoneally.

One hour after infection, the mice were treated subcutaneously with 10 mg/kg bodyweight of a 1 mg/mL solution of compounds of the invention in a 10% solution of Captisol® in PBS. The negative control groups were treated SC with 0.2 mL of galenic diluent only. In the positive control group Enrofloxacin was used in a commercial formulation ad usum veterinarium (Baytril® 2.5%, Bayer Animal Health), that was diluted with physiological saline for injection to achieve a concentration of 1 mg/mL and was administered at a dosage of 10 mg/kg bodyweight. The clinical time course of the infection was observed.

Survival of the mice was recorded at the end of the animal phase (D+2). At this timepoint all remaining mice were euthanized. From all animals of this study, a liver tissue sample was taken for quantitative re-isolation of bacteria.

Results:

"Mouse survival" indicates the number of animals (x/6) that survived at the end of the in-vivo phase (D+2) "Bacteriological cured" indicates that no bacteria were re-isolated from liver tissue (LOQ=100 CFU/g tissue). The following table 5-1 shows the results for representative compounds of the invention.

TABLE 5-1

| | No of animals survived | | | No of animals bacteriological cured | | | | |
|---|---|---|---|---|---|---|---|---|
| Compound ID | 4 of 6 | 5 of 6 | 6 of 6 | 2 of 6 | 3 of 6 | 4 of 6 | 5 of 6 | 6 of 6 |
| | C.192 | C.5 C.103 C.105 C.189 C.197 C.231 | | | C.5 C.247 | | C.103 C.105 C.189 C.192 C.197 C.231 C.245 | |
| | C.247 C.329 | C.251 C.364 C.258 | | | | C.259 | C.251 C.329 C.258 | C.364 |
| | C.259 | | | | | | C.326 | C.320 C.327 |
| | C.360 C.412 | C.320 C.326 C.327 | | | C.360 C.412 C.413 C.415 | | | |
| | | C.413 C.415 C.467 | | | | | C.467 | |
| | C.469 C.521 C.522 C.552 | | | | C.469 | | C.521 C.522 C.552 | |
| | | C.553 C.518 | | | | | C.518 | C.553 |
| | | C.500 C.582 C.583 C.601 | | | C.500 C.582 C.583 | | C.601 | |
| | | C.60.2 C.605 C.613 | | | | | C.605 C.613 | |
| | C.615 | C.616 | | | C.615 | C.616 | | |
| | C.607 C.668 C.687 | C.620 | | | C.620 C.607 C.668 C.687 | | C.689 | |
| | C.695 | C.689 | | | C.695 | | | |

Example 8

Antiinfective Efficacy of Subcutaneous Treatment In the *Mannheimia haemolytica* Cattle Lung Infection Model Material and Methods 15 male Holstein black pied cattle calves of ca. 4 months age were randomly assigned to the study groups ensuring an equal distribution of body weight. The animal weight was approximately 98-133.5 kg on D-1.

Calves were infected on Day 0 via intratracheal instillation of approximately 300 mL of a *M. haemolytica* PBS suspension containing approximately $3 \times 10^9$ CFU *M. haemolytica* in late log phase.

| Species | Ref.-no. | Serotype | ID | Origin/description |
|---|---|---|---|---|
| M. haemolytica | M7/2 | A:1 | 6357 | Isolate from cattle, United Kingdom |

Three animals each were treated one hour after infection by subcutaneous (SC) administration of Compound 329 in an aqueous 30% (w/v) Captisol® solution for injection at a dose of 10 mg/kg BW.

The respective dose volume was injected on the sides of the thoracic wall. Injection volumes exceeding 10 mL were divided into one portion of 10 mL administered to the left side and the remaining rest administered at different injection sites on the other side. Animals in one control group were treated with a commercially available Enrofloxacin solution (Baytril 10%, Bayer Animal Health) at the recommended dose of 10 mg/kg BW. The second control group was treated with the galenic diluent (30% (w/v) Captisol®, dissolved in water) as placebo.

Animals were observed for clinical parameters for two days. Food consumption was measured. Single individual blood samples were collected from the 12 animals at the following time points: D-1 (predose), 30 minutes, 2, 4, 6, 24 h and at D2 (ca. 45 h) after administration. After the day 2 blood sampling, the infected cattle were slaughtered. The lungs were weighted. Lung states and lung scores were observed morphologically.

At necropsy from animals treated with test items or the positive control, samples of epithelial lining fluid (ELF), lung tissue, and additionally tissue of liver and kidney were collected. From each lung two bacteriological swaps were taken from the left and right bronchus.

Epithelial lining fluid was collected by inserting sterile paper strips caudally behind the tracheal bifurcation directly onto the bronchial mucous membrane in the left and right bronchus and allowed to moisten with bronchial fluid. The paper strip was left in place (resting on the bronchial mucosa) for approximately 1 minute before being placed back into the plastic container.

From each lung two tissue samples were collected by clipping from at least two locations, one from morphologically unchanged tissue, one from the edge of pathomorphologically changed areas.

Plasma, ELF, lung tissue and additional tissue samples were analyzed for concentrations of Compound 329 and Enrofloxacin/Ciprofloxacin respectively using a HPLC-MS/MS method.

Results

Before infection, all calves showed no clinical symptoms of any infectious disease. After infection and administration of the items, 3 animals in the negative control group died before the end of the scheduled observation time. *Mannheimia* spp. lung infection was established in all calves in the experiment.

The following clinical observations were recorded:

With regard to the clinical parameters general behavior and food uptake it was observed that Compound 329 treated groups behaved comparable to the positive control-Enrofloxacin treated group.

TABLE 6-1

General behavior before and after infection with *M. haemolytica*

| Treatment | Animal number | General behavior, score* | | | | |
|---|---|---|---|---|---|---|
| | | D 0 am | D 0 pm | D 1 am | D 1 pm | D 2 am |
| C.329 | C 7 | 0 | 2 | 1 | 1 | 0 |
| SC 10 | C 8 | 0 | 1 | 0 | 1 | 0 |
| mg/kg | C 9 | 0 | 1 | 0 | 0 | 0 |
| | mean | 0.0 | 1.3 | 0.3 | 0.7 | 0.0 |
| Enrofloxacin | D 10 | 0 | 0 | 0 | 0 | 0 |
| SC 10 | D 11 | 0 | 0 | 0 | 0 | 0 |
| mg/kg | D 12 | 0 | 0 | 0 | 0 | 0 |
| | mean | 0.0 | 0.0 | 0.0 | 0.0 | 0.0 |
| Placebo | E 13 | 0 | 2 | 3 | 3 | n.a. |
| | E 14 | 0 | 1 | 2 | 2 | n.a. |
| | E 15 | 0 | 2 | 3 | 3 | n.a. |
| | mean | 0.0 | 1.7 | 2.7 | 2.7 | n.a. |

*0 = normal;
1 = slightly depressive,
2 = moderately depressive,
3 = highly depressive,
4 = recumbency.
n.a. = not available

TABLE 6-2

Food consumption [g], cumulated for all animals in the group

| | Food consumption/g | | | | |
|---|---|---|---|---|---|
| Treatment | D −1 | D 0 am* | D 0 pm | D +1 am | D +1 pm |
| C.329 | 4800 | 470 | 1800** | 4800 | 4800 |
| Enrofloxacin | 4800 | 660 | 4800 | 4800 | 4800 |
| Physiological saline | 4800 | 524 | 0 | 0 | 0 |

*after infection and treatment.
**at this time point a reduced ratio of 1800 g food was offered, due to reduced appetite.

The following pathomorphological findings were recorded:

Upon section the lung-body-weight-ratio and the levels of re-isolated bacteria confirmed the initial clinical results. Average ratios of nearly 1.3% for lungs of the C. 329 treated and the Enrofloxacin treated groups were clearly below the above 2.5% for the placebo treated groups.

TABLE 6-3

Lung weight and lung/body weight ratios

| Treatment with | Animal number | Body weight [kg] | Lung weight [g] | Lung/body weight ratio [%] |
|---|---|---|---|---|
| C.329 | C 7 | 132.0 | 1717 | 1.30 |
| SC 10 mg/kg | C 8 | 114.0 | 1549 | 1.36 |
| | C 9 | 112.0 | 1583 | 1.41 |
| | mean | 119.3 | 1616 | 1.36 |
| Enrofloxacin | D 10 | 102.0 | 1334 | 1.31 |
| SC 10 mg/kg | D 11 | 131.5 | 1765 | 1.34 |
| | D 12 | 118.5 | 1429 | 1.21 |
| | mean | 117.3 | 1509 | 1.29 |
| Placebo | E 13 | 119.0 | 2836 | 2.38 |
| | E 14 | 132.5 | 3141 | 2.37 |
| | E 15 | 108.0 | 2992 | 2.77 |
| | mean | 119.8 | 2990 | 2.51 |

TABLE 6-4

Lung consolidations and lung score

| Treatment with | Animal number | Lung consolidations [%] | Lung score (including grade* and percent Lung consolidation) |
|---|---|---|---|
| C.329 | C 7 | 14.8 | 29.5 |
| SC 10 mg/kg | C 8 | 21.6 | 37.7 |
|  | C 9 | 20.9 | 32.4 |
|  | mean | 19.1 | 33.2 |
| Enrofloxacin | D 10 | 13.0 | 21.2 |
| SC 10 mg/kg | D 11 | 10.8 | 16.9 |
|  | D 12 | 15.3 | 20.4 |
|  | mean | 13.0 | 19.5 |
| Placebo | E 13 | 54.1 | 108.2 |
|  | E 14 | 43.8 | 87.0 |
|  | E 15 | 59.6 | 119.1 |
|  | mean | 52.5 | 104.8 |

*The degree of lung consolidation score was graded from 0 to 3: 0 no visible changes, 1 low graded colour changes or induration, 2 medium graded induration, 3 high graded induration, hepatisation, necrosis.

The bacteriological re-isolations are described in Table 6-5:

Very low mean bacterial re-isolation in the C. 329 treated group and the Enrofloxacin treated group confirmed comparable antiinfective efficacy in the calf-*Mannheimia*-in-vivo-model for the two compounds.

TABLE 6-5

Re-isolation of bacteria from individual animals

| Treatment with | Animal number | Left Bronchial swab* | Right Bronchial swab |
|---|---|---|---|
| C.329, | C 7 | − | − |
| SC, single | C 8 | − | − |
| 10 mg/kg | C 9 | − | − |
| Enrofloxacin, | D 10 | − | − |
| SC, single | D 11 | − | − |
| 10 mg/kg | D 12 | − | − |
| Placebo, | E 13 | ++ | ++ |
| SC | E 14 | +++ | +++ |
|  | E 15 | +++ | +++ |

*no bacterial growth, + low, ++ medium, +++ high amount of bacterial growth.
**The detection of M. haemolytica for these samples was below the limit of quantification.

Analytical Detection of Test Item

Serum and tissue samples collected were analyzed for their content of C. 329. Compound concentrations above the plasma concentration were detected in the tissue samples. The detected levels are displayed in table 6-6.

TABLE 6-6

Measured concentrations of test compounds

| Treatment with | number Plasma | Concentration (ng/mL) | | | | | | |
|---|---|---|---|---|---|---|---|---|
|  |  | 0 h | 0.5 h | 2 h | 4 h | 6 h | 24 h | 48 h |
| C.329, | C 7 | 0 | 2340 | 1930 | 1200 | 692 | 146 | 60.5 |
| SC, single | C 8 | 0 | 1520 | 1410 | 856 | 928 | 187 | 57.4 |
| 10 mg/kg | C 9 | 0 | 1280 | 2330 | 1310 | 718 | 176 | 85.2 |
|  | mean | 0 | 1713 | 1890 | 1122 | 779 | 170 | 67.7 |

| Tissue (48 h) | ELF | Lung | Liver | Kidney |
|---|---|---|---|---|
| C 7 | 320 | 8290 | 7760 | 22800 |
| C 8 | 356 | 9410 | 7850 | 25500 |
| C 9 | 1370 | 7570 | 5130 | 17100 |
| mean | 682 | 8423 | 6913 | 21800 |

BLQ = below limit of quantification

An analysis of the measured plasma concentrations of C. 329 in Phoenix WinNonlin Ver 6.3 resulted in the parameters as displayed in table 6-7.

TABLE 6-7

Pharmacokinetic parameters from plasma concentrations

| Treatment with | | $AUC_{last}$ (h*ng/mL) | $C_{max}$ (ng/mL) | $T_{max}$ (h) | $MRT_{last}$ ** (h) | HL_Lambda_z * (h) | Vz_F_obs l/kg |
|---|---|---|---|---|---|---|---|
| C.329, SC 10 mg/kg | Mean | 19434 | 2063 | 1.0 | 9.7 | 11.1 | 7.8 |
|  | Standard deviation | 542 | 471 | 0.87 | 0.65 | 0.65 | 0.21 |

* Half life time,
** Mean retention time till last measured value.

Conclusion

For a single SC treatment with 10 mg/kg BW of Compound 329 good efficacy was observed in the lung model infection with *M. haemolytica* in calves.

The administered compound 329 was detected at high concentrations in plasma and section tissue samples.

Example 9

Antiinfective Efficacy of Subcutaneous Treatment in the *Mannheimia haemolytica* Cattle Lung Infection Model Unless otherwise described the study was conducted as described in Example 8.

Calves were infected via intratracheal instillation of appr. 300 mL of *M. haemolytica* PBS suspension containing approximately $4 \times 10^9$ CFU *M. haemolytica* in late log phase on Day 0.

Three animals each were treated one hour after infection by a single subcutaneous injection with 10 mg/kg of Compound 105 (referred to as C.105), F40 (80 mg/mL in 10% Poloxamer 188), Compound 189 (referred to as C.189) F40 (80 mg/mL in 10% Poloxamer 188) or Compound 326 (referred to as C. 326) F25 (80 mg/mL in 30% Captisol).

Results

The following clinical findings were recorded: The general behavior scores of the animals before (D0 am) and after infection with *M. haemolytica* in the different treated and control groups are indicated in FIG. 7-1: 0=normal;

1=slightly depressive, 2=moderately depressive, 3=highly depressive, 4=recumbency. The food consumption is indicated in Table 7-1.

The following pathomorphological findings after section on Day 2 were recorded: After measuring the body weight and the lung weight the the Lung body mass ratio was calculated as shown in in FIG. 7-2. A healthy animal has a lung body mass ration around 1.7 or lower. The area percentage of lung consolidations compared to the total lung tissue and the lung score determined that is a combined score of such percentage of lung consolidations and the grade. For the "grade" the degree of lung consolidation score was graded from 0 to 3 for each of eight lung lobes: 0 no visible changes, 1 low graded colour changes or induration, 2 medium graded induration, 3 high graded induration, hepatisation, necrosis. The calculated Lung consolidations and lung score" is indicated in FIG. 7-3

The geometrical means (CFU/g tissue) of bacteriological re-isolations of *Mannheimia haemolytica* from lung tissue are illustrated in FIG. 7-4.

TABLE 7-1

Food consumption [g], cumulated for all animals in the group

| Group | treated with | D − 1 | D 0 am * | D 0 pm | D + 1 am | D + 1 pm |
|---|---|---|---|---|---|---|
| A | C.105 SC 10 mg/kg BW | 4800 | 4800 | 4800 | 4800 | 4800 |
| B | C.189 SC 10 mg/kg BW | 4800 | 4800 | 4800 | 4800 | 4800 |
| C | C.326 SC 10 mg/kg BW | 4800 | 3911 | 4800 | 4800 | 4800 |
| D | Enrofloxacin SC 10 mg/kg BW | 4800 | 4027 | 4800 | 4737 | 4800 |
| E | Placebo SC, 10 mL | 4800 | 3060 | 24 | 5 | 0 |

* after infection and treatment.
** at this time point a reduced ratio of 1800 g food was offered, due to reduced appetite.

Analytical Detection of Test Items

TABLE 7-2

Measured concentrations of test compounds

| Treatment with | Animal number | Concentration (ng/mL) | | | | | | |
|---|---|---|---|---|---|---|---|---|
| | Plasma | 0 h | 0.5 h | 2 h | 4 h | 6 h | 24 h | 48 h |
| C.105 SC, single 10 mg/kg | A 1 | BLQ | 564 | 333 | 179 | 82.5 | 11.7 | 6.82 |
| | A 2 | BLQ | 540 | 346 | 178 | 176 | 14.8 | 8.7 |
| | A 3 | BLQ | 555 | 391 | 20.2 | 141 | 11.9 | 6.08 |
| | mean | / | 553 | 357 | 186 | 133 | 12.8 | 7.2 |
| | Tissue (48 h) | ELF | Lung | Liver | | Kidney | Muscle | |
| | A 1 | BLQ | BLQ | 41.7 | | 56.8 | 20.7 | |
| | A 2 | BLQ | BLQ | 38.1 | | 39.4 | BLQ | |
| | A 3 | BLQ | BLQ | 40.4 | | 42.9 | BLQ | |
| | mean | / | / | 40.1 | | 46.4 | / | |
| | Plasma | 0 h | 0.5 h | 2 h | 4 h | 6 h | 24 h | 48 h |
| C.189 SC, single 10 mg/kg | B 4 | BLQ | 916 | 465 | 433 | 339 | 31.3 | BLQ |
| | B 5 | BLQ | 892 | 663 | 300 | 293 | 20.3 | BLQ |
| | B 6 | BLQ | 1350 | 788 | 430 | 289 | 21.8 | BLQ |
| | mean | / | 1050 | 639 | 388 | 307 | 24.5 | / |
| | Tissue (48 h) | ELF | Lung | Liver | | Kidney | Muscle | |
| | B 4 | BLQ | BLQ | BLQ | | BLQ | BLQ | |
| | B 5 | BLQ | BLQ | 22.5 | | BLQ | BLQ | |
| | B 6 | BLQ | BLQ | BLQ | | 25.1 | BLQ | |
| | mean | / | / | / | | / | / | |
| | Plasma | 0 h | 0.5 h | 2 h | 4 h | 6 h | 24 h | 48 h |
| C.326 SC, single 10 mg/kg | C 7 | BLQ | 1470 | 754 | 434 | 535 | 10.8 | 39.5 |
| | C 8 | BLQ | 968 | 866 | 560 | 381 | 98.1 | BLQ |
| | C 9 | BLQ | 3070 | 1450 | 636 | 323 | 52.6 | 33.4 |
| | mean | / | 1840 | 1020 | 543 | 413 | 84.6 | 24.3 |
| | Tissue (48 h) | ELF | Lung | Liver | | Kidney | Muscle | |
| | C 7 | 426 | 3300 | 3760 | | 4990 | 217 | |
| | C 8 | 152 | 979 | 4310 | | 3520 | 251 | |
| | C 9 | 233 | 1280 | 2870 | | 5720 | 169 | |
| | mean | 270 | 1850 | 3650 | | 4740 | 212 | |

An analysis of the measured plasma concentrations in Phoenix WinNonlin Ver 6.3 resulted in the parameters as displayed in table 7-3.

TABLE 7-3

Pharmacokinetic parameters from plasma concentrations

| Treatment with | | $AUC_{last}$ h*ng/mL | $C_{max}$ ng/mL | $T_{max}$ h | $MRT_{last}$ ** h | HL_Lambda_z * h | Vz_F_obs L/kg | Cl_F_obs mL/h/kg |
|---|---|---|---|---|---|---|---|---|
| C.105, SC 10 mg/kg | Mean | 3207 | 553 | 0.5 | 6.34 | 7.77 | 34.8 | 3098 |
| | SD | 520.8 | 12.1 | 0 | 0.36 | 0.46 | 6.85 | 530.5 |
| C.189 SC 10 mg/kg | Mean | 6236 | 1053 | 0.5 | 4.75 | 4.98 | 11.2 | 1565 |
| | SD | 455.9 | 258 | 0 | 0.44 | 0.27 | 1.12 | 115.8 |
| C.326 SC 10 mg/kg | Mean | 10404 | 1836 | 0.5 | 7.25 | 9.58 | 6.21 | 453.6 |
| | SD | 1826 | 1098 | 0 | 1.74 | 1.03 | 0.18 | 63.63 |

* Half life time, SD = Standard deviation,
** Mean retention time till last measured value.

TABLE 7-4

Numeric results summary

| Compound No. | Route of administration | Intended Dose (mg/kg BW) | Survival (x of n)* | Bacteriological Cure (x of n) |
|---|---|---|---|---|
| C.105 | SC, single | 10 | 3/3 | 0/3 |
| C.189 | SC, single | 10 | 3/3 | 1/3 |
| C.326 | SC, single | 10 | 3/3 | 3/3 |

*x = number of animals, n = total number of animals in group

Conclusion

All three tested compounds Compound 105, Compound 189 and Compound 326 were found effective against an artificial lung infection with *M. haemolytica* M7/2 in the calf in the tested dosage of 10 mg/kg.

The test compounds were detected at high concentrations in plasma and section tissue samples.

Example 10

Antiinfective Efficacy of Subcutaneous Treatment in the *Mannheimia haemolytica* Cattle Lung Infection Model Material and Methods Unless otherwise described the study was conducted as described in Clinical Example 8

Calves were infected via intratracheal instillation of appr. 300 mL of *M. haemolytica* PBS suspension containing approximately 4×10$^9$ CFU *M. haemolytica* in late log phase on Day 0.

One hour later three animals each were treated with 10 mg/kg of Compound 231 (referred to as C. 231) (80 mg/mL in 10% Poloxamer 188), or 10 mg/kg or 5 mg/kg Compound 329 (referred to as C. 329) (150 mg/mL in 35% Cavitron).

Results

The following clinical findings were recorded: The general behavior scores of the animals before (D0 am) and after infection with *M. haemolytica* in the different treated and control groups are indicated in FIG. 8-1: 0=normal; 1=slightly depressive, 2=moderately depressive, 3=highly depressive, 4=recumbency. The food consumption is indicated in Table 8-1.

The following pathomorphological findings after section on Day 2 were recorded: After measuring the body weight and the lung weight the the Lung body mass ratio was calculated as shown in in FIG. 8-2. A healthy animal has a lung body mass ration around 1.7 or lower. The area percentage of lung consolidations compared to the total lung tissue and the lung score determined that is a combined score of such percentage of lung consolidations and the grade. For the "grade" the degree of lung consolidation score was graded from 0 to 3 for each of eight lung lobes: 0 no visible changes, 1 low graded colour changes or induration, 2 medium graded induration, 3 high graded induration, hepatisation, necrosis. The calculated Lung consolidations and lung score" is indicated in FIG. 8-3

The geometrical means (CFU/g tissue) of bacteriological re-isolations of *Mannheimia haemolytica* from lung tissue are illustrated in FIG. 8-4.

TABLE 8-1

Food consumption [g], cumulated for all animals in the group

| | | Food consumption/g | | | |
|---|---|---|---|---|---|
| Group | treated with | D − 1 D 0 am * | D 0 pm | D + 1 am | D + 1 pm |
| A | C.231, 10 mg/kg | 4800 1800** | 4800 | 4800 | 4800 |
| B | C.329, 10 mg/kg | 4800 1800** | 4800 | 4800 | 4800 |
| C | C.329, 5 mg/kg | 4800 1213 | 4800 | 4800 | 4800 |
| D | Enrofloxacin 10 mg/kg | 4800 1667 | 4800 | 4800 | 4800 |
| E | Placebo | 4800 659 | 114 | 0 | / |

* after infection and treatment.
**at this time point a reduced ratio of 1800 g food was offered, due to reduced appetite.

Analytical Detection of Test Items

TABLE 8-2

Measured concentrations of test compounds

| Treatment with | Animal number | Concentration (ng/mL) | | | | | | |
|---|---|---|---|---|---|---|---|---|
| | Plasma | 0 h | 0.5 h | 2 h | 4 h | 6 h | 24 h | 48 h |
| C.231, SC, single 10 mg/kg | A 1 | BLQ | 1150 | 448 | 179 | 83.9 | 6.21 | BLQ |
| | A 2 | BLQ | 1320 | 468 | 171 | 82.8 | 10.8 | 7.16 |
| | A 3 | BLQ | 1150 | 447 | 180 | 10.2 | 7.47 | 5.74 |
| | mean | / | 1210 | 454 | 177 | 89.6 | 8.16 | 4.3 |
| | Tissue (48 h) | ELF | Lung | Liver | Kidney | | Muscle | |
| | A 1 | BLQ | 26.6 | 48.7 | 56 | | BLQ | |
| | A 2 | BLQ | BLQ | 41.2 | 53.8 | | 27 | |
| | A 3 | BLQ | 22.4 | 66.9 | 79.3 | | BLQ | |
| | mean | / | 16.3 | 52.3 | 63 | | / | |
| | Plasma | 0 h | 0.5 h | 2 h | 4 h | 6 h | 24 h | 48 h |
| C.329 SC, single 10 mg/kg | B 4 | BLQ | 1160 | 476 | 310 | 210 | 69.1 | 49.3 |
| | B 5 | BLQ | 1610 | 439 | 267 | 172 | 42.9 | 38.5 |
| | B 6 | BLQ | 1400 | 550 | 282 | 174 | 57.5 | 32.4 |
| | mean | / | 1390 | 488 | 286 | 185 | 56.5 | 40.1 |
| | Tissue (48 h) | ELF | Lung | Liver | Kidney | | Muscle | |
| | B 4 | 1090 | 2780 | 3930 | 6570 | | 75.3 | |
| | B 5 | 372 | 3370 | 3650 | 20800 | | 68.5 | |
| | B 6 | 250 | 2790 | 2730 | 4620 | | 85.9 | |
| | mean | 571 | 2980 | 3440 | 10700 | | 76.6 | |
| | Plasma | 0 h | 0.5 h | 2 h | 4 h | 6 h | 24 h | 48 h |
| C.239 SC, single 5 mg/kg | C 7 | BLQ | 1140 | 327 | 146 | 110 | 32.2 | 16.1 |
| | C 8 | BLQ | 830 | 326 | 210 | 156 | 35.1 | 18.2 |
| | C 9 | BLQ | 945 | 221 | 130 | 78.7 | 22.8 | 12.8 |
| | mean | / | 972 | 291 | 162 | 115 | 30 | 15.7 |
| | Tissue (48 h) | ELF | Lung | Liver | Kidney | | Muscle | |
| | C 7 | 91.8 | 1560 | 2060 | 8890 | | 53.3 | |
| | C 8 | 214 | 1320 | 1550 | 3990 | | 45.7 | |
| | C 9 | 324 | 1360 | 1740 | 4940 | | 54.4 | |
| | mean | 210 | 1410 | 1780 | 5940 | | 51.1 | |

TABLE 8-3

| Compound No. | Route of administration | Intended Dose (mg/kg BW) | Survival (x of n)* | Bacteriological Cure (x of n) |
|---|---|---|---|---|
| C.231 | SC, single | 10 | 3/3 | 2/3 |
| C. 329 | SC, single | 10 | 3/3 | 3/3 |
| C.329 | SC, single | 5 | 3/3 | 1/3 |

*x = number of animals, n = total number of animals in group

Conclusion

The compounds were found effective against an artificial lung infection with M. haemolytica in the calf in the tested dosages 10 mg/kg for Compound C 231 and 10 mg/kg and 5 mg/kg for Compound C 329. The test compounds were detected at high concentrations in plasma and section tissue samples.

Example 11

Efficacy of a Representative Compound of the Invention Under "Field Like" Setting of Stress Typical for Commercial Feedyards in the United States Materials and Methods The effectiveness and safety of compound 329 for the treatment of naturally occurring bovine respiratory disease (BRD) under typical U.S. feedlot conditions when administered subcutaneously was investigated. The therapeutic efficacy of the two antibacterials was compared to a negative control group (sterile saline) and a positive control group (Nuflor® Injectable Solution).

Weaned beef cattle calves (crossbreds of Angus, Charolais and Limousin) were enrolled in the study and were allocated to groups of 20 animals per treatment group. Calves were enrolled in the study with body weights that ranged from 123 to 262 kg.

The bovine respiratory disease observed in this 10-day natural infection study was moderate to severe across the treatment groups and typical of that observed in commercial feed yards in the U.S.

Animals were dosed subcutaneously once on the day of enrollment (Day 0) with compound 329 or the control groups. Compound 329 was dosed at 10 mg/kg body weight. Nuflor® was dosed at 40 mg/kg body weight. Sterile saline was dosed at 2 mL/15 kg body weight.

Results

Mortalities during the study were 25% for the negative control (saline) group, and 5% for the compound 329 group. There were no mortalities in the positive control-Nuflor® group. Table 9-1 shows the removals of animals from the study.

TABLE 9-1

| Removals from the study | | | | | | | | | | | | | |
|---|---|---|---|---|---|---|---|---|---|---|---|---|---|
| Treatment Group (a) | Study Day: | D 0 | D 1 | D 2 | D 3 | D 4 | D 5 | D 6 | D 7 | D 8 | D 9 | D 10 | Total | Percentage |
| Saline | | 0 | 0 | 1 | 0 | 0 | 0 | 0 | 3 | 0 | 0 | 1 | 5 | 25% |
| Nuflor® | | 0 | 0 | 0 | 0 | 0 | 0 | 0 | 0 | 0 | 0 | 0 | 0 | 0% |
| C.329 | | 0 | 0 | 0 | 0 | 0 | 0 | 0 | 0 | 0 | 1 | 0 | 1 | 5% |

(a) 20 calves were enrolled in each group.

Average body weights were higher at the end of the study than at enrollment for all groups. Average daily body weight gain calculated for every animal individually resulted in an average negative performance for animals in the negative control group treated with saline. Animals in the positive control group, treated with Nuflor® or compound 329 exhibited positive daily body weight gains over the study period as shown in Table 9-2.

TABLE 9-2

| Average body weights | | | |
|---|---|---|---|
| Weights in lb | Saline | Nuflor ® | C.329 |
| Average Body weight on D 0 | 406.7 | 408.7 | 401.2 |
| Average Body weight on last day in study* | 411.3 | 431.7 | 406.3 |
| Average daily body weight gain* | −0.6 | 2.3 | 0.5 |

*The body weights and daily body weight gains of calves that were removed from the study before D 10 are included.

Bacteriology results showed an infective pressure of predominantly Mannheimia haemolytica, followed by Pasteurella multocida, and sporadically Histophilus somnus and Mycoplasma bovis at enrollment on Day 0. Gram-negative infection pressure was reduced by treatment in all groups, with remaining isolation of Mycoplasma bovis.

Conclusion

Efficacy of compound 329 was demonstrated in a "field like" setting of stress typical for commercial feedyards in the U.S. to induce naturally occurring bovine respiratory disease compared to negative and positive controls of saline and Nuflor®, respectively.

The invention claimed is:

1. A compound of the following formula

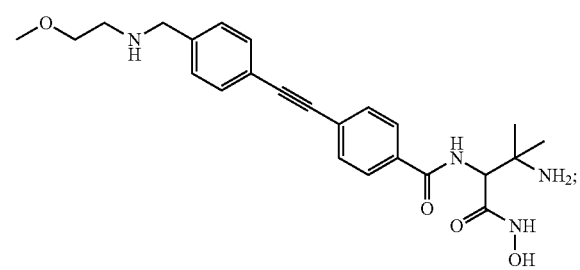 [SMILES: COCCNCc1ccc(C#Cc2ccc(C(=O)NC(C(=O)NO)C(C)(C)N)cc2)cc1]

or a pharmaceutically acceptable salt thereof.

2. A method of treatment of bovine respiratory disease or swine respiratory disease comprising administering to an animal a compound according to claim 1.

* * * * *